(12) United States Patent
Dang et al.

(10) Patent No.: US 9,079,930 B2
(45) Date of Patent: Jul. 14, 2015

(54) SUBSTITUTED PYRIMIDINES

(71) Applicant: MERCK SHARP & DOHME CORP., Rahway, NJ (US)

(72) Inventors: Qun Dang, Westfield, NJ (US); Changyou Zhou, Princeton, NJ (US); Wuxin Zou, Beijing (CN); Yuxia Hua, Beijing (CN)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/346,513

(22) PCT Filed: Sep. 19, 2012

(86) PCT No.: PCT/US2012/055961
§ 371 (c)(1),
(2) Date: Mar. 21, 2014

(87) PCT Pub. No.: WO2013/043624
PCT Pub. Date: Mar. 28, 2013

(65) Prior Publication Data
US 2014/0349972 A1 Nov. 27, 2014

Related U.S. Application Data

(60) Provisional application No. 61/555,693, filed on Nov. 4, 2011.

(30) Foreign Application Priority Data

Sep. 23, 2011 (WO) ................ PCT/CN2011/080118

(51) Int. Cl.
| C07D 413/14 | (2006.01) |
| A61K 31/505 | (2006.01) |
| C07F 9/6558 | (2006.01) |
| C07F 9/6503 | (2006.01) |
| C07F 9/6521 | (2006.01) |
| C07F 9/653 | (2006.01) |

(52) U.S. Cl.
CPC .......... *C07F 9/65583* (2013.01); *C07D 413/14* (2013.01); *C07F 9/65037* (2013.01); *C07F 9/65217* (2013.01); *C07F 9/65312* (2013.01); *A61K 31/505* (2013.01)

(58) Field of Classification Search
CPC .............. C07D 413/04; C07F 9/65037; C07F 9/65217; C07F 9/65312; C07F 6/65583; A61K 31/505
USPC .............................. 544/243, 319; 514/86, 269
See application file for complete search history.

(56) References Cited

U.S. PATENT DOCUMENTS

| 7,166,609 B2 | 1/2007 | Klingler et al. |
| 2007/0072876 A1 | 3/2007 | Tadiparthi et al. |
| 2009/0239876 A1 | 9/2009 | Clements et al. |
| 2011/0046132 A1 | 2/2011 | Hocutt et al. |

FOREIGN PATENT DOCUMENTS

| WO | WO2006094292 | 9/2006 |
| WO | WO2007038571 | 4/2007 |
| WO | WO2007150011 | 12/2007 |
| WO | WO2009086044 | 7/2009 |
| WO | WO2009117269 | 9/2009 |
| WO | WO2013040789 | 3/2013 |
| WO | WO2013043621 | 3/2013 |

OTHER PUBLICATIONS

Denny, Giving Anemia a Boost with Inhibitors of Prolyl Hydroxylase, Journal of Medicinal Chemistry, 55, pp. 2943-2944 (2012).*
Muchnik et al., HIF prolyl hydroxylase inhibitors for anemia, Expert Opinion Investig. Drugs, 20(5), pp. 645-656 (2011).*
Mole, David R. et al, 2-Oxoglutarate Analogue Inhibitors of HIF Prolyl Hydroxylase, Bioorganic & Medicinal Chemistry Letters, 2003, 2677-2680, 13, Elsevier Ltd., Oxford, UK.

* cited by examiner

*Primary Examiner* — Deepak Rao
(74) *Attorney, Agent, or Firm* — Matthew A. Leff; John C. Todaro

(57) ABSTRACT

The present invention relates to substituted pyrimidines useful as HIF prolyl hydroxylase inhibitors to treat anemia and like conditions.

16 Claims, No Drawings

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: PHD Substrate

<400> SEQUENCE: 1

Asp Leu Asp Leu Glu Met Leu Ala Pro Tyr Ile Pro Met Asp Asp Asp
 1               5                  10                  15

Phe Gln Leu
```

SUBSTITUTED PYRIMIDINES

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN$_2$, or egg laying abnormal 9 homolog 2, PHD2 (EGLN$_1$), and PHD3 (EGLN$_3$). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

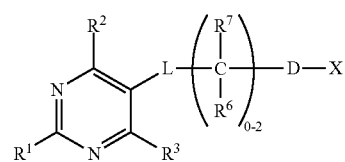

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts thereof:

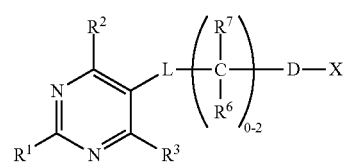

$R^1$ is a heteroaryl selected from isoxazolyl, pyrazolyl, imidazolyl, oxazolyl, thiazolyl, pyridinyl, pyradizinyl, and pyrimidinyl;

$R^2$ and $R^3$ are each independently chosen from hydrogen, hydroxy, —OR, —OCOR, —OCOOR, —OCONHR, and $C_{1-6}$alkyl;

X is selected from —$(C_{0-3}$alkyl$)PO(R')OR$, —$(C_{0-3}$alkyl$)PO(OR)_2$, —$(C_{0-3}$alkyl$)PO(NRR)_2$, —$SO_3R$, —$(C_{0-3}$alkyl$)PO(C_{1-10}$alkyl$)OR$, —$(C_{0-3}$alkyl$)PO(C_{3-10}$cycloalkyl$)OR$, —$(C_{0-3}$alkyl$)PO(H)OR$, —$(C_{0-3}$alkyl$)PO(NHCR'R''COOR)_2$ and —COOR;

R is independently selected from hydrogen, $C_{1-10}$ alkyl, —$C_{1-5}$ alkylaryl, —CR'R'—OCO—$C_{1-10}$ alkyl, and —CR'R'—OCO—O—$C_{1-10}$ alkyl;

R' and R" are independently selected from hydrogen and $C_{1-10}$ alkyl;

L is chosen from a bond, —$CONR^4$—, —$NR^4CO$—, aryl and heteroaryl;

D is chosen from a bond, aryl, and heteroaryl, provided that when L is a bond then D is aryl or heteroaryl;

$R^4$, $R^6$, and $R^7$ are each independently selected from
  hydrogen,
  halogen,
  carboxyl $C_{0-10}$ alkyl,
  $C_{1-10}$ alkyl,
  $C_{2-10}$ alkenyl, $C_{2-10}$ alkynyl,
$C_{1-10}$ alkenylamino,
$C_{1-10}$ alkyl(oxy)$_{0-1}$ carbonyl$C_{1-10}$ alkyl,
aryl $C_{0-10}$ alkyl(oxy)$_{0-1}$ carbonyl$C_{1-10}$ alkyl,
$C_{3-8}$ cycloalkyl $C_{0-10}$ alkyl(oxy)$_{0-1}$carbonyl $C_{1-10}$ alkyl,
$(C_{3-8})$heterocyclyl$C_{0-10}$ alkyl(oxy)$_{0-1}$carbonyl $C_{1-10}$ alkyl,
$(C_{3-8})$heterocycloalkyl $C_{0-10}$ alkyl(oxy)$_{0-1}$ carbonyl $C_{1-10}$ alkyl,
aryl(oxy)$_{0-1}$$C_{0-10}$ alkyl,
$C_{3-8}$ cycloalkyl(oxy)$_{0-1}$$C_{0-10}$ alkyl,
$C_{3-8}$ heterocyclyl(oxy)$_{0-1}$$C_{0-10}$ alkyl,
$C_{3-8}$ heterocycloalkyl(oxy)$_{0-1}$$C_{0-10}$ alkyl,
$C_{1-10}$ alkoxyl,
aryl$C_{1-10}$ alkoxyl, and
hydroxy$C_{0-10}$ alkyl;

wherein $R^1$, $R^2$, $R^3$, $R^4$, $R^6$, $R^7$, and D are optionally substituted with 1, 2, or 3 substituent $R^5$ chosen from:
halogen,
(carbonyl)$_{0-1}$$C_{1-10}$ alkyl,
(carbonyl)$_{0-1}$$C_{2-10}$ alkenyl,
(carbonyl)$_{0-1}$$C_{2-10}$ alkynyl,
$C_{1-10}$ alkylcarbonyl,
$C_{2-10}$ alkenylcarbonyl,
$C_{2-10}$ alkynylcarbonyl,
aryl $C_{0-10}$ alkyl,
$(C_{3-8})$heterocyclyl $C_{0-10}$ alkyl,
$C_{3-8}$ cycloalkyl $C_{0-10}$ alkyl,
$(C_{3-8})$heterocycloalkyl $C_{0-10}$ alkyl,
$C_{1-4}$acylamino $C_{0-10}$ alkyl,
$C_{0-10}$ alkylamino $C_{0-10}$ alkyl,
aryl$C_{0-10}$ alkylamino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
$C_{1-10}$alkyloxy $C_{0-10}$ alkyl,
$(C_{1-10}$ alkyl$)_2$aminocarbonyloxy,
hydroxy $C_{0-10}$ alkyl,
$C_{1-10}$ alkylsulfonyl,
$C_{1-10}$ alkylsulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
cyano,
nitro,
perfluoro$C_{1-6}$alkyl, and
perfluoro$C_{1-6}$alkoxy;

wherein $R^5$ is optionally substituted with 1, 2, or 3 substituents chosen from hydrogen, hydroxy, $(C_{1-6})$alkoxyl, halogen, $CO_2H$, CN, $O(C=O)C_1-C_6$ alkyl, $NO_2$, trifluoromethoxy, trifluoroethoxy,
—$O_{(0-1)}(C_{1-10})$perfluoroalkyl, and $NH_2$ and provided that when X is —COOR then L is isoxazoldiyl and D is phenyl.

Illustrative but nonlimiting examples of compounds of the invention are the following:

diethyl 4-((4-hydroxy-2-(pyridin-2-yl)pyrimidine-5-carboxamido)(4-methoxyphenyl)methyl)phenylphosphonate;
4-((4-hydroxy-2-(pyridin-2-yl)pyrimidine-5-carboxamido)(4-methoxyphenyl)methyl)phenylphosphonic acid;
(2S,2'S)-diethyl 2,2'-((4-((4-hydroxy-2-(pyridin-2-yl)pyrimidine-5-carboxamido)(4-methoxyphenyl)methyl)phenyl)phosphoryl)bis(azanediyl)dipropanoate;
diethyl 2,2'-((4-((4-hydroxy-2-(pyridin-2-yl)pyrimidine-5-carboxamido)(4-methoxyphenyl)methyl)phenyl)phosphoryl)bis(azanediyl)bis(2-methylpropanoate);
diethyl 2,2'-((4-((4-hydroxy-2-(pyridin-2-yl)pyrimidine-5-carboxamido)(4-methoxyphenyl)methyl)phenyl)phosphoryl)bis(azanediyl)diacetate;
4-((4-hydroxy-2-(pyridin-2-yl)pyrimidine-5-carboxamido)(4-methoxyphenyl)methyl)phenylphosphinic acid;
diethyl 4-((4-hydroxy-2-(pyridin-2-yl)pyrimidine-5-carboxamido)(phenyl)methyl)phenyl phosphonate;
4-((4-hydroxy-2-(pyridin-2-yl)pyrimidine-5-carboxamido)(phenyl)methyl)phenyl phosphonic acid;
ethyl 4-((4-hydroxy-2-(pyridin-2-yl)pyrimidine-5-carboxamido)(phenyl)methyl)phenylphosphonate;
ethyl 4-((4-hydroxy-2-(pyridin-2-yl)pyrimidine-5-carboxamido)(phenyl)methyl)phenyl(methyl)phosphinate;
4-((4-hydroxy-2-(pyridin-2-yl)pyrimidine-5-carboxamido)(phenyl)methyl)phenyl(methyl)phosphinic acid;
Diethyl 4-(1-(4-hydroxy-2-(pyridin-2-yl)pyrimidine-5-carboxamido)ethyl)phenyl phosphonate;
4-(1-(4-hydroxy-2-(pyridin-2-yl)pyrimidine-5-carboxamido)ethyl)phenylphosphonic acid;
Ethyl hydrogen 4-(1-(4-hydroxy-2-(pyridin-2-yl)pyrimidine-5-carboxamido)ethyl)phenylphosphonate;
4-(1-(4-Hydroxy-2-(pyridazin-3-yl)pyrimidine-5-carboxamido)ethyl)phenylphosphonic acid;
Diethyl (R)-4-(1-(4-hydroxy-2-(pyridin-2-yl)pyrimidine-5-carboxamido)ethyl)phenyl phosphonate;
(R)-4-(1-(4-hydroxy-2-(pyridin-2-yl)pyrimidine-5-carboxamido)ethyl)phenylphosphonic acid;
(R)-4-(1-(4-hydroxy-2-(pyridazin-3-yl)pyrimidine-5-carboxamido)ethyl)phenylphosphonic acid;
Diethyl (S)-4-(1-(4-hydroxy-2-(pyridin-2-yl)pyrimidine-5-carboxamido)ethyl)phenyl phosphonate;
(S)-4-(1-(4-hydroxy-2-(pyridin-2-yl)pyrimidine-5-carboxamido)ethyl)phenylphosphonic acid;
(S)-4-(1-(4-hydroxy-2-(pyridazin-3-yl)pyrimidine-5-carboxamido)ethyl)phenylphosphonic acid;
Diethyl 5-((4-hydroxy-2-(pyridin-2-yl)pyrimidine-5-carboxamido)(phenyl)methyl)pyridin-2-ylphosphonate;
Ethyl hydrogen 5-((4-hydroxy-2-(pyridin-2-yl)pyrimidine-5-carboxamido)(phenyl)methyl)pyridin-2-ylphosphonate;
3-((4-hydroxy-2-(pyridin-2-yl)pyrimidine-5-carboxamido)(4-methoxyphenyl)methyl)phenylphosphonic acid;
Diisopropyl (4-hydroxy-2-(pyridin-2-yl)pyrimidine-5-carboxamido)(phenyl)methyl phosphonate;
Isopropyl Hydrogen (4-hydroxy-2-(pyridin-2-yl)pyrimidine-5-carboxamido)(phenyl)methylphosphonate;
Isopropyl Hydrogen (4-hydroxy-2-(pyridin-2-yl)pyrimidine-5-carboxamido)(phenyl)methylphosphonate;
Diethyl 4-(1-(4-hydroxy-2-(pyridin-2-yl)pyrimidin-5-ylamino)-1-oxopropan-2-yl)phenyl phosphonate;
Diethyl 4-((4-hydroxy-2-(1H-pyrazol-1-yl)pyrimidine-5-carboxamido)(phenyl)methyl)phenylphosphonate;
Ethyl hydrogen 4-((4-hydroxy-2-(1H-pyrazol-1-yl)pyrimidine-5-carboxamido)(phenyl)methyl)phenylphosphonate;
Ethyl 4-((4-hydroxy-2-(1H-pyrazol-1-yl)pyrimidine-5-carboxamido)(phenyl)methyl)phenyl(methyl)phosphinate;
4-((4-Hydroxy-2-(1H-pyrazol-1-yl)pyrimidine-5-carboxamido)(phenyl)methyl)phenyl(methyl)phosphinic acid;
Diethyl 4-((4-hydroxy-2-(pyridazin-3-yl)pyrimidine-5-carboxamido)(phenyl)methyl)phenylphosphonate;
4-((4-Hydroxy-2-(1H-pyrazol-1-yl)pyrimidine-5-carboxamido)(4-methoxyphenyl)methyl)phenylphosphinic acid;
4-((4-hydroxy-2-(pyridazin-3-yl)pyrimidine-5-carboxamido)(4-methoxyphenyl)methyl)phenylphosphinic acid;
Diethyl (4-hydroxy-2-(1H-pyrazol-1-yl)pyrimidine-5-carboxamido)(4-methoxyphenyl)methylphosphonate;

Diethyl 4-(1-(4-hydroxy-2-(1H-pyrazol-1-yl)pyrimidin-5-ylamino)-1-oxopropan-2-yl)phenylphosphonate;
Diethyl 4-(1-(4-hydroxy-2-(1H-pyrazol-1-yl)pyrimidin-5-ylamino)-2-methyl-1-oxopropan-2-yl)phenylphosphonate;
Diethyl 4-(1-(4-hydroxy-2-(1H-pyrazol-1-yl)pyrimidin-5-ylamino)-3-methyl-1-oxobutan-2-yl)phenylphosphonate;
Diethyl 4-(2-(4-hydroxy-2-(1H-pyrazol-1-yl)pyrimidin-5-ylamino)-2-oxo-1-phenylethyl)phenylphosphonate;
Diethyl 4-(2-(4-hydroxy-2-(pyridazin-3-yl)pyrimidin-5-ylamino)-2-oxo-1-phenylethyl)phenylphosphonate;
4-(1-(4-hydroxy-2-(1H-pyrazol-1-yl)pyrimidine-5-carboxamido)ethyl)phenylphosphonic acid;
(R)-4-(1-(4-hydroxy-2-(1H-pyrazol-1-yl)pyrimidine-5-carboxamido)ethyl)phenyl phosphonic acid;
(S)-4-(1-(4-hydroxy-2-(1H-pyrazol-1-yl)pyrimidine-5-carboxamido)ethyl)phenylphosphonic acid;
4-((4-hydroxy-2-(1H-pyrazol-1-yl)pyrimidine-5-carboxamido)(phenyl)methyl)phenyl(propyl)phosphinic acid;
4-((4-fluorophenyl)(4-hydroxy-2-(1H-pyrazol-1-yl)pyrimidine-5-carboxamido)methyl)phenyl(methyl)phosphinic acid;
4-((R)-(4-fluorophenyl)(4-hydroxy-2-(1H-pyrazol-1-yl)pyrimidine-5-carboxamido)methyl)phenyl(methyl)phosphinic acid;
4-((S)-(4-fluorophenyl)(4-hydroxy-2-(1H-pyrazol-1-yl)pyrimidine-5-carboxamido)methyl)phenyl(methyl)phosphinic acid;
4-((R)-(2,4-difluorophenyl)(4-hydroxy-2-(1H-pyrazol-1-yl)pyrimidine-5-carboxamido)methyl)phenyl(methyl)phosphinic acid;
4-((S)-(2,4-difluorophenyl)(4-hydroxy-2-(1H-pyrazol-1-yl)pyrimidine-5-carboxamido)methyl)phenyl(methyl)phosphinic acid;
4-((S)-(4-hydroxy-2-(1H-pyrazol-1-yl)pyrimidine-5-carboxamido)(phenyl)methyl)phenyl(methyl)phosphinic acid;
4-((R)-(4-hydroxy-2-(1H-pyrazol-1-yl)pyrimidine-5-carboxamido)(phenyl)methyl)phenyl(methyl)phosphinic acid;
3-((R)-(4-hydroxy-2-(1H-pyrazol-1-yl)pyrimidine-5-carboxamido)(phenyl)methyl)phenyl(methyl)phosphinic acid;
3-((S)-(4-hydroxy-2-(1H-pyrazol-1-yl)pyrimidine-5-carboxamido)(phenyl)methyl)phenyl(methyl)phosphinic acid;
4-((R)-cyclohexyl(4-hydroxy-2-(1H-pyrazol-1-yl)pyrimidine-5-carboxamido)methyl)phenyl(methyl)phosphinic acid;
4-((S)-cyclohexyl(4-hydroxy-2-(1H-pyrazol-1-yl)pyrimidine-5-carboxamido)methyl)phenyl(methyl)phosphinic acid;
4-((S)-(2-(4-fluoro-1H-pyrazol-1-yl)-4-hydroxypyrimidine-5-carboxamido)(4-fluorophenyl)methyl)phenyl(methyl)phosphinic acid;
4-((R)-(2-(4-fluoro-1H-pyrazol-1-yl)-4-hydroxypyrimidine-5-carboxamido)(4-fluorophenyl)methyl)phenyl(methyl)phosphinic acid;
(4-hydroxy-2-(pyridazin-3-yl)pyrimidine-5-carboxamido)(phenyl)methylphosphonic acid;
(4-Hydroxy-2-(pyridazin-3-yl)pyrimidine-5-carboxamido)(4-methoxyphenyl)methyl phosphonic acid;
(4-Hydroxy-2-(pyridazin-3-yl)pyrimidine-5-carboxamido)(naphthalen-2-yl)methyl phosphonic acid;
Diethyl 2,2'-((4-((4-hydroxy-2-(pyridazin-3-yl)pyrimidine-5-carboxamido)(4-methoxyphenyl)methyl)phenyl)phosphoryl)bis(azanediyl)diacetate;
(2S,2'S)-Diethyl 2,2'-((4-((4-hydroxy-2-(pyridazin-3-yl)pyrimidine-5-carboxamido)(4-methoxyphenyl)methyl)phenyl)phosphoryl)bis(azanediyl)dipropanoate;
4-((4-hydroxy-2-(pyridazin-3-yl)pyrimidine-5-carboxamido)(4-methoxyphenyl)methyl)benzylphosphonic acid;
4-(5-(2-(4-hydroxy-2-(pyridazin-3-yl)pyrimidine-5-carboxamido)propan-2-yl)pyridine-2-yl)phenylphosphonic acid;
3-((4-hydroxy-2-(pyridazin-3-yl)pyrimidine-5-carboxamido)(4-methoxyphenyl)methyl)phenylphosphonic acid;
3-(2-(4-hydroxy-2-(pyridazin-3-yl)pyrimidin-5-ylamino)-2-oxoethyl)phenyl phosphonic acid
(4-Hydroxy-2-(pyridazin-3-yl)pyrimidine-5-carboxamido)(4-methoxyphenyl)methyl phosphonic acid;
4-(5-(4-Hydroxy-2-(pyridin-2-yl)pyrimidin-5-yl)isoxazol-3-yl)benzoic acid; 4-(5-(4-hydroxy-2-(pyridin-2-yl)pyrimidin-5-yl)isoxazol-3-yl)phenyl(methyl)phosphinic acid; and pharmaceutically acceptable salts thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$-, ($C_0$-$C_6$ alkyl)$S(O)_{0-2}$($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)—NH($C_1$-$C_6$ alkyl), NHC(O)O$C_1$-$C_6$ alkyl, —NH($C_1$-$C_6$ alkyl)NHSO$_2$($C_1$-$C_6$ alkyl), —($C_0$-$C_6$ alkyl)NHSO$_2$($C_1$-$C_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

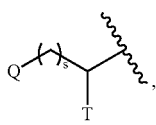

wherein s is an integer equal to zero, 1 or 2, the structure is

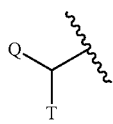

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or $OH$. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

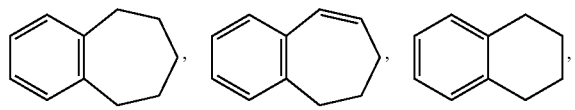

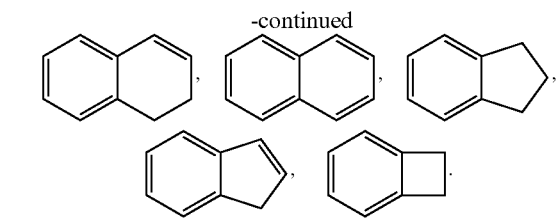

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl (i.e.,

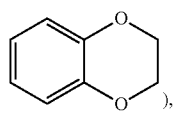), imidazo(2,1-b)(1,3)thiazole, (i.e.,

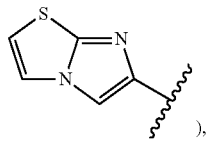 [SMILES: *c1cn2ccsc2n1]), and benzo-1,3-dioxolyl (i.e.,

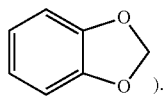).

In certain contexts herein,

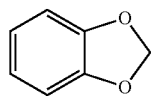

is alternatively referred to as phenyl having as a substituent methylenedioxy attached to two adjacent carbon atoms.

The term "heteroarylene" refers to the diradical group derived from heteroaryl, heterocyclylics, heterocycles, (including substituted heteroaryl, heterocyclylics, heterocycle etc.), as defined above, and are exemplified by the groups pyrazolene, imidazolene, oxazoldylene, thiazoldylene, pyradizindylene, pyrimidinylene, pyridylene, pyridinylene, quinolinylene, benzofuranylene, indolenyl, isoxazolene, and the like.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)$_2$NC(O)—($C_0$-$C_6$alkyl)O($C_1$-$C_6$ alkyl)-, ($C_0$-$C_6$ alkyl)C(O)$_{1-2}$($C_{0-6}$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

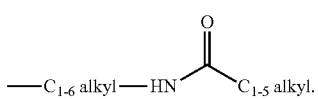

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In one embodiment of the invention is a compound of formula I and pharmaceutically acceptable
salts thereof:
$R^1$ is a heteroaryl selected from isoxazolyl, pyrazolyl, imidazolyl, oxazolyl, thiazolyl, pyridinyl, pyradizinyl, and pyrimidinyl;
$R^2$ and $R^3$ are each independently chosen from hydrogen, hydroxy, and $C_{1-6}$alkyl;
X is selected from —$(C_{0-3}$alkyl$)PO(R')OR$, —$(C_{0-3}$alkyl$)PO(OR)_2$, —$(C_{0-3}$alkyl$)PO(NRR)_2$, —$SO_3R$,
—$(C_{0-3}$ alkyl$)PO(C_{1-10}$alkyl$)OR$, —$(C_{0-3}$ alkyl$)PO(C_{3-10}$ cycloalkyl$)OR$,
—$(C_{0-3}$alkyl$)PO(H)OR$, and —$(C_{0-3}$alkyl$)PO(NHCR'R''COOR)_2$;
R is independently selected from hydrogen, $C_{1-10}$ alkyl, —$C_{1-5}$ alkylaryl, —$CR'R'$—$OCO$—$C_{1-10}$ alkyl, and —$CR'R'$—$OCO$—$O$—$C_{1-10}$ alkyl;
R' and R'' are independently selected from hydrogen and $C_{1-10}$ alkyl;
L is chosen from a bond, —$CONR^4$—, —$NR^4CO$—, aryl and heteroaryl;
D is chosen from a bond, aryl, and heteroaryl provided that when L is a bond, D is aryl or heteroaryl;
$R^4$, $R^6$, and $R^7$ are each independently selected from:
hydrogen, halogen, carboxyl $C_{0-10}$ alkyl, $C_{1-10}$ alkyl, $C_{2-10}$ alkenyl, $C_{2-10}$ alkynyl,
$C_{1-10}$ alkenylamino, $C_{1-10}$ alkyl(oxy)$_{0-1}$ carbonyl$C_{1-10}$ alkyl,
aryl $C_{0-10}$ alkyl(oxy)$_{0-1}$ carbonyl$C_{1-10}$ alkyl,
$C_{3-8}$ cycloalkyl $C_{0-10}$ alkyl(oxy)$_{0-1}$carbonyl $C_{1-10}$ alkyl,
($C_{3-8}$)heterocyclyl $C_{0-10}$ alkyl(oxy)$_{0-1}$carbonyl $C_{1-10}$ alkyl,
($C_{3-8}$)heterocycloalkyl $C_{0-10}$ alkyl(oxy)$_{0-1}$ carbonyl$C_{1-10}$ alkyl, aryl(oxy)$_{0-1}C_{0-10}$ alkyl,
$C_{3-8}$ cycloalkyl(oxy)$_{0-1}C_{0-10}$ alkyl, $C_{3-8}$ heterocyclyl (oxy)$_{0-1}C_{0-10}$ alkyl,
$C_{3-8}$ heterocycloalkyl(oxy)$_{0-1}C_{0-10}$ alkyl, $C_{1-10}$ alkoxyl, aryl$C_{1-10}$ alkoxyl, and
hydroxy$C_{0-10}$alkyl; wherein, $R^1, R^2, R^3, R^4, R^6, R^7$, and D are optionally substituted with 1, 2, or 3 substituent $R^5$ is chosen from:
halogen, (carbonyl)$_{0-1}C_{1-10}$ alkyl, (carbonyl)$_{0-1}C_{2-10}$ alkenyl, (carbonyl)$_{0-1}C_{2-10}$ alkynyl,
$C_{1-10}$ alkylcarbonyl, $C_{2-10}$ alkenylcarbonyl, $C_{2-10}$ alkynylcarbonyl, aryl $C_{0-10}$ alkyl,
($C_{3-8}$)heterocyclyl $C_{0-10}$ alkyl, $C_{3-8}$ cycloalkyl $C_{0-10}$ alkyl,
($C_{3-8}$)heterocycloalkyl $C_{0-10}$ alkyl, $C_{1-4}$acylamino $C_{0-10}$ alkyl, $C_{0-10}$ alkylamino $C_{0-10}$ alkyl,
aryl$C_{0-10}$ alkylamino $C_{0-10}$ alkyl, $C_{3-8}$ cycloalkyl $C_{0-10}$ alkylamino $C_{0-10}$ alkyl, $C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl, $C_{1-10}$alkyloxy $C_{0-10}$alkyl,
($C_{1-10}$ alkyl)$_2$aminocarbonyloxy, hydroxy$C_{0-10}$alkyl, $C_{1-10}$ alkylsulfonyl, $C_{1-10}$ alkylsulfonylamino,
aryl $C_{1-10}$ alkylsulfonylamino, $C_{3-8}$ heterocyclyl $C_{1-10}$ alkylsulfonylamino, $C_{3-8}$ heterocycloalkyl $C_{1-10}$ alkylsulfonylamino, $C_{3-8}$ cycloalkyl $C_{1-10}$ alkylsulfonylamino, cyano, nitro, perfluoro$C_{1-6}$alkyl, and
perfluoro$C_{1-6}$alkoxy; and wherein $R^5$ is optionally substituted with 1, 2, or 3 substituents chosen from hydrogen, hydroxy, ($C_{1-6}$)alkoxyl, halogen, $CO_2H$, CN, $O(C=O)C_1-C_6$ alkyl, $NO_2$, trifluoromethoxy, trifluoroethoxy, —$O_{(0-1)}(C_{1-10})$perfluoroalkyl, and $NH_2$.

In one embodiment of the invention, L is chosen from —$CONR^4$—, and —$NR^4CO$—. Another aspect of the invention, L is chosen from a bond, aryl, and heteroaryl. In a variant of this embodiment, L is heteroaryl.

In one embodiment, L is chosen from isoxazoldiyl oxazoldiyl, pyrazoldiyl, imidazoldiyl, thazoldiyl, pyridindiyl, pyradizindiyl, and pyrimidindiyl. In a variant of this embodiment, L is isoxazoldiyl.

In another embodiment of the invention, $R^1$ is a heteroaryl selected from isoxazolyl, imidazolyl, oxazolyl, pyridinyl, pyradizinyl, and pyrimidinyl, optionally substituted with 1, 2, or 3 $R^5$ substituents. $R^1$ is a heteroaryl selected from pyridinyl, pyradizinyl, and pyrimidinyl, optionally substituted with 1, 2, or 3 $R^5$ substituents.

In one embodiment, $R^2$ is hydroxy.

In another embodiment of the invention, $R^3$ is hydrogen.

In one embodiment, $R^4$, $R^6$, and $R^7$ are each independently selected from hydrogen, aryl $C_{0-10}$ alkyl, ($C_{3-8}$)heterocyclyl$C_{0-10}$ alkyl, $C_{3-8}$ cycloalkyl$C_{0-10}$ alkyl, ($C_{3-8}$) heterocycloalkyl$C_{0-10}$ alkyl, $C_{1-10}$ alkyl, aryl$C_{1-10}$ alkoxyl, and hydroxy$C_{0-10}$alkyl.

In yet another embodiment of the invention, $R^4$, $R^6$, and $R^7$ are each independently selected from napthalene, phenylmethoxy, phenyl, methyl, ethyl, propyl, cyclohexyl, and hydrogen.

In one embodiment of the invention, $R^2$, $R^3$, and $R^6$ are each independently chosen from hydrogen, hydroxy, aryl (oxy)$_{0-1}C_{0-10}$ alkyl, $C_{3-8}$ cycloalkyl(oxy)$_{0-1}C_{0-10}$ alkyl, $C_{3-8}$ heterocyclyl(oxy)$_{0-1}C_{0-10}$ alkyl, $C_{3-8}$ heterocycloalkyl (oxy)$_{0-1}C_{0-10}$ alkyl, and $C_{1-4}$alkyl, wherein $R^2$, $R^3$, and $R^6$ are each independently optionally substituted by 1, 2, or 3, $R^5$ substituents.

In another embodiment, In one embodiment of the invention, $R^2$, $R^3$, and $R^6$ are each independently chosen from hydrogen, hydroxy, aryl(oxy)$_{0-1}C_{0-10}$ alkyl, $C_{3-8}$ cycloalkyl (oxy)$_{0-10}C_{0-10}$ alkyl, and $C_{1-4}$alkyl.

In one embodiment of the invention, $R^6$ is chosen from hydrogen, hydroxy, aryl(oxy)$_{0-10}C_{0-10}$ alkyl, $C_{3-8}$ cycloalkyl (oxy)$_{0-1}C_{0-10}$ alkyl, and $C_{1-4}$alkyl. In a variant of this embodiment, $R^6$ is chosen from hydrogen, phenylmethoxy, methyl ethyl propyl, and cyclohexyl.

In one embodiment of the compounds of Formula I, R is independently selected from hydrogen, $C_{1-10}$ alkyl, —$C_{1-5}$ alkylaryl, and —CR'R'—OCO—$C_{1-10}$ alkyl. In a variant of this embodiment, R is independently selected from hydrogen, $C_{1-10}$ alkyl, and —$C_{1-5}$ alkylaryl.

In one embodiment, R' and R" are independently selected from hydrogen and $C_{1-10}$ alkyl.

In one embodiment, D is chosen from a bond, aryl, heteroaryl, aryl, and heteroaryl, optionally substituted by 1, 2, or 3, $R^5$ substituents. In a variant of this invention, D is chosen from hydrogen, phenylene, and pipidindiyl, pyridindiyl, optionally substituted by 1, 2, or 3, $R^5$ substituents.

Structural representations of compounds having substituents terminating with a methyl group may display the terminal methyl group either using the characters "CH$_3$", e.g. "—CH$_3$" or using a straight line representing the presence of the methyl group, e.g. "———", i.e.,

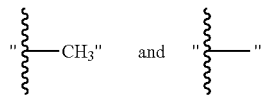

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

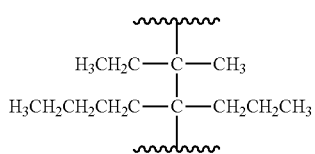

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —CH$_2$C(O)— groups (keto forms) may undergo tautomerism to form hydroxy-CH═C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

ABBREVIATIONS USED IN THE DESCRIPTION
OF THE PREPARATION OF THE COMPOUNDS
OF THE PRESENT INVENTION

~ Approximately
AcOH Acetic acid
$Ag_2O$ Silver oxide
AIBN 2,2'-azobis(2-methylpropionitrile)
Aq Aqueous
Bn Benzyl
BnBr benzylbromide
BnCl benzylchloride
BnOH benzylalcohol
$Boc_2O$ or di-tert-butyl dicarbonate
$BOC_2O$ Brine Saturated aqueous sodium chloride solution
BuLi n-butyl lithium
CDI Carbonyl diimidazole
DBU 1,8-diazabicyclo[5.4.0]undec-7-ene
DCC N,N'-dicyclohexylcarbodiimide
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide
EDC or EDCI 1-(3-dimethylaminopropyl)-3-ethylcarboiimide hydrogenchloride salt
EtOAc or EA Ethyl acetate
Et (et) Ethyl
EtOH Ethanol
$Et_2O$ or ether Diethyl ether
$Et_3N$ triethylamine
g Gram
h or hr Hour
HATU O-(7-Azabenzotriazol-1-yl)-N,N,N',N'-tetramethyluronium hexafluorophosphate
HCl Hydrochloric acid
HOBt 1-hydroxybenzatriazole
HPLC High-performance liquid chromatography
i-propanol Isopropyl alcohol
i-PrOH or IPA Isopropyl alcohol
$K_2CO_3$ Potassium carbonate
KOH Potassium hydroxide
LiOH Lithium hydroxide
Mg Milligrams
mL Milliliters
mmol Millimole
MeCN Acetonitrile
MeOH Methanol
min Minutes
ms or MS Mass spectrum
μg Microgram(s)
μL Microliters
NaOEt Sodium ethoxide
NaOMe Sodium methoxide
$Na_2SO_4$ Sodium sulfate
NBS N-bromosuccinimide
NHAc Acetamido
NHCbz Benzyloxycarboxamido
NaOH Sodium hydroxide
$NaN_3$ Sodium azide
$NH_4OH$ ammonium hydroxide
NMP N-methylpyrrolidone
Pd/C Palladium on carbon
$Pd(OH)_2$ Palladium hydroxide
$Pd(PPh_3)_4$ Palladium tetrakis(triphenylphosphine)
PhLi Phenyl lithium
PG Protecting group
Ph or Ph Phenyl group
PMB Para-methoxybenzyl
PPTs Pyridinium Para-toluenesulfonate
$PPh_3$ Triphenyphosphine
$R_t$ Retention time
RT or rt Room temperature
$SOCl_2$ Thionyl chloride
TEA Triethylamine
TFA Trifluoroacetic acid
THF Tetrahydrofuran
TBTU O-(Benzotriazol-1-yl)-N,N,N',N'-tetramethyluronium tetrafluoroborate
TMS Trimethylsilyl
TMSBr Trimethylsilyl bromide
TMSCN Trimethylsilyl cyanide
$TMSCHN_2$ (trimethylsilyl)diazomethane
TsCl Para-toluenesulfonyl chloride Synthesis The compounds of this invention may be prepared by employing reactions as shown in the following schemes, in addition to other manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The following schemes and descriptions illustrate methods which may be employed for the synthesis of the novel compounds described in this invention. All substituents are as defined above unless indicated otherwise. Several strategies based upon synthetic transformations known in the literature of organic synthesis may be employed for the preparation of the title compounds of general formula I. The choice of the method employed is influenced by the selection of the desired substituent groups ($R^1$ through $R^3$, L, X and A) in the title compounds of general formula I.

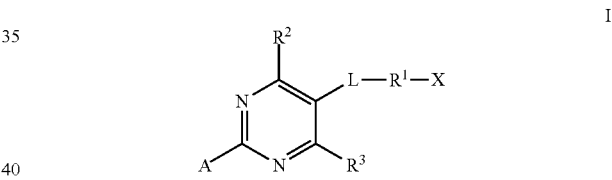

Pyrimidine intermediates useful for the preparation of compounds of formula I of the present invention are either purchased or prepared using suitable procedures reported in the literature (sometimes with minor modifications). The desired X, A and $R^{1-3}$ groups could be introduced at various stages of the synthetic sequence, which will be determined by synthetic feasibility. For example, compounds of formula I wherein L is amide could be prepared from pyrimidine intermediates with a C5-carboxylic acid group (e.g. 1S-6, 2S-10).

One generally useful method for the synthesis of pyrimidines suitable for the preparation of the title compounds of general formula I wherein the substituent $R^2$ is a hydroxy group is illustrated in Scheme 1.

Scheme 1

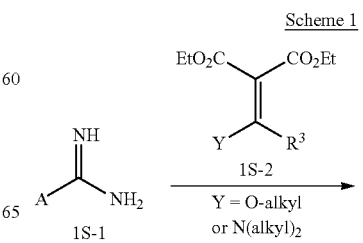

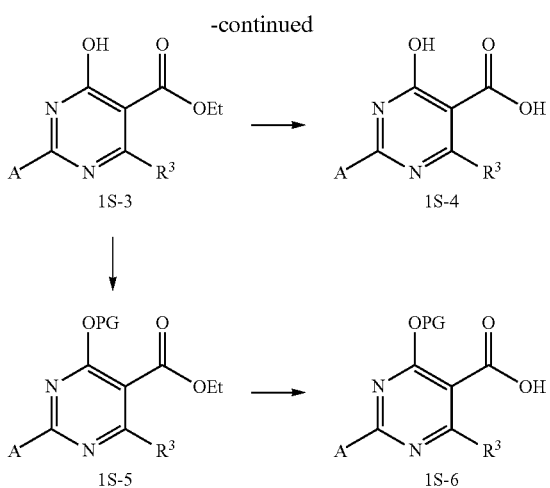

This method involves the initial synthesis of substituted 4-hydroxypyrimidine-5-carboxylates of general formula 1S-4 and 1S-6 (PG denotes protecting group). The synthesis of 4-hydroxypyrimidine-5-carboxylates exemplified in Scheme 1 is based upon reported methods (Dostert, P.; Imbert, T.; Ancher, J. F.; Langlois, M.; Bucher, B.; Mocquet, G. *Eur. J. Med. Chem.* 1982, 17, 437-44. Juby, P. F.; Hudyma, T. W.; Brown, M.; Essery, J. M.; Partyka, R. A. *J. Med. Chem.* 1979, 22, 263-9).

In this method, an amidine or a suitable salt thereof of general formula 1S-1 is reacted with an optionally substituted diethyl methylenemalonate of general formula 1S-2. This reaction is usually conducted using a suitable base such as sodium or potassium ethoxide in ethanol, although other reaction conditions may also be applied. The alkoxide base and the alcohol solvent are chosen to correspond to the esters present in reagent 1S-2 to prevent the formation of mixtures of esters in the product of general formula 1S-3. When required, the reaction is conducted at elevated temperature, typically at the reflux temperature of the solvent until reaction is complete (generally within 1-4 hours). It is also convenient to conduct this reaction under microwave heating in sealed reaction vessels. In this instance, the reaction is generally conducted at temperatures between 80 and 120° C. and the reactions are typically completed in 5-30 minutes.

Compounds of general formula 1S-3 are useful intermediates to prepare compounds of formula I of the present invention. For example, compounds of general formula 1S-3 may be hydrolyzed using a suitable base (e.g. sodium or potassium hydroxide) to give acids of formula 1S-4; alternatively, they are converted to compounds of formula 1S-5, in which the hydroxy group of the pyrimidine core is protected with a desired protecting group (e.g. PG is benzyl, para-methoxy-benzyl, trityl, or tert-butyl-dimethyl silyl); such a protecting group strategy would allow further modifications of A and/or $R^3$ into the desired substituents. Hydrolysis of compounds of formula 1S-5 gives acids of general formula 1S-6, which is readily achieved under suitable ester hydrolysis reaction conditions (Wuts, P. G. M.; Greene, T. W., Protecting Groups in Organic Synthesis, John Wiley and Sons, 4$^{th}$ Edition, 2007).

When amidines of general formula 1S-1 are not commercially available, they may be prepared by a variety of methods known in the literature. Amidines are commonly prepared from nitriles using the Pinner reaction and variations thereof (see Amidines and N-substituted amidines. Dunn, Peter J. in Comprehensive Organic Functional Group Transformations 1995, 5, 741-82, 1161-308 Editor(s): Katrizky, Alan R.; Meth-Cohn, Otto; Rees, Charles Wayne. Publisher: Elsevier, Oxford, UK). Amidines may also be prepared from esters using the method reported by Gielen et al. (Gielen, H.; Alonso-Alija, C.; Hendrix, M.; Niewohner, U.; Schauss, D. *Tetrahedron Lett.* 2002, 43, 419-21).

In instances where the substituent A is selected to be a five-membered heterocyclic ring, it is possible that this heterocyclic group be bonded to the carbon atom at the 2-position of the pyrimidine ring through either a carbon-carbon or a carbon-nitrogen bond. In the case of attachment through a carbon-carbon bond, the precursor for the substituent A is an amidine of general formula 1S-1 and the method using 1S-1 for the synthesis of the title compound of general formula I is as described in the preceding reaction schemes.

When a substituent A is attached through a carbon-nitrogen bond, the precursor for the substituent A is a guanidine of general formula 2S-7. In this example, the synthesis begins with the condensation of the guanidine derivative of general formula 2S-7 with compounds of general formula 2S-8 (or a diethyl ethoxymethylenemalonate of general formula 1S-2 when it is desired that $R^2$=OH) to afford the substituted pyrimidine-5-carboxylate derivative of general formula 2S-9. Ester hydrolysis as described above affords compounds of formula 2S-10, which is useful to prepare compounds of general formula I wherein the group A is a five-membered heterocyclic group attached to the pyrimidine 2-position with a carbon-nitrogen bond.

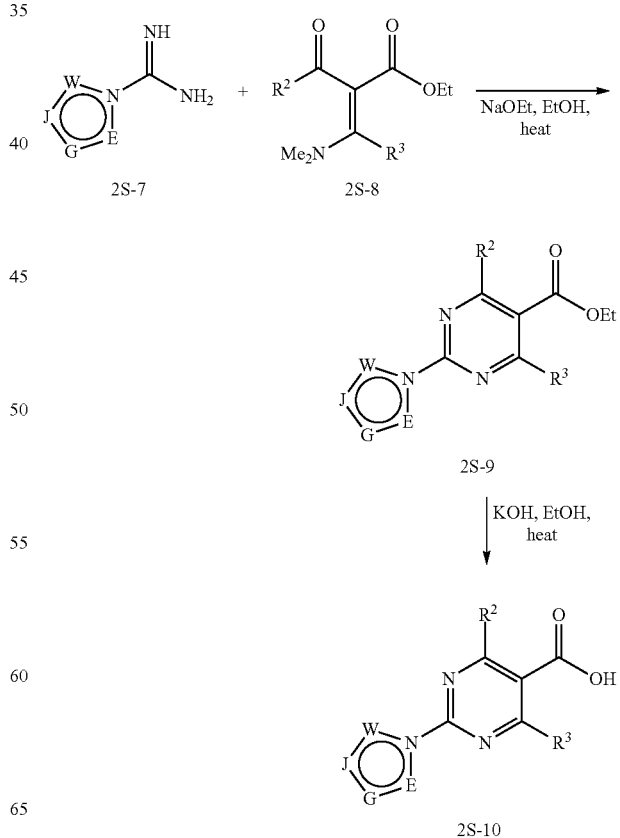

In cases when the guanidine derivative (2S-7) bearing the desired substituents is not commercially available, it may be synthesized using reported methods for guanidine synthesis (e.g. the guanidinylation of amines). Numerous methods for the guanidinylation of amines are reported (see Katritzky, A. R.; Rogovoy, B. V. ARKIVOC 2005, 4, 49-87; http://www.arkat-usa.org/ark/journal/2005/I04_Zefirov/1256/1256.pdf). One general method is shown in Scheme 3, which entails the reaction of compounds of formula 3S-11 with 3,5-dimethyl-1-pyrazolylformamidinium nitrate to afford a guanidine of general formula 3S-12 using the method described by Fletcher et al. (Fletcher, D. I.; Ganellin, C. R.; Piergentili, A.; Dunn, P. M.; Jenkinson, D. H. *Bioorg. Med. Chem.* 2007, 15, 5457-79).

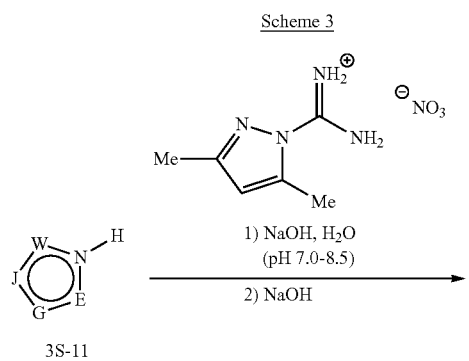

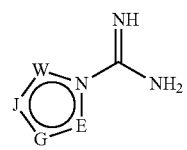

It is recognized that the title compounds of general formula I prepared as described above may be further modified using known methods and that the starting materials selected for use in the reaction schemes above may contain functional groups to enable said further transformation. For instance, aromatic rings in the title compounds of general formula I may be subjected to a variety of aromatic substitution reactions such as nitration, halogenation and the like. Aromatic substituent groups in the title compounds of general formula I bearing leaving groups such as halogens, triflates or the like, can be employed in a variety of metal-catalyzed cross coupling reactions to incorporate new substitution patterns. For example, palladium-catalyzed cross coupling reactions such as those described by Suzuki, Stille, Buchwald and others, may be used to introduce a variety of new substituent groups. Substituent groups that may be introduced using such cross-coupling methods include, but are not limited to, alkyl, alkenyl, alkynyl and aryl groups as well as acyl groups (e.g. carboxylic acids, esters, amides, or ketones), hydroxy and amino or substituted amino groups.

Other pyrimidines with various substituents at the 5-position (wherein R" is not a carboxylate) are also prepared via cyclization reactions described in Schemes 1 & 2, which are exemplified in Scheme 4.

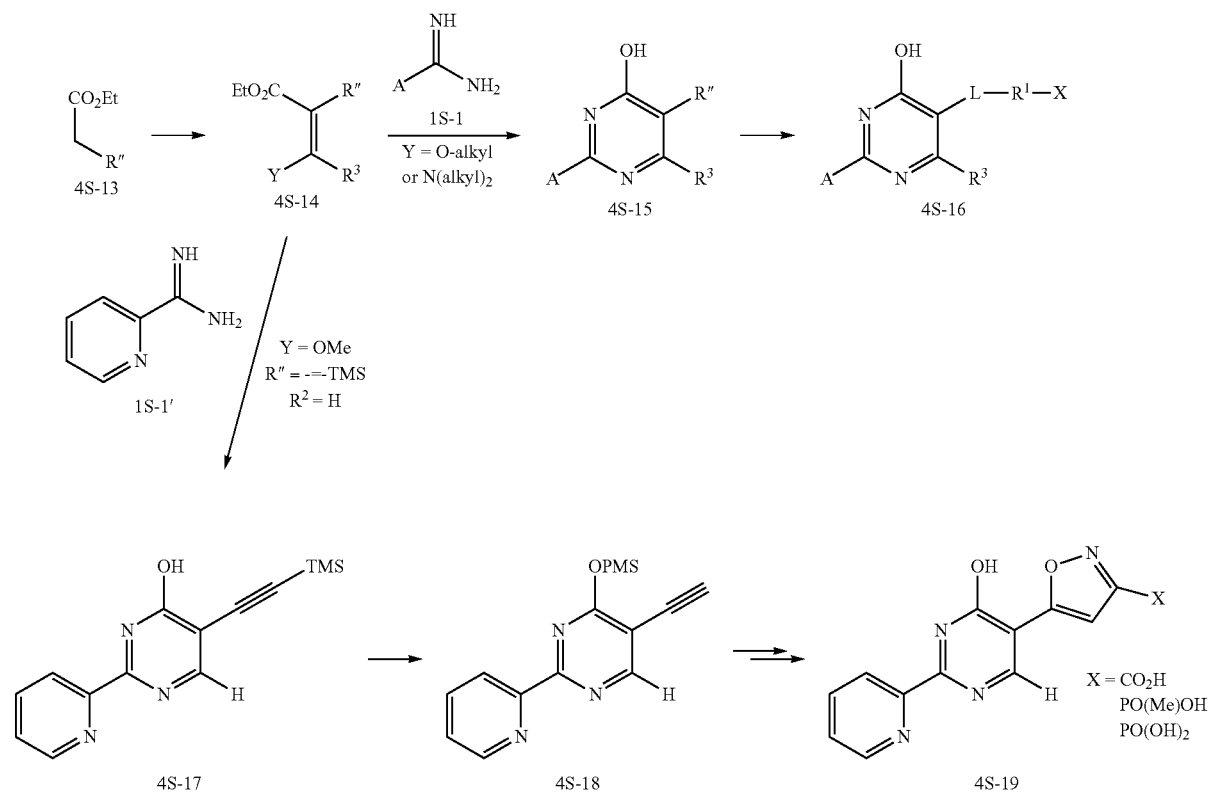

For example, compounds of formula 4S-15 are prepared when amidines 1S-1 are cyclized with esters 4S-14 wherein Y=O-alkyl under reaction conditions exemplified as in Scheme 1. Alternatively, compounds of formula 4S-14 wherein Y=N(alkyl)$_2$ are also cyclized with amidines 1S-1 to give compounds of formula 4S-15 (Chen, W.; Feng, J.; Tu, H. Huaxue Tongbao, 2006, 69, 623-6). The esters 4S-14 can be prepared by reaction of esters 4S-13 with a substituted carboxamide dimethyl acetal.

The synthetic strategy outlined in Scheme 4 could also be adapted for the syntheses of compounds of formula I wherein L is a hetercyclic group, with suitable modifications when needed. For example, compounds 4S-14 wherein Y is OMe, R" is acetylene-TMS, and R$^3$ is H was reacted with compound 1S-1' to give compound 4S-17. Removal of TMS group in compound 4S-17 gave compound 4S-18, which is useful to prepare compounds of formula I wherein A is a 2-pyridyl group, R$^2$ is OH, and R$^3$ is H (such as compounds 4S-19). For example, [3+2]cycloaddition reaction of compound 4-S18 with methyl 4-[chloro(hydroxyimino)methyl]benzoate followed by removal of PMB protecting group using TFA gave compound 4S-19 wherein X is a Phenyl(4-COOMe) group, and hydrolysis of the ester group using a suitable base (e.g. NaOH) gave compound 4S-19 wherein X is -Ph-(4-COOH). Alternatively, [3+2]cycloaddition reaction of compound 4-S18 with ethyl phosphinate (P-[4-[(E)-chloro(hydroxyimino)methyl]phenyl]-P-methyl) followed by removal of PMB protecting group using TFA, and final hydrolysis of the ethyl ester group using a suitable base (e.g. NaOH) gave compound 4S-19 wherein X is -Ph-(4-PO(Me)OH).

The methods presented in reaction Schemes 1 and 2 may be further generalized when it is desired to prepare compounds of general formula I where neither of the R$^3$ or R$^2$ substituents are hydroxy groups.

Scheme 5

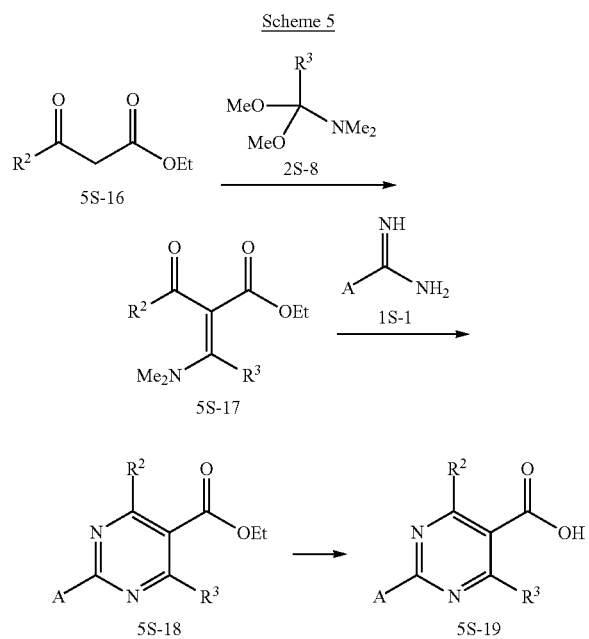

Reaction Scheme 5 illustrates the process beginning with a beta-ketoester of general formula 5S-16 bearing the R$^2$ substituent. The ester of general formula 5S-16 is condensed with a carboxamide dimethyl acetal of general formula 2S-8 to afford the vinylogous amide of general formula 5S-17. The intermediate 5S-17 is then reacted with an amidine derivative of general formula 1S-1 using the method of Schenone et al. (Schenone, P.; Sansebastiano, L.; Mosti, L. J. Heterocyclic Chem. 1990, 27, 295) to afford the alkyl pyrimidine-5-carboxylate of general formula 5S-18. Hydrolysis of compounds of formula 5S-18 under suitable conditions (e.g. KOH or NaOH in EtOH—H$_2$O, heating when necessary) produces compounds of formula 5S-19. The compounds of general formula 5S-19 are then converted to the title compounds of general formula I using the methods described previously.

In one aspect, compounds of formula I are prepared via pyrimidine ring formation reactions (e.g. Schemes 1, 2, 4, 5) with the desired substituents (e.g. X, A, R$^1$, R$^2$, R$^3$ and L) at various positions. In another aspect, the desired substituents on the pyrimidine core can be introduced after the pyrimidine ring is formed, which can be achieved using synthetic methods reported in the literature. For example, the hydroxy group present at the pyrimidine 4-position in compounds of general formulae 1S-3, 1S-4, or 4S-15 may be converted to a halogen substituent upon reaction with a suitable halogenating reagent (e.g. POCl$_3$, BBr$_3$, etc.).

Compounds of general formula I wherein L is an amino or an amino derivative can be prepared from suitable pyrimidine derivatives such as 1S-4, 1S-6, 2S-10 and 5S-19 using synthetic methods reported in the literature. For example, carboxylic acids of formula 5S-19 are converted to their corresponding amines of formula 6S-20 using suitable methods such as Curtis rearrangement reactions, Scheme 6. The amino group in compounds of formula 6S-20 is further derivatized using common synthetic methods such as amide bond formation reactions (e.g. CDI couplings, EDCI couplings, reactions with acyl chlorides, etc.), sulfonamide bond formation reactions (e.g. reactions with sulfonyl chlorides in the presence of a suitable base), reductive amination reactions with a suitable carbonyl compounds (e.g. aldehydes and ketones). For example, compounds of formula I wherein L is —NHCO— and/or —NHSO$_2$— are prepared from compounds of formula 6S-20 as depicted in Scheme 6. In another aspect, carboxylic acids such as compounds of formula 5S-19 can be converted to their corresponding acyl azide such as compounds of formula 6S-22, and under suitable thermal rearrangement reaction conditions acyl azides such as 6S-22 can be converted to their corresponding isocyanate, and subsequent reactions of the resulting isocyanate with various nucleophiles such as alcohols, amines and thiols can produce compounds of formula 6S-23 wherein L is a carbamate (—NHCOO—), urea (—NHCONH—), or thiocarbamate (—NHCOS—). (March's advanced organic chemistry, Wiley-interscience, 2007; Comprehensive Organic Transformations: a guide to functional group preparations by Richard Larock, Wiley-VCH, 2000). Alternatively, compounds 5S-19 is useful to prepare compounds of formula I wherein L is a —CONR'— group via suitable amide formation reactions (e.g. DCC, EDCI, TBTU coupling reactions).

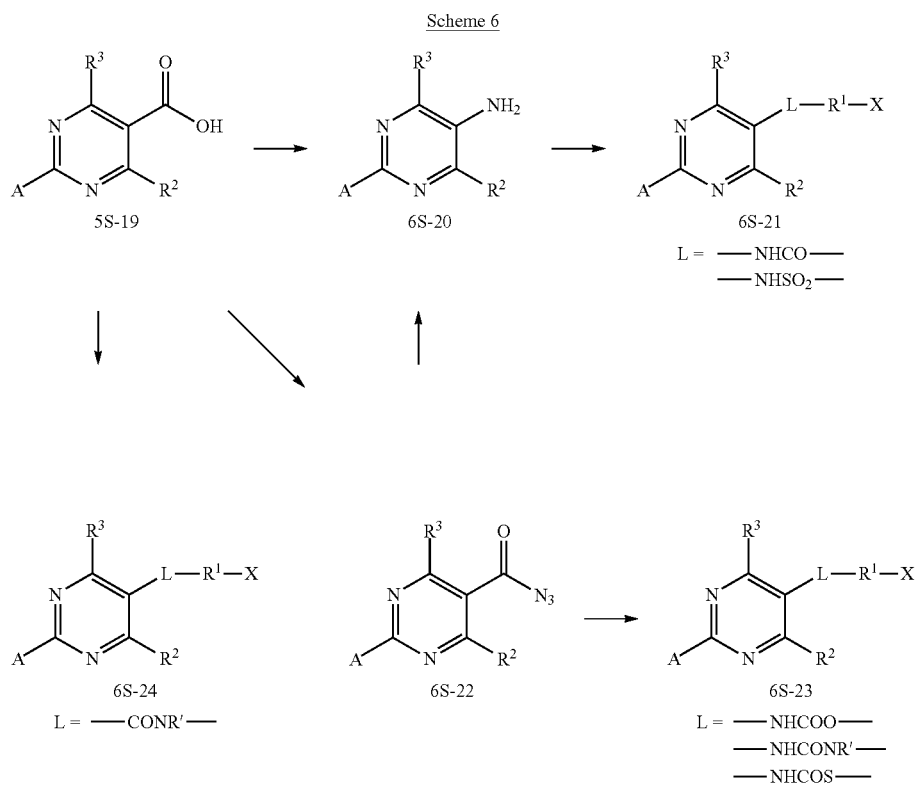

Scheme 6

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60F-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 µm 3.0×50 mm column with gradient 10:90-100 v/v $CH_3CN/H_2O$+v 0.05% TFA over 3.75 min then hold at 100 $CH_2CN$+v 0.05% TFA for 1.75 min; flow rate 1.0 mL/min, UV wavelength 254 nm (all HPLC/MS data was generated with this method unless indicated otherwise). Analytical HPLC/MS—Basic Method: Mass analysis was performed on a Waters Micromass® ZQ™ with electrospray ionization in positive ion detection mode. High performance liquid chromatography (HPLC) was conducted on an Agilent 1100 series HPLC on Waters C18 XBridge 3.5 m 3.0×50 mm column with gradient 10:90-98:2 v/v $CH_3CN/H_2O$+v 0.025% $NH_4OH$ over 3.25 min then hold at 98:2 $CH_3CN$+v 0.025% $NH_4OH$ for 2.25 min; flow rate 1.0 mL/min, UV wavelength 254 nm. Concentration of solutions was carried out on a rotary evaporator under reduced pressure. Flash chromatography was performed using a Biotage Horizon or SP1 Flash Chromatography apparatus (Dyax Corp.) on silica gel (32-63 µM particle size, KP-Sil 60 Å packing material type) in pre-packed cartridges or using an ISCO CombiFlash™ Sq 16× or Combi-Flash® Companion™ apparatus on silica gel (32-63 µM, 60 Å) in pre-packed cartridges. Microwave reactions were carried out on a Biotage Initiator™ 2.0 or CEM Discover™ system.

Preparative HPLC/MS—Standard Method

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 µm 30×100 mm column with gradient 10:90-100 v/v $CH_3CN/H_2O$+v 0.1% TFA over 12 min; flow rate 50 mL/min, UV wavelength 210-400 nm.

Preparative HPLC/MS—Non-Polar Method

Mass analysis was performed on a Waters Micromass® ZQ™ with electrospray ionization in positive ion detection mode. High performance liquid chromatography (HPLC) was conducted on a Waters Prep. HPLC System on Waters C18 Sunfire 5 µm 30×100 mm column with gradient 40:60-100 v/v $CH_3CN/H_2O$+v 0.1% TFA over 10 min then hold at 100 $CH_3CN$+v 0.1% TFA for 4 min; flow rate 50 mL/min, UV wavelength 210-400 nm.

Preparative HPLC/MS—Basic Method

Mass analysis was performed on a Waters Micromass® ZQ™ with electrospray ionization in positive ion detection mode. High performance liquid chromatography (HPLC) was conducted on a Waters Prep. HPLC System on Waters C18 XBridge 5 µm 50×150 mm column with gradient 10:90-35:65 v/v $CH_3CN/H_2O$ (pH=10 with $NH_4OH$) over 10 min; flow rate 120 mL/min, UV wavelength 210-400 nm.

Example 1

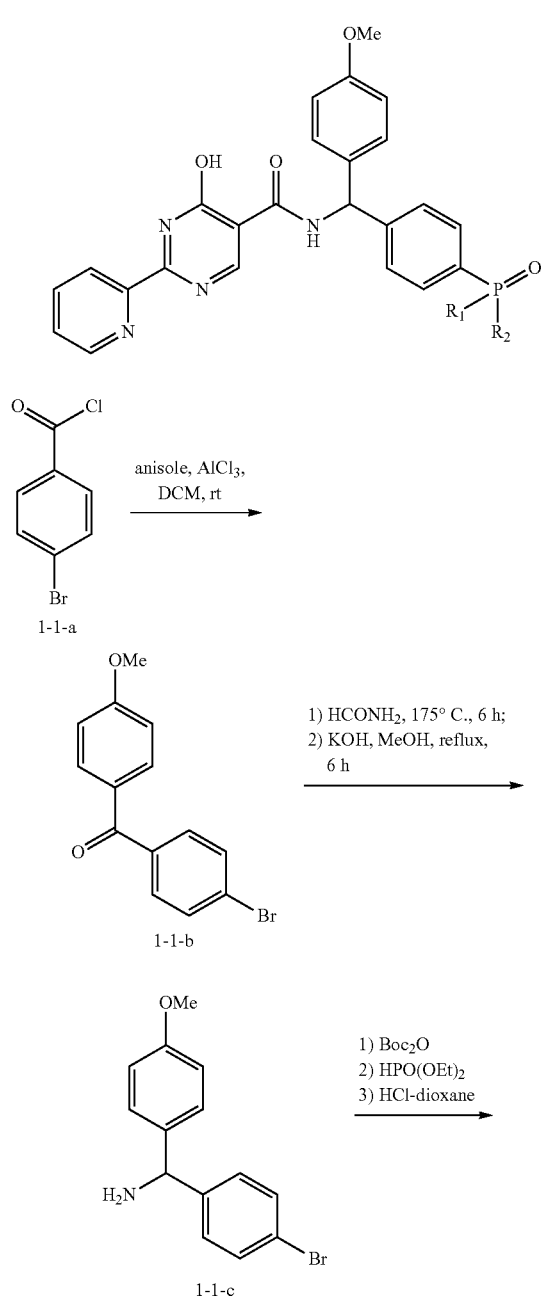

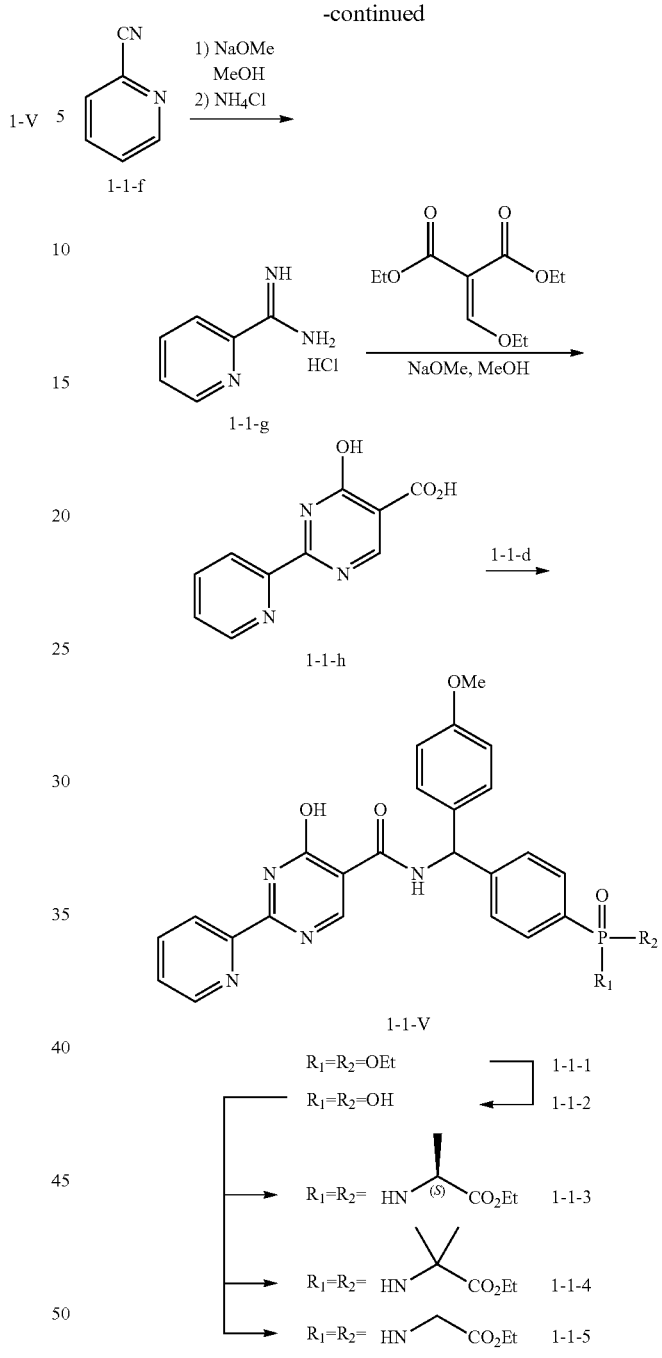

Step A: (4-bromophenyl)(4-methoxyphenyl)methanone (1-1-b)

To a cooled (0° C.) mixture of 4-bromobenzoyl chloride, 1-1-a, (25 g, 0.114 mol) and anisole (15.5 g, 0.143 mol) in DCM (500 ml) was added $AlCl_3$ (19 g, 0.143 mol) portion wise with stirring under $N_2$. The resulting reaction mixture was allowed to stir at r.t for 16 h. The reaction mixture was poured into 20% HCl (500 ml) and the solution stirred for 1 h. After stirring, the resulting solution was allowed to separate into phase layers. The aqueous layer was collected and further extracted with DCM (3×250 ml). The combined organic layer was washed with water (200 ml), brine (200 ml), dried (Na$_2$SO$_{24}$), filtered and concentrated under reduced pressure to yield 30 g of a white solid, 1-1-b. $^1$H NMR (300 MHZ, CDCl$_3$): 3.91 (s, 3H), 6.99 (d, 2H), 7.65 (s, 4H), 7.82 (d, 2H).

Step B: (4-bromophenyl)(4-methoxyphenyl)methanamine (1-1-c)

(4-bromophenyl)(4-methoxyphenyl)methanone, 1-1-b, (3.0 g, 0.01 mol) was heated with formamide (6 ml) for 6 hours at 175° C. The mixture was then poured into water. The product was filtered off, washed with water, dried, and recrystallised from methanol, forming colorless prisms (2.8 g). The above formyl derivative (2.0 g) was heated with potassium hydroxide (3.0 g.) in methanol (16 ml) for 6 hours. After distillation of most of the methanol and pouring the residue into water, the base was taken up in EtOAc, the extract dried with potassium carbonate, the EtOAc removed, and the product recrystallised from light petroleum, forming colorless prisms, 1-1-c, (2.0 g). $^1$H NMR (DMSO-d$_6$, 300 MHz,): δ3.71 (s, 3H), 5.02 (s, 1H), 6.848 (d, 2H), 7.314 (m, 4H), 7.45 (d, 2H).

Step C: Diethyl 4-(amino(4-methoxyphenyl)methyl)phenylphosphonate (1-1-d)

To a mixture of (4-bromophenyl)(4-methoxyphenyl)methanamine, 1-1-c, (2 g, 6.8 mmol), diethyl phosphate (1.1 g, 8.2 mmol) and Et$_3$N (1.3 g, 10.2 mmol) in toluene (25 ml) was added Pd(PPh$_3$)$_4$ (1.5 g, 20%). The mixture was allowed to stir for two days at 100° C. The mixture was then diluted with saturated NH$_4$Cl and extracted with EtOAc. The organic layer was dried over Na$_2$SO$_4$, concentrated, and purified over silica gel (5% MeOH/DCM) to obtain as an oil, 1-1-d, (1.00 g). $^1$HNMR (300 MHZ, DMSO-d): 1.29 (m, 6H), 3.77 (s, 3H), 4.10 (m, 4H), 5.19 (s, 1H), 6.82 (d, 2H), 7.26 (d, 2H), 7.48 (d, 2H), 7.74 (d, 2H).

Step D: Picolinamidine hydrochloride (1-1-g)

Sodium methoxide (2.5 g, 44 mmol) was added to a solution of 2-cyanopyridine (100 g, 0.95 mol) in methanol (1.5 L) under nitrogen. The reaction mixture was stirred at room temperature for 24 hours. Then ammonium chloride (53.5 g, 1 mol) was added. The mixture was stirred at room temperature for 4 h and the solvent was removed in vacuo. The residue was washed with ipropanol/ethyl acetate=1/10 and dried in vacuo to provide the product, 1-1-g, (100 g, 66%).

Step E: 4-hydroxy-2-(pyridin-2-yl)pyrimidine-5-carboxylic acid (1-1-h)

To picolinamidine hydrochloride (1-1-g) (112 g, 0.71 mol) in MeOH (1.1 L) was added sodium methoxide (39.4 g, 0.71 mol) and diethyl ethoxymethylenemalonate (142 g, 0.71 mol). The reaction mixture was heated at reflux overnight and then cooled to room temperature. The resulting mixture was filtered and to the filtrate was added potassium hydroxide (71.4 g, 1.37 mol) in water (265 mL). The reaction was heated at reflux for 2 h. The reaction was cooled to room temperature before adding concentrated HCl (180 mL, 2.35 mol) in portions. The reaction was aged for 2 h. The solids were filtered and rinsed with EtOH, Et$_2$O and then hexane to provide the product, 1-1-h, (110 g, 65%).

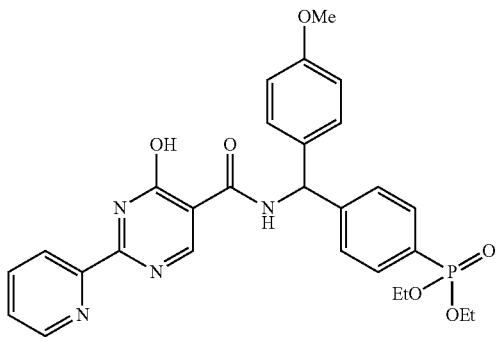

Step F: Diethyl 4-((4-hydroxy-2-(pyridin-2-yl)pyrimidine-5-carboxamido)(4-methoxyphenyl)methyl)phenylphosphonate (1-1-1)

To a solution of 4-hydroxy-2-(pyridin-2-yl)pyrimidine-5-carboxylic acid, 1-1-h, (580 mg, 2.6 mmol) in NMP (2 ml) was added Et$_3$N (540 mg, 5.2 mmol). The mixture was aged for 15 min at room temperature. To the mixture was added CDI (480 mg, 2.86 mmol) and the resulting mixture was heated to 70° C. for 1 h. To the hot homogeneous solution was then added in one portion diethyl 4-(amino(4-methoxyphenyl)methyl)phenylphosphonate, 1-1-d, (940 mg, 2.6 mmol). Heating was continued for 30 min at 70° C. The reaction mixture was then cooled to room temperature and diluted with water (12 ml) and ethyl acetate (5 ml). The resulting aqueous layer was slowly neutralized to pH=7. The neutralized aqueous layer was then extracted with ethyl acetate. The organic layer was concentrated under vacuum and the residue was purified on silica gel column with the eluent of dichloromethane/methanol=50/1 and subsequently prep-HPLC to provide the product as a white solid, 1-1-1, (260 mg, 18%). $^1$H NMR (CD$_3$OD, 300 MHz,): δ 8.60 (m, 2H), 8.40 (m, 1H), 7.90 (m, 1H), 7.60 (m, 2H), 7.50 (m, 1H), 7.40 (m, 2H), 7.20 (m, 2H), 6.84 (m, 2H), 6.24 (s, 1H), 3.99 (m, 4H), 3.68 (s, 3H), 1.08 (t, 6H, J=6 Hz).
(M+Na)$^+$=571.1.

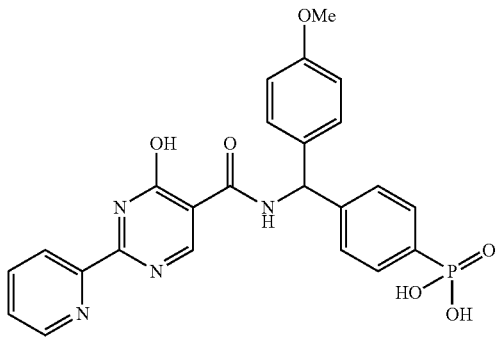

Step G: 4-((4-hydroxy-2-(pyridin-2-yl)pyrimidine-5-carboxamido)(4-methoxyphenyl)methyl)phenylphosphonic acid (1-1-2)

To a solution of ethyl phosphate (1-1-1, 260 mg, 0.47 mmol) in dichloromethane (10 ml) was added TMSBr (2.18 g, 14.2 mmol) dropwise at 0° C. The resulting mixture was stirred at room temperature for 3 days. The mixture was concentrated under vacuum and methanol (20 ml) was added. The mixture was stirred for 15 mins at room temperature and concentrated. The residue was purified on prep-HPLC to provide the product, 1-1-2. (100 mg, 43%). $^1$H NMR (DMSO-d6, 300 MHz,): δ 8.81 (d, 1H, J=6 Hz), 8.40 (m, 1H), 8.10 (m, 1H), 7.60 (m, 4H), 7.35 (m, 2H), 7.25 (m, 2H), 6.95 (m, 2H), 6.23 (d, 1H, J=6 Hz), 3.71 (s, 3H). (M−H)$^-$=491.1.

phosphoryl)bis(azanediyl)bis(2-methylpropanoate) (1-1-4) was prepared from phosphonic acid 1-1-2 (300 mg, 0.61 mmol) in a similar manner as above Step H. 100 mg, 23%. $^1$H NMR (DMSO-d6, 300 MHz,): δ 10.49 (s, 1H), 8.80-8.81 (m, 1H), 8.59 (m, 1H,), 8.36-8.39 (m, 1H), 8.07-8.12 (m, 1H), 7.65-7.74 (m, 3H), 7.36-7.40 (m, 2H), 7.24-7.27 (m, 2H), 6.90-6.93 (m, 2H), 6.24-6.26 (d, J=9 Hz, 1H,), 4.55-4.60 (m, 2H), 3.93-4.00 (m, 5H), 3.72 (s, 3H), 1.38 (s, 6H), 1.31 (s, 6H), 1.09-1.14 (m, 6H). (M+H)$^+$=719.1.

1-1-3

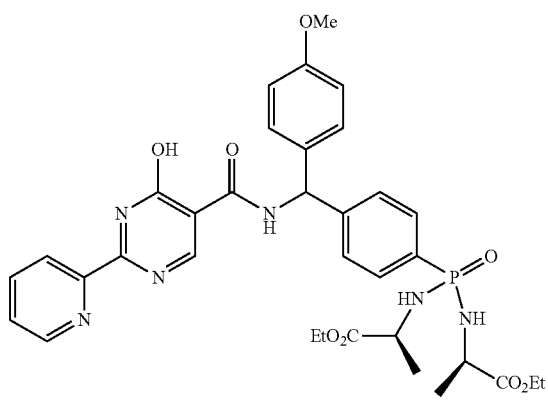

Step H: (2S,2'S)-diethyl 2,2'-((4-((4-hydroxy-2-(pyridin-2-yl)pyrimidine-5-carboxamido)(4-methoxyphenyl)methyl)phenyl)phosphoryl)bis(azanediyl) dipropanoate (1-1-3)

4-((4-hydroxy-2-(pyridin-2-yl)pyrimidine-5-carboxamido)(4-methoxyphenyl)methyl)phenyl phosphonic acid (1-1-2, 200 mg, 0.41 mmol) and L-analine ethyl ester HCl salt (248 mg, 1.62 mmol) in pyridine (6 ml) was added TEA (164 mg, 1.62 mmol). The mixture was stirred for 5 min before the addition of PPh$_3$ (458 mg, 1.75 mmol) and Aldrithiol-2 (385 mg, 1.75 mmol) in pyridine. The resulting mixture was heated at 85° C. overnight. The mixture was then concentrated under vacuum and the residue was purified on silica gel chromatography to provide the product, 1-1-3, (100 mg, 34%). $^1$H NMR (DMSO-d$_6$, 300 MHz,): δ 13.23 (s, 1H), 10.45 (s, 1H), 8.81 (m, 1H,), 8.56 (m, 1H), 8.36 (m, 1H), 8.06 (m, 1H), 7.64 (m, 3H), 7.36 (m, 2H), 7.24 (m, 2H), 6.90 (m, 2H), 6.23 (d, J=6 Hz, 1H,), 4.84 (m, 4H), 4.67 (m, 1H), 3.96 (m, 2H), 3.74 (m, 4H), 3.72 (s, 3H), 1.16 (m, 9H). (M+H)$^+$=691.1.

1-1-4

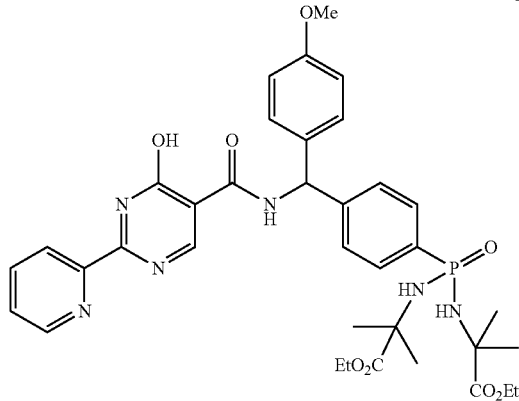

Step IA: diethyl 2,2'-((4-((4-hydroxy-2-(pyridin-2-yl)pyrimidine-5-carboxamido)(4-methoxyphenyl)methyl)phenyl)

1-1-5

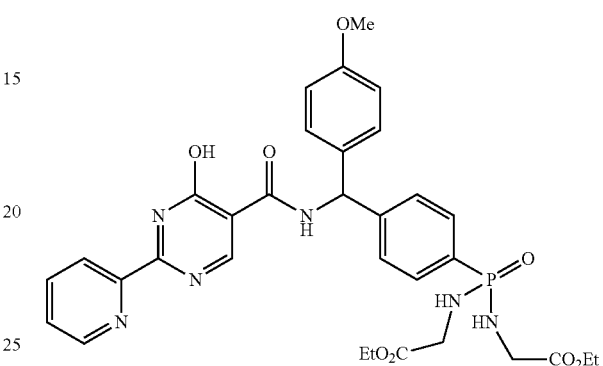

Step IB: diethyl 2,2'-((4-((4-hydroxy-2-(pyridin-2-yl)pyrimidine-5-carboxamido)(4-methoxyphenyl)methyl)phenyl)phosphoryl)bis(azanediyl)acetate(1-1-5) was prepared from phosphonic acid (1-1-2, 300 mg, 0.61 mmol) in a similar manner as Step H. 300 mg, 71%. $^1$H NMR (DMSO-d6, 300 MHz,): δ 13.23 (s, 1H), 10.50 (s, 1H), 8.80-8.81 (m, 1H,), 8.53-8.61 (m, 1H), 8.37-8.39 (m, 1H), 8.07-8.12 (m, 1H), 7.67-7.74 (m, 3H), 7.38-7.41 (m, 2H), 7.23-7.26 (m, 2H), 6.90-6.93 (m, 2H), 6.23-6.26 (d, J=9 Hz, 1H,), 4.75-4.84 (m, 2H), 3.98-4.05 (m, 5H), 3.73 (s, 3H), 3.53-3.63 (m, 4H), 3.31 (s, 2H), 1.11-1.16 (m, 6H). (M+H)$^+$=663.1.

1-1-6

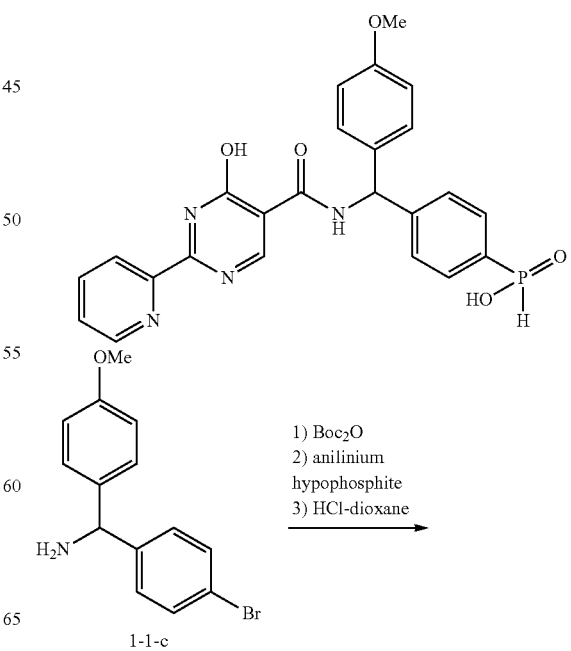

1-1-c

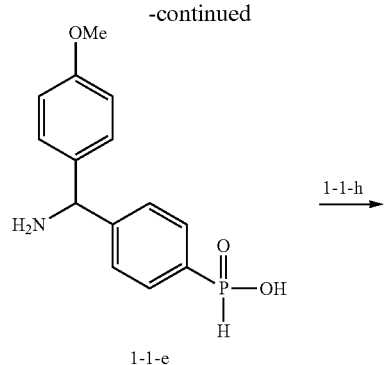

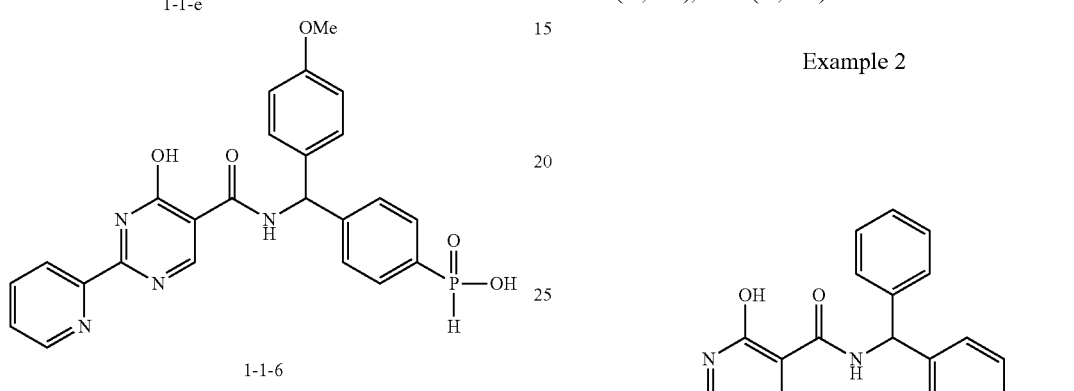

Step A: 4-(amino(4-methoxyphenyl)methyl)phenylphosphinic acid hydrochloride (1-1-e)

Aniline (182 g, 1.95 mol) was added over 30 min via an additional funnel to an ice-cold aqueous solution of hypophosphorus acid (50% wt, 258 g, 1.95 mol). The light brown solution turned into thick slurry. Acetone (500 ml) was added and the resulting mixture was stirred for 5 min before filtration. The solid was washed with acetone to provide the product anilinium hypophosphite (134 g, 43%).

To a mixture of (4-bromophenyl)(4-methoxyphenyl)methylamine, 1-1-c, (2 g, 6.8 mmol) in acetonitrile (25 ml) was added BOC$_2$O (1.5 equivalents) and stirred at room temperature for 24 h. The reaction mixture was evaporated to dryness and purified over silica gel (5% MeOH/DCM) to give N-Boc-(4-bromophenyl)(4-methoxyphenyl)methylamine.

To a solution of N-Boc-(4-bromophenyl)(4-methoxyphenyl)methylamine (39.1 g, 0.1 mmol), anilinium hypophosphite (19.1 g, 0.12 mmol) and TEA (30.3 g, 0.3 mol) in THF was added PdCl$_2$(dppf) (2 g). The mixture was allowed to stir overnight at reflux. The mixture was filtered and the filtrate was concentrated under vacuum. The residue was taken into dichloromethane and washed with sat. NH$_4$Cl. The organic layer was concentrated under vacuum and the residue was purified over silica gel to provide the product as oil (26 g, 69%), which was treated with HCl/dioxane at room temperature overnight to give the product 1-1-e as its HCl form (16 g, 83%). (M+Na)$^+$=300.

Step B: 4-((4-hydroxy-2-(pyridin-2-yl)pyrimidine-5-carboxamido)(4-methoxyphenyl)methyl)phenylphosphinic acid (1-1-6)

To a solution of 4-hydroxy-2-(pyridin-2-yl)pyrimidine-5-carboxylic acid (1-1-h, 1.1 g, 5.1 mmol) in acetonitrile (20 ml) was added Et$_3$N (1.02 g, 10.2 mmol). The mixture was aged for 15 min at room temperature. To the mixture was added CDI (800 mg, 5.1 mmol) and the resulting mixture was heated to 70° C. for 3 h. To the hot homogeneous solution was then added in one portion 4-(amino(4-methoxyphenyl)methyl)phenylphosphinic acid hydrochloride (1-1-e, 1.4 g, 5.1 mmol). Heating was continued for 2 h at 70° C. Then it was concentrated under vacuum and the residue was purified on prep-HPLC to provide the 1-1-6 (160 mg, 6%). $^1$H NMR (CD$_3$OD, 300 MHz,): δ 13.35 (br, 1H), 8.80 (m, 1H), 8.62 (m, 2H), 8.45 (m, 1H), 7.23 (m, 7H), 7.79 (m, 2H), 6.52 (s, 1H), 6.25 (m, 1H), 3.70 (m, 3H).

Example 2

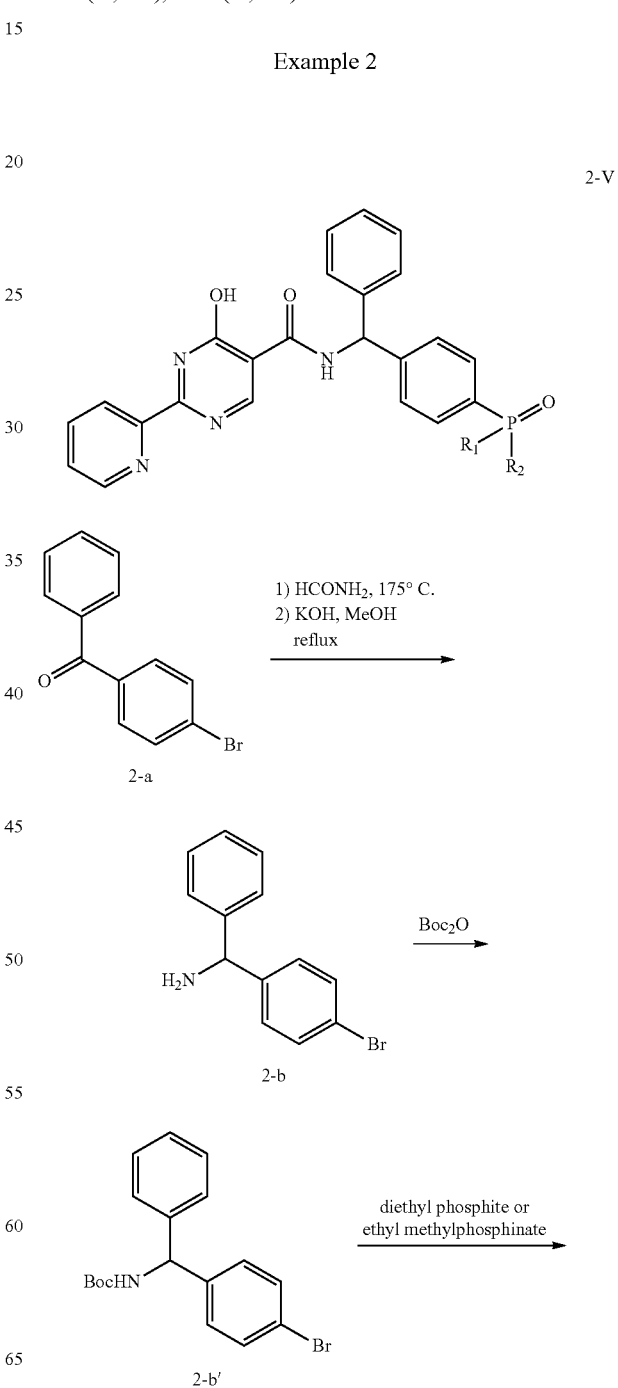

-continued

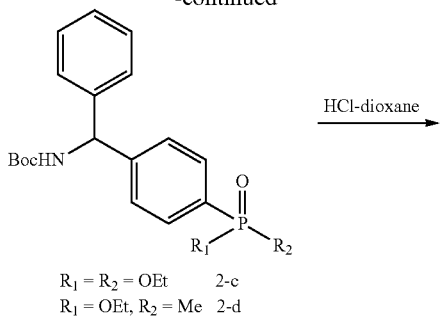

R₁ = R₂ = OEt   2-c
R₁ = OEt, R₂ = Me   2-d

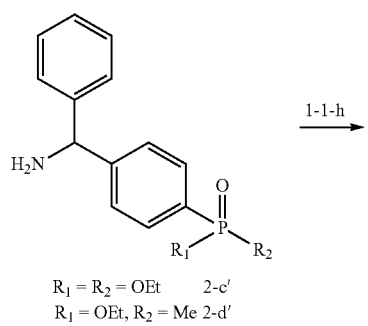

R₁ = R₂ = OEt   2-c'
R₁ = OEt, R₂ = Me   2-d'

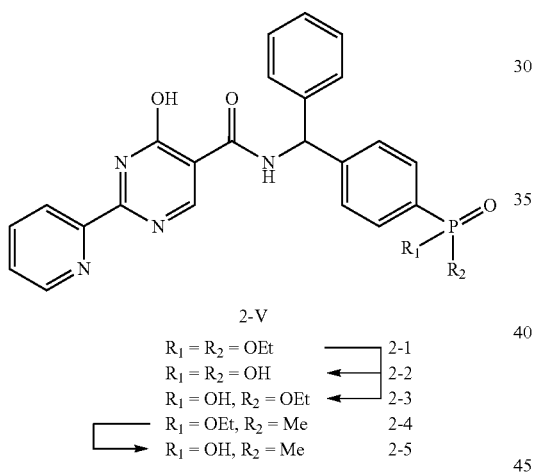

2-V

R₁ = R₂ = OEt → 2-1
R₁ = R₂ = OH ← 2-2
R₁ = OH, R₂ = OEt ← 2-3
R₁ = OEt, R₂ = Me → 2-4
R₁ = OH, R₂ = Me → 2-5

Step A: (4-bromophenyl)(phenyl)methanamine (2-b)

(4-bromophenyl)(phenyl)methanone (200 g, 0.77 mol) was heated with formamide (600 ml) for 24 hours at 185° C., and the mixture was cooled to room temperature before poured into water. The product was filtered off and washed with water. It was recrystallized in EtOH/H₂O to provide an intermediate (120 g, 54%). The above intermediate (100 g, 0.35 mol) was heated at reflux with potassium hydroxide (150 g, 2.6 mol.) in methanol (800 ml) for 8 hours. The mixture was concentrated under vacuum and the residue was diluted with water followed by extraction of ethyl acetate. The organic layer was dried over sodium sulfate and concentrated to provide the product, 2-b, (70 g, 78%). ¹H NMR (CDCl₃, 300 MHz,): δ 7.30 (m, 9H), 5.18 (s, 1H), 1.82 (s, 2H).

Step B: diethyl 4-(amino(phenyl)methyl)phenylphosphonate (2-c)

(4-bromophenyl)(phenyl)methanamine, 2-b, (41.9 g, 0.16 mmol) in DCM was added TEA (38.78 g, 0.38 mmol) and the mixture was cooled to 0° C. Boc₂O (41.84 g, 0.192 mmol) was added at this temperature. Then the resulting mixture was stirred at room temperature overnight. The mixture was washed with water and the organic layer was concentrated under vacuum. The residue was washed with hexane to provide 2-b' (40 g, 69%). ¹H NMR (chloroform-d₃, 300 MHz,): δ 7.43 (m, 2H), 7.21 (m, 6H), 7.12 (m, 2H), 5.85 (s, 1H), 1.42 (s, 9H).

To 2-b' (9 g, 25 mmol), diethyl phosphite (10.5 g, 75 mmol) and Et₃N (8.5 g, 75 mmol) in toluene was added PdCl₂(dppf) (7.5 g). The mixture was allowed to stir overnight at reflux. The mixture was filtered and the filtrate was concentrated under vacuum. The residue was taken into ethyl acetate and washed with saturated NH₃Cl. The organic layer was concentrated under vacuum and the residue was purified over silica gel to provide the crude product 2-c (15 g). (M+Na)⁺=442.

The above crude phosphonate product (2-c, 15 g) was dissolved in HCl/dioxane (100 ml) and the mixture was stirred at room temperature overnight. Then it was concentrated under vacuum and the residue was taken into water and basified with sodium carbonate followed by extraction with ethyl acetate. The organic layer was concentrated under vacuum to provide the product, 2-c', (5 g, 44%). ¹HNMR (300 MHZ, CDCl₃): δ 7.69 (m, 2H), 7.48 (m, 2H), 7.29 (m, 5H), 5.23 (s, 1H), 4.05 (m, 4H), 2.03 (br, 2H), 1.28 (m, 6H).

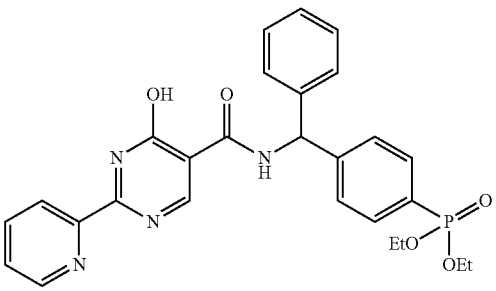

2-1

Diethyl 4-((4-hydroxy-2-(pyridin-2-yl)pyrimidine-5-carboxamido)(phenyl)methyl)phenyl phosphonate (2-1)

To a solution of 4-hydroxy-2-(pyridin-2-yl)pyrimidine-5-carboxylic acid, 1-1-h, (680 mg, 3.13 mmol) in MeCN (10 ml) were added HATU (1.22 g, 3.21 mmol), Et₃N (330 mg, 3.27 mmol) and diethyl 4-(amino(phenyl)methyl)phenylphosphonate, 2-c', (1 g, 3.13 mmol). The resulting mixture was stirred at room temperature for 2 hour. Then it was concentrated under vacuum and the residue was taken into ethyl acetate followed by washing with sat. NH₄Cl. The organic layer was dried over sodium sulfate and concentrated under vacuum. The residue was purified by prep-HPLC to provide the product, 2-1, (300 mg, 18%). ¹H NMR (CD₃OD, 300 MHz,): δ 8.77 (m, 2H), 8.48 (m, 1H), 8.03 (m, 1H), 7.73 (m, 2H), 7.52 (m, 3H), 7.36 (m, 5H), 6.39 (s, 1H), 4.09 (m, 4H), 1.30 (m, 6H).

2-2

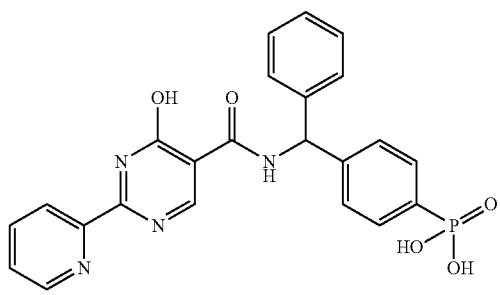

4-((4-hydroxy-2-(pyridin-2-yl)pyrimidine-5-carboxamido)(phenyl)methyl)phenyl phosphonic acid (2-2)

To a solution of diethyl phosphonate (2-1, 100 mg, 0.19 mmol) in dichloromethane was added TMSBr. The resulting mixture was stirred at room temperature for 2 days. The mixture was then concentrated under vacuum and the residue was purified on prep-HPLC to provide the product, 2-2, (40 mg, 46%). $^1$H NMR (CD$_3$OD, 300 MHz,): δ 8.68 (br, 2H), 8.37 (d, 1H), 7.91 (m, 1H), 7.62 (m, 2H), 7.51 (br, 1H), 7.39 (m, 2H), 7.24 (m, 5H), 6.28 (s, 1H).

2-3

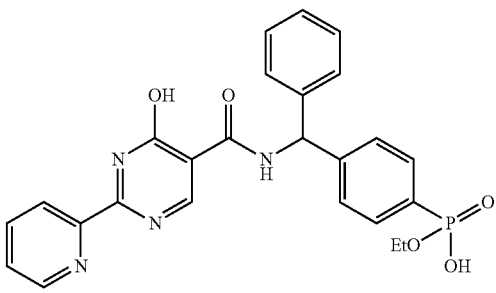

Ethyl 4-((4-hydroxy-2-(pyridin-2-yl)pyrimidine-5-carboxamido)(phenyl)methyl)phenylphosphonate (2-3)

The diethyl phosphonate (2-1, 100 mg, 019 mmol) was dissolved in 5 ml of dioxane and treated with 2 ml of 5N NaOH. The mixture was heated at reflux overnight. Then it was concentrated under vacuum and the residue was treated with 2 ml of trifluoroacetic acid. The mixture was re-evaporated and the residue was purified by prep-HPLC to provide the product, 2-3, (40 mg, 42%). $^1$H NMR (CD$_3$OD, 300 MHz,): δ 8.68 (br, 2H), 8.37 (d, 1H), 7.91 (m, 1H), 7.62 (m, 2H), 7.51 (br, 1H), 7.39 (m, 2H), 7.24 (m, 5H), 6.28 (s, 1H), 3.88 (m, 2H), 1.15 (m, 3H).

2-4

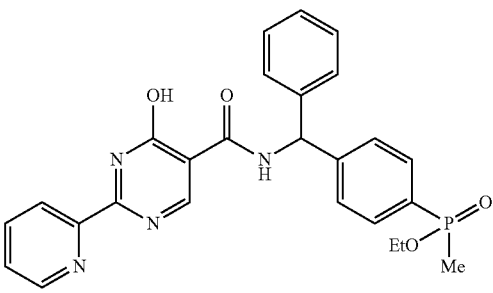

Step A: tert-butyl phenyl(4-phosphono)phenyl)methylcarbamate (2-d)

To 2-b' (1.81 g, 5 mmol), ethyl methylphosphinate (1.62 g, 15 mmol) and Et$_3$N (1.52 g, 15 mmol) in toluene was added PdCl$_2$(dppf) (362 mg). The mixture was allowed to stir overnight at reflux. The mixture was filtered and the filtrate was concentrated under vacuum. The residue was taken into ethyl acetate and washed with sat. NH$_4$Cl. The organic layer was concentrated under vacuum and the residue was purified over silica gel to provide the product 2-d (1.2 g, 62%). (M+Na)$^+$= 412.

The phosphonate 2-d (1.2 g, 2 mmol) was dissolved in HCl/dioxane (30 ml) and the mixture was stirred at room temperature overnight. Then it was concentrated under vacuum and the residue was taken into water and basified with sodium carbonate followed by extraction with ethyl acetate. The organic layer was concentrated under vacuum to provide the product, 2-d', (700 mg, 81%). (M-NH$_2$)$^+$=273.

Step B: ethyl 4-((4-hydroxy-2-(pyridin-2-yl)pyrimidine-5-carboxamido)(phenyl)methyl)phenyl(methyl) phosphinate (2-4)

To a solution of 4-hydroxy-2-(pyridin-2-yl)pyrimidine-5-carboxylic acid, 1-1-h (325.5 mg, 1.5 mmol) in MeCN (10 ml) were added HATU (599 mg, 1.51 mmol), Et$_3$N (159 mg, 1.51 mmol) and ethyl methyl(4-(amino(phenyl)methyl)phenyl)phosphinate (2-d', 433 mg, 1.5 mmol). The resulting mixture was stirred at room temperature for 2 hour. Then it was concentrated under vacuum and the residue was taken into ethyl acetate followed by washing with saturated NH$_4$Cl. The organic layer was dried over sodium sulfate and concentrated under vacuum. The residue was purified by prep-HPLC to provide the product, 2-4, (159 mg, 22%). $^1$H NMR (CD$_3$OD, 300 MHz,): δ 8.67 (m, 2H), 8.39 (m, 2H), 7.94 (m, 1H), 7.46 (m, 5H), 7.26 (m, 5H), 6.29 (s, 1H), 3.76 (m, 2H), 1.57 (d, 3H).

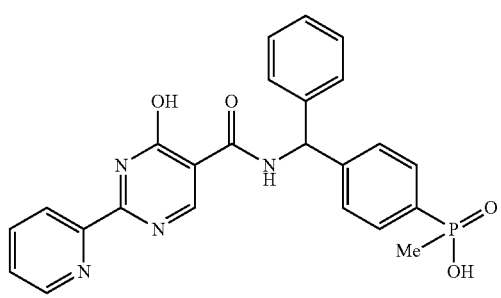

4-((4-hydroxy-2-(pyridin-2-yl)pyrimidine-5-carboxamido)(phenyl)methyl)phenyl(methyl)phosphinic acid (2-5)

The ethyl methylphosphinate 2-4 (130 mg, 0.27 mmol) was dissolved in 5 ml of dioxane and treated with 2 ml of 5N NaOH. The mixture was heated at reflux overnight. The mixture was then concentrated under vacuum and the residue was treated with 2 ml of trifluoroacetic acid. The mixture was re-evaporated and the residue was purified by prep-HPLC to provide the product, 2-5 (80 mg, 64%). $^1$H NMR (CD$_3$OD, 300 MHz,): δ 8.76 (m, 2H), 8.48 (m, 2H), 8.01 (m, 1H), 7.77 (m, 2H), 7.61 (m, 1H), 7.51 (m, 2H), 7.29 (m, 5H), 6.39 (s, 1H), 1.61 (d, 3H).

Example 3

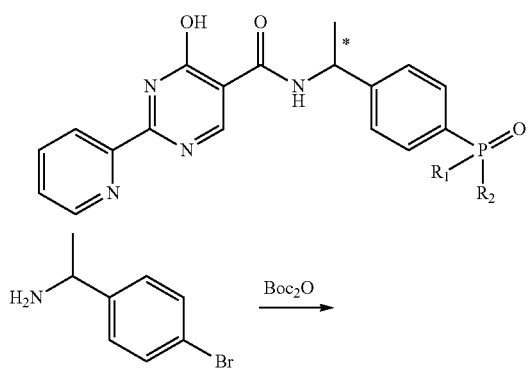

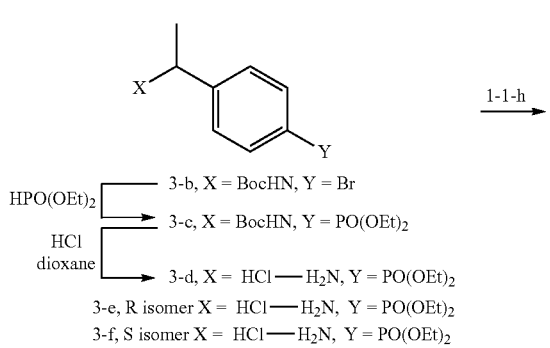

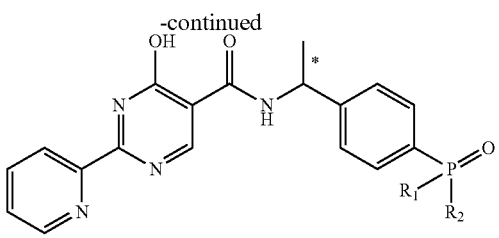

Step A: tert-butyl 1-(4-bromophenyl)ethanamine (3-b)

1-(4-bromophenyl)ethanamine 3-a (5 g, 25 mmol) in DCM (100 ml) was added TEA (5.07 g, 50 mmol) and the mixture was cooled to 0° C. Boc$_2$O (8.13 g, 37 mmol) was added at this temperature. Then the resulting mixture was stirred at room temperature overnight. The mixture was concentrated under vacuum and the residue was washed with hexane to provide 3-b (6.17 g, 82%). (M+H)$^+$=300, 302.

Step B: Diethyl (4-{1-[(tert-butoxycarbonyl)amino]ethyl}phosphonate (3-c)

To tert-butyl 1-(4-bromophenyl)ethylcarbamate (3-b, 2 g, 6.7 mmol), diethyl phosphite (2.77 g, 20 mmol) and Et$_3$N (2.03 g, 20 mmol) in toluene (30 ml) was added Pd(PPh$_3$)$_4$ (2.32 g). The mixture was allowed to stir overnight at 100° C. The mixture was filtered and the filtrate was concentrated under vacuum. The residue was purified over silica gel (petroleum ether/ethyl acetate=20/1) to provide the product 3-c (1.3 g, 56%). (M+H)$^+$=358.

Step C: Diethyl[4-(1-amino)ethyl)phosphonate (3-d)

The Boc derivative (3-c, 1.3 g, 3.8 mmol) was dissolved in HCl/dioxane (20 ml) and the mixture was stirred at room temperature overnight. Then it was concentrated under vacuum to provide the product, 3-d (625 mg, 59%). (M+H)$^+$=258.

Step D: Diethyl (R)-[4-(1-amino)ethyl)phosphonate (3-e)

Compound 3-e was prepared from (R)-(+)-1-(4-bromophenyl)ethylamine in a similar manner as the synthesis of compound 3-d. $^1$H NMR (300 MHz, CDCl$_3$): δ1.27-1.55 (m, 9H), 3.71 (s, 1H), 4.07-4.21 (m, 4H), 7.44-7.48 (m, 2H), 7.75-7.81 (m, 2H). LC-MS (M+H)$^+$=258.

Step E: Diethyl (S)-[4-(1-amino)ethyl)phosphonate (3-f)

Compound 3-f was prepared from (S)-(−)-1-(4-bromophenyl)ethylamine in a similar manner as the synthesis of compound 3-d.

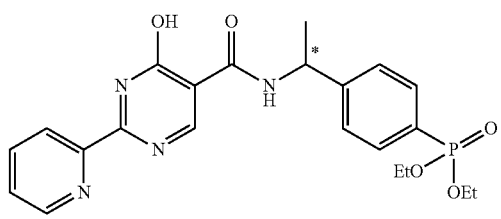

Diethyl 4-(1-(4-hydroxy-2-(pyridin-2-yl)pyrimidine-5-carboxamido)ethyl)phenyl phosphonate (3-1)

To a solution of 4-hydroxy-2-(pyridin-2-yl)pyrimidine-5-carboxylic acid, 1-1-h, (624 mg, 2.88 mmol) in MeCN (15 ml) were added HATU (1.13 g, 2.9 mmol), $Et_3N$ (582 mg, 5.76 mmol) and diethyl 4-(1-aminoethyl)phenylphosphonite hydrochloride, 3-d, (740 mg, 2.88 mmol). The resulting mixture was stirred at room temperature for 2 hours. Then it was filtered before diluted with saturated $NH_4Cl$ solution. The mixture was extracted with dichloromethane. The organic layer was dried over sodium sulfate and concentrated under vacuum. The residue was purified by prep-HPLC to provide the product, 3-1, (190 mg, 15%). $^1$H NMR (DMSO-$d_6$, 300 MHz,): δ 9.98 (s, 1H), 8.81 (s, 1H), 8.56 (s, 1H), 8.38 (m, 1H), 7.70 (m, 1H), 7.56 (m, 5H), 5.15 (m, 1H), 3.98 (m, 4H), 1.50 (m, 3H), 1.20 (m, 6H).

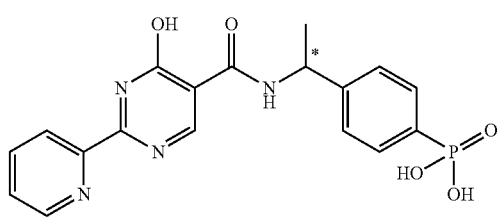

4-(1-(4-hydroxy-2-(pyridin-2-yl)pyrimidine-5-carboxamido)ethyl)phenylphosphonic acid (3-2)

To a solution of ethyl phosphonate 3-1 (130 mg, 0.29 mmol) in dichloromethane (10 ml) was added TMSBr (1.3 g, 8.06 mmol) dropwise at 0° C. The resulting mixture was stirred at room temperature overnight. Subsequently, half of the reaction mixture was concentrated under vacuum and the residue was purified on prep-HPLC to provide the product 4-(1-(4-hydroxy-2-(pyridin-2-yl)pyrimidine-5-carboxamido)ethyl)phenylphosphonic acid, 3-2, (40 mg, 35%). $^1$H NMR (DMSO-$d_6$, 300 MHz,): δ 10.0 (s, 1H), 8.79 (m, 1H), 8.36 (s, 1H), 8.33 (m, 1H), 8.06 (m, 1H), 7.61 (m, 3H), 7.44 (m, 2H), 5.13 (m, 1H), 3.82 (m, 2H), 1.49 (d, 3H), 1.55 (m, 3H).

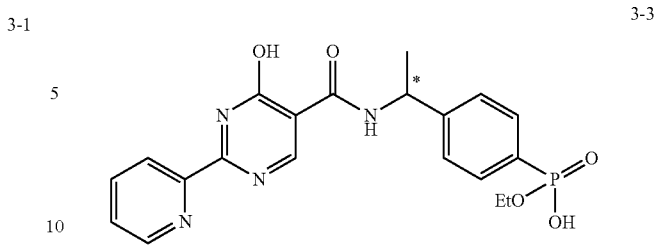

Ethyl hydrogen 4-(1-(4-hydroxy-2-(pyridin-2-yl)pyrimidine-5-carboxamido)ethyl)phenylphosphonate (3-3)

The second half of the unpurified reaction mixture described above in the synthesis of compound 3-2 was stirred at room temperature for an additional day before being concentrated under vacuum. The residue was purified on prep-HPLC to provide the product ethyl hydrogen 4-(1-(4-hydroxy-2-(pyridin-2-yl)pyrimidin-5-carboxamido)ethyl)phenylphosphonate, 3-3, (40 mg, 35%). $^1$H NMR (DMSO-$d_6$, 300 MHz,): δ 10.0 (s, 1H), 8.79 (m, 1H), 8.53 (m, 1H), 8.33 (m, 1H), 8.06 (m, 1H), 7.60 (m, 3H), 7.41 (m, 2H), 5.07 (m, 1H), 3.04 (m, 1H), 1.49 (d, 3H), 1.15 (m, 1H).

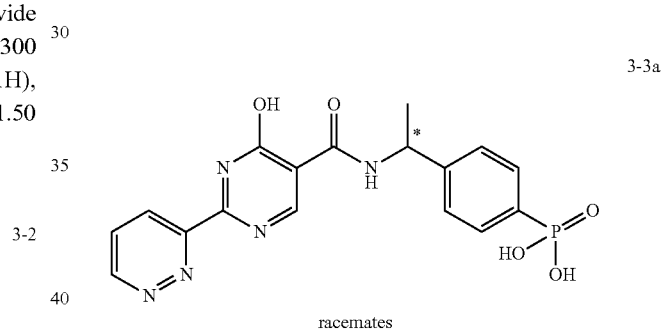

racemates 4-(1-(4-Hydroxy-2-(pyridazin-3-yl)pyrimidine-5-carboxamido)ethyl)phenylphosphonic acid (3-3a) was prepared in a similar manner as compound 3-3. $^1$H NMR (300 MHz, DMSO-$d_6$) δ1.51-1.53 (d, J=6.0 Hz, 3H), 5.15-5.20 (m, 1H), 7.41-7.44 (m, 2H), 761-7.68 (m, 2H), 7.96-8.01 (m, 1H), 8.49-8.58 (m, 2H), 9.51-9.53 (m, 1H), 9.92-9.93 (brs, 1). LC-MS (M+H)$^+$ 402.

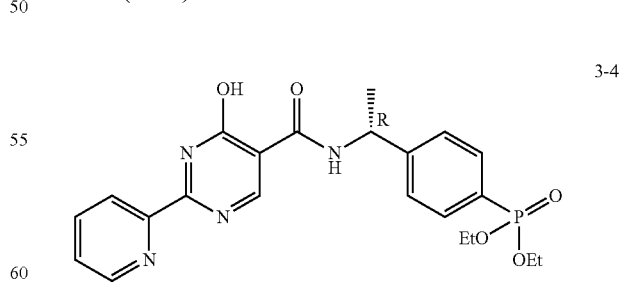

Diethyl (R)-4-(1-(4-hydroxy-2-(pyridin-2-yl)pyrimidine-5-carboxamido)ethyl)phenyl phosphonate (3-4)

4-hydroxy-2-(pyridin-2-yl)pyrimidin-5-carboxylic acid, 1-1-h, (1.185 g, 4.61 mmol) was dissolved in $SOCl_2$ (20 ml), the mixture was stirred at RT for 3 hours, then concentrated under vacuo. The residue was dissolved with 20 ml DCM, and dropwise to a solution of diethyl (R)-4-(1-aminoethyl)phenylphosphonate (3-e) (1 g, 4.61 mmol) and Et₃N (932 mg, 9.22 mmol) in DCM (30 ml) at 0° C., the mixture was stirred at room temperature for overnight. Then added water, the water phase was concentrated under vacuo and purified on silica gel chromatography to provide the product, 3-4, (400 mg).

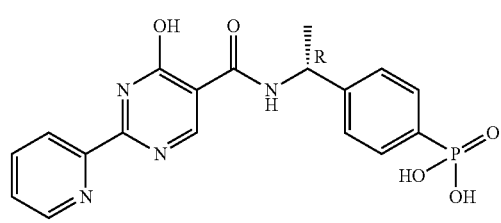

(R)-4-(1-(4-hydroxy-2-(pyridin-2-yl)pyrimidine-5-carboxamido)ethyl)phenylphosphonic acid (3-5)

To a solution of (R)-diethyl 4-(1-(4-hydroxy-2-(pyridin-2-yl)pyrimidine-5-carboxamido)ethyl)phenylphosphonate, 3-4, (400 mg, 0.88 mmol) in DCM (10 ml) was added dropwise TMSBr (2.0 g, 13.15 mmol) at 0° C., and the reaction mixture was stirred at room temperature overnight. The reaction mixture was evaporated to dryness, and the residue was treated with MeCN and water at room temperature. The resulting solid was collected via filtration to obtain the product, 3-5, (200 mg). ¹H NMR (DMSO-d₆, 300 MHz,): δ 11.29 (s, 5H), 9.93-9.96 (m, 1H), 8.80-8.81 (m, 1H), 8.56 (s, 1H), 8.37-8.39 (m, 1H), 8.07-8.12 (m, 1H), 7.61-7.74 (m, 3H), 7.42-7.46 (m, 2H), 5.12-5.16 (m, 1H) 2.07 (s, 1H), 1.48-1.51 (m, 3H), (M+H)⁺=401.2.

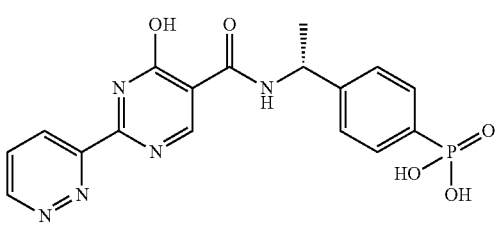

R isomer (R)-4-(1-(4-hydroxy-2-(pyridazin-3-yl)pyrimidine-5-carboxamido)ethyl)phenylphosphonic acid (3-5a) was prepared in a similar manner as compound 3-5. ¹H NMR (300 MHz, DMSO-d₆) δ1.48-1.51 (d, J=6.9 Hz, 3H), 5.12-5.17 (t, J=6.9 Hz, 1H), 7.42-7.45 (m, 2H), 7.61-7.68 (m, 2H), 7.97-8.01 (m, 1H), 8.49-8.52 (m, 2H), 9.47-9.49 (m, 1H). LC-MS (M+H)⁺ 402.

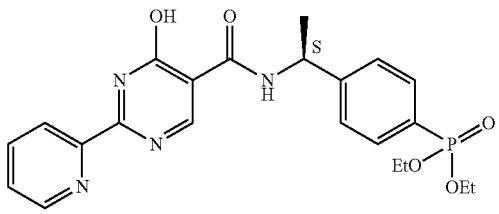

Diethyl (S)-4-(1-(4-hydroxy-2-(pyridin-2-yl)pyrimidine-5-carboxamido)ethyl)phenyl phosphonate (3-6)

4-hydroxy-2-(pyridin-2-yl)pyrimidine-5-carboxylic acid, 1-1-h, (1.185 g, 4.61 mmol) was dissolved in SOCl₂ (20 ml), the mixture was stirred at RT for 3 hours, then concentrated under vacuo. The residue was dissolved in 20 ml DCM, and resulting solution was added dropwisely to a solution of diethyl (S)-4-(1-aminoethyl)phenylphosphonate (3-f) (1 g, 4.61 mmol) and Et₃N (932 mg, 9.22 mmol) in DCM (30 ml) at 0° C., the mixture was stirred at room temperature overnight. Water was then added to the reaction mixture and the water phase was subsequently concentrated under vacuo and purified on silica gel chromatography to provide the product, 3-6, (400 mg).

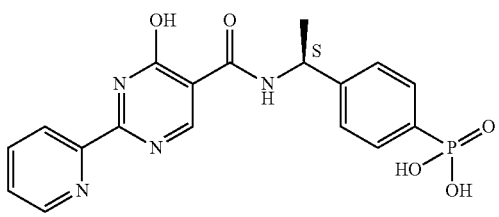

(S)-4-(1-(4-hydroxy-2-(pyridin-2-yl)pyrimidine-5-carboxamido)ethyl)phenylphosphonic acid (3-7)

To a solution of diethyl (S)-4-(1-(4-hydroxy-2-(pyridin-2-yl)pyrimidine-5-carboxamido)ethyl)phenylphosphonate, 3-6, (400 mg, 0.88 mmol) in DCM (10 ml) was added dropwisely TMSBr (2.0 g, 13.15 mmol) at 0° C. The reaction mixture was stirred at room temperature overnight. The reaction mixture was evaporated to dryness and the residue was treated with MeCN and water at room temperature. The resulting solid was collected via filtration to give the product, 3-7, (200 mg). ¹H NMR (DMSO-d₆, 300 MHz,): δ 10.71 (s, 4H), 9.93-9.96 (m, 1H), 8.80-8.81 (m, 1H), 8.56 (s, 1H), 8.37-8.39 (m, 1H), 8.08-8.13 (m, 1H), 7.61-7.74 (m, 3H), 7.42-7.46 (m, 2H), 5.12-5.17 (t, 1H), 2.07 (s, 1H), 1.49-1.51 (d, 3H).

(M+H)⁺=401.2.

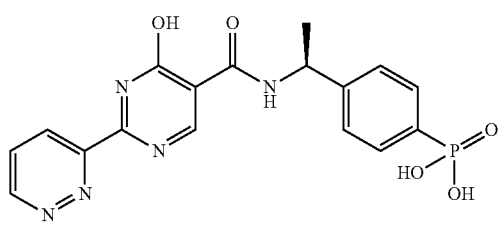

3-7a

S isomer (S)-4-(1-(4-hydroxy-2-(pyridazin-3-yl)pyrimidine-5-carboxamido)ethyl)phenylphosphonic acid (3-7a) was prepared in a similar manner as compound 3-7. $^1$H NMR (300 MHz, DMSO-$d_6$) δ1.51-1.53 (d, J=6.0 Hz, 3H), 5.14-5.19 (q, J=6.0 Hz, 1H), 7.44-7.46 (m, 2H), 764-7.68 (m, 2H), 7.96-8.01 (m, 1H), 8.49-8.53 (m, 2H), 9.51-9.53 (m, 1H), 9.97 (br s, 1H). LC-MS (M+H)$^+$ 402.

Example 4

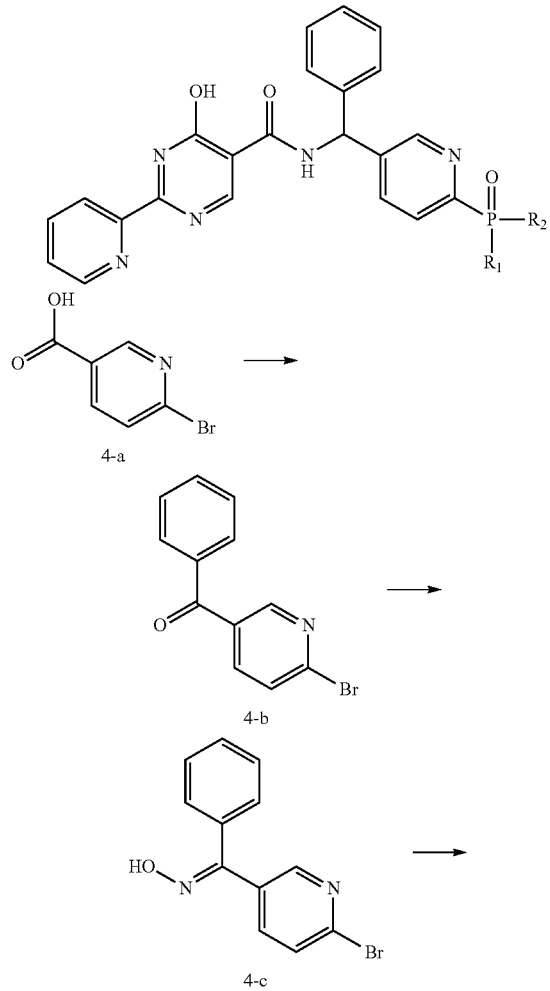

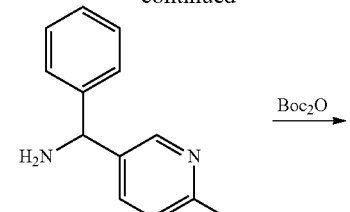

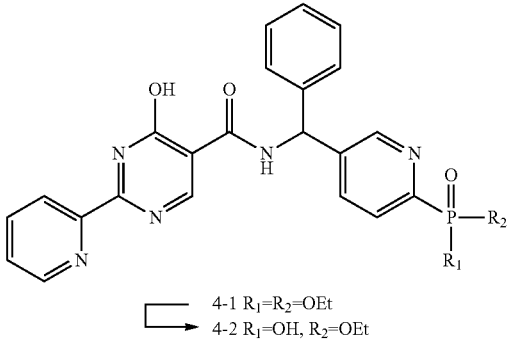

Step A: (6-bromopyridin-3-yl)(phenyl)methanone (4-b)

6-bromopyridine-3-carboxylic acid (50 g, 0.25 mol) in thionyl chloride (4a, 130 ml, 1.76 mol) was heated at reflux for 3 hours. The mixture was then concentrated under vacuum and the residue was co-evaporated with benzene to remove the thionyl chloride. The resulting acid chloride was dissolved in benzene (120 ml, 1.33 mol) and treated with AlCl$_3$ (82.5 g, 0.6 mol) portion wise with stirring at 5° C. After heating at reflux for 6 hours, the reaction mixture was cooled to room temperature and poured into 20% HCl (500 ml), stirred for 1 h, and layers were separated. The aqueous layer was further extracted with ethyl acetate (3×100 mL). The combined organic layer was washed with brine, 50% KOH, and water (100 mL each), dried (Na$_2$SO$_4$), filtered and concentrated under reduced pressure to afford the product, 4-b, (50 g, 77%). $^1$H NMR (CDCl$_3$, 300 MHz,): δ 8.72 (d, J=2.4 Hz, 1H), 8.04 (dd, J$_1$=8.4 Hz, J$_2$=2.7 Hz, 1H), 7.74 (m, 2H), 7.61 (m, 1H), 7.48 (m, 3H).

Step B: (6-bromopyridin-3-yl)(phenyl)methanone oxime (4-c)

A solution of (6-bromopyridin-3-yl)(phenyl)methanone, 4-b, (5.2 g, 20 mmol) in 100 ml of 95% ethanol was treated with N-hydroxylamine hydrochloride (4.2 g, 60 mmol) and sodium carbonate (6.36 g, 60 mmol). The resulting mixture was heated at reflux for 3 hours, cooled to room temperature, and concentrated under vacuum. The residue was taken into ethyl acetate (100 mL) followed by washing with water and brine (50 mL each). The organic layer was dried over sodium sulfate and concentrated. The resulting solid was recrystallized in ethyl acetate/petroleum ether to provide the product, 4-c, (2.7 g, 50%). $^1$H NMR (CD$_3$OD, 300 MHz,): δ 8.34 (s, 1H), 7.78 (m, 1H), 7.32 (m, 7H).

Step C: (6-bromopyridin-3-yl)(phenyl)methylamine (4-d)

The oxime, 4-c, (2.7 g, 10 mmol) was dissolved in 10 ml of DME at room temperature and sodium borohydride (1.59 g, 41 mmol) was added. Titanium tetrachloride (4 g, 21 mmol) was added dropwise under nitrogen at 0° C. Then the mixture was allowed to warm to room temperature and stirred overnight. The mixture was poured into ice water and alkalized with ammonia followed by extraction with ethyl acetate. The organic layer was washed with brine, dried over sodium sulfate and concentrated under vacuum to afford the product, 4-d, (1 g, 38%). $^1$H NMR (CDCl$_3$, 300 MHz,): δ 8.42 (d, J=2.7 Hz, 1H), 7.65 (m, 1H), 7.26 (m, 6H), 5.24 (s, 1H), 1.90 (br, 2H).

Step D: tert-Butyl[(6-bromopyridin-3-yl)(phenyl)methyl]carbamate (4-e)

(6-bromopyridin-3-yl)(phenyl)methylamine, 4-d, (400 mg, 1.52 mmol) and TEA (460 mg, 4.56 mmol) were dissolved in 5 ml of DCM. Boc$_2$O (394 mg, 1.82 mmol) was added at 0° C. and the mixture was then stirred at room temperature overnight. The mixture was concentrated and the residue in 10 ml of DCM was washed with water and diluted HCl. The organic layer was dried over sodium sulfate and concentrated. The residue was purified on column with the eluent of petroleum ether/ethyl acetate=5/1 to provide the product, 4-e, (300 mg, 54%). $^1$H NMR (CD$_3$OD, 300 MHz,): δ 8.13 (s, 1H), 7.54 (d, J=7.8 Hz, 1H), 7.13 (m, 6H), 5.79 (s, 1H), 1.37 (s, 9H).

Step E: Diethyl (5-{[(tert-butoxycarbonyl)amino](phenyl)methyl}pyridin-2-yl)phosphonate (4-f)

To tert-butyl (6-bromopyridin-3-yl)(phenyl)methylcarbamate (4-e) (3.4 g, 9.4 mmol), diethyl phosphite (1.55 g, 11.27 mmol) and Et$_3$N (1.14 g, 11.27 mmol) in THF was added PdCl$_2$(dppf) (200 mg). The mixture was heated at reflux under nitrogen overnight. The mixture was filtered and the filtrate was concentrated under vacuum. The residue was purified over silica gel (DCM/MeOH=20/1) to provide the product, 4-f (3.4 g, 86%).

Step F: Diethyl {5-[amino(phenyl)methyl]pyridin-2-yl}phosphonate (4-g)

A solution of compound 4-f in HCl/dioxane (100 ml) was stirred at room temperature overnight. The mixture was then concentrated under vacuum and the residue was diluted with water followed by extraction with ethyl acetate. The aqueous layer was basified with ammonia and then extracted with ethyl acetate. The organic layer was washed with brine, dried over sodium sulfate and concentrated to provide the product, 4-g, (1.5 g, 58%). $^1$H NMR (CD$_3$OD, 300 MHz,): δ 8.64 (s, 1H), 7.77 (m, 2H), 7.22 (m, 5H), 5.16 (s, 1H), 4.07 (m, 4H), 1.22 (m, 6H). (M+H)$^+$=321.

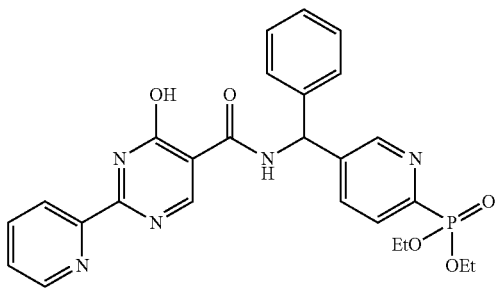

Diethyl 5-((4-hydroxy-2-(pyridin-2-yl)pyrimidine-5-carboxamido)(phenyl)methyl)pyridin-2-ylphosphonate (4-1)

To a solution of 4-hydroxy-2-(pyridin-2-yl)pyrimidine-5-carboxylic acid, 1-1-h, (1 g, 4.6 mmol) in ethyl acetate (20 ml) was added HATU (1.75 g, 4.6 mmol), Et$_3$N (465 mg, 4.6 mmol) and diethyl {5-[amino(phenyl)methyl]pyridin-2-yl}phosphonate (4-g) (1.47 g, 4.6 mmol). The resulting mixture was stirred at room temperature for 2 hour. Then it was filtered before diluted with saturated NH$_4$Cl solution. The mixture was extracted with ethyl acetate. The organic layer was dried over sodium sulfate and concentrated under vacuum. The residue was purified on silica gel chromatography to provide the product, 4-1, (360 mg, 15%). $^1$H NMR (CD$_3$OD, 300 MHz,): δ 10.56 (m, 1H), 8.66 (m, 3H), 8.37 (m, 1H), 7.83 (m, 3H), 7.52 (m, 1H), 7.23 (m, 5H), 6.33 (m, 1H), 4.09 (m, 4H), 1.30 (m, 6H).

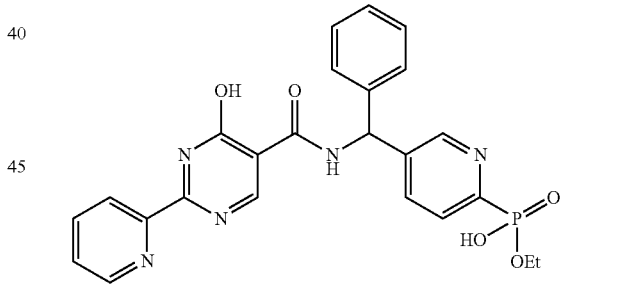

Ethyl hydrogen 5-((4-hydroxy-2-(pyridin-2-yl)pyrimidine-5-carboxamido)(phenyl)methyl)pyridin-2-ylphosphonate (4-2)

The diethyl phosphonate, 4-1, (130 mg, 0.25 mmol) was dissolved in 10 ml of dioxane and treated with 2 ml of 5N NaOH. The mixture was heated at reflux overnight. Then it was concentrated under vacuum and the residue was treated with 2 ml of trifluoroacetic acid. The mixture was re-evaporated and the residue was purified by prep-HPLC to provide the product, 4-2, (80 mg, 65%). $^1$H NMR (CD$_3$OD, 300 MHz,): δ 8.67 (m, 3H), 8.37 (m, 2H), 8.09 (m, 1H), 7.93 (m, 1H), 7.52 (m, 1H), 7.30 (m, 5H), 6.43 (s, 1H), 3.84 (m, 2H), 1.10 (m, 3H).

Example 5

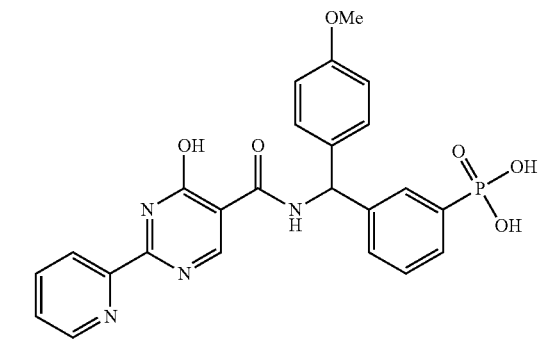

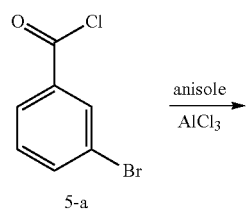

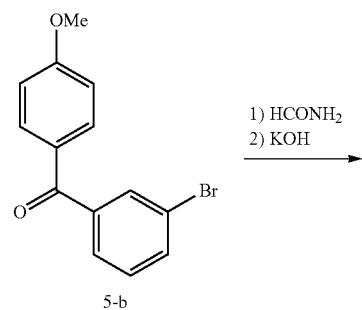

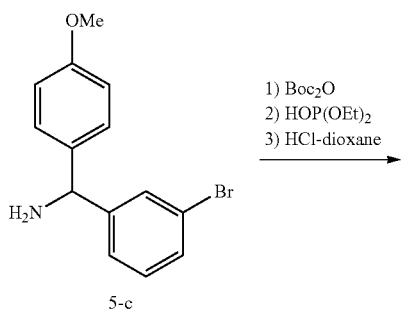

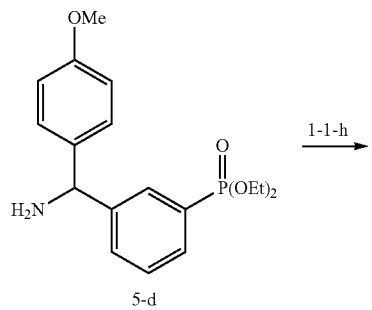

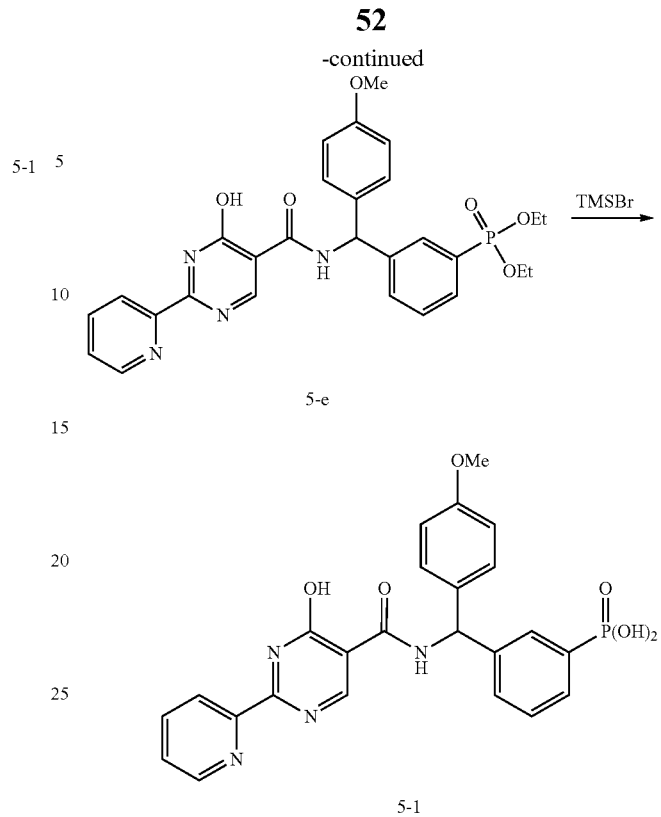

Step A: (3-bromophenyl)(4-methoxyphenyl)methanone (5-b)

To a cooled (0° C.) mixture of 3-bromobenzoyl chloride (5-a, 178 g, 0.82 mol) and anisole (110 g, 1.03 mol) in DCM (2.0 L) was added $AlCl_3$ (138 g, 1.03 mol) portion wise with stirring under $N_2$. The resulting reaction mixture was allowed to stir at r.t overnight. The reaction mixture was poured into 20% HCl (1500 ml), stirred for 1 h, and layers were separated. The aqueous layer was further extracted with DCM (2×750 ml). The combined organic layer was washed with water, brine, dried ($Na_2SO_4$), filtered and concentrated under reduced pressure. The residue was washed with hexane to afford the product, 5-b, (190 g, 84%).

Step B: (3-bromophenyl)(4-methoxyphenyl)methylamine (5-c)

(3-bromophenyl)(4-methoxyphenyl)methanone(5-b) (190 g, 0.66 mol) was heated with formamide (1000 ml) for 24 hours at 185° C., and the mixture was cooled to room temperature before poured into water. The product was filtered off and washed with water to provide Intermediate A (300 g, %). The above formyl derivative, Intermediate A, (300 g, 0.94 mol) was heated with potassium hydroxide (263 g, 4.70 mol) in methanol (1.5 L) and stirred overnight. The mixture was concentrated under vacuum and the residue was diluted with water followed by extraction of ethyl acetate. The organic layer was dried over sodium sulfate and concentrated to provide the product, 5-c, (190 g, 99%).

Step C: diethyl 3-(amino(4-methoxyphenyl)methyl)phenylphosphonate hydrochloride (5-d)

(3-bromophenyl)(4-methoxyphenyl)methylamine, 5-c, (190 g, 0.65 mol) in DCM (1.5 L) was added triethylamine (165 g, 1.63 mol) and the mixture was cooled to 0° C. Boc²O (211 g, 0.98 mol) was added at this temperature. Then the resulting mixture was stirred at room temperature overnight. The mixture was concentrated under vacuum and the residue was washed with hexane to provide Intermediate B (174 g, 68%). (M+H)$^+$=392.

To the above Intermediate B (50 g, 0.128 mol), diethyl phosphite (21.1 g, 0.153 mol) and Et$_3$N (38.8 g, 0.384 mol) in THF (1 L) was added PdCl$_2$(dppf) (5 g). The mixture was allowed to stir overnight at reflux. The mixture was filtered and the filtrate was concentrated under vacuum. The residue was purified over silica gel (petroleum ether/ethyl acetate=10/1) to provide Intermediate C (35 g, 61%). (M+H)$^+$=450.

The above Intermediate C (36.8 g, 82 mmol) was dissolved in HCl/dioxane (500 ml) and the mixture was stirred at room temperature overnight. Then it was concentrated under vacuum to provide the product, 5-d, (27.2 g, 95.4%). (M+H)$^+$=350.

Step D: diethyl 3-((4-hydroxy-2-(pyridin-2-yl)pyrimidine-5-carboxamido)(4-methoxyphenyl)methyl)phenylphosphonate (5-e)

The 4-hydroxy-2-(pyridin-2-yl)pyrimidine-5-carboxylic acid, 1-1-h, (500 mg, 2.3 mmol) was dissolved in SOCl$_2$ (10 ml), the mixture was stirred at RT for 3 hours, then concentrated under vacuo. The residue was dissolved with 20 ml DCM, and dropwise to a solution of diethyl 3-(amino(4-methoxyphenyl)methyl)phenylphosphonate hydrochloride (5-d, 802 mg, 2.30 mmol) and Et$_3$N (464 mg, 4.6 mmol) in DCM (30 ml) at 0° C., the mixture was stirred at room temperature overnight. Then added water, the water phase was concentrated under vacuo and purified on silica gel chromatography to provide the product, 5-e, (990 mg, 78.4%).

Step E: 3-((4-hydroxy-2-(pyridin-2-yl)pyrimidine-5-carboxamido)(4-methoxyphenyl)methyl)phenylphosphonic acid (5-1)

To a solution of diethyl 3-((4-hydroxy-2-(pyridin-2-yl)pyrimidine-5-carboxamido)(4-methoxyphenyl)methyl)phenylphosphonate, 5-e, (0.99 g, 1.81 mmol) in dichloromethane (20 ml) was added TMSBr (5.6 g, 36.2 mmol) dropwise at 0° C. The resulting mixture was stirred at room temperature for 2 days. Then it was concentrated under vacuum and the residue was purified on prep-HPLC to provide the product, 5-1, (400 mg, 45%). $^1$H NMR (DMSO-d$_6$, 300 MHz,): δ 8.80-8.82 (m, 1H), 8.37-8.40 (m, 1H,), 8.07-8.12 (m, 1H), 7.70-7.74 (m, 1H), 7.52-7.64 (m, 2H), 7.38-7.43 (m, 2H), 7.23-7.25 (m, 2H), 6.92-6.95 (m, 2H), 6.25-6.28 (m, 1H), 3.73 (s, 3H). (M−H)$^-$=491.1.

Example 6

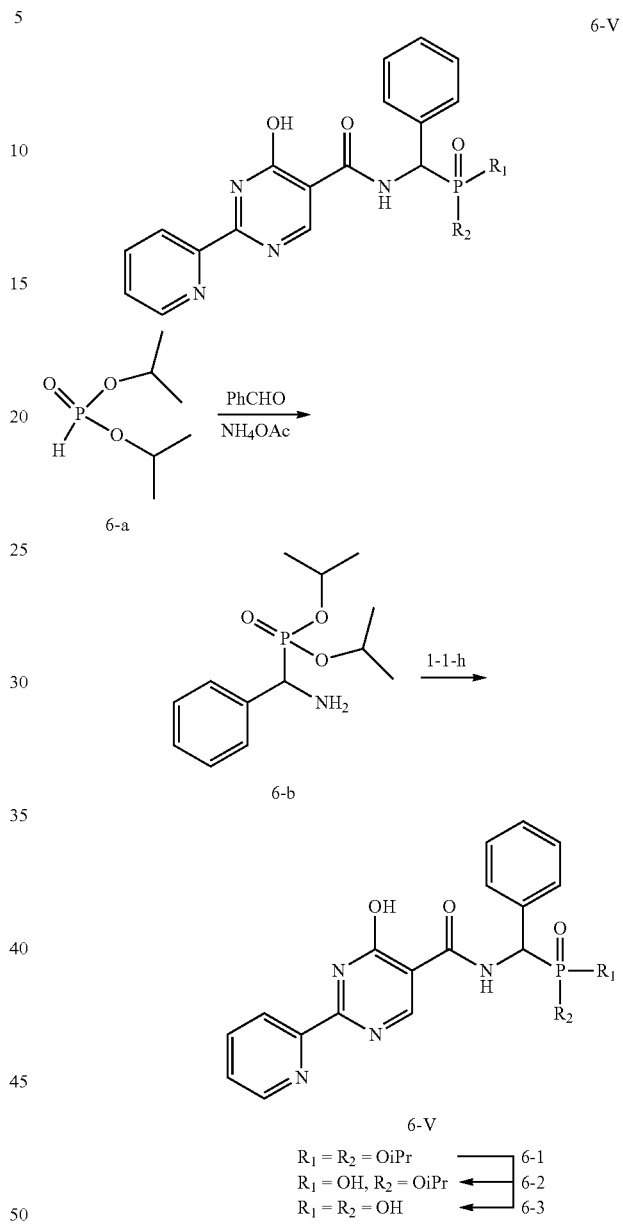

Step A: Diisopropyl amino(phenyl)methylphosphonate (6-b)

To an ethanol solution (1.0 L) of ammonium acetate (37.6 g, 0.5 mol) was added molecular sieves (4 A) (10.0 g), benzaldehyde (53.0 g, 0.5 mol) and diisopropyl phosphate (6-a, 83.1 g, 0.5 mol) at room temperature. The reaction mixture was stirred at 60° C. for 2 days and cooled to room temperature. The reaction mixture was concentrated and ice-water was added. Then the mixture was acidified to pH approximately 1~2 with concentrated HCl; and the solution was washed with Et$_2$O to remove neutral materials. The aqueous phase was then basified to pH 11 with aq NaOH, and the product was extracted with DCM. Combined layers was washed with brine, dried over Na$_2$SO$_4$, and concentrated to give the title compound, 6-b, (253.0 g, 41%). LC-MS: (M+H)$^+$ 272.

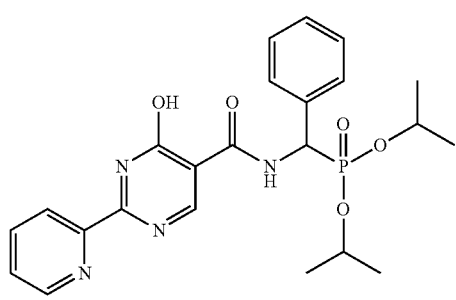

Diisopropyl (4-hydroxy-2-(pyridin-2-yl)pyrimidine-5-carboxamido)(phenyl)methyl phosphonate (6-1)

To a solution of compound 4-hydroxy-2-(pyridin-2-yl)pyrimidine-5-carboxylic acid, 1-1-h, (3.5 g, 16.2 mmol), TBTU (13.0 g, 40.2 mmol) and DIEPA (8.0 g, 61.6 mmol) in DMF (80 mL) was added Diisopropyl amino(phenyl)methylphosphonate, 6-b, (4.4 g, 16.2 mmol). The mixture was stirred at room temperature overnight and concentrated. The residue was taken up in EA and water. The aqueous layer was extracted with EA. Combined layers were washed with brine, dried over Na$_2$SO$_4$, and concentrated to give the crude product, 6-1, which was purified by pre-HPLC (1.3 g, 17%). $^1$H NMR (300 MHz, CD$_3$OD) δ1.16-1.18 (d, J=6.0 Hz, 3H), 1.23-1.25 (d, J=6.0 Hz, 3H), 1.29-1.35 (q, J=6.3 Hz, 6H), 4.55-4.71 (m, 2H), 5.57-5.67 (q, J=9.6 Hz, 1H), 7.28-7.40 (m, 3H), 7.46-7.49 (m, 2H), 7.61-7.65 (m, 1H), 8.01-8.06 (m, 1H), 8.48-8.51 (m, 1H), 8.76-8.78 (m, 2H), 10.80 (s, 1H); LC-MS: (M+H)$^+$ 471.

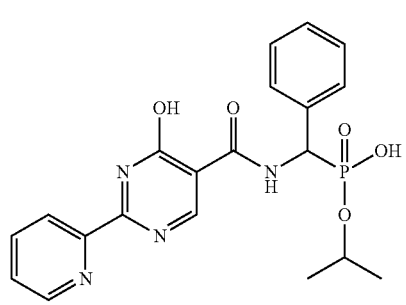

Isopropyl Hydrogen (4-hydroxy-2-(pyridin-2-yl)pyrimidine-5-carboxamido)(phenyl)methylphosphonate (6-2)

A mixture of compound Diisopropyl (4-hydroxy-2-(pyridin-2-yl)pyrimidine-5-carboxamido)(phenyl)methyl phosphonate, 6-1, (200 mg, 0.43 mmol) and NaOH (51 mg, 1.28 mmol) in MeOH (3 mL), THF (1 mL) and H$_2$O (2 mL) was refluxed for 2 days. The resulting mixture was cooled, concentrated and extracted by EA. To the aqueous layer was added HCl (1 M) to adjust the pH to 1~2. The mixture was extracted by EA. Combined organic layers were washed by brine, dried over Na$_2$SO$_4$ and concentrated to afford the title compound, 6-2, as a white solid (40 mg, 22%). $^1$H NMR (300 MHz, DMSO-d$_6$) δ1.12-1.15 (m, 6H), 4.40-4.51 (m, 1H), 5.32-5.42 (m, 1H), 7.23-7.39 (m, 6H), 7.69-7.73 (m, 1H), 8.07-8.12 (m, 1H), 8.36-8.39 (m, 1H), 8.55 (s, 1H), 8.79-8.80 (m, 1H), 10.51 (s, 1H); LC-MS: (M+H)$^+$ 429.

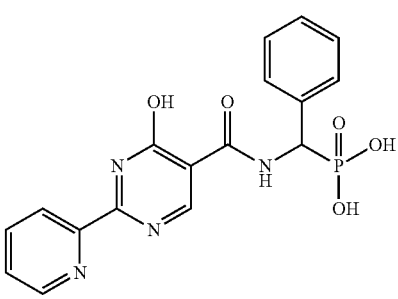

Isopropyl Hydrogen (4-hydroxy-2-(pyridin-2-yl)pyrimidine-5-carboxamido)(phenyl)methylphosphonate (6-3)

To a solution of Diisopropyl (4-hydroxy-2-(pyridin-2-yl)pyrimidine-5-carboxamido)(phenyl)methyl phosphonate, 6-1, (2.3 g, 4.9 mmol) in DCM (50 mL) was added TMSBr (10 mL) at 0° C. The resulting solution was stirred at room temperature under a nitrogen atmosphere overnight. Then ice-water was added and the organic layer was dried over Na$_2$SO$_4$, filtrated, and concentrated to afford a residue, which was purified by washing with hot MeCN, MeOH and Et$_2$O to give the desired compound, 6-3, (2.1 g, 100%) $^1$H NMR (300 MHz, CD$_3$OD) δ5.41-5.48 (m, 1H), 7.14-7.26 (m, 3H), 7.36-7.38 (m, 2H), 7.67-7.72 (m, 1H), 8.11-8.16 (m, 1H), 8.46-8.48 (m, 1H), 8.72-8.75 (m, 2H); LC-MS: 387 (M+H)$^+$.

Example 7

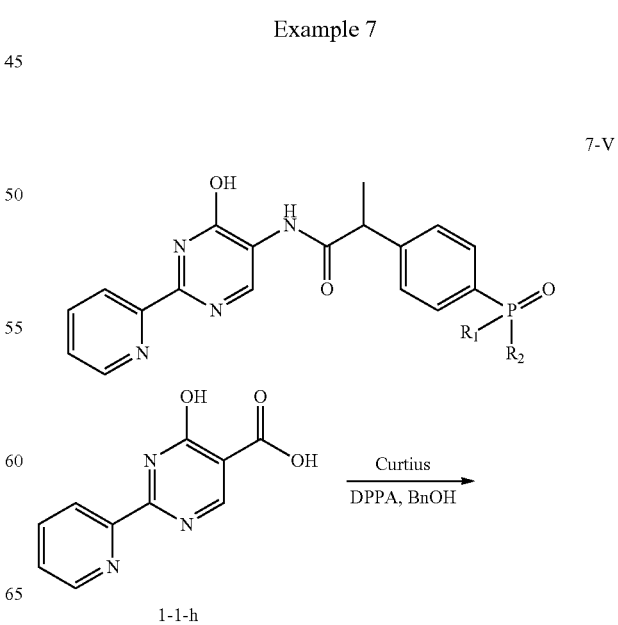

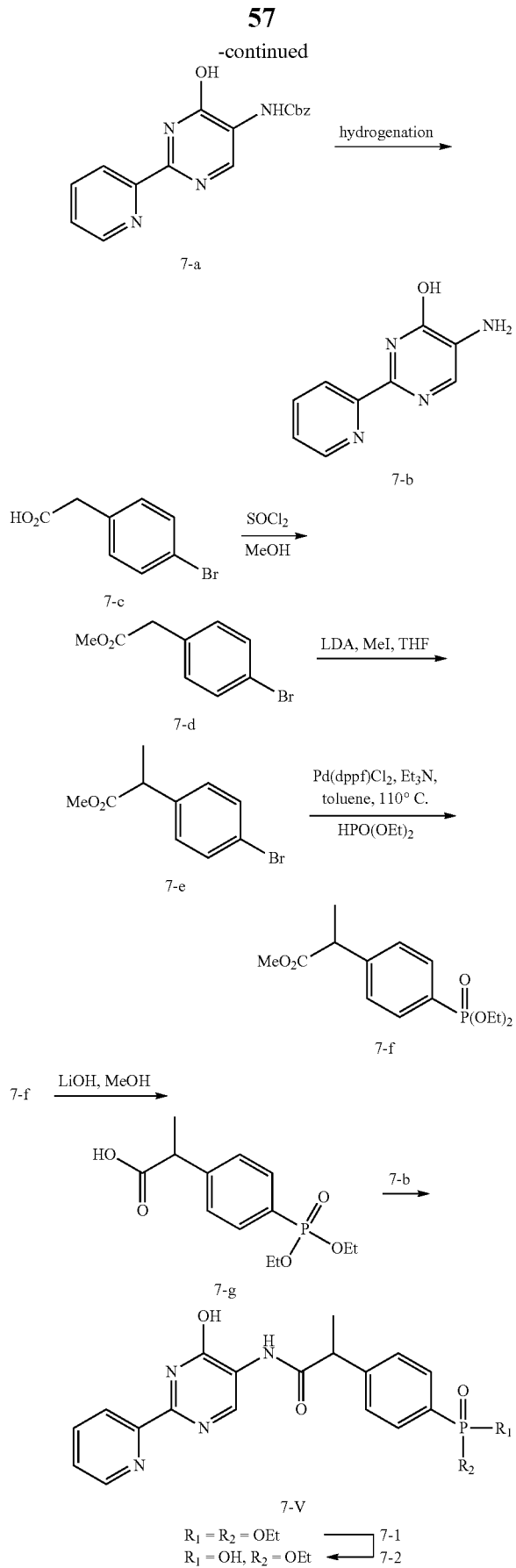

Step A: benzyl 4-hydroxy-2-(pyridin-2-yl)pyrimidin-5-ylcarbamate (7-a)

To a solution of 4-hydroxy-2-(pyridin-2-yl)pyrimidine-5-carboxylic acid, 1-1-h, (10 g, 46 mmol) in toluene (150 ml) was added DPPA (13.94 g, 50.6 mmol), Et$_3$N (9.31, 92.1 mmol) and benzyl alcohol (14.93 g, 0.14 mol). The resulting mixture was heated at reflux overnight. The mixture was then concentrated under vacuum and the residue was purified on silica gel chromatography with the eluent of petroleum ether/ethyl acetate=1/5 (Rf=0.3) to afford the crude product, 7-a, (3.2 g). The sample delivered was re-purified on prep-HPLC. $^1$H NMR (DMSO-d$_6$, 300 MHz,): δ 8.73 (m, 1H), 8.40 (m, 2H), 8.00 (m, 1H), 7.37 (m, 6H), 5.19 (s, 1H).
(M+H)$^+$=323.1.

Step B: 5-amino-2-(pyridin-2-yl)pyrimidin-4-ol (7-b)

Benzyl 4-hydroxy-2-(pyridin-2-yl)pyrimidin-5-ylcarbamate, 7-a, (1 g, 3.1 mmol) in methanol (20 ml) was hydrogenated under 1 atm of hydrogen in the presence of Pd/C (500 mg) overnight. The mixture was filtered and the filtrate was concentrated to provide the crude product, 7-b, (240 mg).

Step C: Methyl 2-(4-bromophenyl) acetate (7-d)

To a solution of 4-bromophenylacetic acid, 7-c, (10 g, 47 mmol) in methanol (100 mL) was added SOCl$_2$ (3.4 mL, 47 mmol) dropwise under a nitrogen atmosphere in an ice-water bath. After stirred in the ice-water bath for 30 min, the resulting solution was refluxed with stirring overnight. The cooled reaction solution was concentrated and treated with cooled saturated NaHCO$_3$ solution. The layers were separated and the aqueous layer was extracted by EA. Combined organic layers were washed by brine, dried over Na$_2$SO$_4$ and concentrated to afford the title compound, 7-d, as pink oil (9.0 g, 85%). $^1$H NMR (300 MHz, CDCl$_3$) δ3.58 (s, 2H), 3.69 (s, 3H), 7.15 (d, J=8.4 Hz, 2H), 7.44 (d, J=8.4 Hz, 2H).

Step D: Methyl 2-(4-bromophenyl)propanoate (7-e)

A solution of methyl 2-(4-bromophenyl)acetate, 7-d, (1.0 g, 4.4 mmol) in THF (5 mL) was cooled to −78° C. under nitrogen, and slowly treated with LDA (2 M in THF, 2.2 mL, 4.4 mmol) at −78° C. The resulting mixture was stirred at −78° C. for 30 min, and then a solution of iodomethane (0.6 g, 4.4 mmol) in THF (10 mL) was added dropwise and the mixture was stirred at −78° C. for another 30 min and then warmed up slowly to room temperature and stirred overnight. The reaction mixture was concentrated and then crush ice was added. Then the mixture was added saturated aqueous ammonium chloride (10 mL) and extracted by EA. Combined organic layers were washed with brine, dried over Na$_2$SO$_4$ and concentrated. The residue was purified by column chromatography to give the title compound, 7-e, (650 mg, 61%). $^1$H NMR (300 MHz, CDCl$_3$) δ1.49 (d, J=7.2 Hz, 2H), 3.67-3.72 (m, 4H), 7.17 (d, J=8.4 Hz, 2H), 7.44 (d, J=8.4 Hz, 2H). LC-MS (M+H)$^+$ 243, 245.

Step E: Methyl 2-(4-(diethoxyphosphoryl)phenyl)propanoate (7-f)

To a solution of methyl 2-(4-bromophenyl)propanoate, 7-e, (500 mg, 2.06 mmol), diethylphosphite (994 mg, 7.20 mmol) and triethylamine (681 mg, 6.7 mmol) in toluene (5 mL) was added [1,1'-bis(diphenylphosphino) ferrocene]dicholoropalladium (54 mg). The resulting reaction mixture was heated at 110° C. under nitrogen overnight. The cooled reaction mixture was filtrated (washed with DCM, 3×10 mL), and the filtrate was concentrated to afford the crude product which was purified by column chromatography to give the title compound, 7-f, as yellow brown oil (500 mg, 99%). $^1$H NMR (300 MHz, CDCl$_3$) δ1.30-1.39 (m, 6H), 1.51 (d, J=7.2 Hz, 3H), 3.67 (s, 3H), 3.77 (q, J=7.2 Hz, 1H), 4.05-4.20 (m, 4H), 7.37-7.41 (m, 2H), 7.72-7.79 (m, 2H). LC-MS (M+H)$^+$ 301.

Step F: 2-(4-(Diethoxyphosphoryl)phenyl)propanoic acid (7-a)

A solution of compound 7-f (100 mg, 0.33 mmol) in methanol (2 mL) and water (2 mL) was treated with LiOH—H$_2$O (14 mg, 0.33 mmol), and the resulting reaction solution was stirred at room temperature overnight. The resulting mixture was concentrated and extracted by EA. The aqueous layers was added HCl (1 M) until pH 1~2. The mixture was extracted by EA. Combined organic layers was washed by brine, dried over Na$_2$SO$_4$ and concentrated to afford the title compound, 7-g, as oil (35 mg, 37%). $^1$H NMR (300 MHz, CDCl$_3$) δ1.30-1.34 (m, 6H), 1.52 (d, J=7.2 Hz, 3H), 3.79 (q, J=7.2 Hz, 1H), 4.07-4.17 (m, 4H), 7.39-7.43 (m, 2H), 7.71-7.78 (m, 2H).

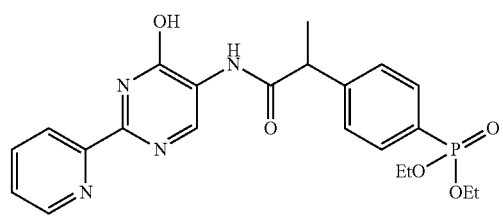

Diethyl 4-(1-(4-hydroxy-2-(pyridin-2-yl)pyrimidin-5-ylamino)-1-oxopropan-2-yl)phenyl phosphonate (7-1)

A mixture of compound 7-b (0.5 g), compound 7-g (0.7 g), HATU (1.5 g, 3.9 mmol) and Et$_3$N (1.2 g, 11.8 mmol) in MeCN (25 mL) was stirred at room temperature overnight. The reaction mixture was concentrated in vacuum. The residue was extracted with EA (100 mL), and then washed with sat. NH$_4$Cl (50 mL), water (50 mL), and brine (50 mL). The organic layer was concentrated and the residue was purified by column chromatography to afford the product 7-1 (280 mg, 25%). $^1$H NMR (300 MHz, CDCl$_3$) δ1.32-1.36 (m, 6H), 1.63 (d, J=7.2 Hz, 3H), 3.89 (q, J=7.2 Hz, 1H), 4.11-4.19 (m, 4H), 7.49-7.57 (m, 3H), 7.77-7.84 (m, 2H), 7.97-8.02 (m, 1H) 8.15 (s, 1H), 8.46 (d, J=7.8 Hz, 1H), 8.64 (d, J=4.8 Hz, 1H), 9.20 (br s, 2H). LC-MS (M+H)$^+$ 457.

Example 8

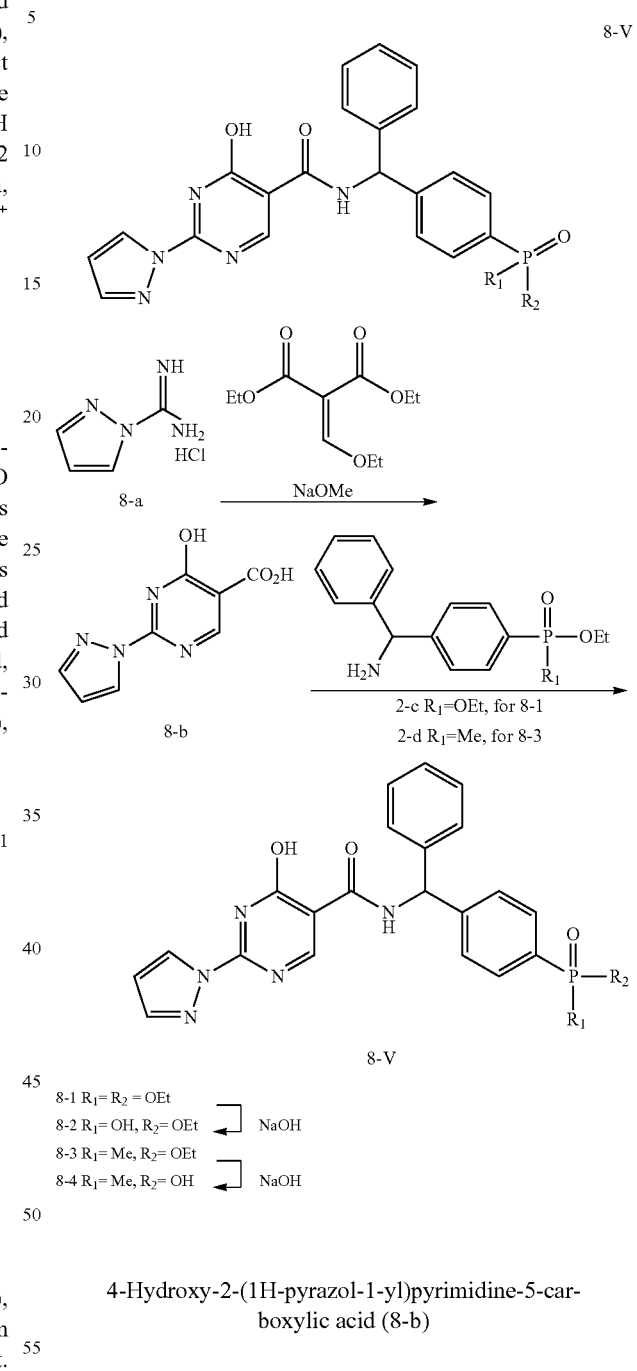

4-Hydroxy-2-(1H-pyrazol-1-yl)pyrimidine-5-carboxylic acid (8-b)

To 1H-pyrazole-1-carboximidamide hydrochloride, 8-a, (44.22 g, 299 mmol) in EtOH (500 mL) was added sodium methoxide (102 mL, 448 mmol, 25 wt % in MeOH) and diethyl ethoxymethylenemalonate (61.0 mL, 299 mmol, 99%). The reaction was heated for about 40 min at 75° C. and then cooled slightly (to 71° C.) before adding potassium hydroxide (33.5 g, 597) in water (125 mL). The reaction was heated to 75° C. again for 1 h. During this time an additional portion of EtOH (100 mL) was added to improve mixing. The reaction was cooled to 40° C. before adding aq. HCl (81.3 mL, 991 mmol, 37%) in portions. The reaction aged for 1 h 40 min and then Et₂O (180 mL) was added. The solids were filtered and rinsed with EtOH, Et₂O and then hexane. The solid was then suspended in aq. HCl (300 mL, 0.67 M), filtered and washed with aq. HCl (300 mL, 1 M), 2:1 Et₂O: EtOH (350 mL), 1:1 Et₂O:EtOH (200 mL), Et₂O (150 mL) and hexane (150 mL) to afford the title compound, 8-b. HPLC/MS: 207.2 (M+1); Rt=0.61 min.

rated and the residue was purified by prep-HPLC to provide the product, 8-2. (100 mg, 42%). ¹H NMR (CD₃OD, 300 MHz,): δ 8.67 (s, 1H), 8.59 (m, 1H), 7.93 (m, 1H), 7.62 (m, 2H), 7.50 (m, 2H), 7.35 (m, 5H), 6.67 (s, 1H), 6.38 (m, 1H), 3.99 (m, 2H), 1.27 (m, 3H).

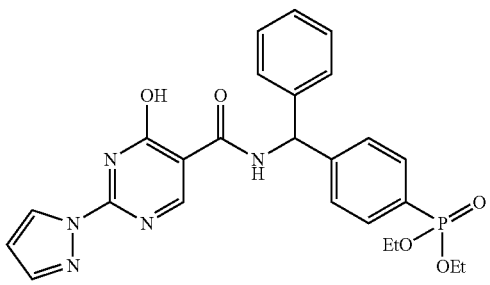

Diethyl 4-((4-hydroxy-2-(1H-pyrazol-1-yl)pyrimidine-5-carboxamido)(phenyl)methyl)phenylphosphonate (8-1)

To a solution of 4-hydroxy-2-(1H-pyrazol-1-yl)pyrimidine-5-carboxylic acid, 8-b, (309 mg, 1.5 mmol) in MeCN (10 ml) were added HATU (599 mg, 1.58 mmol), Et₃N (159 mg, 1.58 mmol) and diethyl 4-(amino(phenyl)methyl)phenylphosphonate, 2-c, (479 mg, 1.5 mmol). The resulting mixture was stirred at room temperature for 2 hours. Then it was concentrated under vacuum and the residue was taken into ethyl acetate followed by washing with sat. NH₄Cl. The organic layer was dried over sodium sulfate and concentrated under vacuum. The residue was purified by prep-HPLC to provide the product, 8-1, (150 mg, 20%). ¹H NMR (CD₃OD, 300 MHz,): δ 10.39 (br, 1H), 8.56 (s, 1H), 8.47 (m, 1H), 7.81 (m, 1H), 7.62 (m, 2H), 7.40 (m, 2H), 7.25 (m, 5H), 6.54 (m, 1H), 6.26 (m, 1H), 3.96 (m, 4H), 1.18 (m, 6H).

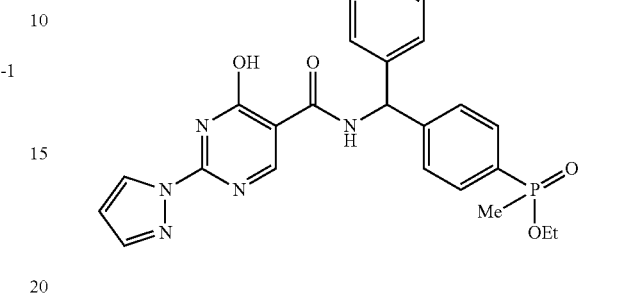

Ethyl 4-((4-hydroxy-2-(1H-pyrazol-1-yl)pyrimidine-5-carboxamido)(phenyl)methyl)phenyl(methyl)phosphinate (8-3)

To a solution of 4-hydroxy-2-(1H-pyrazol-1-yl)pyrimidine-5-carboxylic acid, 8-b, (206 mg, 1 mmol) in MeCN (20 ml) were added HATU (395 mg, 1.04 mmol), Et₃N (105 mg, 1.04 mmol) and ethyl methyl(4-(amino(phenyl)methyl)phenyl)phosphinate, 2-d, (289 mg, 1 mmol). The resulting mixture was stirred at room temperature for 2 hours. Then it was filtered before diluted with saturated NH₄Cl solution. The mixture was extracted with ethyl acetate. The organic layer was dried over sodium sulfate and concentrated under vacuum. The residue was purified on silica gel chromatography to provide the product, 8-3, (150 mg, 31%). ¹H NMR (CD₃OD, 300 MHz,): δ 8.65 (s, 1H), 8.57 (m, 1H), 7.91 (s, 1H), 7.76 (m, 2H), 7.52 (m, 2H), 7.34 (m, 5H), 6.64 (s, 1H), 6.36 (s, 1H), 3.85 (m, 2H), 1.67 (d, 3H), 1.25 (m, 3H).

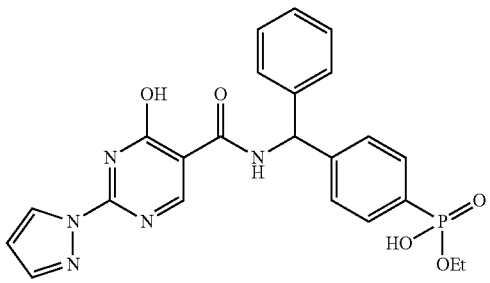

Ethyl hydrogen 4-((4-hydroxy-2-(1H-pyrazol-1-yl)pyrimidine-5-carboxamido)(phenyl)methyl)phenylphosphonate (8-2)

The diethyl phosphonate, 8-1, (253 mg, 0.5 mmol) was dissolved in 5 ml of dioxane and treated with 2 ml of 5N NaOH. The mixture was heated at reflux overnight. Then it was concentrated under vacuum and the residue was treated with 2 ml of trifluoroacetic acid. The mixture was re-evapo-

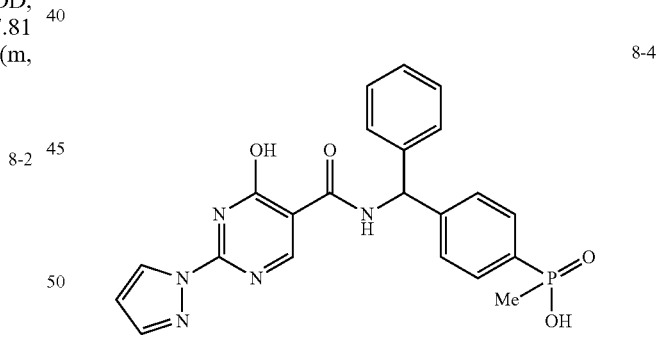

4-((4-Hydroxy-2-(1H-pyrazol-1-yl)pyrimidine-5-carboxamido)(phenyl)methyl)phenyl(methyl)phosphinic acid (8-4)

The ethyl methylphosphinate, 8-3, (144 mg, 0.3 mmol) was dissolved in 5 ml of dioxane and treated with 2 ml of 5N NaOH. The mixture was heated at reflux overnight. Then it was concentrated under vacuum and the residue was treated with 2 ml of trifluoroacetic acid. The mixture was re-evaporated and the residue was purified by prep-HPLC to provide the product, 8-4, (60 mg, 44%). ¹H NMR (CD₃OD, 300 MHz,): δ 9.81 (br, 1H), 8.90 (s, 1H), 8.48 (s, 1H), 7.81 (s, 1H), 7.50 (m, 2H), 7.21 (m, 5H), 6.42 (m, 3H), 1.50 (d, 3H).

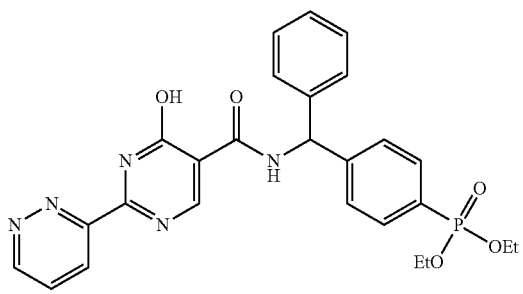

Diethyl 4-((4-hydroxy-2-(pyridazin-3-yl)pyrimidine-5-carboxamido)(phenyl)methyl)phenylphosphonate (8-5)

To a stirred suspension of 4-hydroxy-2-(pyridazin-3-yl)pyrimidine-5-carboxylic acid, 30-ie, (137 mg, 0.63 mmol) in MeCN (10 mL) was added HATU (357 mg, 0.94 mmol), TEA (190 mg, 1.88 mmol) and diethyl 4-(amino(phenyl)methyl)phenylphosphonate, 2-c, (200 mg, 0.63 mmol). The solution was stirred at room temperature for 1 h. The product was precipitated from ice water (50 mL, crush ice). The product was collected by vacuum filtration and dried in a vacuum to afford a syrup, which was purified by pre-HPLC to yield title crude, 8-5, product as pale yellow (100 mg, 31%) $^1$H NMR (300 MHz, DMSO-d$_6$) δ1.19-1.24 (t, J=7.5 Hz, 6H), 3.96-4.01 (q, J=7.5 Hz, 4H), 6.34-6.36 (d, J=6.0 Hz, 1H), 7.37-7.70 (m, 11H), 7.70 (m, 1H), 8.50 (m, 2H), 9.494 (d, J=3.0 Hz, 1H), 10.52 (s, 1H); LC-MS: (M+H)$^+$ 520.

Example 9

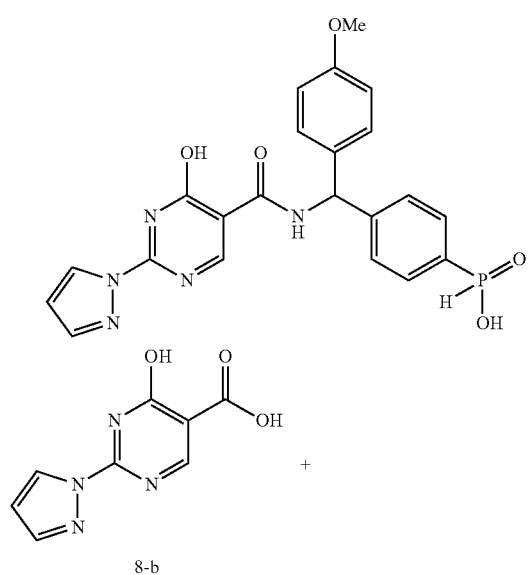

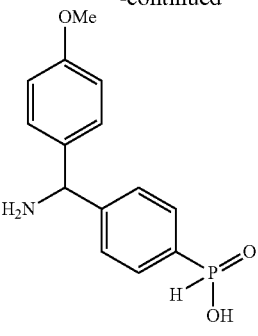

4-((4-Hydroxy-2-(H-pyrazol-1-yl)pyrimidine-5-carboxamido)(4-methoxyphenyl)methyl)phenylphosphinic acid (9-1)

To a solution of 4-hydroxy-2-(1H-pyrazol-1-yl)pyrimidine-5-carboxylic acid, 8-b, (1.1 g, 5.5 mmol) in MeCN (20 ml) were added HATU (2.16 g, 5.68 mmol), Et$_3$N (3.29 g, 32.5 mmol) and 4-(amino(4-methoxyphenyl)methyl)phenylphosphinic acid hydrochloride, 1-1-e, (1.5 g, 5.5 mmol). The resulting mixture was stirred at room temperature for 2 hours. Then it was concentrated under vacuum and the residue was purified on prep-HPLC to provide the product, 9-1, (50 mg, 19%). $^1$H NMR (DMSO-d6, 300 MHz,): δ 8.61 (s, 1H), 8.35 (m, 1H), 8.06 (s, 1H), 7.63 (m, 1H), 7.44 (m, 2H), 7.22 (m, 2H), 6.90 (m, 2H), 6.72 (m, 1H), 6.52 (s, 1H), 6.23 (m, 1H), 3.72 (s, 3H), 2.06 (s, 1H).

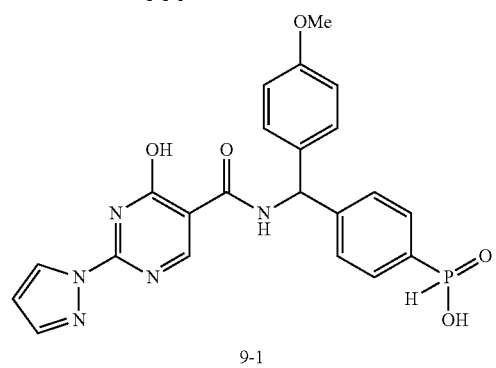

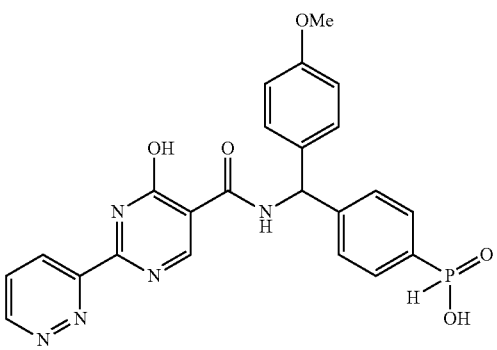

4-((4-hydroxy-2-(pyridazin-3-yl)pyrimidine-5-carboxamido)(4-methoxyphenyl)methyl)phenylphosphinic acid (9-2)

4-hydroxy-2-(pyridazin-3-yl)pyrimidine-5-carboxylic acid, 30-ie, (545 mg, 2.5 mmol) in 5 ml of thionyl chloride was heated at reflux overnight. Then it was concentrated under vacuum and the residue was dissolved in 10 ml of dichloromethane. To the mixture was added 4-(amino(4-methoxyphenyl)methyl)phenylphosphinic acid hydrochloride (1-1-e, 782.5 mg, 2.5 mmol) and TEA (505 mg, 5 mmol) in 10 ml of dichloromethane at 0° C. The mixture was stirred for 3 hours and then it was washed with sat. NH₄Cl. The organic layer was concentrated under vacuum and the residue was purified on prep-HPLC to provide the product 9-2 (150 mg, 12%). $^1$H NMR (CD$_3$OD, 300 MHz,): δ 9.37 (m, 1H), 8.83 (s, 1H), 8.51 (m, 1H), 8.15 (m, 1H), 7.80 (m, 2H), 7.53 (m, 2H), 7.23 (m, 2H), 6.79 (m, 2H), 6.56 (s, 1H), 6.34 (s, 1H), 3.77 (s, 3H).

Example 10

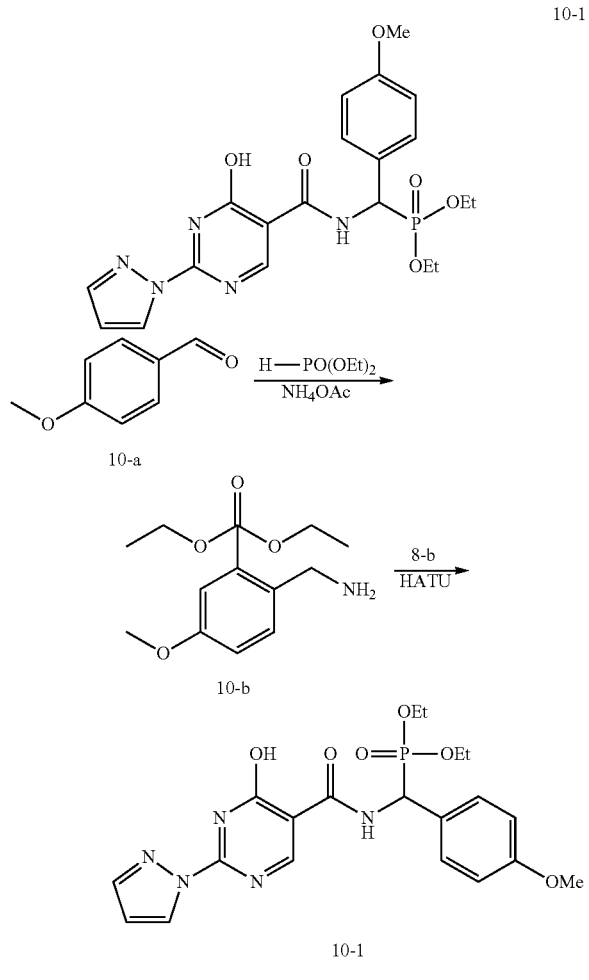

Diethyl amino(4-methoxyphenyl)methylphosphonate (10-b)

To an ethanol solution (400 mL) of ammonium acetate (15 g, 0.2 mol) was added molecular sieves (4 A) (4.0 g), 4-methoxybenzaldehyde (10-a, 27 g, 0.2 mol) and diethyl phosphate (28 g, 0.2 mol) at room temperature. The reaction mixture was stirred at 60° C. for 44 h and cooled to room temperature. The reaction mixture was concentrated and ice-water was added. Then the mixture was acidified to pH 1 with con. HCl; and the solution were washed with Et$_2$O to remove neutral materials. The aqueous phase was basified to pH 11 with aq NaOH, and the product was extracted with DCM. Combined organic layers were washed with brine, dried over Na$_2$SO$_4$, and concentrated to give the title compound 110-b (25 g, 91%). $^1$H NMR (300 MHz, CDCl$_3$) δ1.12-1.26 (m, 6H), 3.76 (s, 3H), 3.77-4.04 (m, 4H), 4.13-4.19 (m, 1H), 6.82-6.85 (m, 2H), 7.30-7.34 (m, 2H); LC-MS: (M+H)⁺ 274.

Diethyl (4-hydroxy-2-(1H-pyrazol-1-yl)pyrimidine-5-carboxamido)(4-methoxyphenyl)methylphosphonate (10-1)

Compound 10-1 was prepared from compound 10-b and compound 8-b in a similar manner as the synthesis of compound 8-1. $^1$H NMR (300 MHz, DMSO-d$_6$) δ1.09-1.20 (m, 6H), 3.73 (s, 3H), 3.84-4.04 (m, 4H), 5.44-5.54 (m, 1H), 6.71-6.73 (m, 1H), 6.92-6.94 (m, 2H), 7.30-7.33 (m, 2H), 8.06 (s, 1H), 8.41 (brs, 1H), 8.60-8.61 (m, 1H). LC-MS: (M+H)⁺ 462.

Example 11

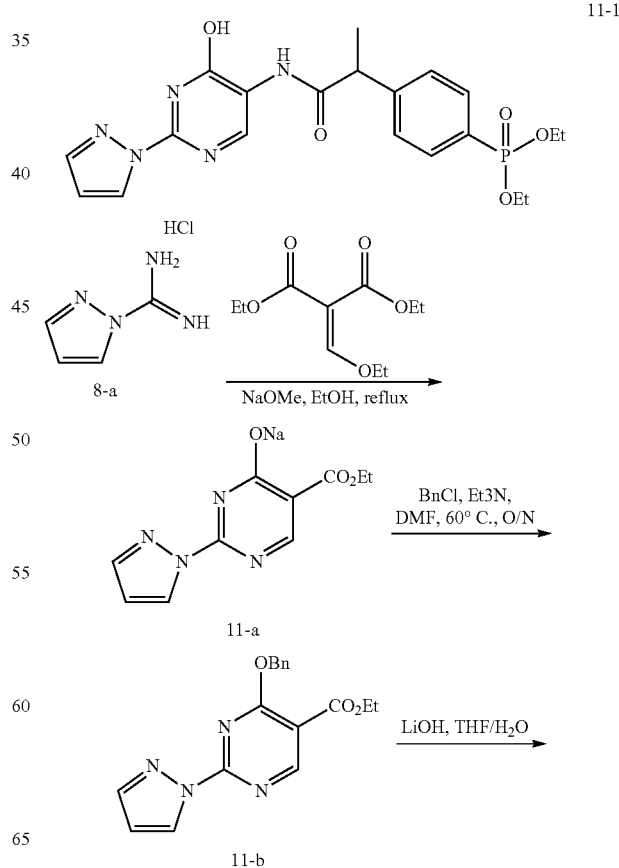

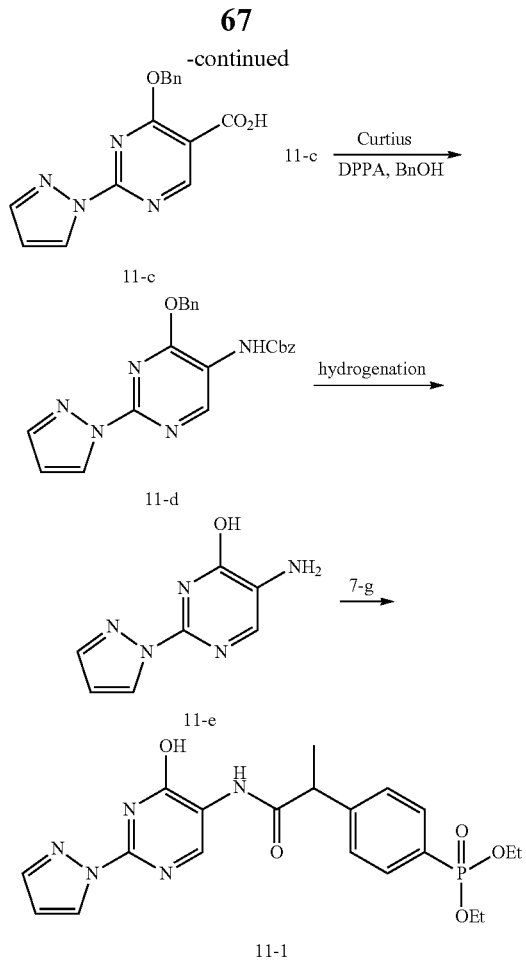

Step A: Ethyl 4-hydroxy-2-(1H-pyrazol-1-yl)pyrimidine-5-carboxylate sodium salt (11-a)

1H-pyrazole-1-carboximidamide hydrochloride, 8-a, (22.11 g, 0.15 mol) in EtOH (250 ml) was added sodium methoxide (12.3 g, 0.23 mol) and diethyl ethoxymethylenemalonate (30 ml, 0.15 mol). The reaction was heated for about 40 min at 75° C. and then cooled to room temperature. The mixture was filtered and the solid was washed with ethanol and ether and dried under vacuum to the product, 11-a, (21 g, 60%). $^1$H NMR (DMSO-d6, 300 MHz,): δ 8.50 (m, 2H), 7.70 (s, 1H), 6.47 (m, 1H), 4.13 (m, 2H), 1.24 (m, 3H).

Step B: Ethyl 4-(benzyloxy)-2-(1H-pyrazol-1-yl) pyrimidine-5-carboxylate (11-b)

To a solution of ethyl 4-hydroxy-2-(1H-pyrazol-1-yl)pyrimidine-5-carboxylate, 11-a, (0.62 g, 2.7 mmol) in DMF (7 ml) were added benzyl chloride (0.5 g, 3.99 mmol) and Et$_3$N (0.8 g, 7.97 mmol). The resulting mixture was then heated at 60° C. for 12 hours. Then it was cooled to room temperature and diluted with water followed by extraction with ethyl acetate. The organic layer was washed with brine, dried over sodium sulfate and concentrated under vacuum. The residue was purified on silica gel column with the eluent of ethyl acetate/petroleum ether=1/1 (Rf=0.7) to afford the product, 11-b, (0.36 g, 42%).

Step C: 4-(benzyloxy)-2-(1H-pyrazol-1-yl)pyrimidine-5-carboxylic acid (11-c)

Ethyl 4-(benzyloxy)-2-(1H-pyrazol-1-yl)pyrimidine-5-carboxylate, 11-b, (150 g, 0.46 mol) in THF (1.5 L) was treated with LiOH monohydrate (58 g, 1.39 mol) in water (60 ml) at room temperature for 3 hours. The mixture was concentrated under vacuum and diluted with water (200 ml) followed by extraction with ethyl acetate. The aqueous layer was acidified to pH=2 with 10% HCl and solid crashed out from the solution which was then filtered and washed with water to afford the product, 11-c, (40 g, 29%).

Step D: benzyl 4-(benzyloxy)-2-(1H-pyrazol-1-yl) pyrimidin-5-ylcarbamate (11-d)

To a solution of 4-(benzyloxy)-2-(1H-pyrazol-1-yl)pyrimidine-5-carboxylic acid, 11-c, (2 g, 6.76 mmol) in dry THF (40 ml) and toluene (40 ml) were added Et$_3$N (2.04 g, 20.3 mmol), DPPA (2.04 g, 7.43 mmol) and benzyl alcohol (1.1 g, 10.1 mmol). The resulting mixture was heated at 60° C. for 12 hours. The mixture was concentrated under vacuum and the residue was purified on silica gel column with the eluent of ethyl acetate/petroleum ether=1/5 (Rf=0.6) to provide the product, 11-d, (1.96 g, 72.6%). $^1$H NMR (DMSO-d$_6$, 300 MHz,): δ 9.39 (br, 1H), 8.73 (s, 1H), 8.62 (s, 1H), 7.83 (s, 1H), 7.56 (m, 2H), 7.33 (m, 8H), 6.57 (m, 1H), 5.58 (s, 2H), 5.16 (s, 2H).

Step E: 5-amino-2-(1H-pyrazol-1-yl)pyrimidin-4-ol (11-e)

Benzyl 4-(benzyloxy)-2-(1H-pyrazol-1-yl)pyrimidin-5-ylcarbamate, 11-d, (1.96 g, 4.9 mmol) was hydrogenated with hydrogen ballon in THF (20 ml) and Pd/C (200 mg) at room temperature for 12 hours. The mixture was filtered through a celite pad and the filtrate was concentrated under vacuum to provide the product, 11-e, (0.8 g, 93%). 1H NMR (DMSO-d$_6$, 300 MHz,): δ 8.39 (s, 1H), 7.80 (s, 1H), 7.20 (s, 1H), 6.56 (m, 1H), 5.00 (br, 2H).

Step F: Diethyl 4-(1-(4-hydroxy-2-(1H-pyrazol-1-yl) pyrimidin-5-ylamino)-1-oxopropan-2-yl)phenylphosphonate (11-1)

To a solution of compound, 7-g, (837 mg, 2.93 mmol), HATU (1.39 g, 3.66 mmol) and triethylamine (740 mg, 7.31 mmol) in CH$_3$CN (25 mL) was added 5-amino-2-(1H-pyrazol-1-yl)pyrimidin-4-ol (11-e, 432 mg, 2.43 mmol). The mixture was stirred at room temperature overnight and concentrated. The residue was taken up in EA and water. The aqueous layers were extracted with EA. Combined layers were washed with brine, dried over Na$_2$SO$_4$, and concentrated to give the crude product which was purified by pre-HPLC, 11-1, (200 mg, 19%). $^1$H NMR (300 MHz, DMSO-d$_6$) δ1.19-1.24 (m, 6H), 1.40 (d, J=7.2 Hz, 3H), 3.93-4.03 (m, 4H), 4.35 (q, J=7.2 Hz, 1H), 6.93-6.64 (m, 1H), 7.53-7.57 (m, 2H), 7.63-7.70 (m, 2H), 7.95 (s, 1H), 8.50-8.51 (m, 1H), 8.59-8.60 (m, 1H), 9.59 (s, 1H). LC-MS (M+H)$^+$ 446.

Example 12

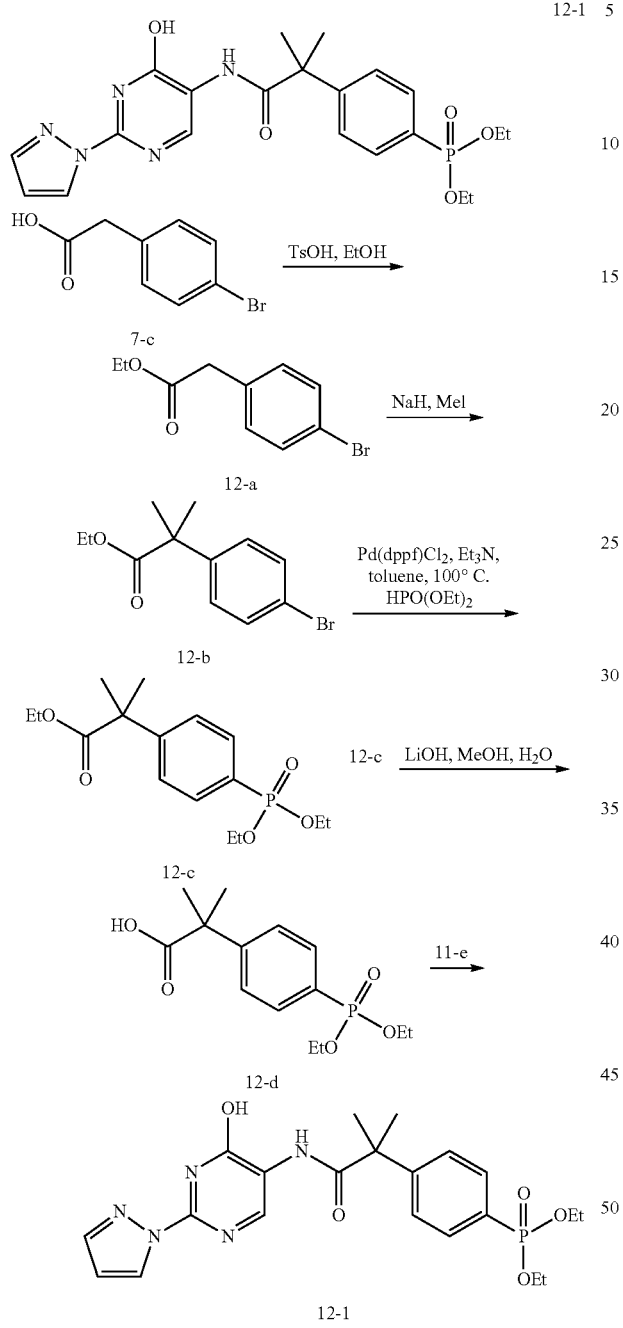

Step A: Ethyl 2-(4-bromophenyl)acetate (12-a)

4-Bromophenylacetic acid, 7-c, (30 g, 0.14 mol) was dissolved in ethanol (150 mL) at reflux along with p-toluenesulphonic acid (2.4 g, 0.014 mol). The reaction mixture was then stirred overnight. The ethanol was the removed in vacuo and the residue was taken up in EA. Combined organic layers were washed with water and the aqueous layer was re-extracted with EA. Combined organic layers were then dried over $Na_2SO_4$ and concentrated to afford the titled compound, 12-a, (25 g, 74%). $^1$H NMR (300 MHz, $CDCl_3$) δ 1.23-1.29 (m, 3H), 3.56 (s, 2H), 4.11-4.18 (m, 2H), 7.16 (d, J=8.1 Hz, 2H), 7.44 (d, J=8.1 Hz, 2H). LC-MS (M+H)$^+$ 243, 245.

Step B: Ethyl 2-(4-bromophenyl)-2-methylpropanoate (12-b)

To a mixture of NaH (0.96 g, 40 mmol) in THF (30 mL) was added compound, 12-a, (2.43 g, 10 mmol) in THF (10 mL) at 0° C. under a nitrogen atmosphere. After stirring for 1 h, iodomethane (1.6 g, 4.0 mmol) was added dropwise. The resulting mixture was stirred at room temperature overnight. The solvent was removed in vacuo and the residue was dissolved with EA, filtrated and the filtration was concentrated to afford the crude product which was purified by column chromatography to give the title compound, 12-b, (1.92 g, 71%). $^1$H NMR (300 MHz, $CDCl_3$) δ1.16-1.20 (m, 3H), 1.55 (s, 6H), 4.10-4.12 (m, 2H), 7.20-7.23 (m, 2H), 7.42-7.45 (m, 2H). LC-MS (M+H)$^+$ 271, 273.

Step C: Ethyl 2-(4-(diethoxyphosphoryl)phenyl)-2-methylpropanoated (12-c)

Compound 12-c was prepared from 12-b in a similar manner as the synthesis of 7-f. $^1$H NMR (300 MHz, $CDCl_3$) δ1.16-1.21 (m, 3H), 1.30-1.39 (m, 6H), 1.58 (s, 6H), 4.09-4.18 (m, 6H), 7.40-7.44 (m, 2H), 7.72-7.79 (m, 2H). LC-MS (M+H)$^+$ 329.

Step D: 2-(4-(diethoxyphosphoryl)phenyl)-2-methylpropanoic acid (12-d)

Compound 12-d was prepared from 12-c in a similar manner as the synthesis of 7-g. $^1$H NMR (300 MHz, $CDCl_3$) δ1.27-1.35 (m, 6H), 1.60 (s, 6H), 4.11-4.15 (m, 4H), 7.44-7.47 (m, 2H), 7.69-7.76 (m, 2H), 10.61 (br s, 1H); LC-MS (M+H)$^+$ 301.

Step E: Diethyl 4-(1-(4-hydroxy-2-(1H-pyrazol-1-yl)pyrimidin-5-ylamino)-2-methyl-1-oxopropan-2-yl)phenylphosphonate (12-1)

Compound 12-1 was prepared from 12-d and 11-e in a similar manner as the synthesis of 7-1. $^1$H NMR (300 MHz, DMSO-$d_6$) δ1.20-1.25 (m, 6H), 1.60 (s, 6H), 3.98-4.02 (m, 4H), 6.65 (s, 1H), 7.56-7.60 (m, 2H), 7.67-7.74 (m, 2H), 7.97 (s, 1H), 8.09 (s, 1H), 8.46-8.52 (s, 2H); LC-MS (M+H)$^+$ 460.

Example 13

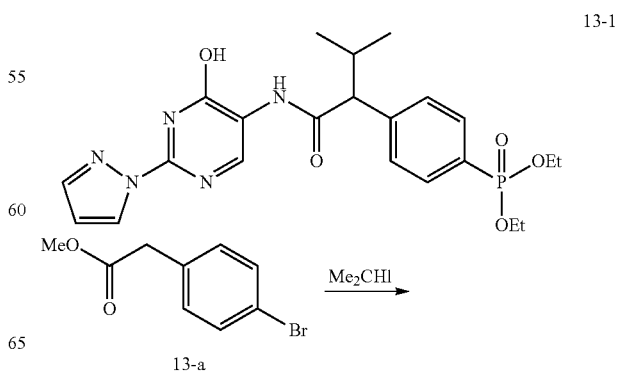

71

-continued

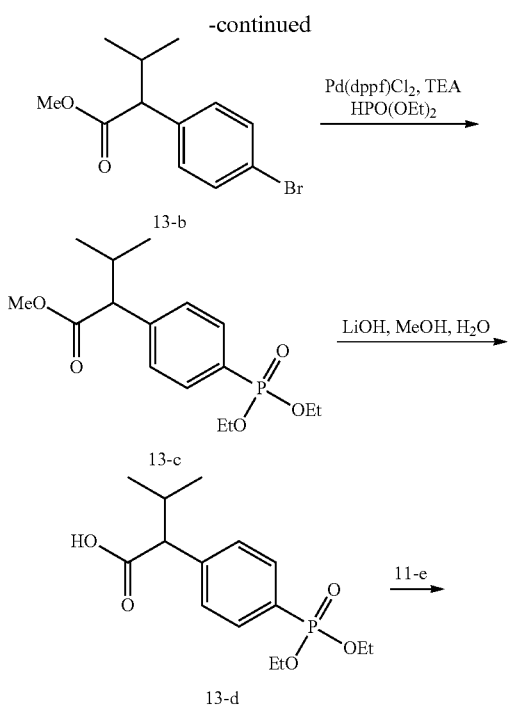

Step C: 2-(4-(diethoxyphosphoryl)phenyl)-3-methylbutanoic acid (13-d)

Compound 13-d was prepared from 13-c in a similar manner as the synthesis of 7-g. $^1$H NMR (300 MHz, CDCl$_3$) δ0.70 (d, J=6.6 Hz, 3H), 1.10 (d, J=6.6 Hz, 3H), 1.27-1.34 (m, 6H), 2.31-2.39 (m, 1H), 3.20 (d, J=10.5 Hz, 1H), 4.08-4.19 (m, 4H), 7.41-7.44 (m, 2H), 7.68-7.75 (m, 2H). LC-MS: (M+H)$^+$ 315.

Step D: Diethyl 4-(1-(4-hydroxy-2-(1H-pyrazol-1-yl)pyrimidin-5-ylamino)-3-methyl-1-oxobutan-2-yl)phenylphosphonate (13-1)

Compound 13-1 was prepared from 13-d and 11-e in a similar manner as the synthesis of 7-1. $^1$H NMR (300 MHz, DMSO-d$_6$) δ0.61 (d, J=6.9 Hz, 3H), 0.97 (d, J=6.9 Hz, 3H), 1.17-1.22 (m, 6H), 2.06 (s, 1H), 2.28-2.31 (m, 1H), 43.87-4.02 (m, 4H), 6.63 (s, 1H), 7.54-7.69 (m, 4H), 7.95 (s, 1H), 8.50 (s, 1H), 8.61 (br s, 1H), 9.65 (s, 1H). LC-MS: (M+H)$^+$ 474.

Example 14

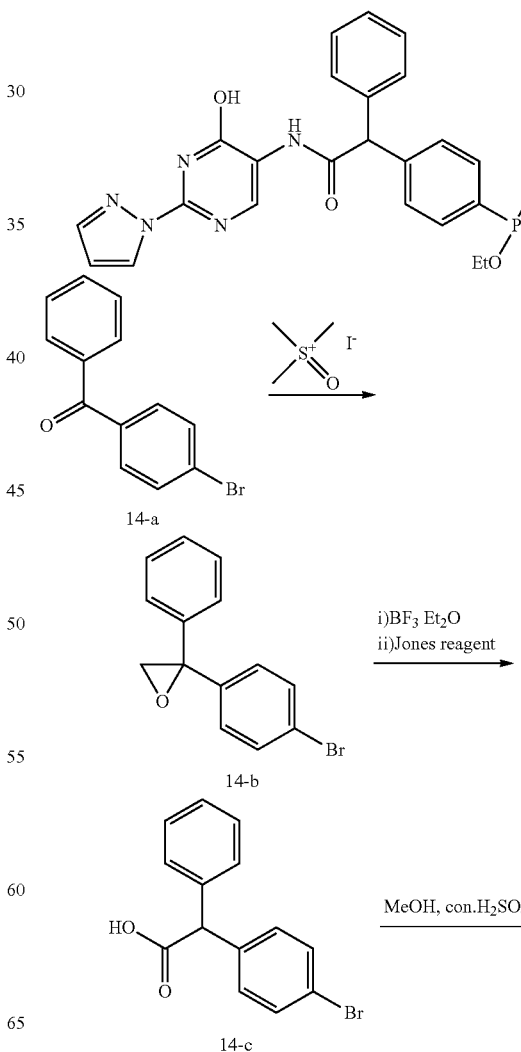

Step A: Methyl 2-(4-bromophenyl)-3-methylbutanoate (13-b)

To a solution of methyl 2-(4-bromophenyl)acetate, 13-a, (2.29 g, 10 mmol) in DMF (40 ml) was added dropwise a mixture of t-BuOK (1.12 g, 10 mmol) in DMF (20 mL) with stirring at 0° C. under a nitrogen atmosphere. After stirring at 0° C. for 30 min, 2-iodopropane (1.70 g, 10 mmol) was added dropwise. Then the resulting solution was stirred overnight and ice-water was added. The aqueous layer was extracted by EA. The combined organic layers were washed by brine, dried over Na$_2$SO$_4$ and concentrated. The crude product was purified by column chromatography to afford the title compound, 13-b, (1.3 g, 48%). $^1$H NMR (300 MHz, CDCl$_3$) δ 0.70-0.72 (m, 3H), 1.02-1.04 (m, 3H), 2.27-2.32 (m, 1H), 3.10-3.14 (m, 1H), 3.65 (s, 3H), 7.19-7.24 (m, 2H), 7.42-7.45 (m, 2H). LC-MS: (M+H)$^+$ 254, 256.

Step B: Methyl 2-(4-(diethoxyphosphoryl)phenyl)-3-methylbutanoate (13-c)

Compound 13-c was prepared from 13-b in a similar manner as the synthesis of 7-f. $^1$H NMR (300 MHz, CDCl$_3$) δ0.69 (d, J=6.6 Hz, 3H), 1.04 (d, J=6.6 Hz, 3H), 1.20-1.39 (m, 6H), 2.31-2.39 (m, 1H), 3.17-3.23 (m, 1H), 4.04-4.20 (m, 4H), 7.42-7.45 (m, 2H), 7.71-7.78 (m, 2H). LC-MS: (M+H)$^+$ 329.

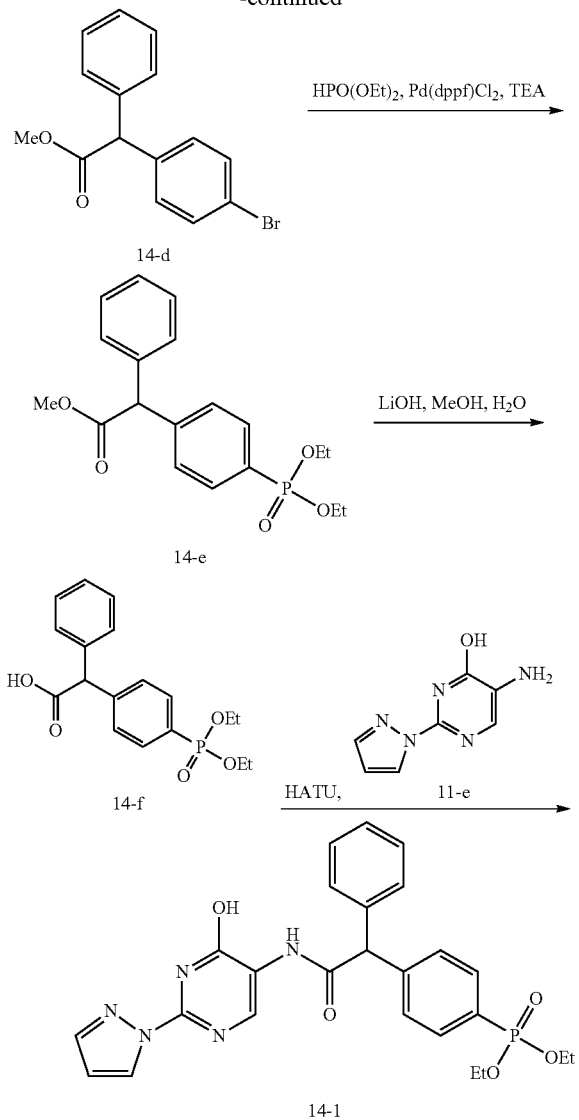

Step A: 2-(4-Bromophenyl)-2-phenyloxirane (14-b)

A slurry of sodium hydride (5.0 g, 125 mmol) and trimethylsulfoxonium iodide (27.5 g, 125 mmol) in THF (50 mL) was stirred overnight under a nitrogen atmosphere at 55° C. Then 4-bromobenzophene, 14-a, (26.11 g, 100 mmol) in THF (50 mL) was added. After being stirred at 55° C. for 16 h, the reaction mixture was quenched with water and extracted with ether and water. The organic layer was washed with brine, dried over sodium sulfate and concentrated to yield the desired compound, 14-b, (27.5 g, 99%). $^1$H NMR (300 MHz, CDCl$_3$): δ3.20-3.30 (m, 2H), 7.18-7.23 (m, 2H), 7.32-7.33 (m, 4H), 7.43-7.46 (m, 2H).

Step B: 2-(4-Bromophenyl)-2-phenylacetic acid (14-c)

To a solution of compound 2-(4-Bromophenyl)-2-phenyloxirane, 14-b, (27.5 g, 100 mmol) in dry toluene (160 mL) was added boron trifluoride etherate (15.3 mL, 121 mmol) at −10° C. Then the mixture was allowed to stir at room temperature for 30 min and stand for 10 min. The mixture was extracted twice with saturated aqueous sodium bicarbonate. Combined organic layers were washed with brine, dried over sodium sulfate and concentrated to afford a crude solid intermediate (30.0 g).

To a solution of the above solid intermediate in acetone (400 mL) was added dropwise Jones' reagent (2.67 M, 20.4 mL, 54.5 mmol) at −10° C. After stirring for 30 min, isopropyl alcohol was added dropwise until the solution turned right green. The chromium salts were removed by filtration through Cellite. The filtrate was concentrated and dissolved in 1:1 petroleum ether-ether solvent and made basic with NaOH and extracted with more petroleump ether. The aqueous layer was acidified and extracted with EA. Combined organic layers were washed with brine, dried over sodium sulfate and concentrated to yield the title compound, 14-c, (9.1 g, 31%). $^1$H NMR (300 MHz, CDCl$_3$): δ5.09 (s, 1H), 7.25-7.32 (m, 7H), 7.49-7.52 (m, 2H); LC-MS: (M+H)$^+$ 290, 292

Step C: Methyl 2-(4-bromophenyl)-2-phenylacetate (14-d)

To a solution of compound 2-(4-Bromophenyl)-2-phenylacetic acid, 14-c, (5.6 g, 19.3 mmol) in methanol (200 mL) was added concentrated sulfuric acid (6 mL) and the reaction mixture was stirred at 60° C. for 14 h. The resulting solution was concentrated and ice-water was added. The aqueous layer was extracted by EA. The combined organic layers were washed with brine, dried over sodium sulfate and concentrated to yield title compound, 14-d, (5.5 g, 93%). $^1$H NMR (300 MHz, CDCl$_3$) δ3.73 (s, 3H), 4.96 (s, 1H), 7.16 (d, J=8.4 Hz, 2H), 7.25-7.30 (m, 5H), 7.42 (d, J=8.4 Hz, 2H). LC-MS: (M+H)$^+$ 304, 306.

Step D: Diethyl 4-[(methoxycarbonyl)(phenyl)methyl]phenylphosphonate (14-e)

To a solution of compound Methyl 2-(4-bromophenyl)-2-phenylacetate, 14-d, (1.52 g, 5.0 mmol), diethylphosphite (2.42 g, 17.5 mmol) and triethylamine (3.13 g, 31 mmol) in toluene (20 mL) was added [1,1'-bis(diphenylphosphino)ferrocene]dicholoropalladium (100 mg). The mixture was allowed to stir overnight at 110° C. and filtrated. The solution was concentrated to afford the crude product which was purified by column chromatography to give compound 14-e as colorless oil (1.7 g, 94%). $^1$H NMR (300 MHz, CDCl$_3$) δ1.29-1.35 (m, 6H), 3.73 (s, 3H), 4.10-4.13 (m, 4H), 5.03 (s, 1H), 7.23-7.40 (m, 7H), 7.69-7.77 (m, 2H). LC-MS: (M+H)$^+$ 363.

Step E: 2-(4-(Diethoxyphosphoryl)phenyl)-2-phenylacetic acid (14-f)

A mixture of Diethyl 4-((methoxycarbonyl)(phenyl)methyl)phenylphosphonate, 14-e, (1.7 g, 5.0 mmol) and LiOH.H$_2$O (0.3 g, 7 mmol) in methanol (10 mL) and H$_2$O (10 mL) was stirred overnight. The resulting mixture was concentrated and extracted by EA. The aqueous layers were added HCl (1 M) until pH 1~2. The mixture was extracted by EA. Combined organic layers were washed with brine, dried over Na$_2$SO$_4$ and concentrated to afford the title compound, 14-f, as colorless oil (1.18 g, 72%). $^1$H NMR (300 MHz, CDCl$_3$) δ1.22-1.31 (m, 6H), 4.03-4.14 (m, 4H), 5.05 (s, 1H), 7.25-7.31 (m, 5H), 7.38-7.42 (m, 2H), 7.68-7.75 (m, 2H); LC-MS: (M+H)$^+$ 349.

Step F: Diethyl 4-(2-(4-hydroxy-2-(1H-pyrazol-1-yl)pyrimidin-5-ylamino)-2-oxo-1-phenylethyl)phenylphosphonate (14-1)

To a solution of 2-(4-(Diethoxyphosphoryl)phenyl)-2-phenylacetic acid, 14-f, (1.18 g, 3.4 mmol), HATU (1.86 g, 4.9 mmol) and triethylamine (989 mg, 9.8 mmol) in CH₃CN (20 mL) was added 5-amino-2-(1H-pyrazol-1-yl)pyrimidin-4-ol (11-e, 577 mg, 3.30 mmol). The mixture was stirred at room temperature overnight and concentrated. The residue was taken up in EA and water. The aqueous layer was extracted with EA. The combined layers were washed with brine, dried over Na₂SO₄, and concentrated to give the crude product of 14-1 which was purified by pre-HPLC (766 mg, 45%). ¹H NMR (300 MHz, DMSO-d₆) δ1.18-1.23 (m, 6H), 3.92-4.03 (m, 4H), 6.64 (s, 1H), 7.25-7.35 (m, 6H), 7.47-7.51 (m, 2H), 7.64-7.71 (m, 2H), 7.97 (s, 1H), 8.61-8.52 (m, 1H), 8.63 (br s, 1H); LC-MS: (M+H)⁺ 508.

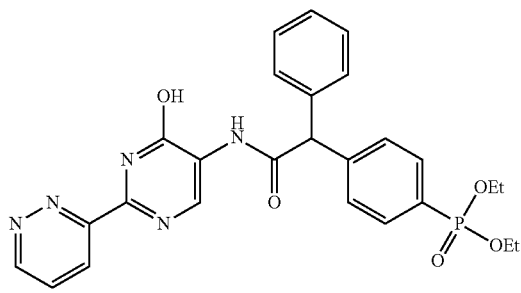

Diethyl 4-(2-(4-hydroxy-2-(pyridazin-3-yl)pyrimidin-5-ylamino)-2-oxo-1-phenylethyl)phenylphosphonate (14-2)

Compound 14-2 was prepared from 14-f and 36i-h in a similar manner as the synthesis of 14-1. ¹H NMR (300 MHz, DMSO) δ 1.19-1.24 (t, J=6.0 Hz, 6H), 3.99-4.03 (d, J=6.0 Hz, 4H), 5.45 (s, 1H), 7.29-7.66 (m, 10H), 8.98 (br s, 1H), 9.22 (s, 1H), LC-MS: (M+H)⁺ 520.2.

Example 15

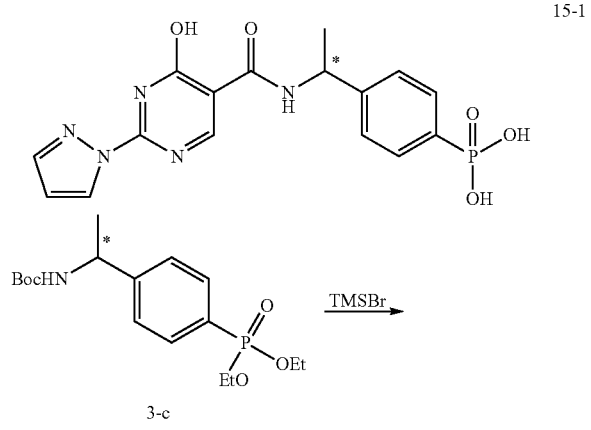

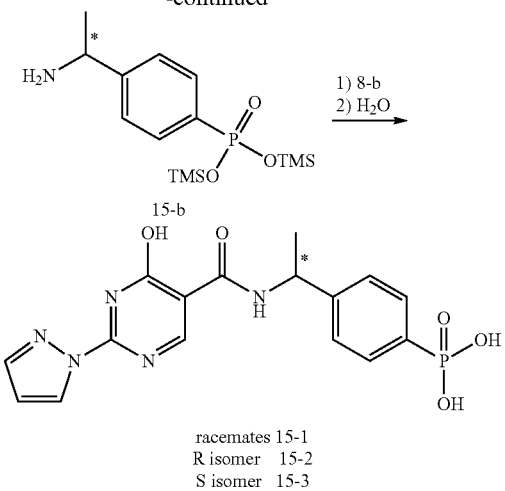

4-(1-(4-hydroxy-2-(1H-pyrazol-1-yl)pyrimidine-5-carboxamido)ethyl)phenylphosphonic acid (15-1)

To a solution of tert-butyl 1-(4-(diethoxyphosphoryl)phenyl)ethylcarbamate, 3-c, (1 g, 2.8 mmol) in DCM (30 ml) was added dropwise TMSBr (8.6 g, 56 mmol) at 0° C., the reaction mixture was stirred at room temperature for overnight. Then evaporated the solvent and added ether, and the solid was filtered to give the TMS intermediate, 15-b.

4-hydroxy-2-(1H-pyrazol-1-yl)pyrimidine-5-carboxylic acid, (8-b) (111 mg, 0.54 mmol) was dissolved in SOCl₂ (3 ml), the mixture was stirred at 50° C. for 3 hours, then concentrated under vacuo. The residue was dissolved with 5 ml DCM, and dropwise to a solution of the TMS intermediate (230 mg, 0.54 mmol) and Et₃N (218.6 mg, 2.16 mmol) in DCM (10 ml) at 0° C., the mixture was stirred at room temperature for overnight. Then added water, the water phase was concentrated under vacuo and purified by Prep-HPLC to give the product, 15-1. ¹H NMR (DMSO-d₆, 300 MHz,): δ 9.88 (s, 1H), 8.63 (s, 1H), 8.42 (s, 1H), 8.06 (s, 1H), 7.41-7.70 (m, 4H), 6.71 (s, 1H), 5.13 (t, 1H), 1.43 (d, 3H). (M+H)⁺=390.

(R)-4-(1-(4-hydroxy-2-(1H-pyrazol-1-yl)pyrimidine-5-carboxamido)ethyl)phenyl phosphonic acid (15-2)

To a solution of (R)-diethyl 4-(1-aminoethyl)phenylphosphonate (3-e, 300 mg, 1.17 mmol) in DCM (10 ml) was added dropwise TMSBr (2.7 g, 17.51 mmol) at 0° C., the reaction mixture was stirred at room temperature for overnight. Then evaporated the solvent and added ether, and the solid was filtered to give the TMS intermediate.

4-hydroxy-2-(1H-pyrazol-1-yl)pyrimidine-5-carboxylic acid (8-b, 300 mg, 1.46 mmol) was dissolved in SOCl₂ (7 ml), the mixture was stirred at 50° C. for 3 hours, then concentrated under vacuo. The residue was dissolved with 5 ml DCM, and dropwise to a solution of the above TMS intermediate (502 mg, 1.46 mmol) and Et₃N (295 mg, 2.92 mmol) in DCM (10 ml) at 0° C., the mixture was stirred at room temperature for overnight. Then added water, the water phase was concentrated under vacuo and purified by Prep-HPLC to provide the product, 15-2 (70 mg). 1H NMR (DMSO-d₆, 300 MHz,): δ 9.81 (s, 1H), 8.62-8.63 (m, 1H), 8.40-8.41 (m, 1H), 8.06 (s, 1H), 7.60-7.67 (m, 2H), 7.42-7.44 (m, 2H), 6.71-6.72 (m, 1H), 5.10-5.15 (m, 1H), 1.47-1.50 (m, 3H). (M+H)⁺=390.2.

(S)-4-(1-(4-hydroxy-2-(1H-pyrazol-1-yl)pyrimidine-5-carboxamido)ethyl)phenylphosphonic acid (15-3)

To a solution of (S)-diethyl 4-(1-aminoethyl)phenylphosphonate (3-f, 300 mg, 1.17 mmol) in DCM (10 ml) was added dropwise TMSBr (2.7 g, 17.51 mmol) at 0° C., the reaction mixture was stirred at room temperature for overnight. Then evaporated the solvent and added ether, and the solid was filtered to give the TMS intermediate.

4-hydroxy-2-(1H-pyrazol-1-yl)pyrimidine-5-carboxylic acid (8-b, 300 mg, 1.46 mmol) was dissolved in SOCl$_2$ (7 ml), the mixture was stirred at 50° C. for 3 hours, then concentrated under vacuo. The residue was dissolved with 5 ml DCM, and added dropwise to a solution of the above TMS intermediate (502 mg, 1.46 mmol) and Et$_3$N (295 mg, 2.92 mmol) in DCM (10 ml) at 0° C., the mixture was stirred at room temperature for overnight. Water was then added to the reaction mixture. The water phase was concentrated under vacuo and purified by Prep-HPLC to provide the product, 15-3 (20 mg). $^1$H NMR (DMSO-d$_6$, 300 MHz,): δ 9.76 (m, 1H), 8.61-8.62 (m, 1H), 8.39-8.43 (m, 1H), 8.06 (s, 1H), 7.60-7.67 (m, 2H), 7.41-7.44 (m, 2H), 6.71-6.72 (m, 1H), 5.10-5.15 (m, 1H), 1.47-1.50 (m, 3H). (M+H)$^+$=390.2.

Example 16

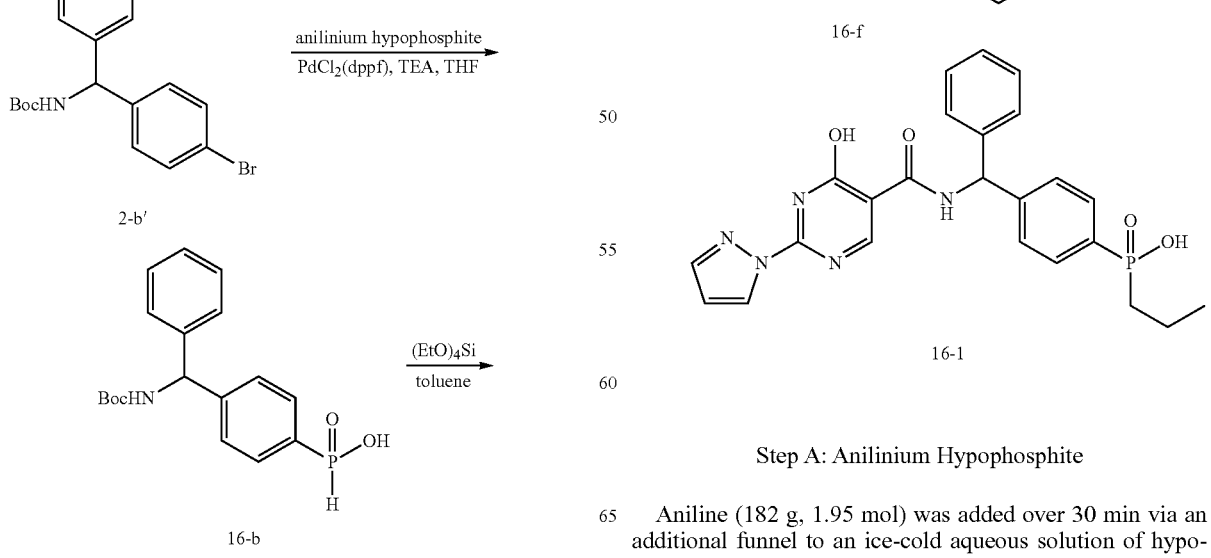

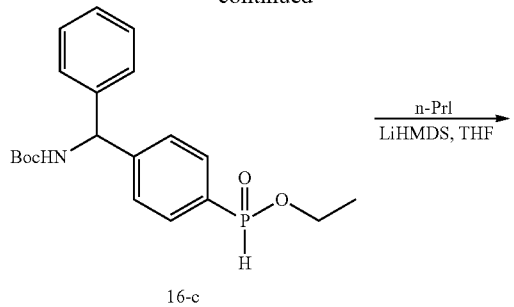

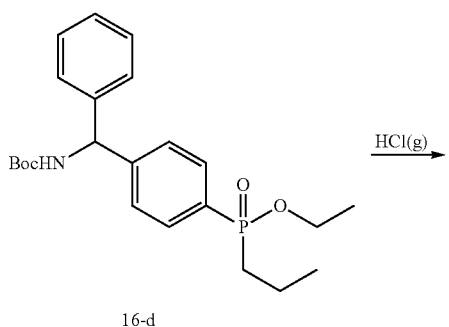

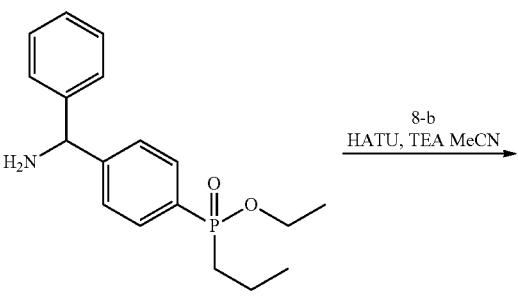

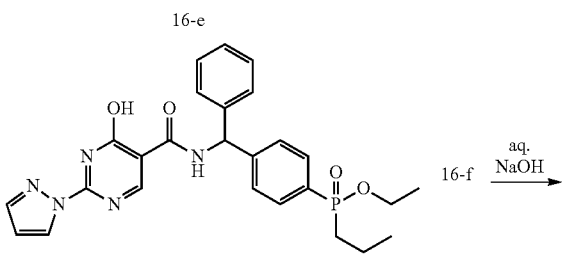

Step A: Anilinium Hypophosphite

Aniline (182 g, 1.95 mol) was added over 30 min via an additional funnel to an ice-cold aqueous solution of hypophosphorus acid (50% wt, 258 g, 1.95 mol). The light brown solution turned into thick slurry. Acetone (500 ml) was added and the resulting mixture was stirred for 5 min before filtration. The solid was washed with acetone to provide the product anilinium hypophosphite (134 g, 43%).

Step B: 4-((tert-butoxycarbonylamino)(phenyl)methyl)phenylphosphinic acid (16-b)

To a solution of tert-butyl(4-bromophenyl)(phenyl)methylcarbamate (2-b', 10 g, 27.7 mmol) in dry THF (150 ml) was added anilinium hypophosphite (8.8 g, 55.4 mmol), $PdCl_2$ (dppf) (2.58 g, 2.77 mmol) and $Et_3N$ (8.4 g, 3 eq), and with nitrogen protected, the mixture was refluxed for 3-4 h. Filtered and evaporated THF and the residue was diluted with water (200 ml), washed with $Et_2O$ (50 ml×3) and the aqueous phase was acidified with aqueous $KHSO_4$ (1M. saturated with NaCl). The resulting aqueous phase was extracted with ethyl acetate (200 ml×3), and the organic layer was dried and concentrated under vacuo to give the title compound, 16-b (7.0 g, 73%).

Step C: Tert-butyl (4-(ethoxyhydrophosphoryl)phenyl)phenyl)methylcarbamate (16-c)

To a solution of 4-((tert-butoxycarbonylamino)(phenyl)methyl)phenylphosphinic acid, 16-b, (2.2 g, 6.3 mmol) in dry toluene (150 ml) was added $(EtO)_4Si$ (1.58 g, 7.6 mmol). The mixture was refluxed overnight. The toluene was evaporated and the residue was purified by silica gel (petroleum:ethyl acetate=1:1) to afford the title compound, 16-c, (1.5 g, 64%).

Step D: Tert-butyl (4-(ethoxy(propyl)phosphoryl)phenyl)(phenyl)methylcarbamate (16-d)

To a solution of tert-butyl (4(ethoxyhydrophosphoryl)phenyl)(phenyl)-methylcarbamate, 16-c, (1.6 g, 4.3 mmol) in dry THF (20 ml) was added dropwise LiHMDS (9.4 g, 9.4 mmol) at −78° C. with $N_2$ protection. After 10 mins, 1-iodopropane (0.87 g, 5.1 mmol) was added dropwise. After addition, the mixture was allowed to warm to room temperature and stirred for 2 hours. The mixture was then diluted with brine and THF, and the organic layer was separated and dried. The organic layer was concentrated under vacuo to give the title compound, 16-d, which was used in the next step without further purification.

Step E: Ethyl 4-(amino(phenyl)methyl)phenyl(propyl)phosphinate (16-e)

Tert-butyl (4-(ethoxy(propyl)phosphoryl)phenyl)(phenyl) methylcarbamate, 16-d, (1.8 g) was added to HCl (g) in dioxane (20 ml). The resulting mixture was stirred at rt for 3-5 hours. Evaporated the solvent and water was added (20 ml), extracted with ethyl acetate (20 ml) and the separated aqueous phase was adjusted to pH=12-13 with 1N NaOH. The resulting aqueous solution was then extracted whit ethyl acetate (30 ml×3). The organic layer was dried and concentrated under vacuo to give the title compound, 16-e, (810 mg, 59%).

Step F: Ethyl 4-((4-hydroxy-2-(1H-pyrazol-1-yl)pyrimidine-5-carboxamido)(phenyl)methyl)phenyl(propyl)phosphinate (16-f)

To a solution of 4-hydroxy-2-(1H-pyrazol-1-yl)pyrimidine-5-carboxylic acid (8-b, 526 mg, 2.56 mmol) in MeCN (10 ml) was added $Et_3N$ (645 mg, 6.39 mmol), then added HATU (1068 mg, 2.81 mmol). After 5 mins, ethyl 4-(amino (phenyl)methyl)phenyl(propyl)phosphinate, 16-e, (810 mg, 2.56 mmol) was added and the resulting mixture was stirred at rt for 2 hours. The mixture was then evaporated and the residue was diluted with ethyl acetate followed by washing with brine. The organic layer was dried and concentrated under vacuo to give the title compound, 16-f, (crude product, 2.1 g).

Step G: 4-((4-hydroxy-2-(1H-pyrazol-1-yl)pyrimidine-5-carboxamido)(phenyl)methyl)phenyl(propyl) phosphinic acid (16-1)

To a solution of ethyl 4-((4-hydroxy-2-(1H-pyrazol-1-yl) pyrimidine-5-carboxamido)(phenyl)methyl)phenyl(propyl) phosphinate, 16-f, (2.1 g, 4.16 mmol) in dioxane (30 ml) was added 2N NaOH (0.83 g, 20.8 mmol). The mixture was stirred at 85° C. for 6-8 hours, then evaporated the solvent and the residue was added water (20 ml) and extracted with ethyl acetate (30 ml) twice. The aqueous phase was adjusted to pH=1~2 with conc. HCl, then filtered, and the filtered solid was washed with water, dried to give the title compound, 16-1, (crude product), which was further purified by prep_H-PLC to give pure 16-1 (400 mg). $^1H$ NMR (300 MHz, DMSO-$d_6$): δ 10.38 (s, 1H), 8.61 (d, 1H), 8.42 (s, 1H), 8.06 (s, 1H), 7.34 (m, 9H), 6.72 (s, 1H), 6.32 (d, 1H), 1.75 (m, 2H), 1.41 (m, 2H), 0.95 (t, 3H). $(M+H)^+=478.2$.

Example 17

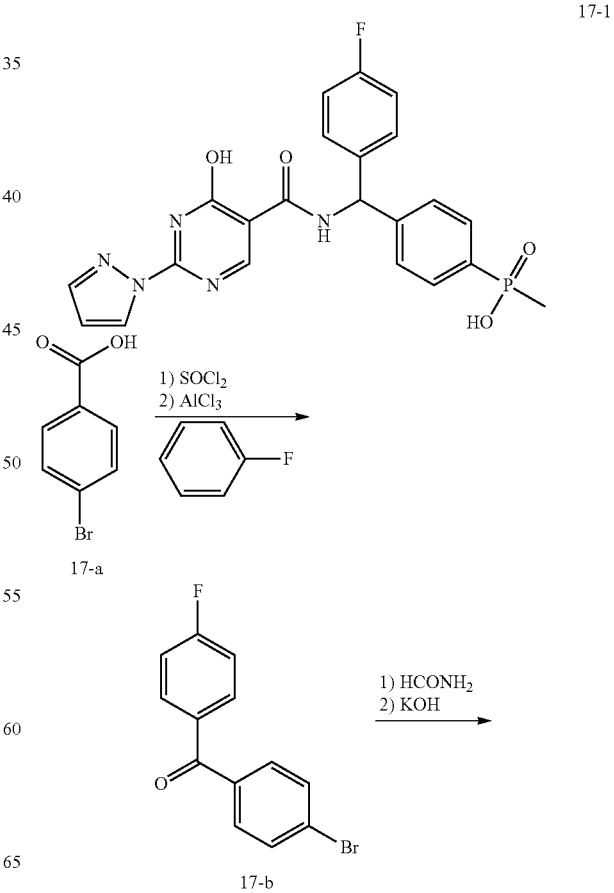

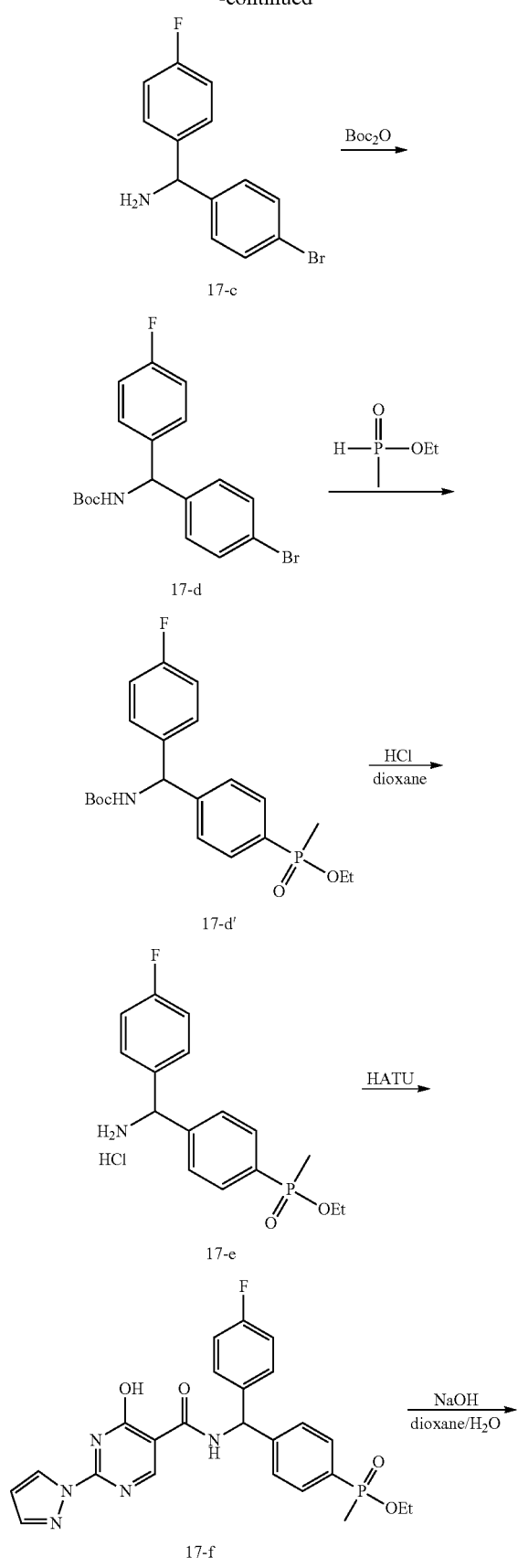

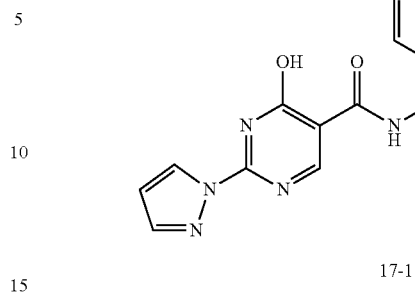

Step A: (4-bromophenyl)(4-fluorophenyl)methanone (17-b)

4-bromobenzoic acid (17-a, 10 g, 0.05 mol) was dissolved in $SOCl_2$ (100 ml) and the resulting mixture was stirred at rt for 3 hours, then concentrated under vacuum. The residue was dissolved in 1-fluorobenzene (24 g, 0.25 mol) and $AlCl_3$ (8.24 g, 0.06 mol) was added portion-wise with stirring under $N_2$. The resulting reaction mixture was refluxed overnight. The reaction mixture was cooled to temperature and poured into 20% HCl (1500 ml), stirred for 1 h, and the layers were separated. The aqueous layer was further extracted with DCM (2×50 ml). The combined organic layer was washed with water, brine, dried ($Na_2SO_4$), filtered and concentrated under reduced pressure. The residue was washed with hexane to afford the product, 17-b, (12.2 g, 85%).

Step B: (4-bromophenyl)(4-fluorophenyl)methanamine (17-c)

(4-bromophenyl)(4-fluorophenyl)methanone (17-b, 1 g, 39.6 mmol) was heated with formamide (50 ml) for 24 hours at 185° C., and the mixture was cooled to room temperature before poured into water. The product was filtered off and washed with water to provide the product (10 g, 82%). The above formyl derivative (4.5 g, 15 mmol) was heated with potassium hydroxide (41 g, 73 mol) in methanol (100 mL) overnight. The mixture was concentrated under vacuum and the residue was diluted with water followed by extraction of ethyl acetate. The organic layer was dried over sodium sulfate and concentrated to provide the product, 17-c, (3.3 g, 80%).

Step C: tert-butyl (4-bromophenyl)(4-fluorophenyl)methylcarbamate (17-d)

(4-bromophenyl)(4-fluorophenyl)methanamine (17-c, 3 g, 10.8 mmol) in DCM (30 mL) was added TEA (3.2 g, 32.2 mmol) and the mixture was cooled to 0° C. $Boc_2O$ (2.8 g, 12.9 mmol) was added at this temperature. Then the resulting mixture was stirred at room temperature overnight. The mixture was concentrated under vacuum and the residue was washed with hexane to provide the product, 17-d (3.7 g, 92%).

Step D: ethyl 4-(amino(4-fluorophenyl)methyl)phenyl(methyl)phosphinate hydrochloride (17-e)

To tert-butyl(4-bromophenyl)(4-fluorophenyl)methylcarbamate (17-d, 500 mg, 0.128 mol), ethyl methylphosphite (21.1 g, 0.153 mol) and Et₃N (38.8 g, 0.384 mol) in THF (1 L) was added PdCl₂(dppf) (5 g). The mixture was allowed to stir overnight at reflux. The mixture was filtered and the filtrate was concentrated under vacuum. The residue was purified over silica gel (petroleum ether/ethyl acetate=10/1) to provide compound 17-d' (417 mg, 78%).

A solution of compound 17-d' (417 mg, 1.02 mmol) in HCl/dioxane (10 ml) was stirred at room temperature overnight. Then it was concentrated under vacuum to provide the product, 17-e, (300 mg, 95%).

Step E: ethyl 4-((4-fluorophenyl)(4-hydroxy-2-(1H-pyrazol-1-yl)pyrimidine-5-carboxamido)methyl)phenyl(methyl)phosphinate (17-f)

To a stirred solution of 4-hydroxy-2-(1H-pyrazol-1-yl)pyrimidine-5-carboxylic acid, 8-b, (275 mg, 1.33 mmol) and Et₃N (404 mg, 4 mmol) in MeCN (6 ml) was added HATU (558 mg, 1.47 mmol). The mixture was stirred for 5 min at room temperature and then compound 17-e (450 mg, 1.47 mmol) was added. The resulting mixture was stirred at room temperature for 1 hour. Then the mixture was concentrated under vacuum and the residue was taken into ethyl acetate followed by washing with 1N HCl. The organic layer was dried over sodium sulfate and concentrated under vacuum. The residue was purified on silica gel chromatography (CH₂Cl₂:CH₃OH=50/1) to provide the product, 17-f, (180 mg, 27%).

Step F: 4-((4-fluorophenyl)(4-hydroxy-2-(1H-pyrazol-1-yl)pyrimidine-5-carboxamido)methyl)phenyl(methyl)phosphinic acid (17-1)

Ethyl 4-((4-fluorophenyl)(4-hydroxy-2-(1H-pyrazol-1-yl)pyrimidine-5-carboxamido)methyl)phenyl(methyl)phosphinate, 17-f, (2 g, 4.03 mmol) was dissolved in 20 ml of dioxane and treated with 10 ml of 3N NaOH. The mixture was heated at 80° C. for one hour. Then the mixture was concentrated under vacuum and the residue was diluted with water and washed with ethyl acetate. The aqueous layer was acidified with conc. HCl to pH=1 and the expected product crashed out (1.7 g of crude). The product can be further purified via prep-HPLC give the title product, 17-1, (1.4 g, 75%). ¹H NMR (300 MHz, CD₃OD): δ 8.66 (s, 1H), 8.59 (s, 1H), 7.93 (s, 1H), 7.81 (m, 2H), 7.50 (m, 2H), 7.36 (m, 2H), 7.10 (m, 2H), 6.66 (s, 1H), 6.38 (s, 1H), 1.66 (d, 3H). (M+H)⁺=468.0.

Example 18

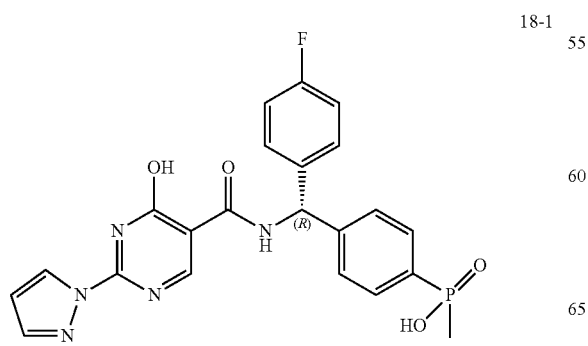

18-1

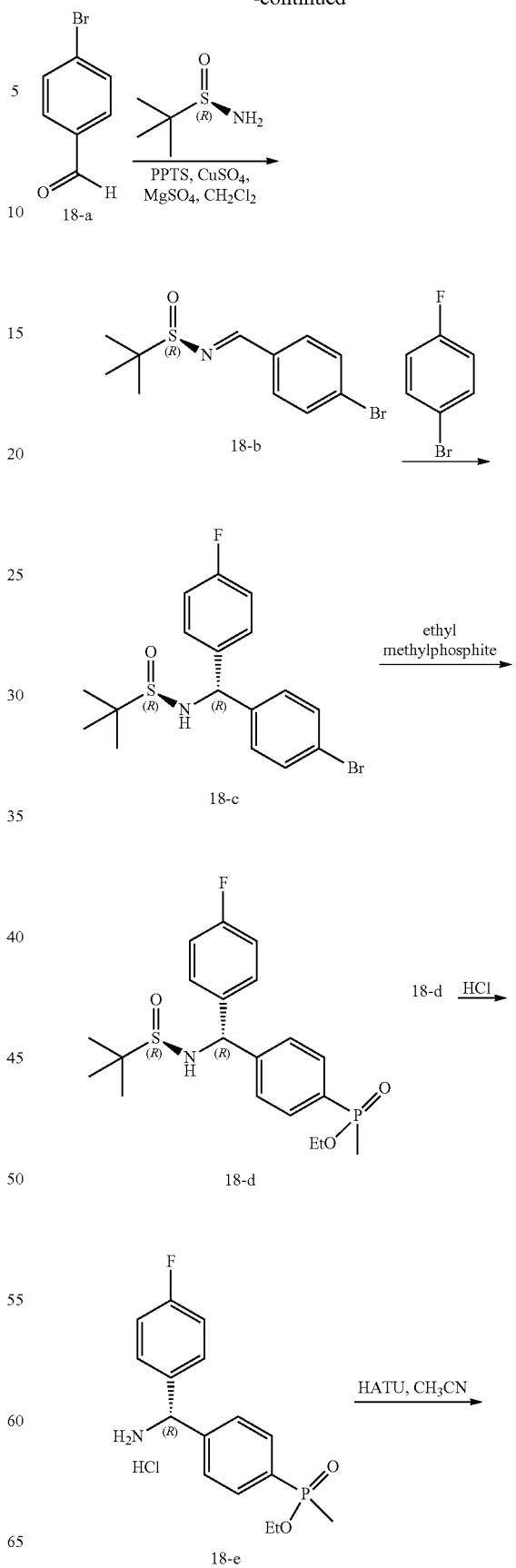

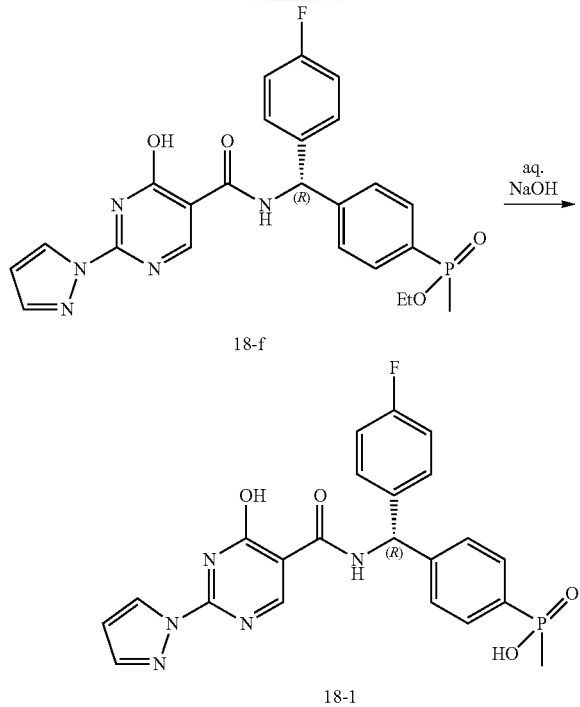

18-f 18-1

Step A: (R)-(E)-N-(4-bromobenzylidene)-2-methyl-propane-2-sulfinamide (18-b)

To a mixture of 4-bromobenzaldehyde, 18-a, (150 g, 0.82 mol) in dichloromethane (1.5 L) were added (R)-2-methylpropane-2-sulfinamide (128 g, 1.06 mol), PPTS (20 g, 0.08 mmol) and anhydrous $CuSO_4$ (394 g, 2.46 mol) and the resulting mixture was stirred at 37° C. overnight. The mixture was then filtrated and the filtrate was concentrated under vacuum. The residue was purified by column chromatography (petroleum ether/ethyl acetate=5/1) to provide the product, 18-b, (200 g, 69%).

Step B: (R)—N—((R)-(4-bromophenyl)(4-fluorophenyl)methyl)-2-methylpropane-2-sulfinamide (18-c)

The solution of 1-bromo-4-fluorobenzene (8-b) (0.95 g, 5.48 mmol) in THF (8 mL) was cooled to −78° C. Then n-BuLi (2.2 mL, 5.48 mol) was dropwise added at −78° C. and maintained at this temperature for about 1 h. (R,E)-N-(4-bromobenzylidene)-2-methylpropane-2-sulfinamide (1 g, 2.74 mol) in anhydrous THF (100 ml) was also dropwise added at −78° C. The mixture was stirred at −78° C. for 1 h, warmed to rt for 2 h, and then quenched by $NH_4Cl$ aq. The organic phase was dried and purified by column chromatography (PE:EA=10:1) to afford the product as light yellow solid, recrystallized by PE:EA=20:1 to give 18-c as a white solid (300 mg, 31%). $(M+1)^+=385$. HPLC indicated that the diastereomer ratio is 95:5 after recrystallization for three times in hexane/ethyl acetate.

Step C: Ethyl 4-((R)-(4-fluorophenyl)((R)-1-methylethylsulfinamido)-methyl)phenyl(methyl)phosphinate (18-d)

To (R)—N—((R)-(4-bromophenyl)(4-fluorophenyl)methyl)-2-methylpropane-2-sulfinamide, 18-c, (10 g, 0.026 mol), ethyl methylphosphite (5.6 g, 0.052 mol) and $Et_3N$ (7.88 g, 0.078 mol) in THF (100 ml) was added $PdCl_2(dppf)$ (2.2 g). The mixture was allowed to stir overnight at reflux. The mixture was filtered and the filtrate was concentrated under vacuum. The residue was taken into dichloromethane and washed with brine. The organic layer was concentrated under vacuum and the residue was purified over silica gel (petroleum ether:ethyl acetate=1/1) to provide the product, 18-d, (6.9 g, 68%).

Step D: Ethyl 4-((R)-amino(4-fluorophenyl)methyl)phenyl(methyl)phosphinate hydrochloride (18-e)

Ethyl 4-((R)—((R)-1,1-dimethylethylsulfinamido)(4-fluorophenyl)methyl)phenyl(methyl)phosphinate, 18-d, (7 g, 18 mmol) was dissolved in HCl/dioxane (50 ml) and the mixture was stirred at room temperature for about 3 h. The mixture was then concentrated under vacuum and the residue was washed with ethyl acetate to provide the product, 18-e, (4.4 g, 80%).

Step E: Ethyl 4-((R)-(4-fluorophenyl)(4-hydroxy-2-(1H-pyrazol-1-yl)pyrimidine-5-carboxamido)methyl)phenyl(methyl)phosphinate (18-f)

To a stirred solution of 4-hydroxy-2-(1H-pyrazol-1-yl)pyrimidine-5-carboxylic acid, 8-b, (5.15 g, 25 mmol) and $Et_3N$ (6.9 g, 68 mmol) in MeCN (100 ml) was added HATU (9.5 g, 25 mmol). The mixture was stirred for 5 min at room temperature and then compound 18-e (7 g, 23 mmol) was added. The resulting mixture was stirred at room temperature for 1 hour. Then it was concentrated under vacuum and the residue was taken into ethyl acetate followed by washing with 1N HCl. The organic layer was dried over sodium sulfate and concentrated under vacuum. The residue was purified on silica gel chromatography (petroleum ether:ethyl acetate=2/1) to provide the product, 18-f, (8.1 g, 65.7%).

Step F: 4-((R)-(4-fluorophenyl)(4-hydroxy-2-(1H-pyrazol-1-yl)pyrimidine-5-carboxamido)methyl)phenyl(methyl)phosphinic acid (18-1)

Ethyl 4-((R)-(4-fluorophenyl)(4-hydroxy-2-(1H-pyrazol-1-yl)pyrimidine-5-carboxamido)methyl)phenyl(methyl)phosphinate, 18-f, (7 g, 14 mmol) was dissolved in 50 ml of dioxane and treated with 5 ml of 3N NaOH. The mixture was heated at 80° C. for one hour. Then the mixture was concentrated under vacuum. The residue was diluted with water and washed with ethyl acetate. The aqueous layer was acidified with conc. HCl to pH=1 and the expected product crashed out (9.2 g of crude). The product can be further purified via prep-HPLC give 4 g of title product, 18-1, (Y=61%). $^1H$ NMR (300 MHz, DMSO-$d_6$): δ 10.32 (br, 1H), 8.62 (s, 1H), 8.43 (s, 1H), 8.05 (s, 1H), 7.46 (m, 2H), 7.37 (m, 4H), 7.20 (m, 2H), 6.72 (s, 1H), 6.33 (d, 1H), 1.50 (d, 3H). $(M+H)^+=468.1$.

Example 19

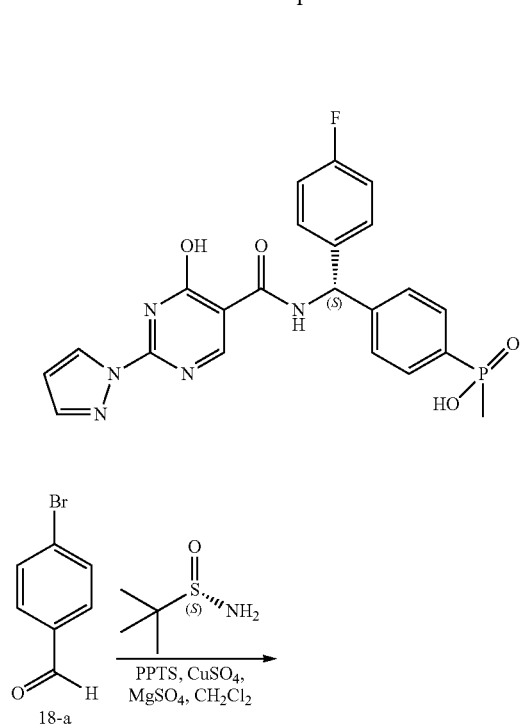

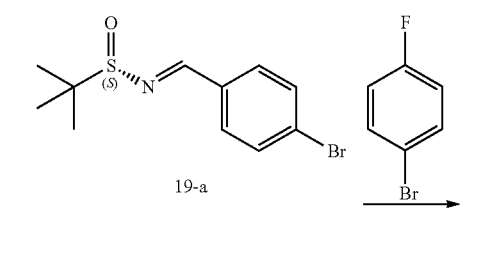

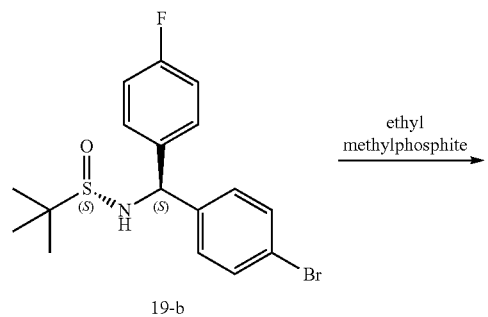

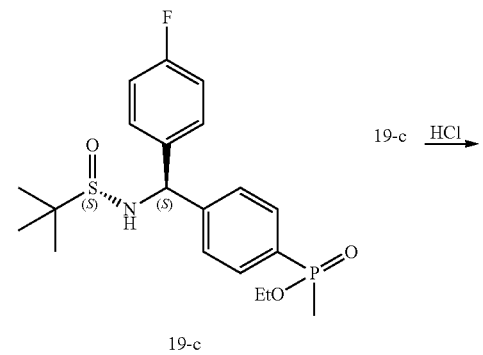

Step A: (S,E)-N-(4-bromobenzylidene)-2-methylpropane-2-sulfinamide (19-a)

To 4-bromobenzaldehyde, 18-a, (50 g, 0.27 mol) in dichloromethane (500 mL) were added (S)-2-methylpropane-2-sulfinamide (43 g, 0.36 mol), PPTS (6.7 g, 0.027 mmol) and anhydrous $CuSO_4$ (131 g, 0.82 mol) and the resulting mixture was stirred at 37° C. overnight. The mixture was then filtrated and the filtrate was concentrated under vacuum. The residue was purified by column chromatography (petroleum ether/ethyl acetate=20/1) to provide the product, 19-a, (70 g, 71%).

Step B: (S)—N—((S)-(4-bromophenyl)(4-fluorophenyl)methyl)-2-methylpropane-2 sulfinamide (19-b)

The solution of 1-bromo-4-fluorobenzene (66.7 g, 0.38 mol) in THF (400 mL) was cooled to −78° C. Then n-BuLi (140 mL, 0.38 mol) was dropwise added at −78° C. and maintained at this temperature for about 1 h. (S,E)-N-(4-bromobenzylidene)-2-methylpropane-2-sulfinamide, 19-a, (70 g, 0.19 mol) in anhydrous THF (100 ml) was also dropwise added at −78° C. The mixture was stirred at −78° C. for 1 h, warmed to rt for 2 h, and then quenched by $NH_4Cl$ aq. The organic phase was dried and purified by column chromatography (PE:EA=10:1) afford the product 19-b as a light yellow solid, recrystallized by PE:EA=20:1 to give the white solid, (26 g, 35%).

(M+1)⁺=385.

Step C: Ethyl 4-((S)—((S)-1,1-dimethylethylsulfinamido)(4-fluorophenyl)methyl)phenyl(methyl)phosphinate (19-c)

To (S)—N—((S)-(4-bromophenyl)(4-fluorophenyl)methyl)-2-methylpropane-2-sulfinamide, 19-b, (10 g, 0.026 mol), ethyl methylphosphite (5.6 g, 0.052 mol) and Et₃N (7.88 g, 0.78 mol) in THF (100 ml) was added PdCl₂(dppf) (2.2 g). The mixture was allowed to stir overnight at reflux. The mixture was filtered and the filtrate was concentrated under vacuum. The residue was taken into dichloromethane and washed with brine. The organic layer was concentrated under vacuum and the residue was purified over silica gel (petroleum ether:ethyl acetate=1/1) to provide the product, 19-c, (6.9 g, 68%).

Step D: Ethyl 4-((S)-amino(4-fluorophenyl)methyl)phenyl(methyl)phosphinate hydrochloride (19-d)

Ethyl 4-((S)—((S)-1,1-dimethylethylsulfinamido)(4-fluorophenyl)-methyl)phenyl(methyl)phosphinate, 19-c, (10.6 g, 27 mmol) was dissolved in HCl/dioxane (100 ml) and the mixture was stirred at room temperature for about 3 h. The mixture was then concentrated under vacuum and the residue was washed with ethyl acetate to provide the product, 19-d, (6.66 g, 80%).

Step E: Ethyl 4-((S)-(4-fluorophenyl)(4-hydroxy-2-(1H-pyrazol-1-yl)pyrimidine-5 carboxamido)methyl)phenyl(methyl)phosphinate (19-e)

To a stirred solution of 4-hydroxy-2-(1H-pyrazol-1-yl)pyrimidine-5-carboxylic acid, 8-b, (5.9 g, 29 mmol) and Et₃N (7.9 g, 78 mmol) in MeCN (100 ml) was added HATU (10.9 g, 29 mmol). The mixture was stirred for 5 min at room temperature and then compound 19-d (8 g, 26 mmol) was added. The resulting mixture was stirred at room temperature for 1 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (petroleum ether: ethyl acetate=2/1) to provide the product, 19-e, (4.39 g, 31%).

Step F: 4-((S)-(4-fluorophenyl)(4-hydroxy-2-(1H-pyrazol-1-yl)pyrimidine-5-carboxamido)methyl)phenyl(methyl)phosphinic acid (19-1)

Ethyl 4-((S)-(4-fluorophenyl)(4-hydroxy-2-(1H-pyrazol-1-yl)pyrimidine-5-carboxamido)methyl)phenyl(methyl) phosphinate, 19-e, (12 g, 0.024 mol) was dissolved in 100 ml of dioxane and treated with 4 ml of 3N NaOH. The mixture was heated at 80° C. for one hour. The mixture was then concentrated under vacuum. The resulting residue was diluted with water and washed with ethyl acetate. The aqueous layer was acidified with conc. HCl to pH=1 and the expected product crashed out, 19-1, (9.2 g of crude). The product can be further purified via prep-HPLC (3.5 g). ¹H NMR (300 MHz, DMSO-d₆): δ 8.62 (s, 1H), 8.43 (s, 1H), 8.07 (s, 1H), 7.46 (m, 2H), 7.38 (m, 4H), 7.21 (m, 2H), 6.73 (s, 1H), 6.38 (d, 1H), 1.52 (d, 3H). (M+H)⁺=468.1.

Example 20

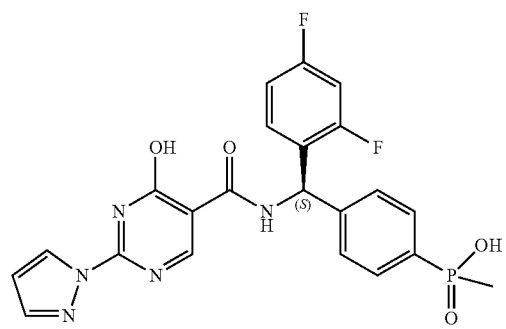

20-1

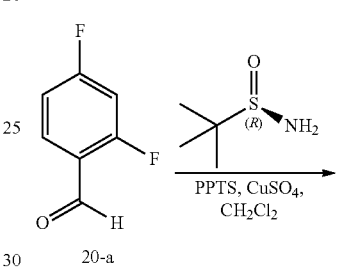

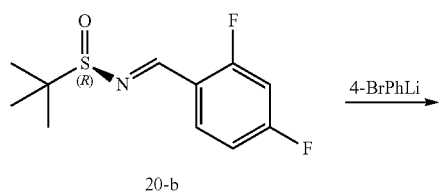

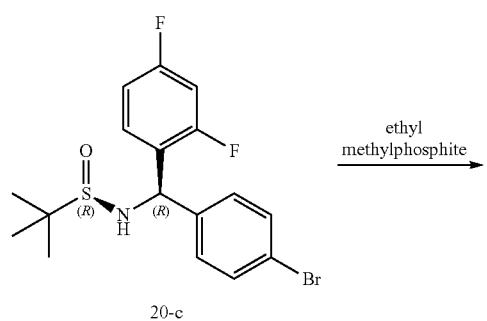

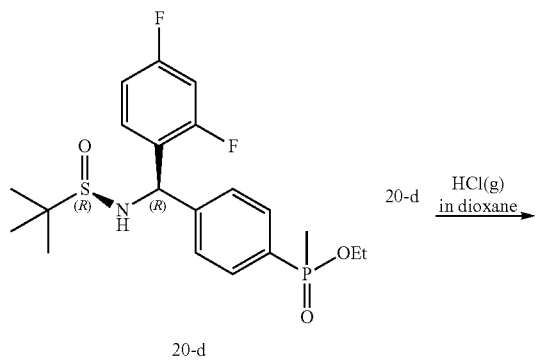

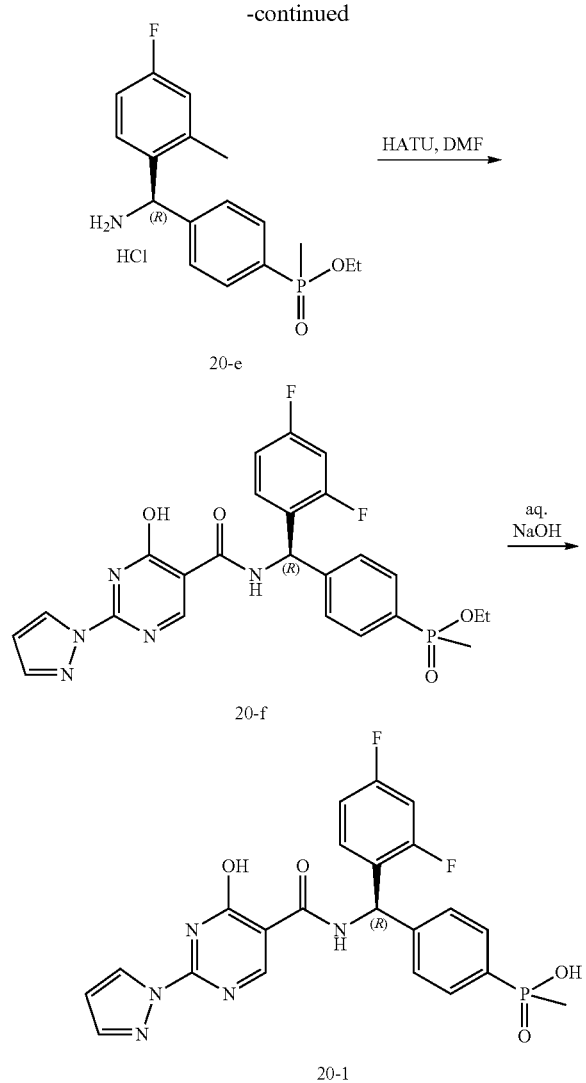

anhydrous THF was added dropwise below −60° C. Then the mixture was allowed to stir at room temperature for 6 h. The mixture was quenched with saturated NH₄Cl followed by extraction with ethyl acetate. The organic layer was dried over sodium sulfate and concentrated under vacuum. The residue was purified by column chromatography (petroleum ether/ethyl acetate=4/1) to provide the product, 20-c, (3.6 g, 22%). HPLC indicated that the no obvious diastereomer was observed.

Step C: Ethyl 4-((R)-(2,4-difluorophenyl)((R)-1,1-dimethylethylsulfinamido)methyl)phenyl(methyl)phosphinate (20-d)

To (R)—N—((R)-(4-bromophenyl)(2,4-difluorophenyl)methyl)-2-methylpropane-2-sulfinamide, 20-c, (1 g, 2.5 mmol), ethyl methylphosphite (0.54 g, 5 mmol) and Et₃N (0.63 g, 6.25 mmol) in THF (10 ml) was added PdCl₂(dppf) (183 mg). The mixture was allowed to stir overnight at reflux. The mixture was filtered and the filtrate was concentrated under vacuum. The residue was taken into ethyl acetate and washed with brine. The organic layer was concentrated under vacuum and the residue was purified over silica gel to give compound, 20-d, (dichloromethane:methanol=50/1) to provide the product (866 mg, 81%).

Step D: Methyl 4-((R)-amino(2,4-difluorophenyl)methyl)phenyl(methyl)phosphinate hydrochloride (20-e)

Ethyl 4-((R)-(2,4-difluorophenyl)((R)-1,1-dimethylethylsulfinamido)methyl)-phenyl(methyl)phosphinate, 20-d, (866 mg, 2.5 mmol) was dissolved in HCl/dioxane (5 ml) and the mixture was stirred at room temperature for 1 h. Then it was concentrated under vacuum and the residue was washed with ethyl acetate to provide the product 20-e (781 mg, 96%).

Step E: Ethyl 4-((R)-(2,4-difluorophenyl)(4-hydroxy-2-(1H-pyrazol-1-yl)pyrimidine-5-carboxamido)methyl)phenyl(methyl)phosphinate (20-f)

To a stirred solution of 4-hydroxy-2-(1H-pyrazol-1-yl)pyrimidine-5-carboxylic acid, 8-b, (200 mg, 0.97 mmol) and DIEA (380 mg, 2.91 mmol) in DMF (3 ml) was added HATU (370 mg, 0.97 mmol). The mixture was stirred for 5 min at room temperature and then compound 20-e (351 mg, 0.97 mmol) was added. The resulting mixture was stirred at 60° C. for 3 hour. The mixture was then diluted with water and extracted with ethyl acetate. The organic layer was washed with brine, dried over sodium sulfate and concentrated under vacuum. The residue was purified on silica gel chromatography (dichloromethane:methanol=20/1) to provide the product, 20-f, (400 mg, 80%).

Step F: 4-((R)-(2,4-difluorophenyl)(4-hydroxy-2-(1H-pyrazol-1-yl)pyrimidine-5-carboxamido)methyl)phenyl(methyl)phosphinic acid (20-1)

Ethyl 4-((R)-(2,4-difluorophenyl)(4-hydroxy-2-(1H-pyrazol-1-yl)pyrimidine-5-carboxamido)methyl)phenyl(methyl)phosphinate, 20-f, (400 mg, 0.78 mmol) was dissolved in 5 ml of dioxane and treated with 0.5 ml of 5N NaOH. The mixture was heated at 80° C. for one hour. The mixture was then concentrated under vacuum and the residue was diluted with water and washed with ethyl acetate. The aqueous layer was acidified with AcOH and evaporated to dryness. The residue was used for prep-HPLC to afford the product, 20-1, (100 mg, Step A: (R,E)-N-(2,4-difluorobenzylidene)-2-methylpropane-2-sulfinamide (20-b)

2,4-difluorobenzaldehyde (20-a, 10 g, 70.4 mmol) in dichloromethane (300 ml) were added (R)-2-methylpropane-2-sulfinamide (8.5 g, 70.4 mmol), PPTS (1.85 g, 7.4 mmol) and anhydrous CuSO₄ (22.5 g, 0.14 mol). The resulting mixture was stirred at 37° C. overnight. The mixture was then filtrated and the filtrate was concentrated under vacuum. The residue was purified by column chromatography (petroleum ether/ethyl acetate=8/1) to provide the product, 20-b, (15.77 g, 91%).

Step B: (R)—N—((R)-(4-bromophenyl)(2,4-difluorophenyl)methyl)-2-methylpropane-2-sulfinamide (20-c)

1,4-dibromobenzene (9.6 g, 40.77 mmol) was dissolved in THF (150 ml) and cooled to −78° C. under nitrogen. Then n-BuLi (16.3 ml, 40.77 mmol) was added dropwise below −60° C. After addition, the mixture was stirred at −78° C. for additional 1 h and then (R,E)-N-(2,4-difluorobenzylidene)-2-methylpropane-2-sulfinamide, 20-b, (10 g, 40.77 mmol) in 26%). $^1$H NMR (300 MHz, CD$_3$OD): δ 8.67 (s, 1H), 8.58 (s, 1H), 7.92 (s, 1H), 7.81 (m, 2H), 7.48 (m, 3H), 7.04 (m, 2H), 6.66 (s, 1H), 6.60 (s, 1H), 1.66 (d, 3H). (M−H)$^-$=484.0.

Example 21

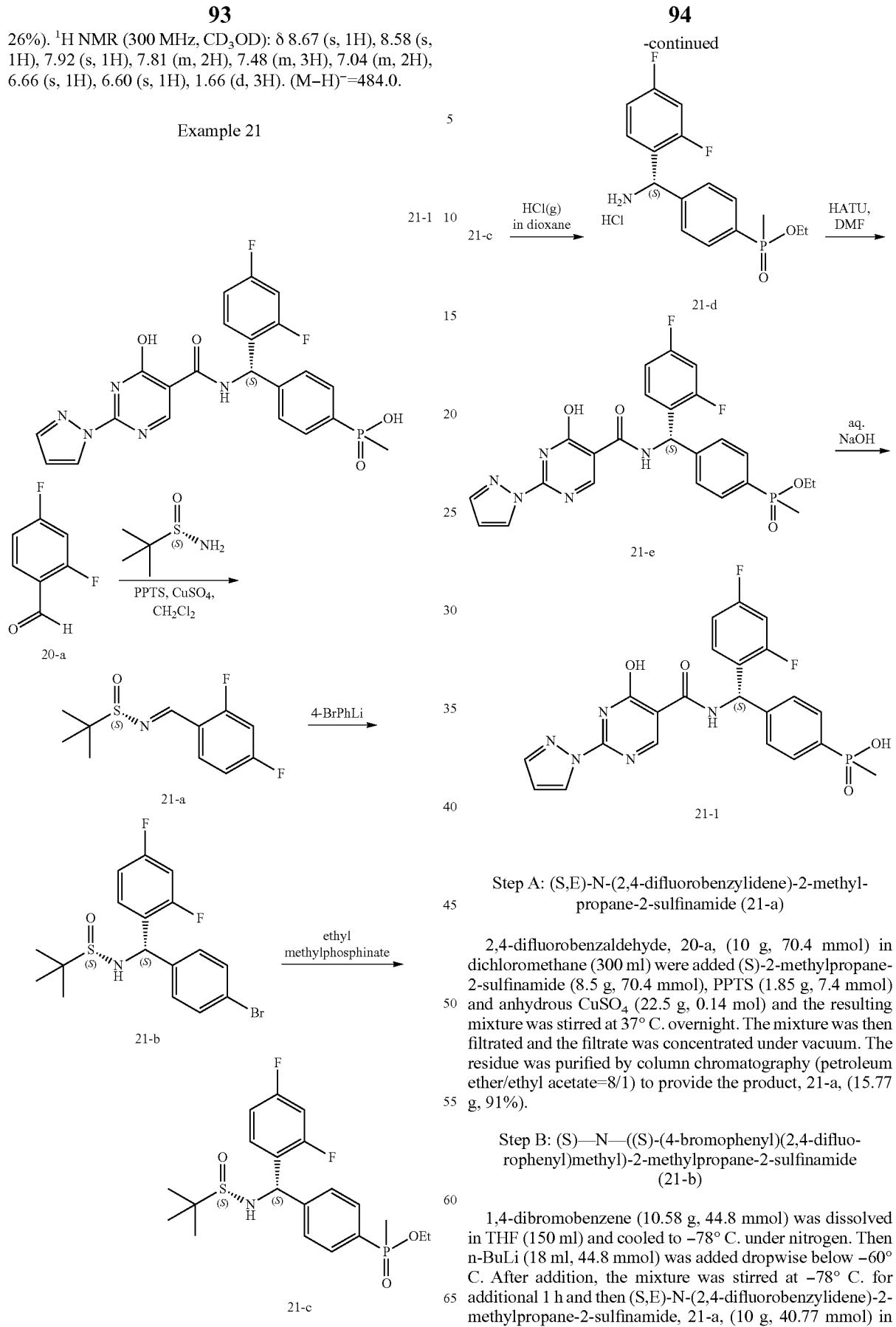

Step A: (S,E)-N-(2,4-difluorobenzylidene)-2-methylpropane-2-sulfinamide (21-a)

2,4-difluorobenzaldehyde, 20-a, (10 g, 70.4 mmol) in dichloromethane (300 ml) were added (S)-2-methylpropane-2-sulfinamide (8.5 g, 70.4 mmol), PPTS (1.85 g, 7.4 mmol) and anhydrous CuSO$_4$ (22.5 g, 0.14 mol) and the resulting mixture was stirred at 37° C. overnight. The mixture was then filtrated and the filtrate was concentrated under vacuum. The residue was purified by column chromatography (petroleum ether/ethyl acetate=8/1) to provide the product, 21-a, (15.77 g, 91%).

Step B: (S)—N—((S)-(4-bromophenyl)(2,4-difluorophenyl)methyl)-2-methylpropane-2-sulfinamide (21-b)

1,4-dibromobenzene (10.58 g, 44.8 mmol) was dissolved in THF (150 ml) and cooled to −78° C. under nitrogen. Then n-BuLi (18 ml, 44.8 mmol) was added dropwise below −60° C. After addition, the mixture was stirred at −78° C. for additional 1 h and then (S,E)-N-(2,4-difluorobenzylidene)-2-methylpropane-2-sulfinamide, 21-a, (10 g, 40.77 mmol) in anhydrous THF was added dropwise below −60° C. Then the mixture was allowed to stir at room temperature for 6 h. The mixture was quenched with saturated NH₄Cl followed by extraction with ethyl acetate. The organic layer was dried over sodium sulfate and concentrated under vacuum. The residue was purified by column chromatography (petroleum ether/ethyl acetate=4/1) to provide the product, 21-b, (7.5 g, 42%). HPLC implicated that only the single isomer was formed.

Step C: Ethyl 4-((S)-(2,4-difluorophenyl)((S)-1,1-dimethylethylsulfinamido)methyl)phenyl(methyl) phosphinate (21-c)

To (S)—N—((S)-(4-bromophenyl)(2,4-difluorophenyl) methyl)-2-methylpropane-2-sulfinamide, 21-b, (2 g, 5 mmol), ethyl methylphosphite (1.08 g, 10 mmol) and Et₃N (1.25 g, 12.5 mmol) in THF (20 ml) was added PdCl₂(dppf) (360 mg). The mixture was allowed to stir overnight at reflux. The mixture was filtered and the filtrate was concentrated under vacuum. The residue was taken into ethyl acetate and washed with brine. The organic layer was concentrated under vacuum and the residue was purified over silica gel (dichloromethane:methanol=50/1) to provide the product, 21-c, (950 mg, 44%).

Step D: Ethyl 4-((S)-amino(2,4-difluorophenyl)methyl)phenyl(methyl)phosphinate hydrochloride (21-d)

Ethyl 4-((S)-(2,4-difluorophenyl)((S)-1,1-dimethylethylsulfinamido)methyl)phenyl(methyl)phosphinate, 21-c, (950 mg, 2.2 mmol) was dissolved in HCl/dioxane (5 ml) and the mixture was stirred at room temperature for 1 h. Then it was concentrated under vacuum and the residue was washed with ethyl acetate to provide the product, 21-d, (700 mg, 88%).

Step E: Ethyl 4-((S)-(2,4-difluorophenyl)(4-hydroxy-2-(1H-pyrazol-1-yl)pyrimidine-5-carboxamido)methyl)phenyl(methyl)phosphinate (21-e)

To a stirred solution of 4-hydroxy-2-(1H-pyrazol-1-yl)pyrimidine-5-carboxylic acid, 8-b, (285 mg, 1.38 mmol) and DIEA (540 mg, 4.14 mmol) in DMF (5 ml) was added HATU (525 mg, 1.38 mmol). The mixture was stirred for 5 min at room temperature and then compound 21-d (500 mg, 1.38 mmol) was added. The resulting mixture was stirred at 60° C. for 3 hours, diluted with water and then extracted with ethyl acetate. The organic layer was washed with brine, dried over sodium sulfate, and concentrated under vacuum. The residue was purified on silica gel chromatography (dichloromethane:methanol=20/1) to provide the product, 21-e, (400 mg, 56%).

Step F: 4-((S)-(2,4-difluorophenyl)(4-hydroxy-2-(1H-pyrazol-1-yl)pyrimidine-5-carboxamido)methyl)phenyl(methyl)phosphinic acid (21-1)

Ethyl 4-((S)-(2,4-difluorophenyl)(4-hydroxy-2-(1H-pyrazol-1-yl)pyrimidine-5-carboxamido)methyl)phenyl(methyl) phosphinate, 21-e, (400 mg, 0.78 mmol) was dissolved in 2 ml of dioxane and treated with 0.2 ml of 5N NaOH. The mixture was heated at 80° C. for 30 min. Then the mixture was concentrated under vacuum. The residue was diluted with water and washed with ethyl acetate. The aqueous layer was acidified with AcOH and evaporated to dryness. The residue was used for prep-HPLC to afford the product, 21-1, (250 mg, 66%). ¹H NMR (300 MHz, CD₃OD): δ 8.67 (s, 1H), 8.58 (s, 1H), 7.92 (s, 1H), 7.81 (m, 2H), 7.48 (m, 3H), 7.01 (m, 2H), 6.66 (s, 1H), 6.60 (s, 1H), 1.67 (d, 3H). (M−H)⁻=484.0.

Example 22

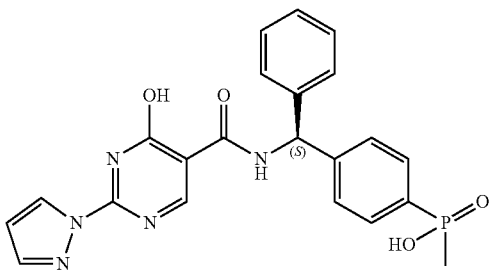

22-1

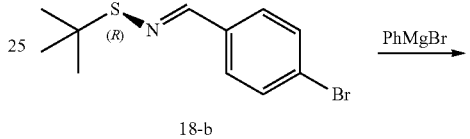

18-b

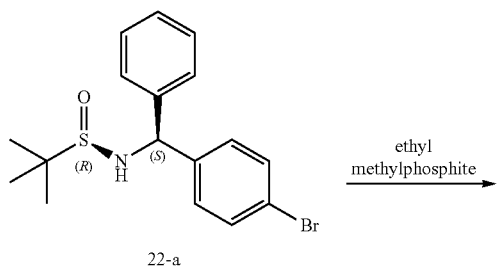

22-a

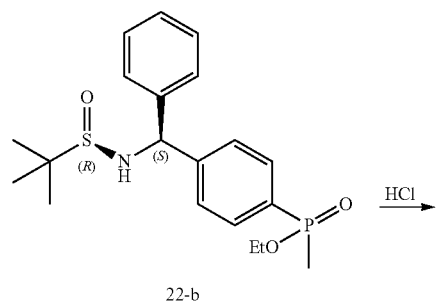

22-b

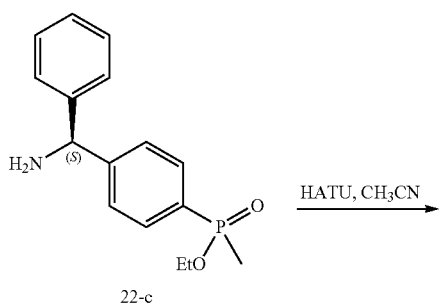

22-c

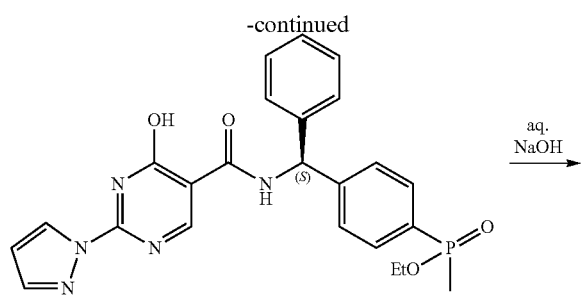

22-d

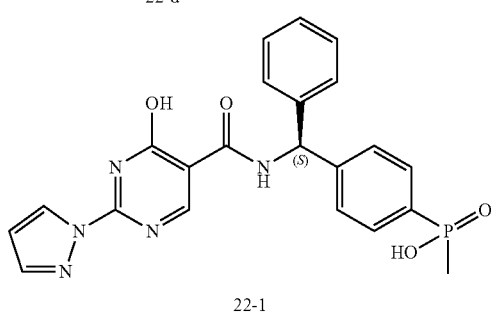

22-1

Step A: (S)—N—((R)-(4-bromophenyl)(phenyl)methyl)-2-methylpropane-2-sulfinamide (22-a)

(R,E)-N-(4-bromobenzylidene)-2-methylpropane-2-sulfinamide, 18-b, (10 g, 34.84 mmol) was dissolved in anhydrous THF (100 ml). The mixture was then cooled to −45° C. and PhMgBr (34.84 ml, 69.68 mmol) was added dropwise. After addition, the mixture was allowed to stir at −45° C. for additional 4 h and warm to room temperature for another 2 h. TLC monitored the reaction and the time was prolonged if necessary. The mixture was quenched with saturated NH$_4$Cl followed by extraction with ethyl acetate. The organic layer was dried over sodium sulfate and concentrated under vacuum. The residue was purified by column chromatography (petroleum ether/ethyl acetate=4/1) to provide the product, 22-a, (8 g, 63%). HPLC indicated that the diastereomer ratio is 96:4 after recrystallization once in hexane/ethyl acetate.

Step B: Ethyl 4-((S)—((R)-1,1-dimethylethylsulfinamido)(phenyl)methyl)phenyl(methyl)phosphinate (22-b)

To (S)—N—((R)-(4-bromophenyl)(phenyl)methyl)-2-methylpropane-2-sulfinamide, 22-a, (16 g, 43.83 mmol), ethyl methylphosphite (9.47 g, 87.67 mmol) and Et$_3$N (13.3 g, 132 mmol) in THF (200 ml) was added PdCl$_2$(dppf) (1.6 g). The mixture was allowed to stir overnight at reflux. The mixture was filtered and the filtrate was concentrated under vacuum. The residue was taken into dichloromethane and washed with brine. The organic layer was concentrated under vacuum and the residue was purified over silica gel (petroleum ether:ethyl acetate=1/1) to provide the crude product, 22-b, (9.5 g, 55%).

Step C: Ethyl 4-((S)-amino(phenyl)methyl)phenyl(methyl)phosphinate hydrochloride (22-C)

Ethyl 4-((S)—((R)-1,1-dimethylethylsulfinamido)(phenyl)methyl)phenyl(methyl)phosphinate, 22-b, (9.5 g, 24.1 mmol) was dissolved in HCl/dioxane (100 ml) and the mixture was stirred at room temperature overnight. The mixture was then concentrated under vacuum and the residue was washed with ethyl acetate to provide the product, 22-c, (7.16 g, 91%).

Step D: Ethyl 4-((S)-(4-hydroxy-2-(1H-pyrazol-1-yl)pyrimidine-5-carboxamido)(phenyl)methyl)phenyl(methyl)phosphinate (22-d)

To a stirred solution of 4-hydroxy-2-(1H-pyrazol-1-yl)pyrimidine-5-carboxylic acid, 8-b, (2.5 g, 12.1 mmol) and Et$_3$N (4.3 mg, 43 mmol) in MeCN (50 ml) was added HATU (4.83 mg, 12.72 mmol). The mixture was stirred for 5 min at room temperature and then compound 22-c (3.5 g, 12.1 mmol) was added. The resulting mixture was stirred at room temperature for 1 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (petroleum ether:ethyl acetate=2/1) to provide the product, 22-d, (4 g, 69%).

Step E: 4-((S)-(4-hydroxy-2-(1H-pyrazol-1-yl)pyrimidine-5-carboxamido)(phenyl)methyl)phenyl(methyl)phosphinic acid (22-1)

Ethyl 4-((S)-(4-hydroxy-2-(1H-pyrazol-1-yl)pyrimidine-5-carboxamido)(phenyl)methyl)phenyl(methyl)phosphinate, 22-d, (2 g, 4.32 mmol) was dissolved in 7.2 ml of dioxane and treated with 7.2 ml of 3N NaOH. The mixture was heated at 80° C. for one hour. Then it was concentrated under vacuum and the residue was diluted with water and washed with ethyl acetate. The aqueous layer was acidified with conc. HCl to pH=1 and the expected product, 22-1, crashed out (1.4 g of crude). The product can be further purified via prep-HPLC. $^1$H NMR (300 MHz, DMSO-d$_6$): δ 10.40 (br, 1H), 8.64 (s, 1H), 8.44 (s, 1H), 8.06 (s, 1H), 7.60 (m, 2H), 7.38 (m, 7H), 6.73 (s, 1H), 6.32 (d, 1H), 1.51 (d, 3H). (M−H)$^-$=448.1.

Example 23

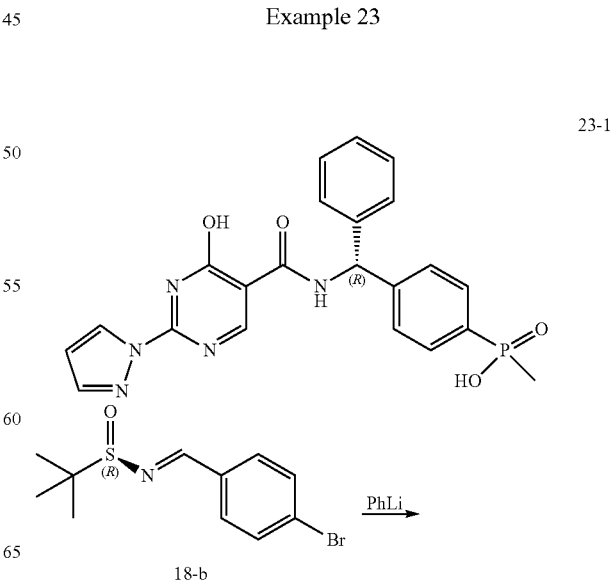

23-1

18-b

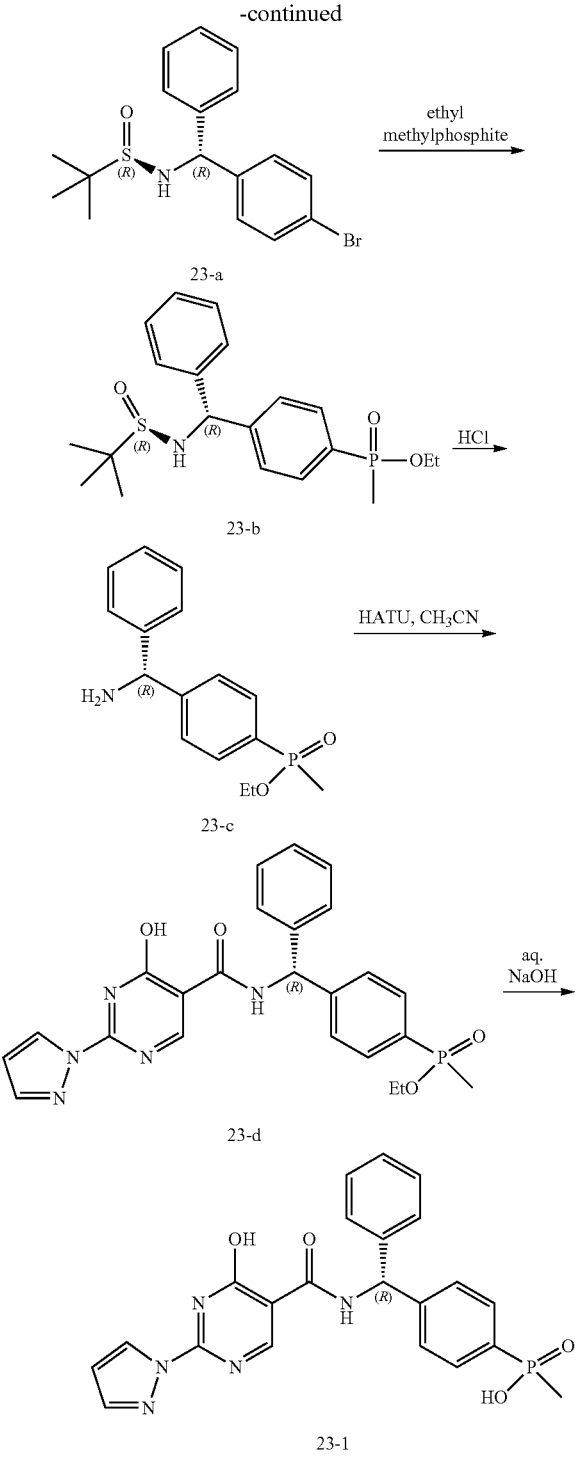

necessary. The mixture was quenched with saturated NH$_4$Cl followed by extraction with ethyl acetate. The organic layer was dried over sodium sulfate and concentrated under vacuum. The residue was purified by column chromatography (petroleum ether/ethyl acetate=2/1) to provide the product, 23-a, (8 g, 63%). HPLC indicated that the diastereomer ratio is 80:20 and recrystallization once in hexane/ethyl acetate can increase it to above 95:5 with around 40% material lost in the mother liquid.

Step B: Ethyl 4-((R)—((R)-1,1-dimethylethylsulfinamido)(phenyl)methyl)phenyl(methyl)phosphinate (23-b)

To (R)—N—((R)-(4-bromophenyl)(phenyl)methyl)-2-methylpropane-2-sulfinamide, 23-a, (16 g, 43.83 mmol), ethyl methylphosphite (9.47 g, 87.67 mmol) and Et$_3$N (13.3 g, 132 mmol) in THF (200 ml) was added PdCl$_2$(dppf) (1.6 g). The mixture was allowed to stir overnight at reflux. The mixture was filtered and the filtrate was concentrated under vacuum. The residue was taken into dichloromethane and washed with brine. The organic layer was concentrated under vacuum and the residue was purified over silica gel (petroleum ether:ethyl acetate=1 1/1) to provide the crude product, 23-b, (9.5 g, 55%).

Step C: Ethyl 4-((R)-amino(phenyl)methyl)phenyl(methyl)phosphinate hydrochloride (23-c)

Ethyl 4-((R)—((R)-1,1-dimethylethylsulfinamido)(phenyl)methyl)phenyl(methyl)phosphinate, 23-b, (9.5 g, 24.1 mmol) was dissolved in HCl/dioxane (100 ml) and the mixture was stirred at room temperature overnight. Then it was concentrated under vacuum and the residue was washed with ethyl acetate to provide the product, 23-c, (7.16 g, 91%).

Step D: Ethyl 4-((R)-(4-hydroxy-2-(1H-pyrazol-1-yl)pyrimidine-5-carboxamido)(phenyl)methyl)phenyl(methyl)phosphinate (23-d)

To a stirred solution of 4-hydroxy-2-(1H-pyrazol-1-yl)pyrimidine-5-carboxylic acid, 8-b, (2.5 g, 12.11 mmol) and Et$_3$N (4.3 mg, 43 mmol) in MeCN (50 ml) was added HATU (4.83 mg, 12.72 mmol). The mixture was stirred for 5 min at room temperature and then ethyl 4-((R)-amino(phenyl)methyl)phenyl(methyl)phosphinate hydrochloride, 23-c, (3.5 g, 12.1 mmol) was added. The resulting mixture was stirred at room temperature for 1 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (petroleum ether:ethyl acetate=2/1) to provide the product, 23-d, (4 g, 69%).

Step E: 4-((R)-(4-hydroxy-2-(1H-pyrazol-1-yl)pyrimidine-5-carboxamido)(phenyl)methyl)phenyl methyl)phosphinic acid (23-1)

Ethyl 4-((R)-(4-hydroxy-2-(1H-pyrazol-1-yl)pyrimidine-5-carboxamido)(phenyl)methyl)phenyl(methyl)phosphinate, 23-d, (2 g, 4.32 mmol) was dissolved in 7.2 ml of dioxane and treated with 7.2 ml of 3N NaOH. The mixture was heated at 80° C. for one hour. Then it was concentrated under vacuum and the residue was diluted with water and washed with ethyl acetate. The aqueous layer was acidified with conc. HCl to pH=1 and the expected product crashed out, Step A: (R)—N—((R)-(4-bromophenyl)(phenyl)methyl)-2-methylpropane-2-sulfinamide (23-a)

(R,E)-N-(4-bromobenzylidene)-2-methylpropane-2-sulfinamide, 18-b, (10 g, 34.84 mmol) was dissolved in anhydrous THF (100 ml). The mixture was then cooled to −78° C. and PhLi (34.84 ml, 69.68 mmol) was added dropwise. After addition the mixture was allowed to stir at −78° C. for additional 4 h and warmed to room temperature for another 2 h. The reaction was TLC monitored and prolonged the time if 23-1, (1.4 g of crude). The product can be further purified via prep-HPLC. $^1$H NMR (300 MHz, DMSO-$d_6$): δ 10.36 (br, 1H), 8.62 (s, 1H), 8.42 (s, 1H), 8.06 (s, 1H), 7.60 (m, 2H), 7.35 (m, 7H), 6.72 (s, 1H), 6.32 (s, 1H), 2.10 (s, 2H), 1.52 (d, 2H). (M–H)$^-$=448.0.

Example 24

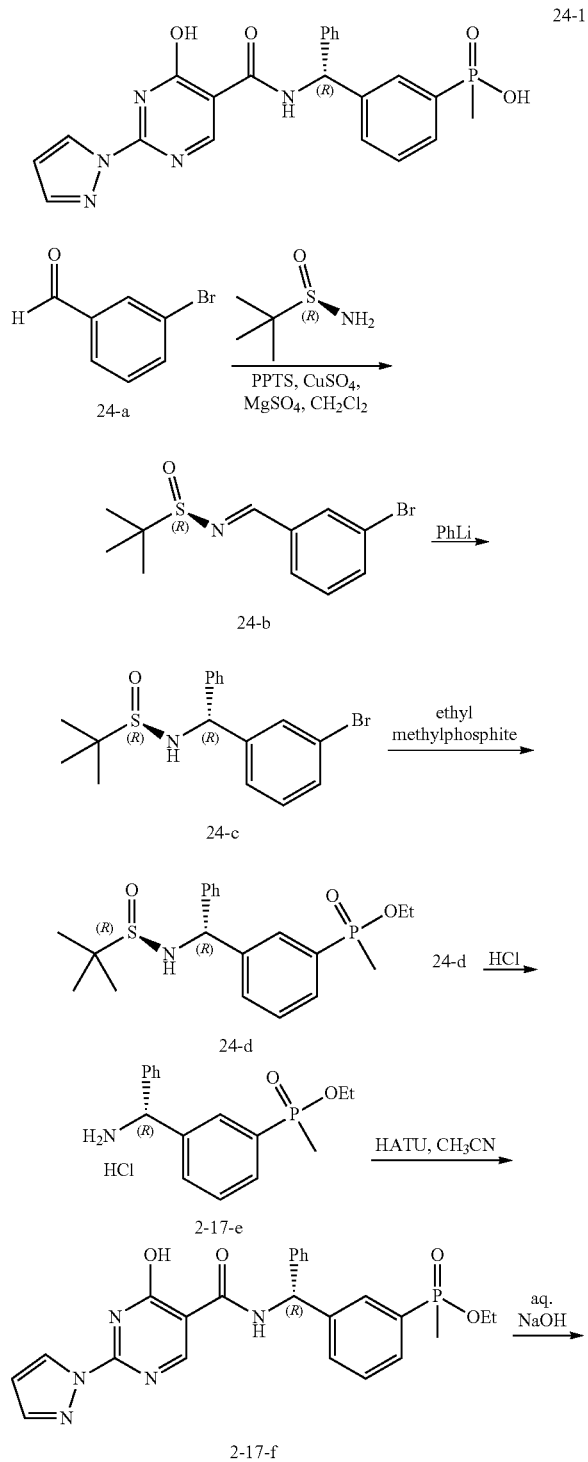

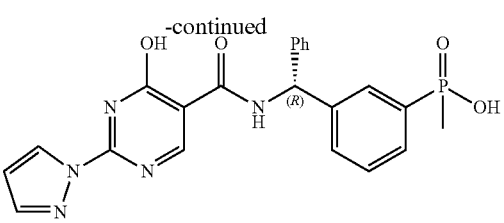

Step A: (R,E)-N-(3-bromobenzylidene)-2-methyl-propane-2-sulfinamide (24-b)

3-bromobenzaldehyde, 24-a, (10 g, 53.9 mmol) in dichloromethane (300 ml) were added (R)-2-methylpropane-2-sulfinamide (7.84 g, 64.8 mmol), PPTS (1.97 g, 7.85 mmol) and anhydrous CuSO$_4$ (25.8 g, 161 mmol) and the resulting mixture was stirred at 37° C. overnight. The mixture was then filtrated and the filtrate was concentrated under vacuum. The residue was purified by column chromatography (petroleum ether/ethyl acetate=5/1) to provide the product, 24-b, (14.4 g, 93%).

Step B: (R)—N—((R)-(3-bromophenyl)(phenyl)methyl)-2-methylpropane-2-sulfinamide (24-c)

(R,E)-N-(3-bromobenzylidene)-2-methylpropane-2-sulfinamide, 24-b, (12 g, 41.64 mmol) was dissolved in anhydrous THF (120 ml). The mixture was then cooled to −78° C. and PhLi (41 ml, 83.28 mmol) was added dropwise. After addition the mixture was allowed to stir at −78° C. for additional 2 h and warmed to room temperature for another 2 h. The mixture was quenched with saturated NH$_4$Cl followed by extraction with ethyl acetate. The organic layer was dried over sodium sulfate and concentrated under vacuum. The residue was purified by column chromatography (petroleum ether/ethyl acetate=5/1) to provide the product, 24-c, (11.8 g, 77%). HPLC indicated that the diastereomer ratio is 90:10 and the product was used for the next step directly.

Step C: Ethyl 3-((R)—((R)-1,1-dimethylethylsulfinamido)(phenyl)methyl)phenyl(methyl)phosphinate (24-d)

To (R)—N—((R)-(3-bromophenyl)(phenyl)methyl)-2-methylpropane-2-sulfinamide, 24-c, (11.8 g, 32.3 mmol), ethyl methylphosphite (6.5 g, 64.6 mmol) and Et$_3$N (9.09 g, 96.9 mmol) in THF (100 ml) was added PdCl$_2$(dppf) (2.1 g, 3.23 mmol). The mixture was allowed to stir overnight at reflux. The mixture was filtered and the filtrate was concentrated under vacuum to provide the crude product, 24-d, (15 g). The crude product was used to the next step directly.

Step D: Ethyl 3-((R)-amino(phenyl)methyl)phenyl(methyl)phosphinate (24-e)

Ethyl 3-((R)—((R)-1,1-dimethylethylsulfinamido)(phenyl)methyl)phenyl(methyl)phosphinate, 24-d, (15 g, 80% purity, 32.3 mmol) was dissolved in HCl/dioxane (70 ml, 4 mol/L) and the mixture was stirred at room temperature for 2 h. The mixture was concentrated under vacuum and the residue was dissolved with H$_2$O (90 ml) and HCl (10 ml). The aqueous phase was extracted with EA (80 ml*5). The pH of the aqueous layer was adjusted to about pH=12 and extracted with EA (100 ml*3). The organic was dried over Na$_2$SO$_4$ and the crude product was purified with column (DCM/MeOH=100/1~30/1) to provide the product, 24-e, (6.77 g, 74%).

Step E: Ethyl 3-((R)-(4-hydroxy-2-(1H-pyrazol-1-yl)pyrimidine-5-carboxamido)(phenyl)methyl)phenyl (methyl)phosphinate (24-f)

To a stirred solution of 4-hydroxy-2-(1H-pyrazol-1-yl)pyrimidine-5-carboxylic acid, 8-b, (7.9 g, 25.7 mmol) and Et$_3$N (7.09 g, 70.2 mmol) in MeCN (50 ml) was added HATU (10.7 g, 28.2 mmol). The mixture was stirred for 10 min at room temperature and then ethyl 3-((R)-amino(phenyl)methyl)phenyl(methyl)phosphinate, 24-e, (6.79 g, 23.4 mmol) was added. The resulting mixture was stirred at room temperature for 1 hour. The mixture was then concentrated under vacuum and the residue was taken into ethyl acetate followed by washing with saturated NH$_4$Cl. The organic layer was dried over sodium sulfate and concentrated under vacuum to provide the crude product, 24-f, (18.8 g) as red oil. The crude product was used for the next step directly.

Step F: 3-((R)-(4-hydroxy-2-(1H-pyrazol-1-yl)pyrimidine-5-carboxamido)(phenyl)methyl)phenyl(methyl)phosphinic acid (24-1)

Ethyl ((R)-(4-hydroxy-2-(1H-pyrazol-1-yl)pyrimidine-5-carboxamido)(phenyl)methyl)phenyl(methyl)phosphinate, 24-f, (18.8 g, 390 mmol) was dissolved in 200 ml of dioxane and treated with 50 ml of 3N NaOH. The mixture was heated at 80° C. for one hour. The mixture was then concentrated under vacuum and the residue was diluted with water and washed with ethyl acetate. The aqueous layer was acidified with conc. HCl to pH=1 and the expected product crashed out, 24-1, (11 g of crude). The product can be further purified via prep-HPLC. $^1$H NMR (300 MHz, DMSO-d$_6$): δ 8.63 (s, 1H), 8.44 (s, 1H), 8.07 (s, 1H), 7.50 (m, 2H), 7.38 (m, 7H), 6.73 (s, 1H), 6.35 (d, 1H), 1.53 (d, 3H). (M+H)$^+$=450.1.

Example 25

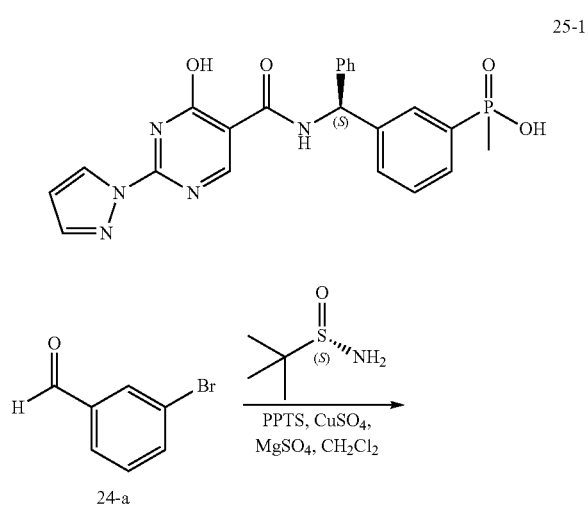

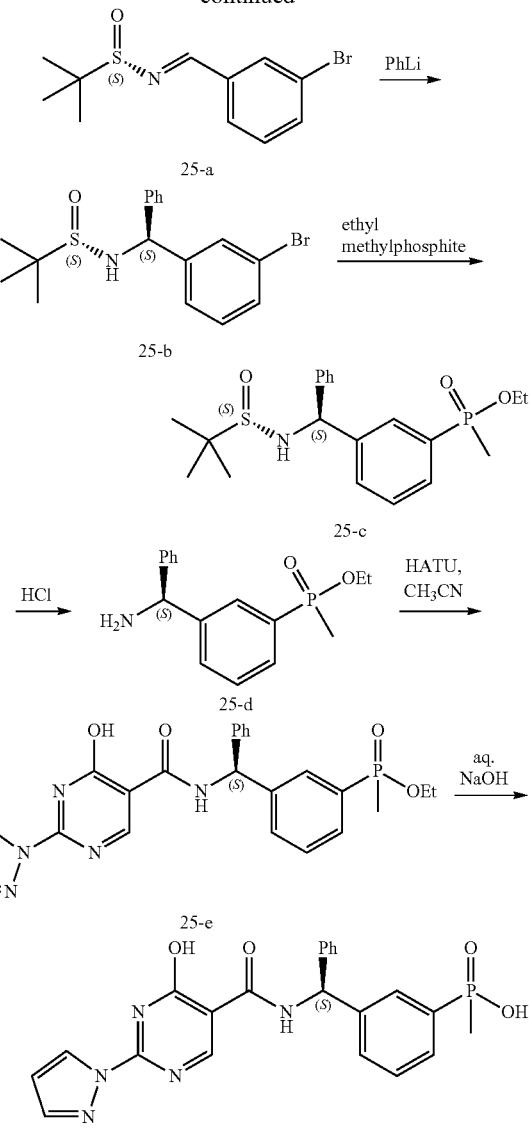

Step A: (S,E)-N-(3-bromobenzylidene)-2-methylpropane-2-sulfinamide (25-a)

3-bromobenzaldehyde, 24-a, (30 g, 162 mmol) in dichloromethane (600 ml) were added (S)-2-methylpropane-2-sulfinamide (23.52 g, 194.5 mmol), PPTS (5.97 g, 16.2 mmol) and anhydrous CuSO$_4$ (78 g, 486 mmol) and the resulting mixture was stirred at 37° C. overnight. The mixture was then filtrated and the filtrate was concentrated under vacuum. The residue was purified by column chromatography (petroleum ether/ethyl acetate=5/1) to provide the product, 25-a, (24.5 g, 52%).

Step B: (S)—N—((S)-(3-bromophenyl)(phenylmethyl)-2-methylpropane-2-sulfinamide (25-b)

(S,E)-N-(3-bromobenzylidene)-2-methylpropane-2-sulfinamide, 25-a, (24.5 g, 85 mmol) was dissolved in anhydrous THF (300 ml). The mixture was then cooled to −78° C. and PhLi (85 ml, 170 mmol) was added dropwise. After addition, the mixture was allowed to stir at −78° C. for an additional 3 h and warmed to room temperature for another 2 h. The mixture was quenched with saturated NH₄Cl followed by extraction with ethyl acetate. The organic layer was dried over sodium sulfate and concentrated under vacuum. The residue was purified by column chromatography (petroleum ether/ethyl acetate=5/1) to provide the product, 25-b, (17.8 g, 57%). HPLC indicated that the diastereomer ratio is 80:20 and the product was used for the next step directly. HPLC indicated that the diastereomer ratio is 89:11.

Step C: Ethyl 3-((S)—((S)-1,1-dimethylethylsulfinamido)(phenyl)methyl)phenyl(methyl)phosphinate (25-c)

To (S)—N—((S)-(3-bromophenyl)(phenyl)methyl)-2-methylpropane-2-sulfinamide, 25-b, (17.8 g, 48.7 mmol), ethyl methylphosphite (7.9 g, 730 mmol) and Et₃N (14.75 g, 146 mmol) in THF (150 ml) was added PdCl₂(dppf) (3.55 g, 4.87 mmol). The mixture was allowed to stir overnight at reflux. The mixture was filtered and the filtrate was concentrated under vacuum to provide the crude product, 25-c, (25 g). The crude product was used to the next step directly.

Step D: Ethyl 3-((S)-amino(phenyl)methyl)phenyl(methyl)phosphinate (25-d)

Ethyl 3-((S)—((S)-1,1dimethylethylsulfinamido)(phenyl)methyl)phenyl(methyl)phosphinate, 25-c, (25 g, 76% purity, 48.7 mmol) was dissolved in HCl/dioxane (150 ml, 4 mol/L) and the mixture was stirred at room temperature for 2 h. The mixture was then concentrated under vacuum and the residue was dissolved in H₂O (90 ml) and HCl (10 ml). The aqueous phase was extracted with EA (80 ml×5). The pH of the aqueous phase was adjusted to about pH=12 and extracted with EA (100 ml*3). The organic layer was dried over Na₂SO₄. The solvent was removed to provide crude product, 25-d, (10.55 g) and the crude product was used for the next step directly.

Step E: Ethyl 3-((S)-(4-hydroxy-2-(1H-pyrazol-1-yl)pyrimidine-5-carboxamido)(phenyl)methyl)phenyl(methyl)phosphinate (25-e)

To a stirred solution of 4-hydroxy-2-(1H-pyrazol-1-yl)pyrimidine-5-carboxylic acid, 8-b, (12.3 g, 40 mmol) and Et₃N (11 g, 109 mmol) in MeCN (200 ml) was added HATU (16.6 g, 43.8 mmol). The mixture was stirred for 10 min at room temperature and then ethyl 3-((S)-amino(phenyl)methyl)phenyl(methyl)phosphinate, 25-d, (10.55 g, 36.5 mmol) was added. The resulting mixture was stirred at room temperature for 1 hour. The mixture was then concentrated under vacuum and the residue was taken into ethyl acetate followed by washing with saturated NH₄Cl. The organic layer was dried over sodium sulfate and concentrated under vacuum to provide the crude product, 25-e, (33 g) as red oil. The crude product was used for the next step directly.

Step F: 3-((S)-(4-hydroxy-2-(1H-pyrazol-1-yl)pyrimidine-5-carboxamido)(phenyl)methyl)phenyl(methyl)phosphinic acid (25-1)

Ethyl ((S)-(4-hydroxy-2-(1H-pyrazol-1-yl)pyrimidine-5-carboxamido)(phenyl)methyl)phenyl(methyl)phosphinate, 25-e, (33 g, 69 mmol) was dissolved in 400 ml of dioxane and treated with 100 ml of 3N NaOH. The mixture was heated at 80° C. for one hour. The mixture was then concentrated under vacuum and the residue was diluted with water and washed with ethyl acetate. The aqueous layer was acidified with conc. HCl to pH=1 and the expected product crashed out, 25-1, (11 g of crude). The product can be further purified via prep-HPLC. ¹H NMR (300 MHz, DMSO-d₆): δ 10.39 (br, 1H), 8.62 (s, 1H), 8.45 (s, 1H), 8.07 (s, 1H), 7.37 (m, 9H), 6.73 (s, 1H), 6.33 (d, 1H), 1.52 (d, 3H). (2M+H)⁺=899.0.

Example 26

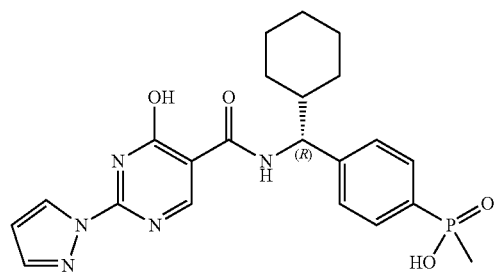

26-1

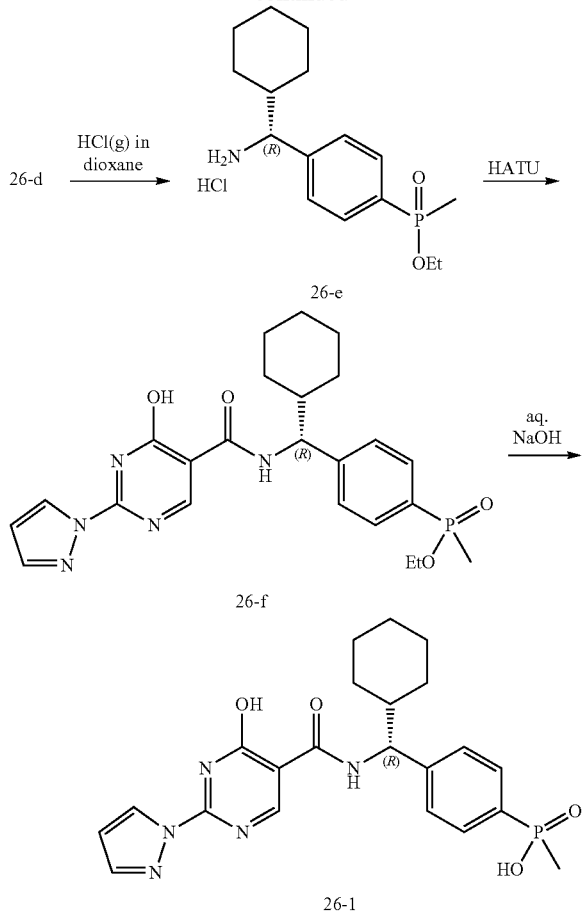

Step A: (R,E)-N-(cyclohexylmethylene)-2-methyl-propane-2-sulfinamide (26-b)

Cyclohexanecarbaldehyde, 26-a, (13.58 g, 0.121 mol) in dichloromethane (250 mL) were added (R)-2-methylpropane-2-sulfinamide (17.6 g, 0.145 mol), PPTS (3.03 g, 0.0121 mmol) and anhydrous CuSO₄ (58 g, 0.363 mol). The resulting mixture was stirred at 37° C. overnight. The mixture was then filtrated and the filtrate was concentrated under vacuum. The residue was purified by column chromatography (petroleum ether/ethyl acetate=5/1) to provide the product, 26-b, (23 g, 88%).

Step B: (R)—N—((R)-(4-bromophenyl)(cyclohexyl)methyl)-2-methylpropane-2-sulfinamide 26-c)

A solution of 1,4-dibromobenzene (16.5 g, 69.7 mmol) in anhydrous Et₂O (200 ml) was cooled to −70° C., and BuLi (31.6 mL, 79 mmol) was added dropwisely. The mixture was stirred at −70° C. for 1 hour, then (R,E)-N-(cyclohexylmethylene)-2-methylpropane-2-sulfinamide, 26-b, (10 g, 46.5 mmol) in anhydrous THF (100 ml) was added dropwise into the mixture at −70° C. The mixture was then stirred overnight with a temperature range from −70° C.~10° C. After the overnight stirring, the mixture was quenched with saturated NH₄Cl followed by extraction with ethyl acetate. The organic layer was dried over sodium sulfate and concentrated under vacuum. The residue was purified by column chromatography (petroleum ether/ethyl acetate=30/1) to provide the product, 26-c, (1.5 g, 43%). HPLC indicated that the diastereomer ratio is nearly 99:1.

Step C: Ethyl-4-((R)-cyclohexyl((R)-1,1-dimethyl-ethylsulfinamido)methyl)phenyl(methyl)phosphinate (26-d)

To compound 26-c (2.6 g, 6.98 mmol), ethyl methylphosphite (1.5 g, 13.978 mmol) and Et₃N (2.11 g, 21 mmol) in THF (250 ml) was added PdCl₂(dppf) (0.805 g) and the resulting mixture was stirred overnight at reflux. The mixture was cooled to room temperature and filtered and the filtrate was concentrated under vacuum. The residue was taken into dichloromethane and washed with brine. The organic layer was concentrated under vacuum and the residue was purified over silica gel (petroleum ether:ethyl acetate=1/100) to provide the product, 26-d, (1.7 g, 61%).

Step D: Ethyl 4-((R)-amino(cyclohexyl)methyl)phenyl(methyl)phosphinate hydrochloride (26-e)

A solution of compound 26-d (1.7 g, 4.26 mmol) in HCl/dioxane (30 mL) was stirred at room temperature for 2 h. The mixture was then concentrated under vacuum and the residue was washed with ethyl acetate to provide the product, 26-e, (1.6 g, 80%).

Step E: Ethyl 4-((R)-cyclohexyl(4-hydroxy-2-(1H-pyrazol-1-yl)pyrimidine-5-carboxamido)methyl)phenyl(methyl)phosphinate (26-f)

To a stirred solution of 4-hydroxy-2-(1H-pyrazol-1-yl)pyrimidine-5-carboxylic acid, 8-b, (1.187 g, 5.76 mmol) and Et₃N (1.75 mg, 17.3 mmol) in DMF (15 mL) was added HATU (2.62 mg, 6.9 mmol). The mixture was stirred for 5 min at room temperature and then compound 26-e (1.7 g, 5.76 mmol) was added. The resulting mixture was stirred at room temperature for 15 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (ethyl acetate:MeOH=5/1) to provide the product, 26-f, (1.05 g, 49%).

Step F: 4-((R)-cyclohexyl(4-hydroxy-2-(1H-pyrazol-1-yl)pyrimidine-5-carboxamido)methyl)phenyl(methyl)phosphinic acid (26-1)

A solution of 26-f (0.98 g, 2.03 mmol) in 15 ml of dioxane was treated with 2 ml of 5N NaOH and heated at 80° C. for 2 hour. The reaction solution was cooled to room temperature and then concentrated under vacuum and the residue was diluted with water and washed with ethyl acetate. The aqueous layer was acidified with conc. HCl to pH=1 and the resulting solids were collected via filtration to give 26-1 (170 mg 38.4%). $^1$H NMR (300 MHz, DMSO-$d_6$): δ 10.06 (s, 1H), 8.60 (s, 1H), 8.37 (s, 1H), 8.04 (s, 1H), 7.70 (m, 2H), 7.50 (m, 2H), 6.70 (s, 1H), 4.87 (m, 1H), 1.52 (m, 9H), 1.15 (m, 5H). (M+H)⁺=456.1.

Example 27

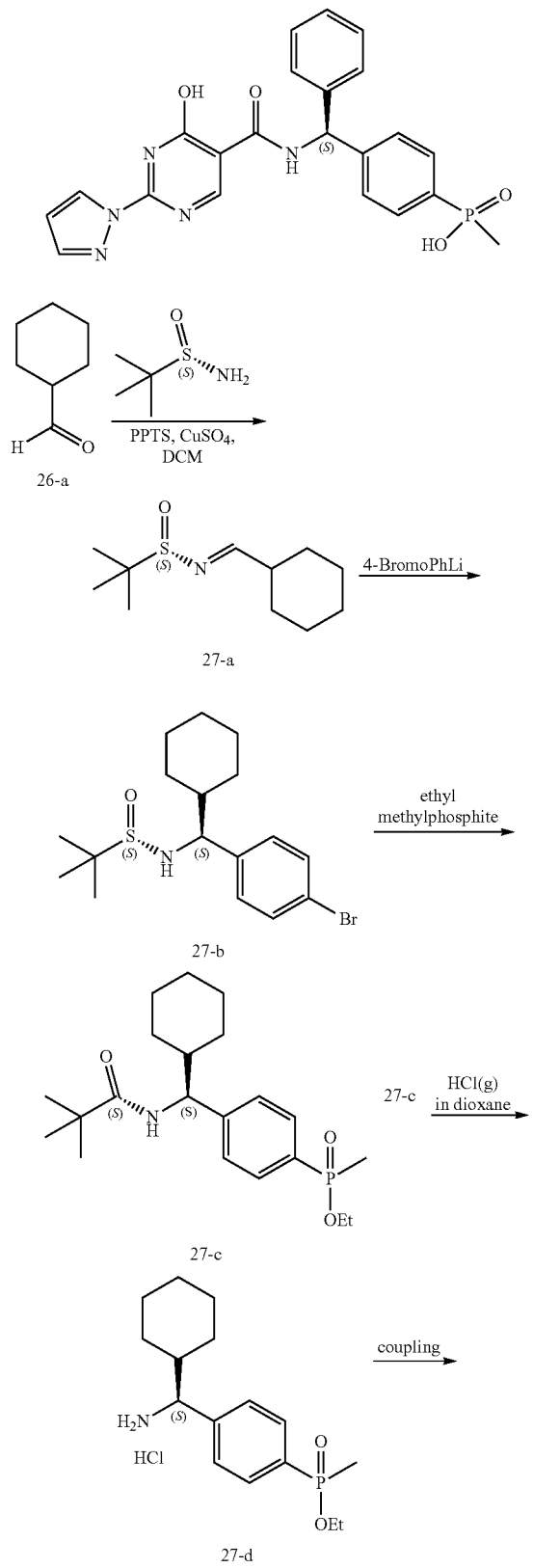

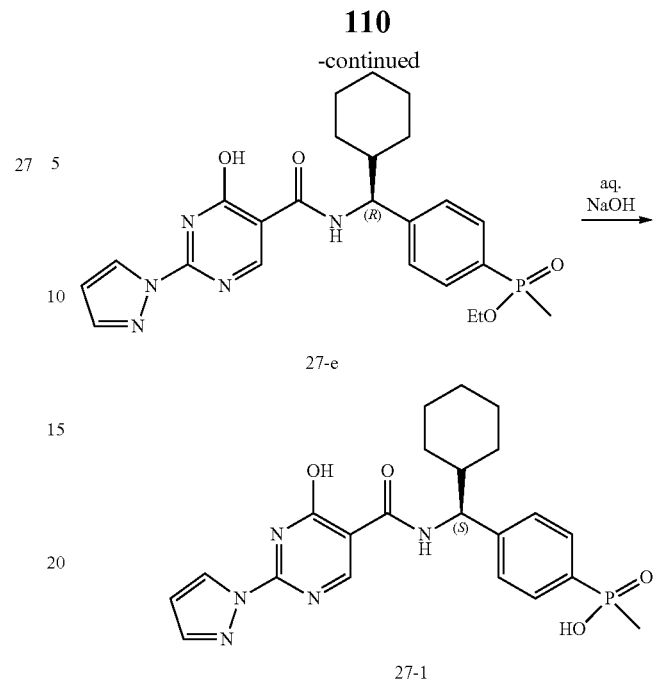

Step A: (S,E)-N-(cyclohexylmethylene)-2-methyl-propane-2-sulfinamide (27-a)

Cyclohexanecarbaldehyde, 26-a, (13.6 g, 0.121 mol) in dichloromethane (250 mL) were added (S)-2-methylpropane-2-sulfinamide (17.6 g, 0.145 mol), PPTS (3.03 g, 0.0121 mmol) and anhydrous $CuSO_4$ (58 g, 0.363 mol) and the resulting mixture was stirred at 37° C. overnight. The mixture was then filtrated and the filtrate was concentrated under vacuum. The residue was purified by column chromatography (petroleum ether/ethyl acetate=100/1) to provide the product, 27-a, (14 g, 31.1%).

Step B: (S)—N—((S)-(4-bromophenyl(cyclohexyl)methyl)-2-methylpropane-2-sulfinamide (27-b)

1,4-dibromobenzene (20 g, 84.7 mmol) was dissolved in anhydrous THF (300 ml) and the resulting mixture was then cooled to −70° C. Then BuLi (34 mL, 84.6 mmol) was added dropwise at that temperature. The mixture was stirred at −70° C. for 1 hour, then (S,E)-N-(cyclohexylmethylene)-2-methylpropane-2-sulfinamide, 27-a, (14 g, 65 mmol) in anhydrous THF (30 ml) was added dropwise into the mixture at −70° C. The mixture was then stirred overnight from −70° C. to 10° C. The mixture was quenched with saturated $NH_4Cl$ followed by extraction with ethyl acetate. The organic layer was dried over sodium sulfate and concentrated under vacuum. The residue was purified by column chromatography (petroleum ether/ethyl acetate=30/1) to provide the product, 27-b, (5.4 g, 22.33%). HPLC indicated that the reaction underwent excellent stereoselectivity.

Step C: Ethyl 4-((S)-cyclohexyl((S)-1,1-dimethylethylsulfinamido)methyl)phenyl(methyl)phosphinate (27-c)

To (S)—N—((S)-(4-bromophenyl)(cyclohexyl)methyl)-2-methylpropane-2-sulfinamide, 27-b. (4.887 g, 13.13 mmol), ethyl methylphosphite (2.84 g, 26.26 mmol) and $Et_3N$ (3.98 g, 39.4 mmol) in THF (100 ml) was added $PdCl_2(dppf)$ (1.5 g). The mixture was allowed to stir overnight at reflux. The mixture was filtered and the filtrate was concentrated under vacuum. The residue was taken into dichloromethane and washed with brine. The organic layer was concentrated under vacuum and the residue was purified over silica gel (diluting with ethyl acetate) to provide the product, 27-c, (5.0 g, 90%).

Step D: Ethyl 4-((S)-amino(cyclohexyl)methyl)phenyl(methyl)phosphinate hydrochloride (27-d)

Ethyl 4-((S)-cyclohexyl((S)-1,1-dimethylethylsulfinamido)methyl)phenyl(methyl)phosphinate, 27-c, (5.0 g, 12.5 mmol) was dissolved in HCl/dioxane (100 mL) and the mixture was stirred at room temperature for 2 h. The reaction mixture was then concentrated under vacuum and the residue was washed with ethyl acetate to provide the product, 27-d, (4.2 g, 90%).

Step E: Ethyl 4-((S)-cyclohexyl(4-hydroxy-2-(1H-pyrazol-1-yl)pyrimidine-5-carboxamido)methyl)phenyl(methyl)phosphinate (27-e)

To a stirred solution of 8-b (2.6 g, 12.6 mmol) and Et$_3$N (3.8 g, 37.8 mmol) in DMF (50 mL) was added HATU (5.8 g, 15.2 mmol). The mixture was stirred for 5 min at room temperature and then ethyl 4-((S)-amino(cyclohexyl)methyl)phenyl(methyl)phosphinate hydrochloride, 27-d, (4.2 g, 12.6 mmol) was added. The resulting mixture was stirred at room temperature for 15 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (ethyl acetate: MeOH=10/1) to provide the product, 27-e, (3.3 g, 54.1%).

Step F: 4-((S)-cyclohexyl(4-hydroxy-2-(1H-pyrazol-1-yl)pyrimidine-5-carboxamido)methyl)phenyl(methyl)phosphinic acid (27-1)

A solution of 27-e (0.90 g, 1.86 mmol) in 30 ml of dioxane was treated with 3 ml of 3N NaOH and heated at 80° C. for 2 hour. The mixture was cooled to room temperature and then concentrated under vacuum and the residue was diluted with water and washed with ethyl acetate. The aqueous layer was acidified with conc. HCl to pH=1 and resulting solids were collected via filtration to give 27-1 (400 mg 47.2%). $^1$H NMR (300 MHz, DMSO-d$_6$): δ 10.06 (br, 1H), 8.62 (s, 1H), 8.38 (s, 1H), 8.07 (s, 1H), 7.70 (m, 2H), 7.39 (m, 2H), 6.73 (s, 1H), 4.88 (m, 1H), 1.52 (m, 9H), 1.16 (m, 5H). (M+H)$^+$=456.2.

Example 28

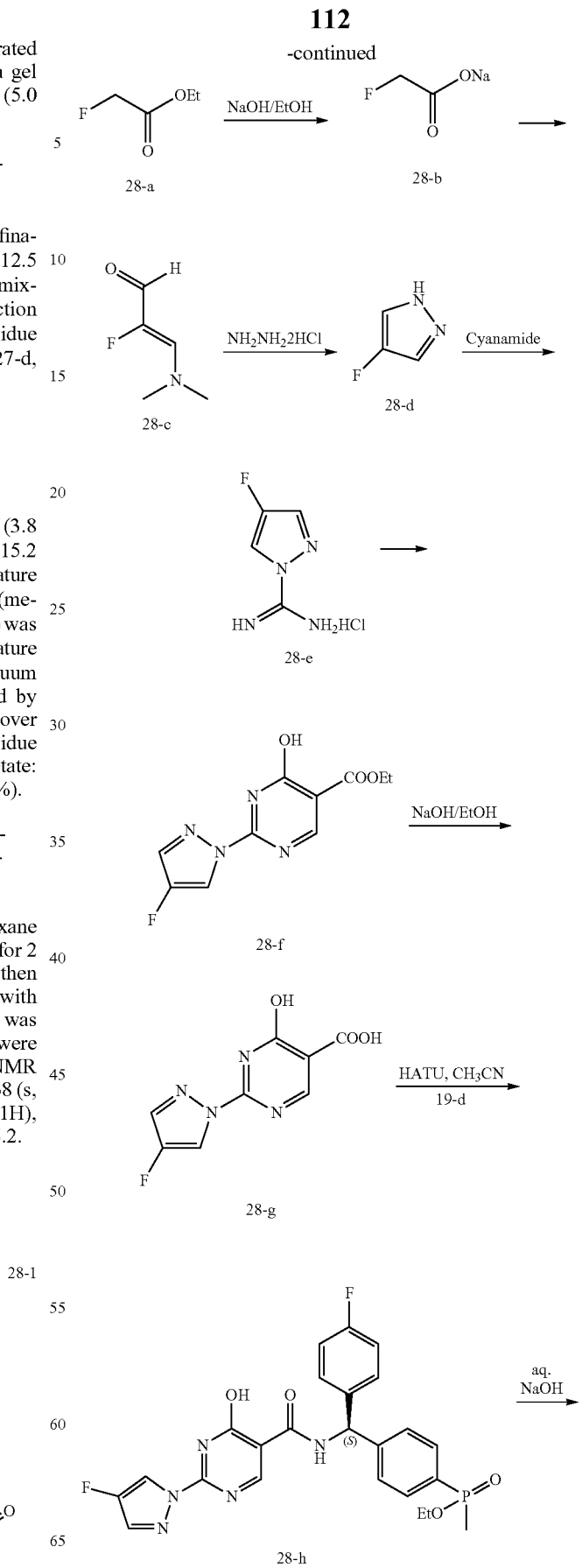

113

-continued

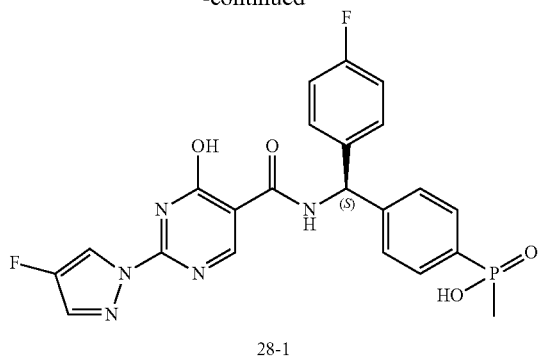

28-1

Step A: Sodium 2-fluoroacetate (28-b)

Ethyl 2-fluoroacetate, 28-a, (107 g, 1 mol) was dissolved in absolute EtOH (1 L), cooled to 0° C. and NaOH (40 g, 1 mol) in EtOH was added. The reaction was stirred overnight after which petroleum ether was added. The reaction solution was cooled to −20° C. and filtered giving 104 g of title compound, 28-b, as white solid (yield 99%).

Step B: (Z)-3-(dimethylamino)-2-fluoroacrylaldehyde (28-c)

A suspension of sodium 2-fluoroacetate, 28-b, (50 g, 0.5 mol) in DMF was cooled to 0° C. and oxalyl chloride was added dropwise over 40 minutes. The reaction mixture was stirred for 30 minutes at room temperature, then heated to 60° C. for a further 30 minutes, and $Et_3N$ was added dropwise over 20 minutes while the temperature was at 0° C. The reaction mixture was stirred at 0° C. for 30 minutes and at 50° C. for 30 minutes. The reaction mixture was cooled to 0° C. and 100 mL of ice water was added, then 650 mL of saturated $K_2CO_3$ solution was added. The reaction mixture was heated at 80° C. for 30 minutes, then 350 mL of brine was added while the temperature was at room temperature. The aqueous phase was extracted with $CH_2Cl_2$, then the organic layer was dried with $Na_2SO_4$. The crude was purified by column chromatography (EA) giving 21 g of the title compound, 28-c.

Step C: 4-fluoro-1H-pyrazole (28-d)

Hydrazine dihydrochloride (4.48 g, 0.043 mol) was added to a solution of (Z)-3-(dimethylamino)-2-fluoroacrylaldehyde, 28-c, (5 g, 0.043 mol) in 100 mL of 40% V/V solution of EtOH in water, then the mixture was heated at 55° C. for 30 minutes. The reaction was cooled to room temperature, basified to pH=9 with a saturated solution of $NaHCO_3$ and the aqueous layer was extracted with $Et_2O$. The organic layers were combined and dried with $Na_2SO_4$, the solvent was removed to give 3.6 g of the titled product, 28-d, as a yellow oil (77%).

Step D: 4-fluoro-1H-pyrazole-1-carboxamidine hydrochloride (28-e)

To 4-fluoro-1H-pyrazole, 28-d, (2 g, 23 mmol) and cyanamide (0.97 g, 23 mmol) in dioxane (5 mL) was added 4N HCl

114 in dioxane (15 mL). The mixture was gently refluxed with stirring for 2 h under nitrogen. During the course of the reaction the product crystallizes. After cooling to room temperature, 10 mL of anhydrous ether was added and the mixture was allowed to stand for 30 min. The white solid was collected by filtration, washed with anhydrous ether and dried to constant weight in vacuuo providing the product, 28-e, (3 g, 80%).

Step E: Ethyl 2-(4-fluoro-1H-pyrazol-1-yl)-4-hydroxypyrimidine-5-carboxylate (28-f)

To a solution of 28-e (2 g, 12 mmol) in EtOH was added sodium methoxide (1 g, 18 mmol) and diethyl ethoxymethylenemalonate (2.64 g, 12 mmol). The reaction was cooled to room temperature, filtered and washed with EtOH and $Et_2O$ to afford the title product, 28-f, (1.9 g, 61%).

Step F: 2-(4-fluoro-1H-pyrazol-1-yl)-4-hydroxypyrimidine-5-carboxylic acid (28-g)

Ethyl 2-(4-fluoro-1H-pyrazol-1-yl)-4-hydroxypyrimidine-5-carboxylate, 28-f, (1 g, 3.9 mmol) was dissolved in EtOH (7 mL) and KOH (0.67 g, 11.9 mmol) in $H_2O$ (3 mL) was added. The mixture was stirred at 78° C. for 1.5 h. Then the solvent was evaporated, and the residue was added about 10 mL of $H_2O$ and filtered. The solid was dried and washed by EtOH (5 mL) to give the title product, 28-g, (0.7 g).

Step G: Ethyl 4-((S)-(2-(4-fluoro-1H-pyrazol-1-yl)-4-hydroxypyrimidine-5-carboxamido)(4-fluorophenyl)methyl)phenyl(methyl)phosphinate (28-h)

To a stirred solution of 28-g (2.8 g, 12 mmol) and $Et_3N$ (3.5 g, 34 mmol) in MeCN (30 ml) was added HATU (4.8 g, 12 mmol). The mixture was stirred for 5 min at room temperature and then ethyl 4-((S)-amino(4-fluorophenyl)methyl)phenyl(methyl)phosphinate, 19-d, (3.5 g, 1 mmol) was added. The resulting mixture was stirred at room temperature for 1 hour. Then it was concentrated under vacuum and the residue was taken into ethyl acetate followed by washing with 1N HCl. The organic layer was dried over sodium sulfate and concentrated under vacuum. The residue was purified on silica gel chromatography (petroleum ether:ethyl acetate=1/1) to provide the product, 28-h, (1.2 g, 18.7%).

Step H: 4-((S)-(2-(4-fluoro-1H-pyrazol-1-yl)-4-hydroxypyrimidine-5-carboxamido)(4-fluorophenyl) methyl)phenyl(methyl)phosphinic acid (28-1)

A solution of 28-h (3.8 g, 7.4 mmol) in 25 ml of dioxane was treated with 7.2 ml of 3N NaOH and heated at 80° C. for one hour. The mixture was cooled to room temperature and then concentrated under vacuum and the residue was diluted with water and washed with ethyl acetate. The aqueous layer was acidified with conc. HCl to pH=1 and the resulting solid was collected via filtration to give compound 28-1 (1.4 g of crude), which was further purified via prep-HPLC (150 mg, 4%). $^1$H NMR (300 MHz, $CD_3OD$): δ 8.72 (s, 1H), 8.17 (s, 1H), 7.81 (m, 3H), 7.43 (m, 2H), 7.20 (m, 2H), 7.11 (m, 2H), 6.71 (s, 1H), 1.65 (d, 3H). $(M+H)^+=486.0$.

Example 29

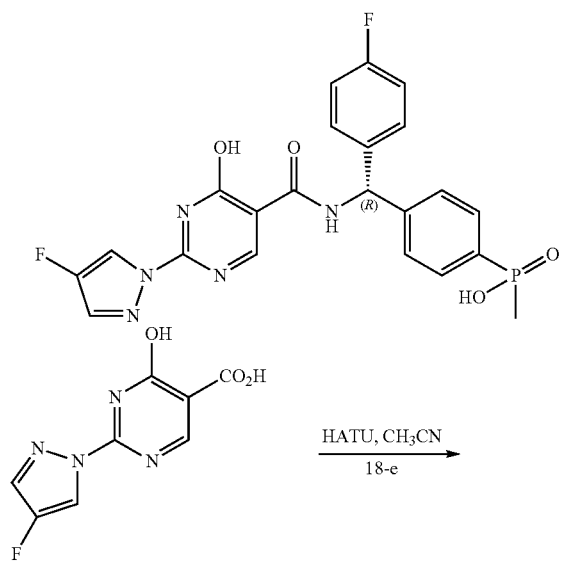

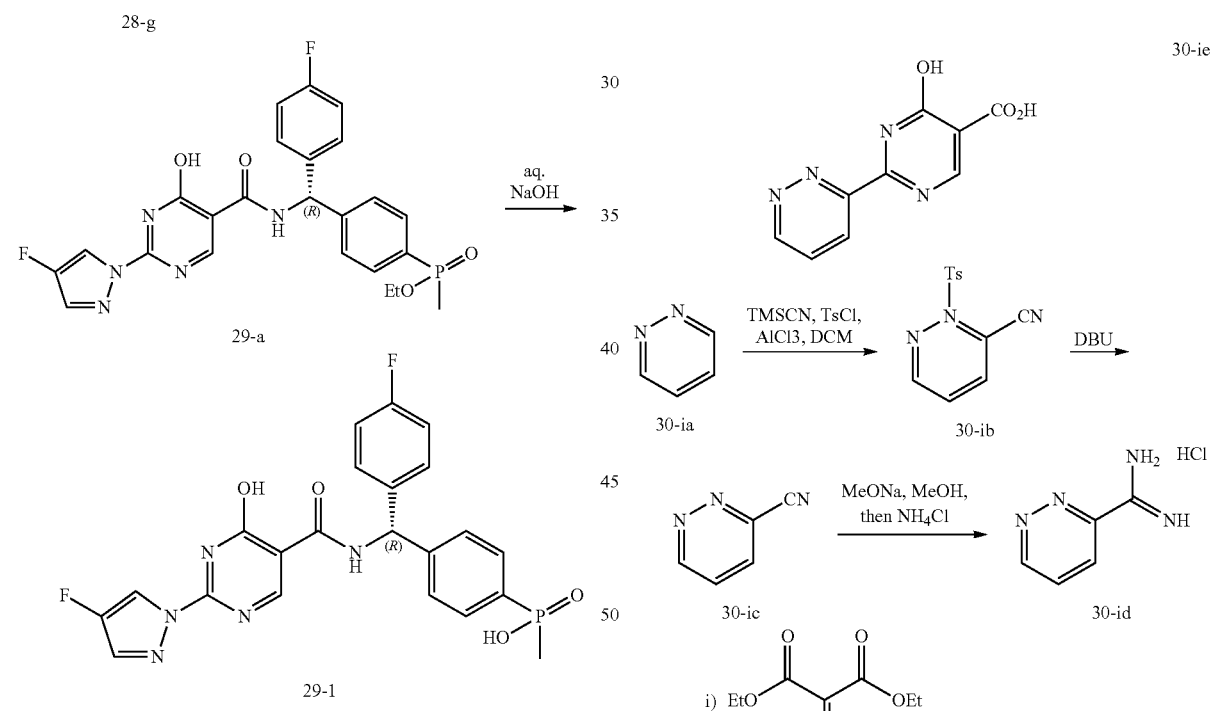

Step A: Ethyl 4-((R)-(2-(4-fluoro-1H-pyrazol-1-yl)-4-hydroxypyrimidine-5-carboxamido)(4-fluorophenyl)methyl)phenyl(methyl)phosphinate (29-a)

To a stirred solution of 28-g (2.8 g, 12 mmol) and Et$_3$N (3.5 g, 34 mmol) in MeCN (30 ml) was added HATU (4.8 g, 12 mmol). The mixture was stirred for 5 min at room temperature and then ethyl 4-((R)-amino(4-fluoro phenyl)methyl)phenyl (methyl)phosphinate, 18-e, (3.5 g, 11 mmol) was added. The resulting mixture was stirred at room temperature for 1 hour. The mixture was then concentrated under vacuum and the residue was taken into ethyl acetate followed by washing with 1N HCl. The organic layer was dried over sodium sulfate and concentrated under vacuum. The residue was purified on silica gel chromatography (petroleum ether:ethyl acetate=1/1) to provide the product, 29-a, (1 g, 15.7%).

Step B: 4-((R)-(2-(4-fluoro-1H-pyrazol-1-yl)-4-hydroxypyrimidine-5-carboxamido)(4-fluorophenyl)methyl)phenyl(methyl)phosphinic acid (29-1)

A solution of compound 29-a (4 g, 7.8 mmol) in 30 ml of dioxane was treated with 7 ml of 3N NaOH. The mixture was heated at 80° C. for one hour. The mixture was then concentrated under vacuum and the resulting residue was diluted with water and washed with ethyl acetate. The aqueous layer was acidified with conc. HCl to pH=1 and the expected product, 29-1, crashed out (700 mg of crude). The product can be further purified via prep-HPLC (152 mg, 5%). $^1$H NMR (300 MHz, CD$_3$OD): δ 8.66 (s, 1H), 8.57 (d, 1H), 7.81 (d, 1H), 7.77 (m, 2H), 7.52 (m, 2H), 7.20 (m, 2H), 7.13 (m, 2H), 6.38 (s, 1H), 1.65 (d, 3H). (M+H)$^+$=486.2.

Example 30

Intermediate 30-ie

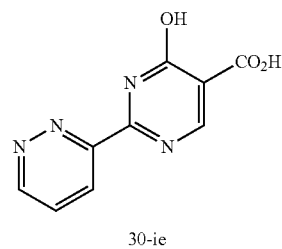

Step A: 2-Tosyl-2,3-dihydropyridazine-3-carbonitrile (30-ib)

A solution of pyridazine, 30-ia, (5 mL, 69.12 mmol), aluminum chloride (28 mg, 0.21 mmol) and TMSCN (16.75 mmol) in DCM (60 mL) was stirred under a nitrogen atmosphere at 0° C. for 20 min. A solution of TsCl (22.75 g, 119.7 mmol) in DCM (40 mL) was added dropwise. The reaction was warmed to room temperature, stirred for an additional 60 h, and concentrated in vacuo. The residue was washed with EtOH (150 mL) and the resulting solids were filtered to afford the title compound, 30-ib, (15 g, 83%). $^1$H NMR (300 MHz, CDCl$_3$) δ7.93 (d, J=8.4 Hz, 2H), 7.38 (d, J=1.8 Hz, 2H), 6.23-6.21 (m, 2H), 5.79 (d, J=6.3 Hz, 1H), 2.44 (s, 3H). LC-MS: (M+H)$^+$ 262.

Step B: Pyridazine-3-carbonitrile (30-ic)

To a solution of compound 30-ib (9.0 g, 34.4 mmol) in THF (100 mL) was added DBU (6.5 ml, 68.9 mmol). The reaction mixture was stirred at room temperature under a nitrogen atmosphere for 1 h. The reaction was quenched with saturated aqueous NH$_4$Cl (100 mL) and water (150 mL). The layers were separated and the aqueous layer was extracted with EtOAc (2×150 mL). The combined organic extracts were dried, filtered, and concentrated, and the residue was washed with hexane (100 mL) to afford the title compound, 30-ic, (2.7 g, 75%). $^1$H NMR (300 MHz, CDCl$_3$) δ9.40 (dd, J=1.5, 5.1 Hz), 7.88 (dd, J=1.8, 8.4 Hz), 7.70 (dd, J=5.1, 8.4 Hz). LC-MS: (M+H)$^+$ 106.

Step C: Pyridazine-3-carboximidamide hydrochloride (30-id)

To a solution of Pyridazine-3-carbonitrile, 30-ic, (2.7 g, 25.7 mmol) in MeOH (25 mL) was added sodium methoxide (139 mg, 0.257 mmol). The reaction was stirred at room temperature overnight when ammonium chloride (1.65 g, 30.8 mmol) was added. The reaction was refluxed for 3 h, cooled to room temperature and concentrated to afford the crude product, 30-id, (4.2 g, crude). $^1$H NMR (300 MHz, DMSO-d$_6$) δ9.38 (dd, J=1.5, 5.1 Hz, 1H), 8.30 (dd, J=1.5, 8.7 Hz, 1H), 7.92 (dd, J=5.1, 8.4 Hz, 1H). LC-MS: (M+H)$^+$ 123.

Step D: 4-Hydroxy-2-(pyridazin-3-yl)pyrimidine-5-carboxylic acid (30-ie)

A mixture of crude Pyridazine-3-carboximidamide hydrochloride, 30-id, (4.2 g, 34.4 mmol), diethyl ethoxymethylenemalonate (6.5 mL, 34.4 mmol) and sodium methoxide (1.85 g, 41.3 mmol) in MeOH (100 mL) was refluxed overnight. The reaction mixture was added with KOH (3.8 g, 68.8 mmol) and refluxed for 4 h. The reaction was concentrated. The residue was dissolved with water (30 mL) and extracted with EtOAc. The aqueous layer was adjusted to pH=2 by addition of concentrated aq. HCl. The solids was filtered and rinsed with water and hexane to afford the title compound, 30-ie, (3 g, 40%). $^1$H NMR (300 MHz, CD$_3$OD) δ14.7 (s, 1H), 9.50 (dd, J=1.6, 5.0 Hz), 8.57 (s, 1H), 8.51 (dd, J=1.6, 8.4 Hz, 1H), 8.01 (dd, J=5.0, 8.4 Hz, 1H), 3.44 (s, 1H). LC-MS: (M+H)$^+$ 219.

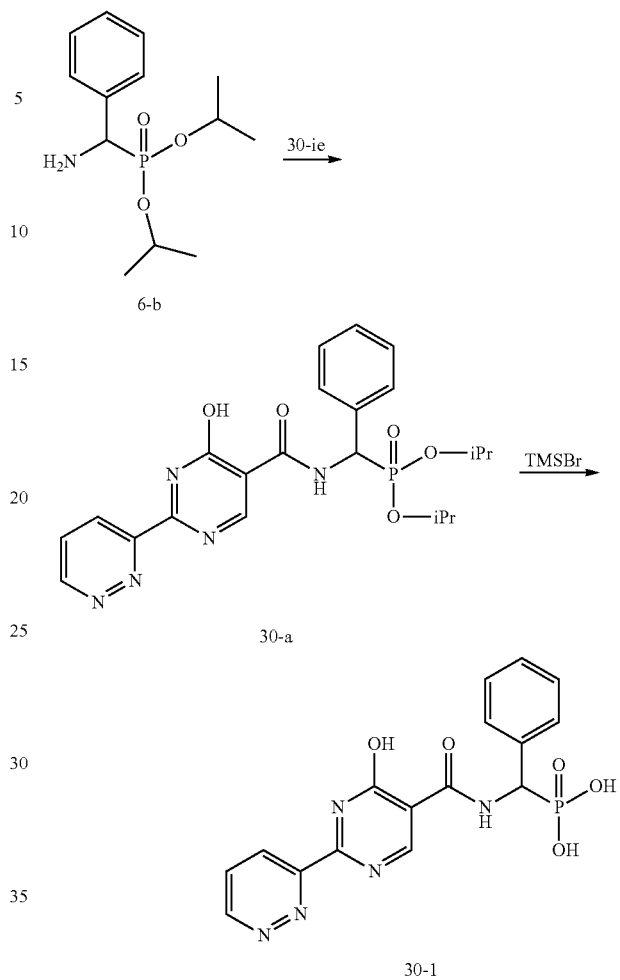

Example 30

Step A: Diisopropyl (4-hydroxy-2-(pyridazin-3-yl)pyrimidine-5-carboxamido)(phenyl)methyl phosphonate (30-a)

A solution of 4-hydroxy-2-(pyridazin-3-yl)pyrimidine-5-carboxylic acid, 30-ie, (1.0 g, 4.6 mmol) in SOCl$_2$ (20 mL was stirred at 65° C. for 4 h. The solution was then concentrated in vacuum to remove the solvent to afford a residue, which was added dropwise to a solution of diisopropyl amino(phenyl)methylphosphonate, 6-b, (2.49 g, 9.2 mmol) and TEA (1.85 g, 18.3 mmol) in anhydrous DCM (40 mL). The mixture was stirred at 25° C. overnight, extracted with DCM (100 mL×3), washed with water (50 mL×3), dried over Na$_2$SO$_4$ and concentrated in vacuum. The residue was purified by column chromatography on silica gel using petroleum ether:ethyl acetate=1:1 (volumn:volumn) as the eluent to give the desired compound, 30-a, as a yellow solid (700 mg, 32%). $^1$H NMR (300 MHz, CDCl$_3$) δ11.87-11.66 (m, 1H); 10.11-10.06 (m, 1H), 9.42-9.40 (m, 1H), 9.04 (s, 1H), 8.63-8.60 (m, 1H), 7.79-7.75 (m, 1H), 7.49-7.47 (m, 2H), 7.35-7.27 (m, 2H), 5.71-5.61 (m, 1H), 4.70-4.59 (m, 2H), 3.57-3.40 (m, 1H), 1.33-1.11 (m, 12H); LC-MS (M+H)$^+$ 472.

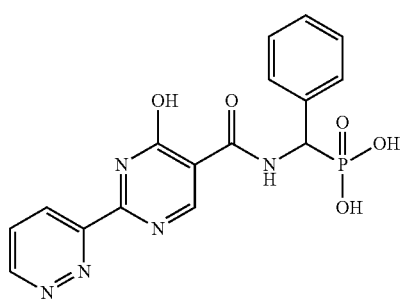

30-1

Step B: (4-hydroxy-2-(pyridazin-3-yl)pyrimidine-5-carboxamido)(phenyl)methylphosphonic acid (30-1)

To a solution of diisopropyl(4-hydroxy-2-(pyridazin-3-yl)pyrimidine-5-carboxamido)(phenyl)methylphosphonate, 30-a, (600 mg, 1.3 mmol) in DCM (50 mL) was added TMSBr (2 mL) at 0° C. The resulting solution was stirred at room temperature under a nitrogen atmosphere overnight. Then ice-water was added and organic layer was dried over $Na_2SO_4$, filtrated, and concentrated to afford a residue, which was purified by washing with hot MeCN, MeOH and $Et_2O$ to give the desired compound, 30-1, as a yellow solid (410 mg, 83%). $^1$H NMR (300 MHz, DMSO-$d_6$) δ9.51-9.48 (m, 1H), 8.55-8.51 (m, 1H), 8.03-7.98 (m, 1H), 7.38-7.31 (m, 5H), 7.27-7.22 (m, 1H), 5.36-5.26 (m, 1H), LC-MS (M+H)$^{388}$.

The following compounds (30-2 and 30-3) were prepared in a similar manner as the synthesis of compound 30-1.

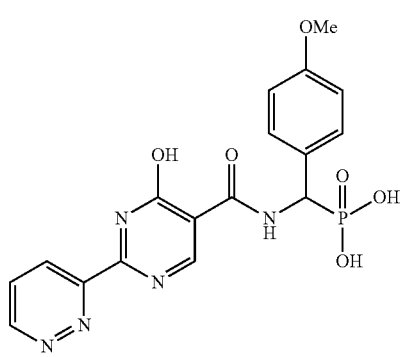

30-2

(4-Hydroxy-2-(pyridazin-3-yl)pyrimidine-5-carboxamido)(4-methoxyphenyl)methyl phosphonic acid (30-2)

$^1$H NMR (300 MHz, DMSO-$d_6$) δ3.72 (s, 3H), 5.19-5.29 (m, 1H), 6.89 (d, J=8.4 Hz, 2H), 7.26-7.28 (m, 2H), 7.97-8.02 (m, 1H), 8.50-8.53 (d, J=8.4 Hz, 2H), 9.47-9.49 (m, 1H). LC-MS: (M+H)$^+$ 418.

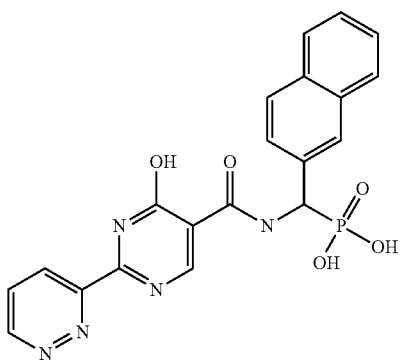

30-3

(4-Hydroxy-2-(pyridazin-3-yl)pyrimidine-5-carboxamido)(naphthalen-2-yl)methyl phosphonic acid (30-3)

$^1$H NMR (300 MHz, DMSO-$d_6$) δ5.40-5.50 (m, 1H), 7.44-7.56 (m, 3H), 7.83-8.02 (m, 5H), 8.51-8.54 (m, 2H), 9.43-9.49 (m, 1H), 10.59-10.71 (m, 1H), 11.25-11.61 (m, 1H); LC-MS: (M+H)$^+$ 438.

Example 31

General Procedure for the Synthesis of Phosphonic Diamides (31-1 and 31-2)

The phosphonic acid (200 mg, 0.4 mmol) and amino acid ethyl ester HCl salt (1.6 mmol) in pyridine (5 mL) was added TEA (164 mg, 1.6 mmol). The mixture was stirred for 5 min before the addition of PPh$_3$ (478 mg, 1.8 mmol) and Aldrithiol-2 (402 mg, 1.8 mmol) in pyridine. The resulting mixture was heated at 60° C. overnight. The mixture was then concentrated under vacuum and the residue was purified on silica gel chromatography to provide the desired compound. The following phosphonic diamides were prepared according to this procedure:

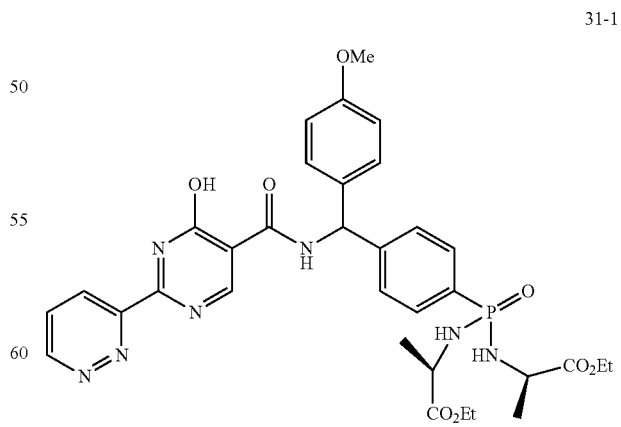

31-1

Diethyl 2,2'-((4-((4-hydroxy-2-(pyridazin-3-yl)pyrimidine-5-carboxamido)(4-methoxyphenyl)methyl)phenyl)phosphoryl)phosphoryl)bis(azanediyl)diacetate (31-1), the yield was 59%. $^1$H NMR (CDCl$_3$, 300 MHz,): δ 9.96-9.91 (m, 1H), 9.43-9.41 (m, 1H), 9.10 (s, 1H), 8.66-8.63 (m, 1H), 7.88-7.77 (m, 3H), 7.46-7.43 (m, 2H), 7.27-7.22 (d, J=8.4 Hz, 2H), 6.90-6.87 (d, J=8.4 Hz, 2H), 6.45-6.42 (d, J=8.4 Hz, 1H), 4.21-4.14 (m, 4H), 3.90-3.83 (m, 2H,), 3.80 (s, 3H), 3.75-3.64 (m, 2H), 1.28-1.23 (m, 6H), LC-MS: (M+H)$^+$ 664.
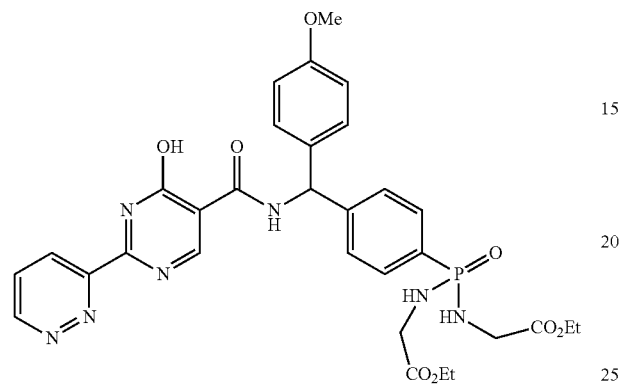
31-2
(2S,2'S)-Diethyl 2,2'-((4-((4-hydroxy-2-(pyridazin-3-yl)pyrimidine-5-carboxamido)(4-methoxyphenyl)methyl)phenyl)phosphoryl)bis(azanediyl)dipropanoate (31-2), the yield was 30%. $^1$H NMR (CD$_3$OD, 300 MHz,): δ 9.38-9.37 (s, 1H), 8.83 (s, 1H), 8.66-8.63 (d, J=8.4 Hz, 1H), 7.96-7.91 (m, 1H), 7.84-7.77 (m, 2H), 7.47-7.45 (m, 2H), 7.26-7.23 (d, J=8.4 Hz, 2H), 6.91-6.88 (d, J=8.4 Hz, 2H), 6.32 (s, 1H), 4.14-4.10 (m, 2H), 3.96-3.91 (m, 4H,), 3.76 (s, 3H), 1.36-1.32 (m, 6H), 1.26-1.21 (m, 3H), 1.09-1.03 (m, 3H), LC-MS: (M+H)$^+$ 692.
Example 32
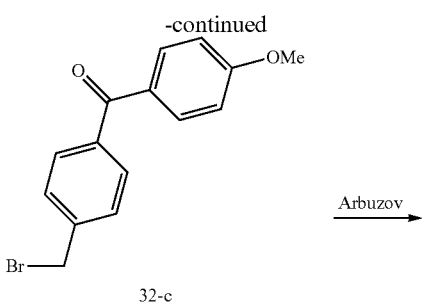
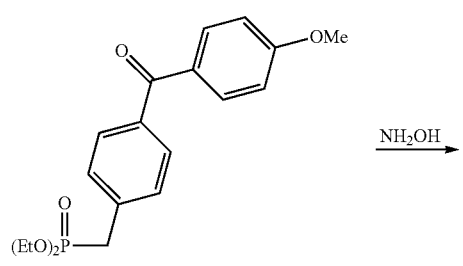
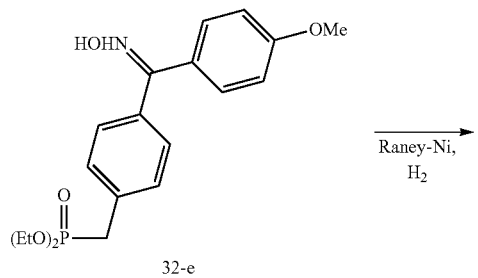
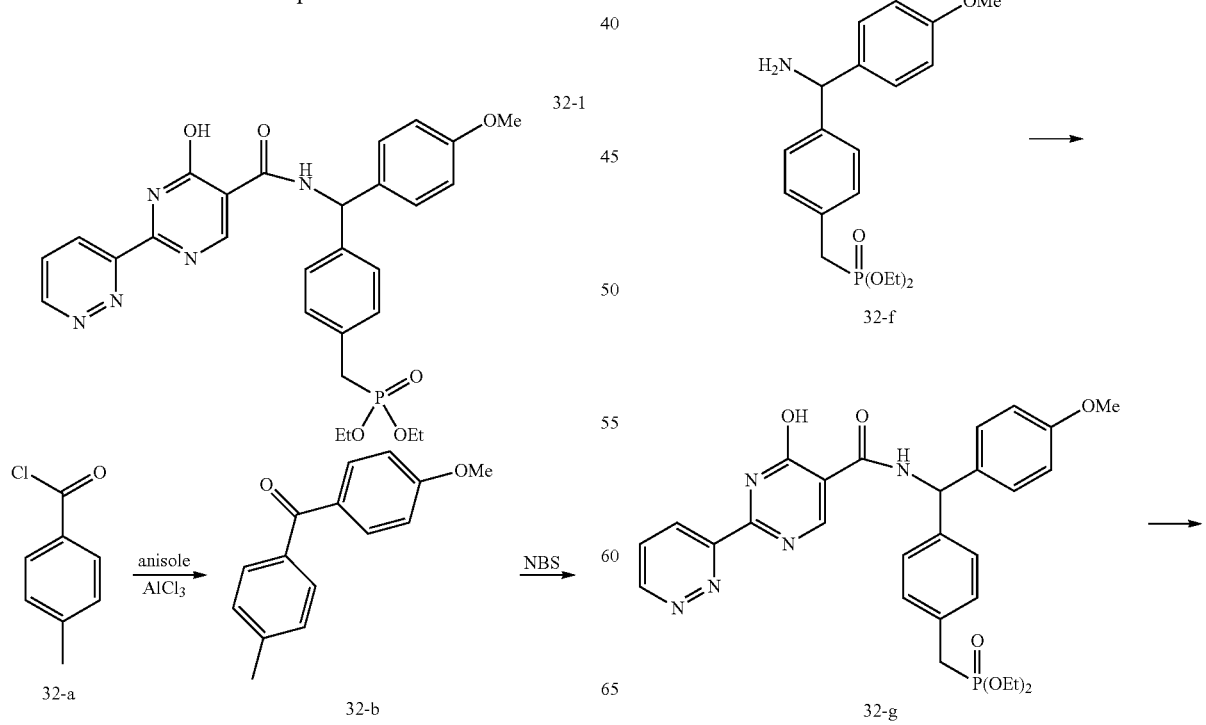

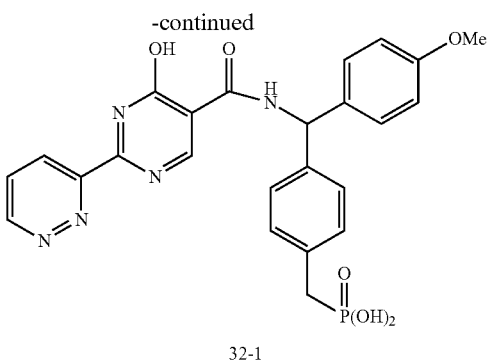

32-1

Step A: (4-methoxyphenyl)(p-tolyl)methanone (32-b)

To a solution of 4-methylbenzoyl chloride, 32-a, (10 g, 65 mmol) and anisole (8.8 g, 81 mmol) in DCM anhydrous was added aluminum(III) chloride (10.8 g, 81 mmol), the reaction mixture was then stirred for 10 h at ambient temperature. The resulting mixture was concentrated under reduce pressure, 100 ml of water was added, filtered, the residue was dried in vacuo. The product was obtained as a white solid, 32-b, (14 g, 95% yield). $^1$H NMR (300 MHz, DMSO-$d_6$) δ 2.25 (s, 3H), 3.71 (s, 3H), 6.85-6.89 (m, 2H), 7.11-7.19 (m, 6H). LC-MS 227 [MH]$^+$.

Step B: (4-(bromomethyl)phenyl)(4-methoxyphenyl)methanone (32-c)

To a solution of (4-methoxyphenyl)(p-tolyl)methanone, 32-b. (3 g, 13.3 mmol) in CCL$_4$ (30 ml) was added NBS (2.8 g, 16 mmol) and AIBN (50 mg), the reaction mixture was then stirred for 3 h under refluxed. The resulting mixture was cooled to ambient temperature, filtered, and filtrate was concentrated under reduce pressure. Purified by column chromatography on silica gel (petroleum ether/ethyl acetate=6:1), the pure product, 32-c, was obtained as a colorless oil (3 g, 74% yield). $^1$H NMR (300 MHz, DMSO-$d_6$) δ 3.84 (s, 3H), 4.49 (s, 2H), 6.90-6.94 (m, 2H), 7.43-7.61 (m, 2H), 7.67-7.79 (m, 4H). LC-MS 305 [MH]$^+$.

Step C: Diethyl 4-(4-methoxybenzoyl)benzylphosphonate (32-d)

(4-(bromomethyl)phenyl)(4-methoxyphenyl)methanone, 32-c, (3 g, 10 mmol) and triethyl phosphite (2 g, 11.9 mmol) was dissolved in DMF (20 ml), and then stirred for 10 h at 150° C. The resulting mixture was cooled to ambient temperature, diluted with water (50 ml) and extracted with ethyl acetate (3×50 ml). The organic layer was combined, washed with brine (2×100 ml), dried over Na$_2$SO$_4$ anhydrous, purified by chromatography on silica gel (petroleum ether/ethyl acetate=1:1.5). The pure product, 32-d, was obtained as a colorless oil (2.6 g, 72% yield). $^1$H NMR (300 MHz, CDCl$_3$) δ 1.20-1.27 (m, 6H), 2.80-2.88 (d, J=22.8, 2H) 3.81 (s, 3H), 3.93-4.07 (m, 4H), 6.86-6.90 (m, 2H), 7.31-7.35 (m, 2H), 7.62-7.93 (m, 4H). LC-MS 363 [MH]$^+$.

Step D: Diethyl 4-((hydroxyimino)(4-methoxyphenyl)methyl)benzylphosphonate (32-e)

Diethyl 4-(4-methoxybenzoyl)benzylphosphonate, 32-d, (500 mg, 1.38 mmol) was dissolved in 95% EtOH (5 ml). Hydroxylamine hydrochloride (288 mg, 4.14 mmol) and Na$_2$CO$_3$ (439 mg, 4.14 mmol) was added to the solution. The reaction mixture was then stirred for 10 h under reflux. The resulting mixture was cooled to ambient temperature, filtered. The filtrate was concentrated under reduce pressure, extracted with ethyl acetate/H$_2$O (3×10 ml). The organic layer was combined and washed with brine (2×10 ml) dried over Na$_2$SO$_4$ anhydrous, concentrated under reduce pressure to dry. The pure product, 32-e, was obtained as colorless oil (460 mg, 88% yield). $^1$H NMR (300 MHz, CDCl$_3$) δ 0.67-0.85 (m, 6H), 2.628-3.306 (m, 2H), 3.30-3.35 (d, J=46.8, 3H), 3.51-3.63 (m, 4H), 6.31-6.33 (m, 1H), 6.44-6.47 (m, 1H), 6.74-6.92 (m, 6H). LC-MS 378 [MH]$^+$.

Step E: Diethyl 4-(amino(4-methoxyphenyl)methyl)benzylphosphonate (32-f)

Diethyl 4-((hydroxyimino)(4-methoxyphenyl)methyl)benzylphosphonate, 32-e, (450 mg, 1.2 mmol) was dissolved in EtOH (10 ml), Raney Ni (50 mg) was added, and the resulting mixture was then stirred for 12 h at ambient temperature under hydrogen. The solution was filtered, filtrate was concentrated under reduce pressure, purified by column chromatography (DCM/MeOH=20:1). The product was obtained as a white solid, 32-f, (400 mg, 92%). $^1$H NMR (300 MHz, CDCl$_3$) δ 1.18-1.23 (t, J=6.9 Hz 6H), 2.27 (s, 2H), 3.04-3.11 (d, J=21.6 Hz 2H) 3.74 (s, 3H), 3.93-3.99 (m, 4H), 5.12 (s, 1H), 6.78-6.81 (d, J=8.7 Hz, 2H), 7.18-7.28 (m, 6H). LC-MS 364 [MH]$^+$.

Step F: Diethyl 4-((4-hydroxy-2-(pyridazin-3-yl)pyrimidine-5-carboxamido)(4-methoxy phenyl)methyl)benzylphosphonate (32-g)

4-hydroxy-2-(pyridazin-3-yl)pyrimidine-5-carboxylic acid, 30-ie, (325 mg, 1.5 mmol) and diethyl 4-(amino(4-methoxyphenyl)methyl)benzylphosphonate, 32-f, (540 mg, 1.5 mmol) was dissolved in DMF (5 ml), HATU (570 mg, 1.5 mmol) and DIEA (590 mg, 4.5 mmol) were then added, the reaction mixture was stirred for 2 h at 50° C. under nitrogen. The resulting mixture was cooled to ambient temperature, diluted with water (10 ml), filtered, the residue was washed with water for 3 times, a brown solid was obtained, 32-g, (500 mg, 60% yield). $^1$H NMR (300 MHz, DMSO-$d_6$) δ 1.14-1.18 (t, J=4.2 Hz 6H), 3.16-3.23 (d, J=21.3 Hz 2H), 3.73 (s, 3H) 3.89-3.98 (m, 4H), 6.20-6.22 (d, J=7.8 Hz, 1H), 6.89-6.92 (m, 2H), 7.20-7.24 (m, 6H), 7.99-8.02 (m, 1H), 8.49-8.58 (m, 2H), 9.48-9.50 (m, 1H), 14.00 (s, 1H). LC-MS 564 [MH]$^+$.

Step G: 4-((4-hydroxy-2-(pyridazin-3-yl)pyrimidine-5-carboxamido)(4-methoxyphenyl)methyl)benzylphosphonic acid (32-1)

diethyl 4-((4-hydroxy-2-(pyridazin-3-yl)pyrimidine-5-carboxamido)(4-methoxyphenyl)methyl)benzylphosphonate (32-g, 450 mg, 0.8 mmol) was dissolved in DCM (10 ml), TMSBr (1.8 g, 12 mmol) was then added, the reaction mixture was stirred for 14 h at ambient temperature, monitored by TLC. The resulting mixture was concentrated under reduce pressure, the residue was dissolved in CH$_3$CN (5 ml), diluted with water (10 ml), stirred for 10 min, filtered, washed with water, purified by pre-HPLC, the pure product 32-1 was obtained as a white solid (104 mg, 26% yield). $^1$H NMR (300 MHz, CD$_3$OD) δ2.97-3.04 (d, J=21.6 Hz 2H) 3.67 (s, 1H) 6.17 (s, 1H), 6.78-6.81 (m, 2H) 7.12-7.20 (m, 6H), 7.80-7.90 (m, 1H), 8.49-8.58 (m, 1H), 8.75 (s, 1H), 9.28 (m, 1H). LC-MS 508 [MH]$^+$.

Example 33

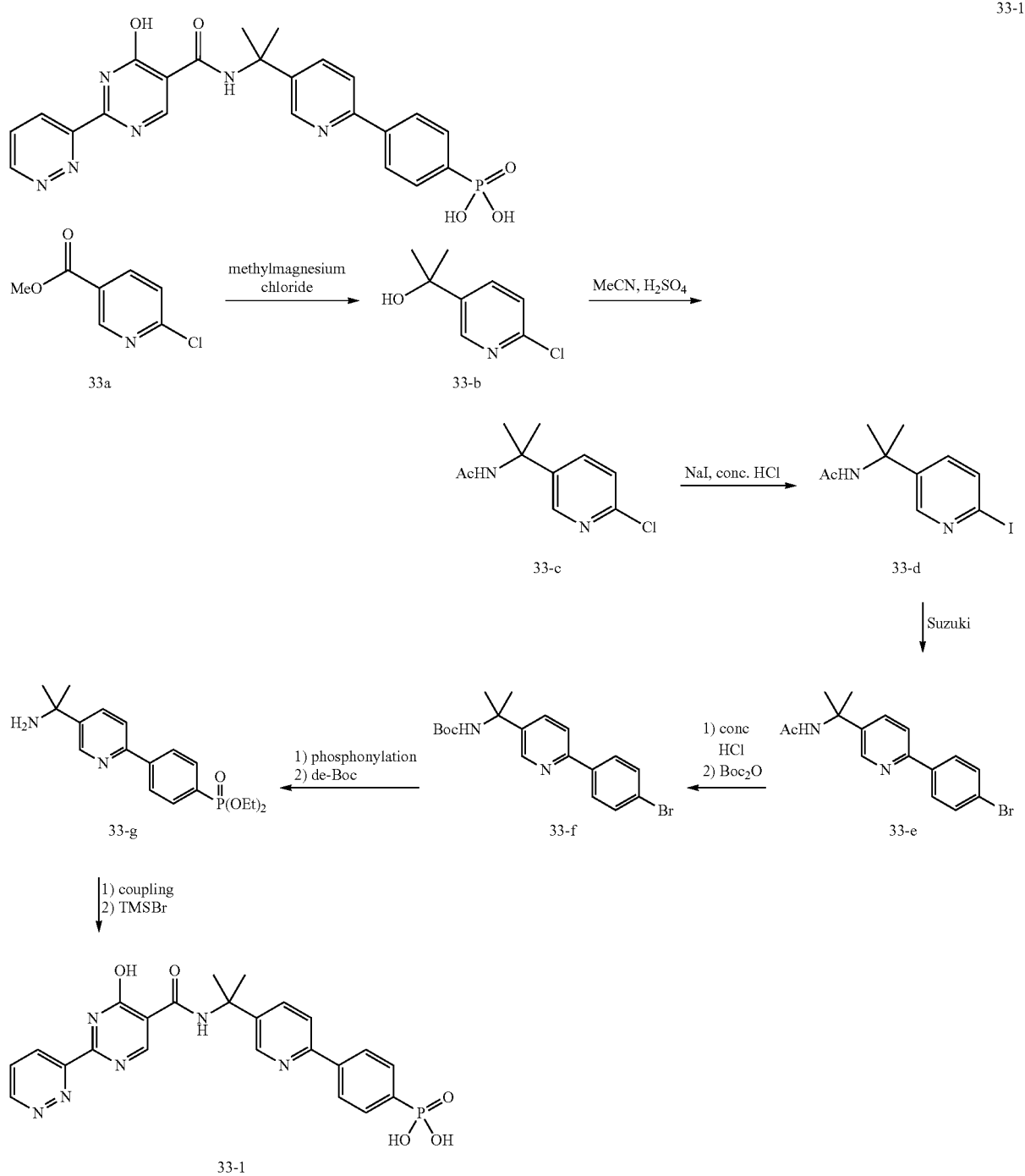

Step A: 2-(6-chloropyridin-3-yl)propan-2-ol (33-b)

The methylmagnesium chloride (58.3 ml, 174.8 mmol) was added to a 1 L 3-neck flask and diluted with 100 ml THF and cooled to 0° C. The methyl 6-chloronicotinate, 33-a, (10 g, 58.3 mmol) was dissolved in THF (50 ml) and added dropwisely to the Grignard reagent. The reaction solution was stirred at room temperature for 30 mins while being monitored by TLC. The reaction mixture was poured into 500 ml of 1N HCl and extracted with ether (2×200 mL). The combined organic extracts were washed with brine, dried with MgSO$_4$, and concentrated under vacuum to give 33-b (10 g, 100%).

Step B: N-(2-(6-chloropyridin-3-yl)propan-2-yl) acetamide (33-c)

To a solution of 2-(6-chloropyridin-3-yl)propan-2-ol, 33-b, (10 g, 58.3 mmol) in MeCN (100 ml) was added dropwise H$_2$SO$_4$ (40 g, 408 mmol) at 0° C., while keeping the internal temperature below 15° C. After the addition was completed, the reaction mixture was warmed to room temperature and stirred for 24 hours. The reaction mixture was then cooled to 0° C. and diluted with NH₄OH slowly. The reaction mixture was then extracted with ether (3×100 mL), dried, and concentrated. The product was purified by silica gel (DCM-DCM:MeOH=30:1) to give a white solid, 33-c, (9 g, 72.6%)

Step C: N-(2-(6-iodopyridin-3-yl)propan-2-yl)acetamide (33-d)

To a solution of N-(2-(6-chloropyridin-3-yl)propan-2-yl)acetamide, 33-c, (25 g, 0.12 mol) in MeCN (400 ml) was added NaI (353 g, 2.35 mol) and concentrated HCl (48 ml, 0.59 mol). The reaction mixture was then refluxed for 60 hours. Product conversion was monitored by LC-MS. The reaction mixture was filtered and the cake was washed with MeCN. The filtrate was concentrated under vacuo and the residue was diluted with ethyl acetate, washed with saturated aqueous Na₂S2O3 and brine, dried and concentrated to give the product, 33-d, as a white solid (22 g, 61%).

Step D: N-(2-(6-(4-bromophenyl)pyridin-3-yl)propan-2-yl)acetamide (33-e)

To a solution of N-(2-(6-iodopyridin-3-yl)propan-2-yl)acetamide, 33-d, (22 g, 72.4 mmol) in dioxane (100 ml) was added 4-bromophenylboronic acid (16 g, 79.6 mmol) and Pd(PPh₃)₄ (4.2 g, 3.62 mmol) and aq Na₂CO₃ (2N) (25.3 g, 238.8 mmol). The reaction mixture was then stirred at 95° C. for 3 hours. The reaction mixture was then cooled to room temperature and concentrated under vacuo. The concentrate was extracted with ethyl acetate, washed with brine, and re-concentrated. Purification by silica gel (petroleum ether: ethyl acetate=1:1-ethyl acetate) gave the solid, 33-e, (18 g, 75%).

Step E: Tert-butyl 2-(6-(4-bromophenyl)pyridin-3-yl)propan-2-ylcarbamate (33-f)

To a solution of compound 33-e (5 g, 15 mmol) in H₂O (25 ml) was added concentrated HCl (12.3 ml, 150 mmol). The reaction mixture was then refluxed for 60 hours. The reaction mixture was then cooled to room temperature and extracted with ethyl acetate. The water phase was adjusted to a pH of about 8-10 by aqueous NaOH (2N), then extracted with ethyl acetate and washed with brine, dried and concentrated to give 2-(6-(4-bromophenyl)pyridin-3-yl)propan-2-amine (2.6 g, 59%).

To a solution of 2-(6-(4-bromophenyl)pyridin-3-yl)propan-2-amine (2.6 g, 8.93 mmol) and Et₃N (2.3 g, 22.3 mmol) in DCM (30 ml) was added (Boc)₂O (2.9 g, 13.4 mmol) in DCM (10 ml). Then the reaction mixture was stirred at room temperature for overnight. The mixture was washed with brine, dried and concentrated, purified by silica gel (DCM~DCM:MeOH=50:1) to give compound 33-f (1.26 g, 36%).

Step F: Diethyl 4-(5-(2-aminopropan-2-yl)pyridin-2-yl)phenylphosphonate (33-g)

To a solution of tert-butyl 2-(6-(4-bromophenyl)pyridin-3-yl)propan-2-ylcarbamate, 33-f, (850 mg, 2.17 mmol) in toluene (15 ml) was added diethyl phosphonate (900 mg, 6.52 mmol) and Et₃N (660 mg, 6.52 mmol) and PdCl₂(dppf) (85 mg) under N₂, and the reaction mixture was refluxed for 8 hours. The reaction solution was then evaporated and diluted with EtOAc. The organic phase was washed with brine, dried and concentrated. Purified by silica gel (DCM-DCM: MeOH=50:1) to give tert-butyl 2-(6-(4-(diethoxyphosphoryl)phenyl)pyridin-3-yl)propan-2-ylcarbamate (900 mg, 92.4%).

tert-butyl 2-(6-(4-(diethoxyphosphoryl)phenyl)pyridin-3-yl)propan-2-ylcarbamate (5.3 g, 11.8 mmol) was dissolved in HCl in dioxane (30 ml), the mixture was stirred at 50° C. for 4 hours. Then evaporated the solvent and the residue diluted with H₂O (5 ml), extracted with ethyl acetate and the water phase was adjusted to pH=9 with 1N aqueous NaOH, extracted with ethyl acetate and the organic phase washed with brine and dried, concentrated under vacuo to give the product 33-g.

Step G: 4-(5-(2-(4-hydroxy-2-(pyridazin-3-yl)pyrimidine-5-carboxamido)propan-2-yl)pyridine-2-yl)phenylphosphonic acid (33-1)

4-hydroxy-2-(pyridazin-3-yl)pyrimidine-5-carboxylic acid, 30-ie, (200 mg, 0.92 mmol) was dissolved in SOCl₂ (5 ml). The mixture was stirred at 60° C. for 4 hours, then concentrated under vacuo. The residue was dissolved with 5 ml of DCM, and added dropwise to a solution of diethyl 4-(5-(2-aminopropan-2-yl)pyridin-2-yl)phenylphosphonate, 33-g, (353 mg, 0.92 mmol) and Et₃N (371 mg, 3.7 mmol) in DCM (10 ml) at 0° C. The mixture was stirred at room temperature for 5 hours and then washed with brine, dried, and concentrated under vacuo to give diethyl 4-(5-(2-(4-hydroxy-2-(pyridazin-3-yl)pyrimidine-5-carboxamido) propan-2-yl)pyridin-2-yl)phenylphosphonate (220 mg, 44%).

To a solution of diethyl 4-(5-(2-(4-hydroxy-2-(pyridazin-3-yl)pyrimidine-5-carboxamido) propan-2-yl)pyridin-2-yl) phenylphosphonate (180 mg, 0.33 mmol) in DCM (5 ml) was added dropwise TMSBr (1.50 g, 9.85 mmol) at 0° C., the reaction mixture was stirred at room temperature for overnight. Then evaporated the solution and diluted with 20 ml MeOH, and stirred at room temperature for 30 mins, concentrated under vacuo, purified by Pre-HPLC to give product 33-1. $^1$H NMR (CDCl₃-d₆, 300 MHz,): δ 9.50 (s, 1H), 8.71 (s, 1H), 8.50 (d, 1H), 8.11 (m, 2H), 7.72-8.02 (m, 5H), 3.15 (s, 1H), 1.76 (s, 6H). (M+H)⁺=493.1.

Example 34

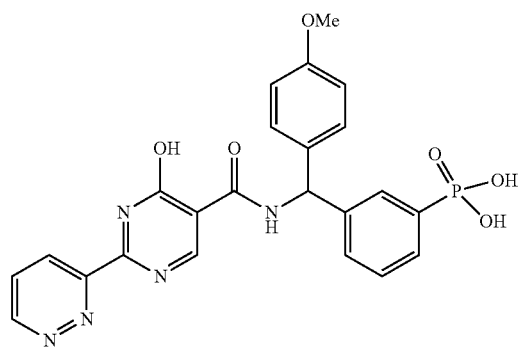

34-1

3-((4-hydroxy-2-(pyridazin-3-yl)pyrimidine-5-carboxamido)(4-methoxyphenyl)methyl)phenylphosphonic acid (34-1)

Compound 34-1, was prepared from compound 5-d and 30-ie in a similar manner as the synthesis of compound 5-1. $^1$H NMR (DMSO-d₆, 300 MHz,): δ 10.41 (s, 1H), 9.48-9.50 (m, 1H,), 8.50-8.53 (m, 1H), 7.98-8.03 (m, 1H), 7.52-7.65 (m, 2H), 7.43-7.46 (m, 2H), 7.24-7.26 (d, J=6 Hz 2H), 6.93-9.6 (m, 2H), 6.27-6.29 (d, J=6 Hz 2H), 3.74 (s, 3H). (M−H)⁻=492.1.

Example 35

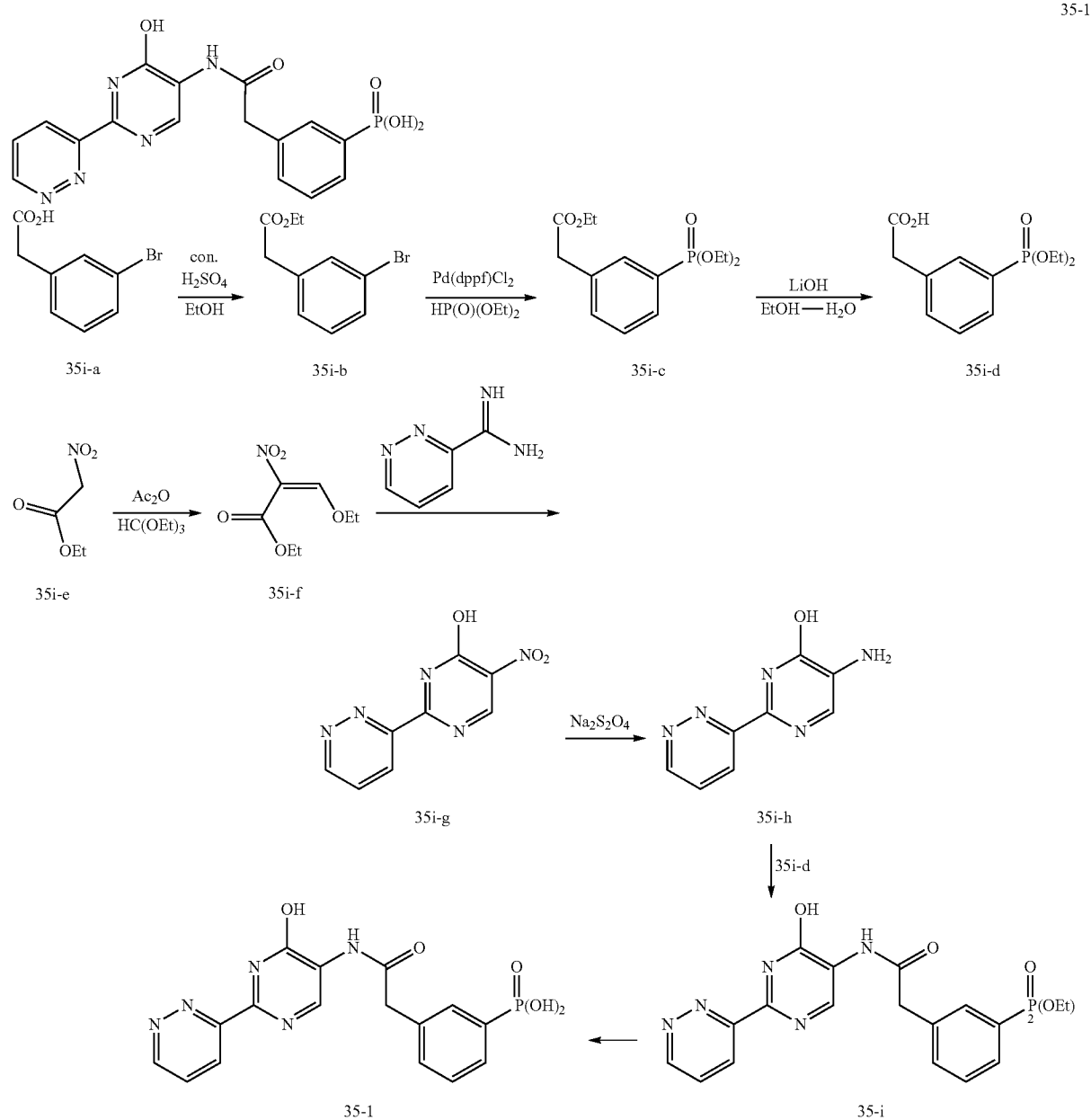

Step A: Ethyl 2-(3-bromophenyl)acetate (35i-b)

3-Bromophenylacetic acid, 35i-a, (50 g, 0.23 mol) was dissolved in ethanol (250 mL) and sulfuric acid was added drop-wise. The mixture was heated to reflux and stirred overnight. The solution was adjusted to about a pH of 7-8 with sodium hydroxide solution and concentrated in vacuo. The water phase was extracted with ethyl acetate (3×150 mL) and the combined organics was washed with brine (50 mL) and dried, concentrated to give the compound, 35i-b, (52.6 g, 93%) as colorless oil. $^1$H NMR (300 MHz, CDCl$_3$) δ 1.24-1.29 (m, 3H), 3.58 (s, 2H), 4.11-4.19 (m, 2H), 7.18-7.25 (m, 2H), 7.38-7.44 (m, 2H). LC-MS (M+H)$^+$ 243, 245.

Step B: Ethyl 2-(3-(diethoxyphosphoryl)phenyl)acetate (35i-c)

To a solution of ethyl 2-(3-bromophenyl)acetate, 35i-b, (22.1 g, 90 mmol), diethylphosphite (25.1 g, 180 mmol) and triethylamine (27.5 g, 270 mmol) in toluene (300 mL) was added [1,1'-bis(diphenylphosphino) ferrocene]dicholoropalladium (3 g). The mixture was allowed to stir overnight at 110° C. and was filtered. The solution was concentrated to afford the crude product which was purified by column chromatography to give the title compound, 35i-c as yellow brown oil (26 g, crude). $^1$H NMR (300 MHz, CDCl$_3$): δ 1.20-1.32 (m, 9H), 3.62 (s, 2H), 4.00-4.16 (m, 6H), 7.36-7.47 (m, 2H), 7.64-7.71 (m, 2H). LC-MS (M+H)$^+$ 301.

Step C: 2-(3-(diethoxyphosphoryl)phenyl)acetic acid (35i-d)

A mixture of ethyl 2-(3-(diethoxyphosphoryl)phenyl)acetate, 35i-c, (26 g, 86.7 mmol) and LiOH.H$_2$O (5.5 g, 130 mmol) in ethanol (40 mL) and H$_2$O (40 mL) was stirred overnight. The resulting mixture was concentrated and washed by ethyl acetate. The aqueous layers were adjusted to about pH 1-2 with HCl. The mixture was extracted by ethyl acetate. The combined organic layers were washed by brine, dried over Na$_2$SO$_4$ and concentrated to afford the title compound, 35i-d, as brown oil (19 g, 81%). $^1$H NMR (300 MHz, CDCl$_3$) δ 1.15-1.25 (m, 6H), 3.68 (s, 2H), 3.95-4.06 (m, 4H), 7.43-7.64 (m, 4H), 12.32 (s, 1H). LC-MS (M+H)$^+$ 273.

Step D: Ethyl 3-(dimethylamino)-2-nitroacrylate (35i-f)

A mixture of ethyl 2-nitroacetate, 35i-e, (20 mL, 179 mmol) and triethoxymethane (48 mL, 359 mmol) was stirred at room temperature for 2 h, and then stirred at 100° C. for 3 h. The reaction mixture was concentrated in vacuum to afford the crude dark orange liquid, 35i-f, (40 g). LC-MS (M+H)$^+$ 189.1.

Step E: 5-nitro-2-(pyridazin-3-yl)pyrimidin-4-ol (35i-g)

A mixture of ethyl 3-(dimethylamino)-2-nitroacrylate, 35i-f, (1 g, 5.3 mmol) and pyridazine-3-carboximidamide (0.8 g, 5.3 mmol) in CH$_3$OH (30 mL) was added with NaOCH$_3$ (3.4 g, 6.36 mmol) and refluxed overnight. The pH of reaction mixture was adjusted to 7 by addition of concentrated HCl. The solids were filtered to afford the product, 35i-g, (1 g, 86%). $^1$H NMR (300 MHz, DMSO) δ 7.77 (dd, J=4.8, 7.5 Hz, 2H), 8.29 (d, J=8.4 Hz, 1H), 8.77 (s, 1H), 9.26 (d, J=4.5 Hz, 1H). LC-MS (M+H)$^+$ 220.1

Step F: 5-amino-2-(pyridazin-3-yl)pyrimidin-4-ol (35i-h)

To a solution of 5-nitro-2-(pyridazin-3-yl)pyrimidin-4-ol, 35i-g, (3.0 g, 13.6 mmol) in THF/H$_2$O (100 mL, V$_{THF/H2O}$=1:1) was added Na$_2$S$_2$O$_4$ (4.77 g, 27.4 mmol) and stirred at room temperature for 4 h. The reaction mixture was extracted with EA (100 mL), washed with brine (50 mL), and concentrated under vacuum. The residue was purified by column chromatography to afford the product, 35i-h, (0.8 g, 30%) as a yellow solid. $^1$H NMR (300 MHz, CD$_3$OD) δ 5.66 (s, 2H), 7.39 (s, 1H), 7.80 (dd, J=4.8, 8.4 Hz, 1H), 8.29 (d, J=8.4 Hz, 1H), 9.26 (d, J=4.8 Hz), LC-MS (M+H)$^+$ 190.1.

Step G: Diethyl 3-(2-(4-hydroxy-2-(pyridazin-3-yl)pyrimidin-5-ylamino)-2-oxoethyl)phenyl-phosphonate (35i)

A mixture of 5-amino-2-(pyridazin-3-yl)pyrimidin-4-ol, 35i-h, (0.5 g, 2.6 mmol), 2-(3-(diethoxyphosphoryl)phenyl) acetic acid, 35i-d, (0.7 g, 2.6 mmol), HATU (1.5 g, 3.9 mmol) and Et$_3$N (1.2 g, 11.8 mmol) in MeCN (25 mL) was stirred at room temperature overnight. The reaction mixture was concentrated in vacuum. The residue was extracted with EA (100 mL), and then washed with sat. NH$_4$Cl (50 mL), water (50 mL), and brine (50 mL). The organic layer was concentrated and the residue was purified by column chromatography to afford the product, 35i, (280 mg, 25%). LC-MS (M+H)$^+$ 444.1.

Step H: 3-(2-(4-hydroxy-2-(pyridazin-3-yl)pyrimidin-5-ylamino)-2-oxoethyl)phenyl phosphonic acid (35-1)

A solution of diethyl 3-(2-(4-hydroxy-2-(pyridazin-3-yl)pyrimidin-5-ylamino)-2-oxoethyl)phenyl-phosphonate (35i, 280 mg, 0.63 mmol) in DCM (20 mL) was added with TMSBr (1.9 g, 12.6 mmol) and stirred at 30° C. for overnight. The reaction mixture was concentrated in vacuum. The residue was added with MeOH (50 mL), stirred for 20 min, and concentrated. The residue was added with water (20 mL) and MeCN (0.5 mL). The solids were filtered to afford the pure product, 35-1, as a white solid (70 mg, 29%). $^1$H NMR (300 MHz, DMSO) δ 3.9 (s, 2H), 7.39-7.58 (m, 3H), 7.70 (d, J=12.9 Hz, 1H), 7.93 (m, 1H), 8.42 (d, J=8.7 Hz, 1H), 8.86 (m, 1H), 9.40 (d, J=4.2 Hz, 1H), 9.84 (m, 1H), LC-MS (M+H)$^+$ 388.1

Example 36

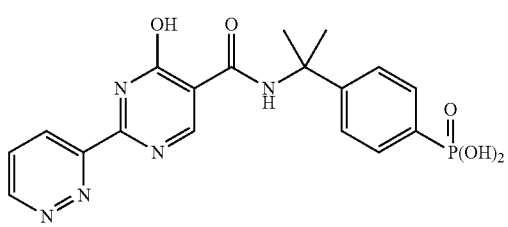

36-1

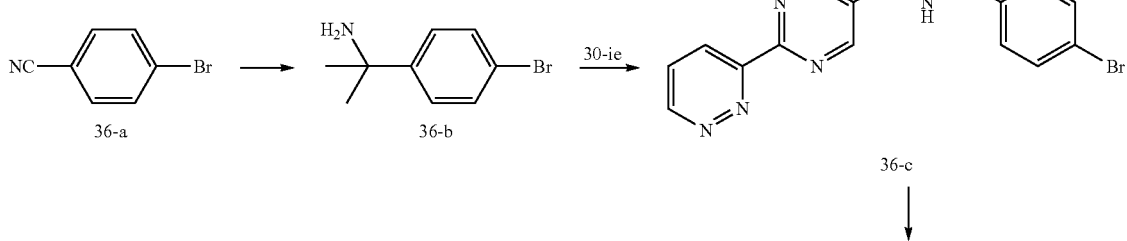

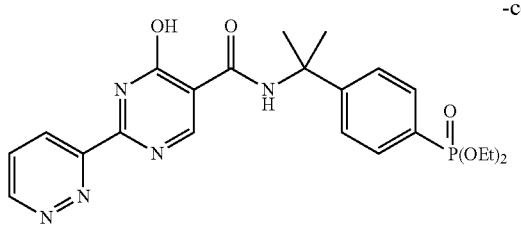

36-d

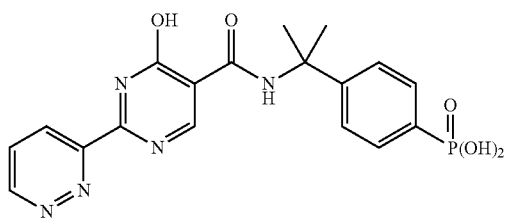

36-1

Step A: 2-(4-Bromophenyl)propan-2-amine (36-b)

A mixture of cerium chloride (8.0 g, 10.9 mmol) in THF (80 mL) was cooled to −70° C. using a dry ice bath. Then methyl lithium (1.5M, 22 mL, 33 mmol) was added and the resulting mixture was stirred for 90 min at −70° C. before adding a solution of 4-bromobenzonitile (36-a, 2.0 g, 10.9 mmol). The mixture was stirred for additional 2 h at −70° C., then warmed to room temperature. Aqueous ammonium hydroxide solution was added and the mixture was filtered. The filtrate was concentrated, then treated with aqueous hydrochloric acid (2 N, 50 mL). The aqueous layer was washed with DCM (2×30 mL), and then adjusted to pH 10 by adding aqueous ammonium hydroxide solution. The mixture was extracted with DCM (3×50 mL). The combined organic layers were dried, concentrated, and purified by chromatography (DCM:MeOH=100:1 as the eluent) to afford compound, 36-b, (700 mg, 30%). $^1$H NMR (300 MHz, CDCl$_3$) δ7.52-7.30 (m, 4H), 2.33 (s, 2H), 1.62 (s, 3H), 1.50 (s, 3H). LC-MS: (M+H—NH$_3$)$^+$ 198.

Step B: N-(2-(4-bromophenyl)propan-2-yl)-4-hydroxy-2-(pyridazin-3-yl)pyrimidine-5-carboxamide (36-c)

A mixture of 4-hydroxy-2-(pyridazin-3-yl)pyrimidine-5-carboxylic acid, 30-ie, (110 mg, 0.5 mmol), 2-(4-bromophenyl)propan-2-amine, 36-b, (70 mg, 0.32 mmol), HATU (290 mg, 0.76 mmol) and DIEA (82 mg, 0.64 mmol) in DMF (3 mL) was stirred at room temperature overnight. The mixture was washed with aqueous NH$_4$Cl (15 mL) and extracted with EtOAc (30 mL). The organic layers were dried and concentrated in vacuo. The residue was washed with hexane to afford compound 36-c (80 mg, 57%). $^1$H NMR (300 MHz, CDCl$_3$) δ11.62 (s, 1H), 9.55 (s, 1H), 9.41 (dd, J=1.5, 4.8 Hz, 1H), 9.00 (d, J=4.2 Hz, 1H), 8.63 (dd, J=1.5, 8.1 Hz, 1H), 7.78 (dd, J=5.1, 8.4 Hz, 1H)), 7.43 (d, J=8.4 Hz, 2H), 7.33 (d, J=8.4 Hz, 2H), 1.78 (s, 6H). LC-MS: (M+H)$^+$ 414.

Step C: Diethyl 4-(2-(4-hydroxy-2-(pyridazin-3-yl)pyrimidine-5-carboxamido)propan-2-yl)phenylphosphonate (36-d)

A mixture of N-(2-(4-bromophenyl)propan-2-yl)-4-hydroxy-2-(pyridazin-3-yl)pyrimidine-5-carboxamide (36-c, 200 mg, 0.484 mmol), diethylphosphite (195 mg, 1.45 mmol), Et$_3$N (146 mg, 1.45 mmol) and Pd (PPh$_3$)$_4$ (0.1 g) in toluene (10 mL) was refluxed overnight. The reaction mixture was concentrated in vacuum. The residue was purified by pre-HPLC to afford the product 36-d, (3.0 mg). $^1$H NMR (300 MHz, DMSO) δ10.85 (s, 1H), 9.08 (s, 1H), 8.75 (d, J=8.4 Hz), 7.86 (m, 1H), 7.61-7.52 (m, 2H), 7.43-7.42 (m, 2H), 4.00-3.92 (m, 4H), 1.61 (s, 6H), 1.20 (t, J=6.9 Hz, 6H). LC-MS: (M+H)$^+$ 472.

Step D: (4-Hydroxy-2-(pyridazin-3-yl)pyrimidine-5-carboxamido)(4-methoxyphenyl)methyl phosphonic acid (36-1)

To a solution of Diethyl 4-(2-(4-hydroxy-2-(pyridazin-3-yl)pyrimidine-5-carboxamido)propan-2-yl)phenylphosphonate, 36-d, (1.50 g, 3.20 mmol) in DCM (50 mL) was added TMSBr (9.7 g, 64 mmol). The resulting mixture was stirred at room temperature under a nitrogen atmosphere for 2 days and concentrated. Then ice water was added into the residue and the resulting mixture was filtered. The solid was washed with methanol to give the title compound, 36-1, (350 mg, 26%). $^1$H NMR (300 MHz, DMSO-d$_6$) δ1.70 (s, 6H), 7.45-7.48 (m, 2H), 7.58-7.65 (m, 2H), 7.98-8.02 (m, 1H), 8.50-8.53 (m, 2H), 9.48-9.50 (m, 1H), 10.05-10.06 (br s, 1H). LC-MS (M+H)$^+$ 416.

Example 37

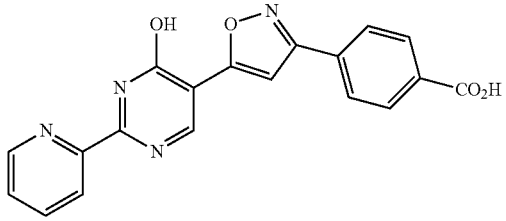

37-1

Step A: Picolinamidine hydrochloride (37-b)

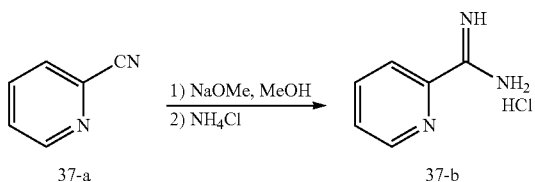 [SMILES: N#Cc1ccccn1 ; N=C(N)c1ccccn1 ; Cl]

To a solution of 2-cyanopyridine (37-a, 100 g, 0.95 mol) in methanol (1.5 L) under nitrogen was added sodium methoxide (2.5 g, 44 mmol). The reaction mixture was stirred at room temperature for 24 h. Then ammonium chloride (53.5 g, 1.0 mol) was added. The mixture was stirred at room temperature for 4 h and the solvent was removed in vacuo. The residue was washed with i-propanol/ethyl acetate=1/10 and dried in vacuo to provide compound 37-b (100 g, 66%).

Step B: Methyl 4-((hydroxyimino)methyl)benzoate (37-d)

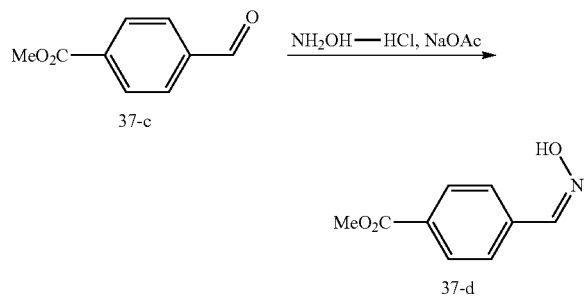

To a solution of methyl 4-formylbenzoate, 37-c, (5.0 g, 30.5 mmol) and hydroxylamine hydrochloride (2.5 g, 36.6 mmol) in THF/H$_2$O (V$_{THF}$:V$_{H2O}$=4:1, 50 mL) was added sodium acetate (3.5 g, 42.7 mmol). The reaction mixture was stirred at room temperature overnight and diluted with dichloromethane (400 mL), washed with water, dried with anhydrous Na$_2$SO$_4$, filtrated and concentrated in vacuo to provide compound, 37-d, (4.9 g, 90%).

Step C: Methyl 4-(chloro(hydroxyimino)methyl)benzoate (37-e)

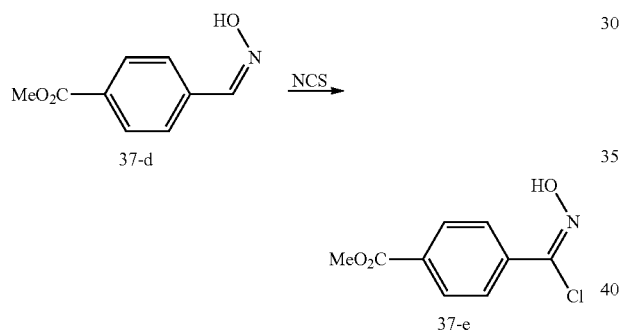

To a solution of compound, 37-d, (2.0 g, 11.2 mmol) in chloroform (30 mL) was added N-chlorosuccinimide (NCS, 1.78 g, 13.4 mmol). The reaction mixture was stirred at room temperature for 4 h. The reaction mixture was diluted with dichloromethane (200 mL), washed with water, dried with anhydrous Na$_2$SO$_4$, filtrated and concentrated in vacuo to provide compound, 37-e, (2.30 g, 96%).

Step D: Methyl 2-iodo-3-methoxyacrylate (37-g)

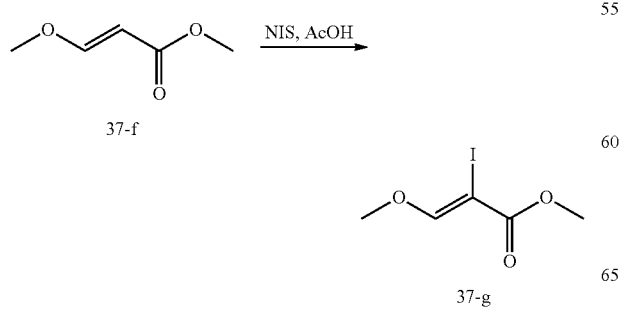

A mixture of methyl-3-methoxypropenoate, 37-f, (13.92 g, 120 mmol), N-iodosuccinimid (32 g, 140 mmol), glacial acetic acid (18 mL, 240 mmol), and dichloromethane (150 mL) was stirred at room temperature for 24 h. Triethylamine (50 mL, 36 mmol) was added, and the reaction mixture was stirred at room temperature for 12 h before water was added. The organic layer was separated and the aqueous layer was extracted with dichloromethane. The combined organic extracts were washed with saturated aqueous sodium thiosulfate, saturated aqueous sodium bicarbonate, and water, and were dried over anhydrous sodium sulfate and concentrated. The residue was purified by flash chromatography (PE:EA=1:5) to afford compound, 37-g (30.5 g, crude). $^1$H NMR (300 MHz, CDCl$_3$) δ 7.69 (s, 1H), 4.01 (s, 3H), 3.80 (s, 3H); LC-MS (ESI): 243 [M+H]$^+$.

Step E: Methyl 2-(methoxymethylene)-4-(trimethylsilyl)but-3-ynoate (37-h)

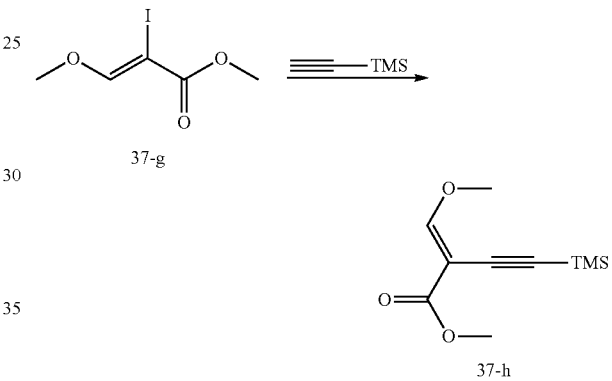

A mixture of compound 37-g (30 g, 124 mmol), ethynyltrimethylsilane (24.3 g, 248 mmol), triethylamine (37.6 g, 372 mmol), copper(I) iodide (2.35 g, 6.2 mmol), Pd(dppf)Cl$_2$ (2.50 g) in DMF (300 mL) was stirred overnight at 80° C. The reaction mixture was cooled to room temperature, poured into ice-water, and extracted with ethyl acetate. The organic layer was washed with water, brine, and dried over sodium sulfate and concentrated. The residue was purified by flash chromatography (PE:EA=1:5) to afford compound 37-h (15 g, 57%) as a yellow solid. $^1$H NMR (300 MHz, CDCl$_3$) δ 7.671 (s, 1H), 3.977 (s, 3H), 3.763 (s, 3H), 0.234 (s, 9H); LC-MS (ESI): 213 [M+H]$^+$.

Step F: 2-(Pyridin-2-yl)-5-((trimethylsilyl)ethynyl)pyrimidin-4-ol (37-i)

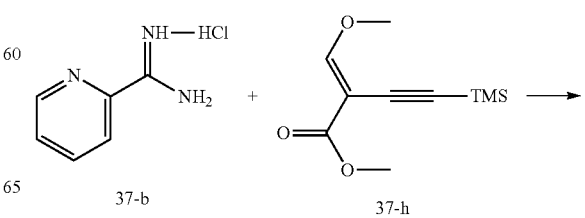

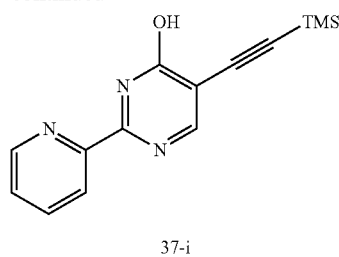

37-i

A mixture of compound 37-b (15 g, 71 mmol), compound 37-h (12.2 g, 77.8 mmol), triethylamine (21.4 g, 212 mmol) in methanol (200 mL) was stirred overnight at room temperature. The residue obtained from removal of the solvent was purified by flash chromatography (DCM) to afford compound 37-i (7.5 g, 39%) as a yellow solid. $^1$H NMR (300 MHz, CDCl$_3$) δ 8.668-8.649 (m, 1H), 8.428-8.395 (m, 1H), 8.257 (s, 1H), 7.937-7.880 (m, 1H), 7.517-7.471 (m, 1H), 0.285 (s, 9H). LC-MS (ESI): 270 [M+H]+

Step G: 5-Ethynyl-4-(4-methoxybenzyloxy)-2-(pyridin-2-yl)pyrimidine (37-j)

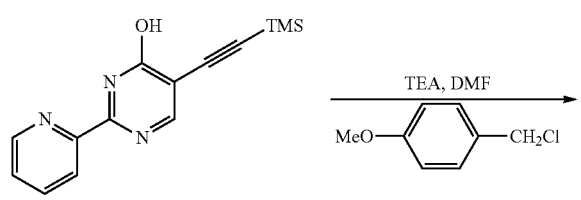

37-i

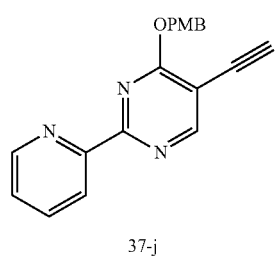

37-j

A mixture of compound 37-i (1.0 g, 3.7 mmol), 1-(chloromethyl)-4-methoxybenzene (0.7 g, 4.4 mmol), and triethylamine (1.5 g, 11.1 mmol) in DMF (10 mL) was stirred overnight at 80° C. The reaction mixture was cooled to room temperature, poured into water, and extracted with ethyl acetate. The combined organic layer was dried over sodium sulfate and concentrated. The residue was purified by flash chromatography (PE:EA=1:3) to afford compound 37-j (300 mg, 25%) as a yellow solid. $^1$H NMR (300 MHz, CDCl$_3$) δ 8.988-8.980 (s, 1H)), 8.775 (s, 1H), 8.581-8.555 (m, 1H), 8.020 (m, 1H), 7.554-7.541 (m, 1H), 7.522-7.493 (d, J=8.7 Hz, 2H), 6.924-6.895 (d, J=8.7 Hz, 2H), 5.741 (s, 2H), 3.807 (s, 1H), 3.509 (s, 1H), LC-MS (ESI): 318 [M+H]+

Step H: Methyl 4-(5-(4-(4-methoxybenzyloxy)-2-(pyridin-2-yl)pyrimidin-5-yl)isoxazol-3-yl)benzoate (37-k)

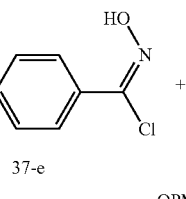

37-e

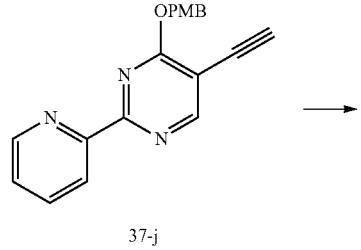

37-j

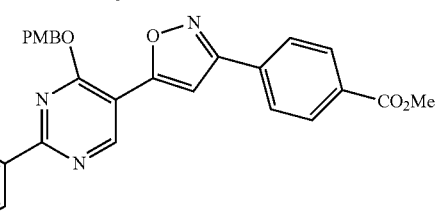

37-k

To a mixture of compound 37-e (517 mg, 2.43 mmol), compound 37-j (700 mg, 2.21 mmol) in THF (5 mL) was added triethylamine (335 mg, 3.31 mmol) dropwise. The mixture was stirred overnight at room temperature. The residue obtained from removal of the solvent was purified by flash chromatography (PE:EA=1:2) to afford compound 37-k (420 mg, 38%) as a yellow solid. $^1$H NMR (300 MHz, CDCl$_3$) δ 8.786 (s, 1H), 8.753-8.731 (d, J=6.6 Hz, 1H), 8.172-8.144 (d, J=8.4 Hz, 2H), 8.004-7.976 (d, J=8.4 Hz, 2H), 7.838-7.806 (m, 1H), 7.645 (s, 1H), 7.615 (s, 1H), 7.495-7.470 (s, 1H), 6.875-6.846 (d, J=8.7 Hz, 2H), 6.697-6.668 (d, J=8.7 Hz, 2H), 5.786 (s, 2H), 3.960 (s, 3H), 3.723 (s, 3H), LC-MS (ESI): 495 [M+H]$^+$.

Step I: Ethyl 4-(5-(4-hydroxy-2-(pyridin-2-yl)pyrimidin-5-yl)isoxazol-3-yl)benzoate (37-m)

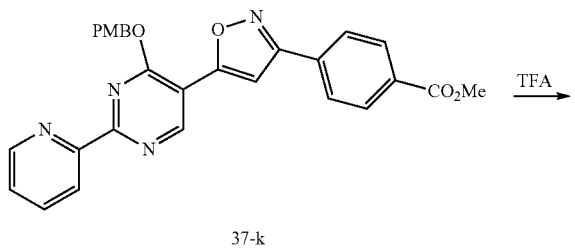

37-k

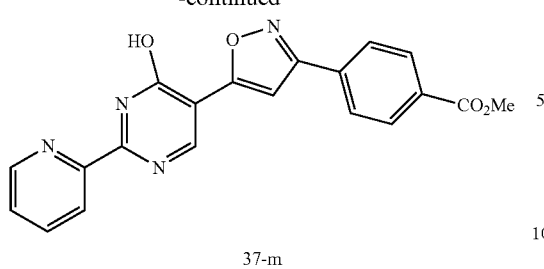

37-m

To a solution of compound 37-k (300 mg, 0.61 mmol) in DCM (5 mL) was added trifluoroactic acid (2.5 mL) dropwise. The mixture was stirred overnight at room temperature. The reaction mixture was evaporated to dryness to give compound 37-m, which was used in the next step without further purification.

Step J: 4-(5-(4-Hydroxy-2-(pyridin-2-yl)pyrimidin-5-yl)isoxazol-3-yl)benzoic acid (37-1)

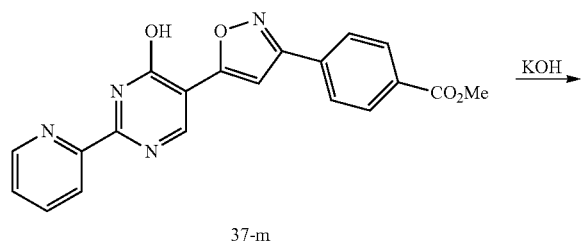

37-m

↓ KOH

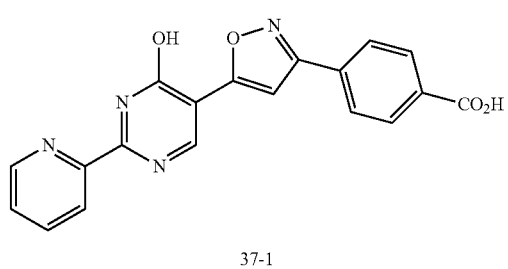

37-1

To a mixture of compound 37-m (300 mg, crude) in MeOH (10 mL) was added a solution of 20% KOH (10 mL). The mixture was stirred at 50° C. for 2 h. The reaction mixture was filtered. The filtrate was concentrated and the aqueous solution was extracted with DCM, and acidified by concentrated HCl to adjust to about pH 2-3. The solid was filtered and washed with water to afford compound 37-1 (110 mg, 73% for two steps) as a yellow solid. $^1$H NMR (300 MHz, DMSO-$d_6$) δ 8.827-8.821 (s, 1H), 8.722 (s, 1H), 8.456-8.431 (m, 1H), 8.103-8.035 (m, 2H), 7.733-7.694 (m, 1H), 7.630 (s, 1H), LC-MS (ESI): 361 [M+H]$^+$.

Example 38

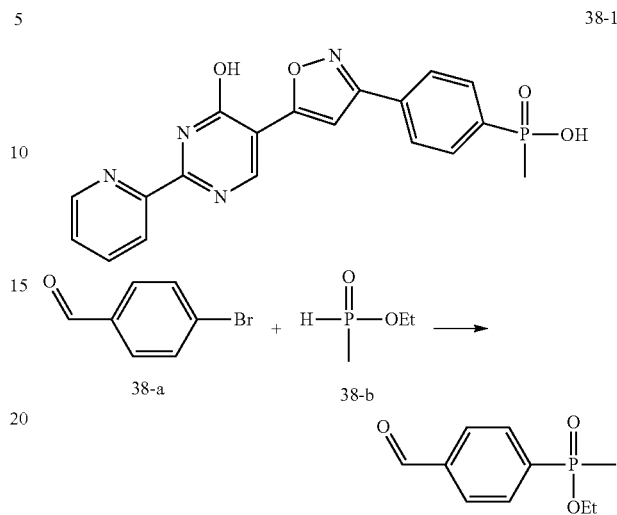

38-1

Step A: Ethyl 4-formylphenyl(methyl)phosphinate (38-c)

To a solution of 4-bromobenzaldehyde, 38-a, (500 mg, 2.7 mmol) and ethyl methylphosphinate, 38-b, (650 mg, 5.4 mmol) in toluene (10 mL) was added triethylamine (1.1 g, 11 mmol). After being allowed to stir for 10 h at 110° C. under nitrogen atmosphere, the mixture was cooled to ambient temperature, concentrated, diluted with water (50 mL) and extracted with ethyl acetate (3×50 mL). The combined organic layers were washed with brine (2×30 mL), dried over Na$_2$SO$_4$, filtrated and concentrated to give a residue, which was purified by chromatography on silica gel (dichloromethane/methanol=70:1) to afford compound 38-c as a colorless oil. (530 mg, 93%). $^1$H NMR (300 MHz, DMSO-$d_6$) δ 10.08 (s, 1H), 7.93-8.05 (m, 4H), 3.90-3.98 (m, 2H), 1.68-1.73 (d, J=14.4 Hz, 3H), 1.16-1.24 (m, 3H). LC-MS 213 [M+H]$^+$ Step B: (E)-Ethyl 4-((hydroxyimino)methyl)phenyl(methyl)phosphinate (38-d)

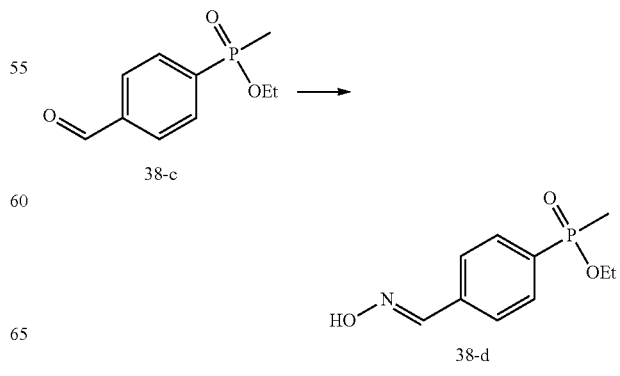

To a solution of compound 38-c (530 mg, 2.5 mmol) in ethanol (10 mL) was added hydroxylamine hydrochloride (230 mg, 3.2 mmol) and NaHCO₃ (360 g, 3.60 mmol). The reaction mixture was then stirred for 10 h at room temperature. The resulting mixture was concentrated under reduce pressure to afford crude compound 38-d (570 mg). LC-MS 228 [M+H]⁺

Step C: (Z)-Ethyl 4-(chloro(hydroxyimino)methyl)phenyl(methyl)phosphinate (38-e)

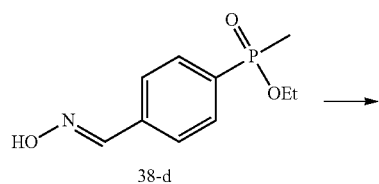

38-d

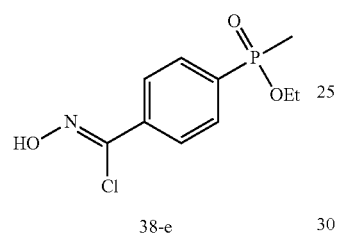

38-e

To a mixture of compound 38-d (570 mg, crude) in chloroform (15 mL) was added N-chlorobutanamide (370 mg, 2.8 mmol). After being stirred for 15 h at room temperature, the reaction mixture was concentrated to give a residue, which was purified by column chromatography on silica gel (DCM:MeOH=30:1) to afford compound 38-e (750 mg, crude) as a yellow solid. LC-MS 218 [M+H]⁺

Step D: Ethyl 4-(5-(4-(4-methoxybenzyloxy)-2-(pyridin-2-yl)pyrimidin-5-yl)isoxazol-3-yl)phenyl(methyl)phosphinate (38-f)

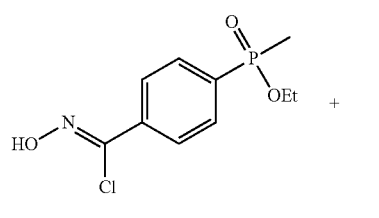

38-e

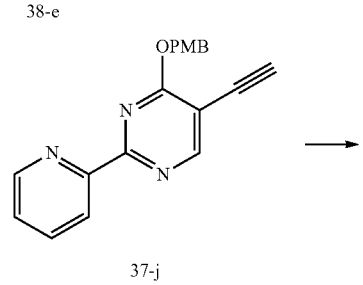

37-j

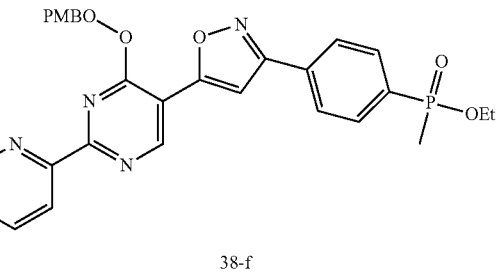

38-f

A mixture of compound 38-e (750 mg, 2.8 mmol), compound 37-j (820 mg, 2.6 mmol) and triethylamine (780 mg, 7.8 mmol) in THF (20 mL) was stirred at room temperature for 12 h. The resulting mixture was concentrated under reduce pressure, purified by column chromatography on silica gel (DCM:MeOH=30:1) to give compound 38-f (780 mg). LC-MS 543 [M+H]⁺

Step E: Ethyl 4-(5-(4-hydroxy-2-(pyridin-2-yl)pyrimidin-5-yl)isoxazol-3-yl)phenyl(methyl)phosphinate (38-g)

38-f 38-g

To a solution of compound 38-f (440 mg, 0.80 mmol) in DCM (5 mL) was added 2,2,2-trifluoroacetic acid (2 mL). After being stir for 10 h at room temperature, the reaction mixture was concentrated under reduce pressure and the residue was purified by pre-TLC (DCM:methanol=15:1) to afford compound 38-g (320 mg, 94%). ¹H NMR (300 MHz, CD₃OD) δ 8.79-8.80 (m, 1H), 8.71 (s, 1H), 8.38-8.41 (m, 1H), 8.10-8.12 (m, 3H), 7.89-7.93 (m, 2H), 7.67-7.72 (m, 2H), 3.91-3.96 (m, 2H), 1.67-1.72 (d, J=14.4 Hz, 3H), 1.18-1.22 (m, 3H). LC-MS 423 [M+H]⁺

Step F: 4-(5-(4-hydroxy-2-(pyridin-2-yl)pyrimidin-5-yl)isoxazol-3-yl)phenyl(methyl)phosphinic acid (38-1)

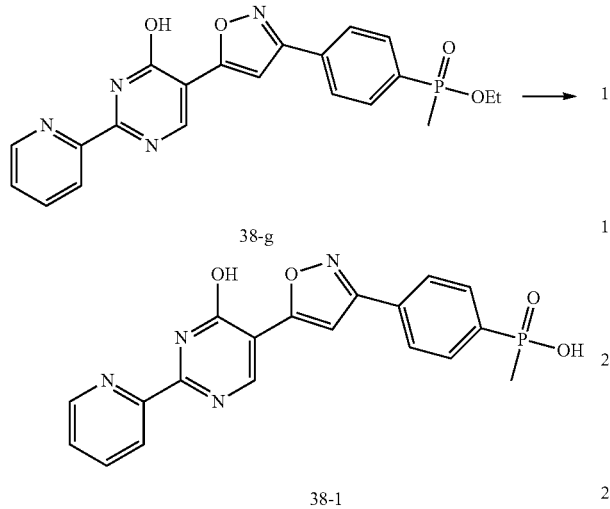

To a solution of compound 38-g (150 mg, 0.35 mmol) in dioxane (5 mL) was added 3 N NaOH aqueous solution (2 mL). The reaction mixture was refluxed for 1 h, and diluted with water, adjusted pH to 2 with concentrated HCl. The reaction mixture was concentrated and purified by pre-HPLC to afford compound 38-1 (2 mg). $^1$H NMR (300 MHz, CD$_3$OD) δ 8.84-8.56 (m, 1H), 8.77 (s, 1H), 8.44-8.46 (m, 1H), 8.10-8.14 (m, 3H), 7.89-7.95 (m, 2H), 7.70-7.77 (m, 2H), 7.34 (s, 1H), 7.00-7.16 (d, J=51.3 Hz, 1H), 1.57-1.62 (d, J=14.4 Hz, 3H). LC-MS 395 [M+H]$^+$ Biological Assays The exemplified compounds, Examples 1 through 13 of the present invention, have been found to inhibit the interaction between PHD2 and a HIF peptide and exhibit IC$_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 96-well plate was added 1 μL of test compound in DMSO and 20 μl of assay buffer (50 mM Tris pH 7.4/0.01% Tween-20/0.1 mg/ml bovine serum albumin/10 μM ferrous sulfate/i mM sodium ascorbate/20 μg/ml catalase) containing 0.15 μg/ml FLAG-tagged full length PHD2 expressed in and purified from baculovirus-infected Sf9 cells. After a 30 min preincubation at room temperature, the enzymatic reactions were initiated by the addition of 4 μL of substrates (final concentrations of 0.2 μM 2-oxoglutarate and 0.5 μM HIF-1α peptide biotinyl-DLDLEMLAPYIPMD-DDFQL (SEQ ID NO: 1)). After 2 hr at room temperature, the reactions were terminated and signals were developed by the addition of a 25 μL quench/detection mix to a final concentration of 1 mM ortho-phenanthroline, 0.1 mM EDTA, 0.5 nM anti-(His)6 LANCE reagent (Perkin-Elmer Life Sciences), 100 nM AF647-labeled streptavidin (Invitrogen), and 2 μg/ml (His)6-VHL complex (S. Tan (2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

Table 6 depicts the inhibition of HIF PHD2 activity expressed as IC$_{50}$ (nM), for the exemplified compounds, 1-1-1, 1-1-2, 1-1-3, 1-1-4, 1-1-5, 1-1-6, 2-1, 2-2, 2-3, 2-4, 2-5, 3-1, 3-2, 3-3, 3-5, 3-7, 3-7a, 4-1, 4-2, 5-1, 6-1, 6-2, 6-3, 7-1, 8-1, 8-2, 8-3, 8-4, 8-5, 9-1, 9-2, 10-1, 11-1, 12-1, 13-1, 14-1, 14-2, 15-1, 15-2, 15-3, 16-1, 17-1, 18-1, 19-1, 20-1, 21-1, 22-1, 23-1, 24-1, 25-1, 26-1, 27-1, 28-1, 29-1, 30-1, 30-2, 30-3, 31-1, 31-2, 32-1, 33-1, 34-1, 35-1, and 36-1 of the present invention.

TABLE 6

PHD2 Inhibition Activity
+ = 0.5 ≤ IC$_{50}$ ≤ 20 (nM)
++ = 20 < IC$_{50}$ ≤ 100 (nM)
+++ = 100 < IC$_{50}$ ≤ 10000 (nM)

| Cmp. No. | Compound IUPAC name | IC$_{50}$ (nM) |
|---|---|---|
| 1-1-1 | Diethyl 4-((4-hydroxy-2-(pyridin-2-yl)pyrimidine-5-carboxamido)(4-methoxyphenyl) methyl)phenylphosphonate | + |
| 1-1-2 | 4-((4-hydroxy-2-(pyridin-2-yl)pyrimidine-5-carboxamido)(4-methoxyphenyl)methyl) phenylphosphonic acid | + |
| 1-1-3 | (2S,2'S)-diethyl 2,2'-((4-((4-hydroxy-2-(pyridin-2-yl)pyrimidine-5-carboxamido)(4-methoxyphenyl) methyl)phenyl)phosphoryl)bis(azanediyl)dipropanoate | ++ |
| 1-1-4 | diethyl 2,2'-((4-((4-hydroxy-2-(pyridin-2-yl)pyrimidine-5-carboxamido)(4-methoxyphenyl)methyl)phenyl)phosphoryl)bis(azanediyl)bis(2-methylpropanoate) | + |
| 1-1-5 | diethyl 2,2'-((4-((4-hydroxy-2-(pyridin-2-yl)pyrimidine-5-carboxamido)(4-methoxyphenyl) methyl)phenyl)phosphoryl)bis(azanediyl)diacetate | ++ |
| 1-1-6 | 4-((4-hydroxy-2-(pyridin-2-yl)pyrimidine-5-carboxamido)(4-methoxyphenyl)methyl) phenylphosphinic acid | + |
| 2-1 | Diethyl 4-((4-hydroxy-2-(pyridin-2-yl)pyrimidine-5-carboxamido)(phenyl)methyl)phenyl phosphonate | + |

TABLE 6-continued

PHD2 Inhibition Activity
+ = 0.5 ≤ IC$_{50}$ ≤ 20 (nM)
++ = 20 < IC$_{50}$ ≤ 100 (nM)
+++ = 100 < IC$_{50}$ ≤ 10000 (nM)

| Cmp. No. | Compound IUPAC name | IC$_{50}$ (nM) |
|---|---|---|
| 2-2 | 4-((4-hydroxy-2-(pyridin-2-yl)pyrimidine-5-carboxamido)(phenyl)methyl)phenyl phosphonic acid | + |
| 2-3 | Ethyl 4-((4-hydroxy-2-(pyridin-2-yl)pyrimidine-5-carboxamido)(phenyl)methyl) phenylphosphonate | + |
| 2-4 | ethyl 4-((4-hydroxy-2-(pyridin-2-yl)pyrimidine-5-carboxamido)(phenyl)methyl phenyl(methyl)phosphinate | + |
| 2-5 | 4-((4-hydroxy-2-(pyridin-2-yl)pyrimidine-5-carboxamido)(phenyl)methyl)phenyl(methyl) phosphinic acid | + |
| 3-1 | Diethyl 4-(1-(4-hydroxy-2-(pyridin-2-yl)pyrimidine-5-carboxamido)ethyl)phenyl phosphonate | ++ |
| 3-2 | 4-(1-(4-hydroxy-2-(pyridin-2-yl)pyrimidine-5-carboxamido)ethyl)phenylphosphonic acid | +++ |
| 3-3 | Ethyl hydrogen 4-(1-(4-hydroxy-2-(pyridin-2-yl)pyrimidine-5-carboxamido)ethyl) phenylphosphonate | +++ |
| 3-3a | 4-(1-(4-Hydroxy-2-(pyridazin-3-yl) pyrimidine-5-carboxamido)ethyl)phenylphosphonic acid | +++ |
| 3-5 | (R)-4-(1-(4-hydroxy-2-(pyridin-2-yl)pyrimidine-5-carboxamido)ethyl)phenylphosphonic acid | +++ |
| 3-5a | (R)-4-(1-(4-hydroxy-2-(pyridazin-3-yl)pyrimidine-5-carboxamido)ethyl)phenylphosphonic acid | ++ |
| 3-7 | (S)-4-(1-(4-hydroxy-2-(pyridin-2-yl)pyrimidine-5-carboxamido)ethyl)phenylphosphonic acid | +++ |
| 3-7a | (S)-4-(1-(4-hydroxy-2-(pyridazin-3-yl) pyrimidine-5-carboxamido) ethyl) phenylphosphonic acid | +++ |
| 4-1 | Diethyl 5-((4-hydroxy-2-(pyridin-2-yl)pyrimidine-5-carboxamido)(phenyl)methyl)pyridin-2-ylphosphonate | + |
| 4-2 | Ethyl hydrogen 5-((4-hydroxy-2-(pyridin-2-yl)pyrimidine-5-carboxamido)(phenyl)methyl) pyridin-2-ylphosphonate | + |
| 5-1 | 3-((4-hydroxy-2-(pyridin-2-yl)pyrimidine-5-carboxamido)(4-methoxyphenyl)methyl) phenylphosphonic acid | + |
| 6-1 | Diisopropyl (4-hydroxy-2-(pyridin-2-yl) pyrimidine-5-carboxamido) (phenyl) methyl phosphonate | + |
| 6-2 | Isopropyl Hydrogen (4-hydroxy-2-(pyridin-2-yl) pyrimidine-5-carboxamido) (phenyl)methylphosphonate | ++ |
| 6-3 | Isopropyl Hydrogen (4-hydroxy-2-(pyridin-2-yl) pyrimidine-5-carboxamido) (phenyl)methylphosphonate | ++ |
| 7-1 | Diethyl 4-(1-(4-hydroxy-2-(pyridin-2-yl)pyrimidin-5-ylamino)-1-oxopropan-2-yl)phenyl phosphonate | +++ |
| 8-1 | Diethyl 4-((4-hydroxy-2-(1H-pyrazol-1-yl)pyrimidine-5-carboxamido)(phenyl)methyl) phenylphosphonate | + |
| 8-2 | Ethyl hydrogen 4-((4-hydroxy-2-(1H-pyrazol-1-yl)pyrimidine-5-carboxamido)(phenyl) methyl)phenylphosphonate | + |
| 8-3 | Ethyl 4-((4-hydroxy-2-(1H-pyrazol-1-yl)pyrimidine-5-carboxamido)(phenyl)methyl)phenyl (methyl)phosphinate | + |
| 8-4 | 4-((4-Hydroxy-2-(1H-pyrazol-1-yl)pyrimidine-5-carboxamido)(phenyl)methyl)phenyl (methyl) phosphinic acid | + |
| 8-5 | Diethyl 4-((4-hydroxy-2-(pyridazin-3-yl)pyrimidine-5-carboxamido)(phenyl)methyl) phenylphosphonate | + |
| 9-1 | 4-((4-Hydroxy-2-(1H-pyrazol-1-yl)pyrimidine-5-carboxamido)(4-methoxyphenyl)methyl) phenylphosphinic acid | + |
| 9-2 | 4-((4-hydroxy-2-(pyridazin-3-yl)pyrimidine-5-carboxamido)(4-methoxyphenyl)methyl) phenylphosphinic acid | + |
| 10-1 | Diethyl (4-hydroxy-2-(1H-pyrazol-1-yl)pyrimidine-5-carboxamido)(4-methoxyphenyl) methylphosphonate | + |
| 11-1 | Diethyl 4-(1-(4-hydroxy-2-(1H-pyrazol-1-yl)pyrimidin-5-ylamino)-1-oxopropan-2-yl) phenylphosphonate | +++ |
| 12-1 | Diethyl 4-(1-(4-hydroxy-2-(1H-pyrazol-1-yl) pyrimidin-5-ylamino)-2-methyl-1-oxopropan-2-yl) phenylphosphonate | +++ |
| 13-1 | Diethyl 4-(1-(4-hydroxy-2-(1H-pyrazol-1-yl)pyrimidin-5-ylamino)-3-methyl-1-oxobutan-2-yl)phenylphosphonate | ++ |
| 14-1 | Diethyl 4-(2-(4-hydroxy-2-(1H-pyrazol-1-yl)pyrimidin-5-ylamino)-2-oxo-1-phenylethyl)phenylphosphonate | + |
| 14-2 | Diethyl 4-(2-(4-hydroxy-2-(pyridazin-3-yl)pyrimidin-5-ylamino)-2-oxo-1-phenylethyl) phenylphosphonate | +++ |
| 15-1 | 4-(1-(4-hydroxy-2-(1H-pyrazol-1-yl)pyrimidine-5-carboxamido)ethyl)phenylphosphonic acid | ++ |
| 15-2 | (R)-4-(1-(4-hydroxy-2-(1H-pyrazol-1-yl)pyrimidine-5-carboxamido)ethyl)phenyl phosphonic acid | + |
| 15-3 | (S)-4-(1-(4-hydroxy-2-(1H-pyrazol-1-yl)pyrimidine-5-carboxamido)ethyl)phenylphosphonic acid | +++ |
| 16-1 | 4-((4-hydroxy-2-(1H-pyrazol-1-yl)pyrimidine-5-carboxamido)(phenyl)methyl) phenyl(propyl)phosphinic acid | + |

TABLE 6-continued

PHD2 Inhibition Activity
+ = 0.5 ≤ IC$_{50}$ ≤ 20 (nM)
++ = 20 < IC$_{50}$ ≤ 100 (nM)
+++ = 100 < IC$_{50}$ ≤ 10000 (nM)

| Cmp. No. | Compound IUPAC name | IC$_{50}$ (nM) |
|---|---|---|
| 17-1 | 4-((4-fluorophenyl)(4-hydroxy-2-(1H-pyrazol-1-yl)pyrimidine-5-carboxamido) methyl)phenyl(methyl)phosphinic acid | + |
| 18-1 | 4-((R)-(4-fluorophenyl)(4-hydroxy-2-(1H-pyrazol-1-yl)pyrimidine-5-carboxamido) methyl)phenyl(methyl)phosphinic acid | + |
| 19-1 | 4-((S)-(4-fluorophenyl)(4-hydroxy-2-(1H-pyrazol-1-yl)pyrimidine-5-carboxamido) methyl)phenyl(methyl)phosphinic acid | + |
| 20-1 | 4-((R)-(2,4-difluorophenyl)(4-hydroxy-2-(1H-pyrazol-1-yl)pyrimidine-5-carboxamido) methyl)phenyl(methyl)phosphinic acid | + |
| 21-1 | 4-((S)-(2,4-difluorophenyl)(4-hydroxy-2-(1H-pyrazol-1-yl)pyrimidine-5-carboxamido)methyl)phenyl(methyl)phosphinic acid | + |
| 22-1 | 4-((S)-(4-hydroxy-2-(1H-pyrazol-1-yl)pyrimidine-5-carboxamido)(phenyl) methyl)phenyl(methyl)phosphinic acid | + |
| 23-1 | 4-((R)-(4-hydroxy-2-(1H-pyrazol-1-yl)pyrimidine-5-carboxamido)(phenyl)methyl) phenyl (methyl)phosphinic acid | + |
| 24-1 | 3-((R)-(4-hydroxy-2-(1H-pyrazol-1-yl)pyrimidine-5-carboxamido)(phenyl) methyl)phenyl(methyl)phosphinic acid | + |
| 25-1 | 3-((S)-(4-hydroxy-2-(1H-pyrazol-1-yl)pyrimidine-5-carboxamido)(phenyl) methyl phenyl(methyl)phosphinic acid | + |
| 26-1 | 4-((R)-cyclohexyl(4-hydroxy-2-(1H-pyrazol-1-yl)pyrimidine-5-carboxamido)methyl) phenyl (methyl)phosphinic acid | + |
| 27-1 | 4-((S)-cyclohexyl(4-hydroxy-2-(1H-pyrazol-1-yl)pyrimidine-5-carboxamido) methyl) phenyl(methyl)phosphinic acid | + |
| 28-1 | 4-((S)-(2-(4-fluoro-1H-pyrazol-1-yl)-4-hydroxypyrimidine-5-carboxamido)(4-fluorophenyl)methyl)phenyl(methyl)phosphinic acid | +++ |
| 29-1 | 4-((R)-(2-(4-fluoro-1H-pyrazol-1-yl)-4-hydroxypyrimidine-5-carboxamido)(4-fluorophenyl)methyl)phenyl(methyl)phosphinic acid | + |
| 30-1 | (4-hydroxy-2-(pyridazin-3-yl)pyrimidine-5-carboxamido)(phenyl)methylphosphonic acid | ++ |
| 30-2 | (4-Hydroxy-2-(pyridazin-3-yl)pyrimidine-5-carboxamido)(4-methoxyphenyl)methyl phosphonic acid | + |
| 30-3 | (4-Hydroxy-2-(pyridazin-3-yl)pyrimidine-5-carboxamido)(naphthalen-2-yl)methyl phosphonic acid | + |
| 31-1 | Diethyl 2,2'-((4-((4-hydroxy-2-(pyridazin-3-yl)pyrimidine-5-carboxamido)(4-methoxyphenyl)methyl)phenyl)phosphoryl)bis(azanediyl)diacetate | + |
| 31-2 | (2S,2'S)-Diethyl 2,2'-((4-((4-hydroxy-2-(pyridazin-3-yl)pyrimidine-5-carboxamido)(4-methoxyphenyl)methyl)phenyl)phosphoryl)bis(azanediyl)dipropanoate | + |
| 32-1 | 4-((4-hydroxy-2-(pyridazin-3-yl)pyrimidine-5-carboxamido)(4-methoxyphenyl)methyl) benzylphosphonic acid | + |
| 33-1 | 4-(5-(2-(4-hydroxy-2-(pyridazin-3-yl)pyrimidine-5-carboxamido)propan-2-yl) pyridine-2-yl)phenylphosphonic acid | + |
| 34-1 | 3-((4-hydroxy-2-(pyridazin-3-yl)pyrimidine-5-carboxamido)(4-methoxyphenyl) methyl) phenylphosphonic acid | + |
| 35-1 | 3-(2-(4-hydroxy-2-(pyridazin-3-yl)pyrimidin-5-ylamino)-2-oxoethyl)phenyl phosphonic acid | +++ |
| 36-1 | (4-Hydroxy-2-(pyridazin-3-yl)pyrimidine-5-carboxamido)(4-methoxyphenyl)methyl phosphonic acid | ++ |

What is claimed is:

1. A compound of formula I or pharmaceutically acceptable salts thereof:

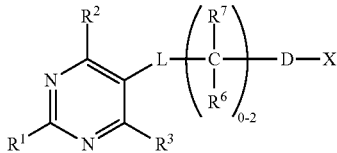

$R^1$ is a heteroaryl selected from isoxazolyl, pyrazolyl, imidazolyl, oxazolyl, thiazolyl, pyridinyl, pyradizinyl, and pyrimidinyl;

$R^2$ and $R^3$ are each independently chosen from hydrogen, hydroxy, —OR, —OCOR, —OCOOR, —OCONHR, and $C_{1-6}$alkyl;

X is selected from —$(C_{0-3}$alkyl)PO(R')OR, —$(C_{0-3}$alkyl)PO(OR)$_2$, —$(C_{0-3}$alkyl)PO(NRR)$_2$, —SO$_3$R, —$(C_{0-3}$alkyl)PO$(C_{1-10}$alkyl)OR, —$(C_{0-3}$alkyl)PO$(C_{3-10}$cycloalkyl)OR, —$(C_{0-3}$alkyl)PO(H)OR, —$(C_{0-3}$alkyl)PO(NHCR'R"COOR)$_2$ and —COOR;

R is independently selected from hydrogen, $C_{1-10}$ alkyl, —$C_{1-5}$ alkylaryl, —CR'R'-OCO—$C_{1-10}$ alkyl, and —CR'R'—OCO—O—$C_{1-10}$ alkyl;

R' and R" are independently selected from hydrogen and $C_{1-10}$ alkyl;

L is chosen from a bond, —CONR$^4$—, —NR$^4$CO—, aryl, and heteroaryl;

D is chosen from a bond, aryl, and heteroaryl, provided that when L is a bond then D is aryl or heteroaryl;

$R^4$, $R^6$, and $R^7$ are each independently selected from
hydrogen,
halogen,
carboxyl $C_{0-10}$ alkyl,
$C_{1-10}$ alkyl,
$C_{2-10}$ alkenyl,
$C_{2-10}$ alkynyl,
$C_{1-10}$ alkenylamino,
$C_{1-10}$ alkyl(oxy)$_{0-1}$ carbonyl$C_{1-10}$ alkyl,
aryl $C_{0-10}$ alkyl(oxy)$_{0-1}$ carbonyl$C_{1-10}$ alkyl,
$C_{3-8}$ cycloalkyl $C_{0-10}$ alkyl(oxy)$_{0-1}$carbonyl $C_{1-10}$ alkyl,
$(C_{3-8})$heterocyclyl $C_{0-10}$ alkyl(oxy)$_{0-1}$carbonyl $C_{1-10}$ alkyl,
$(C_{3-8})$heterocycloalkyl $C_{0-10}$ alkyl(oxy)$_{0-1}$ carbonyl $C_{1-10}$ alkyl,
aryl(oxy)$_{0-1}C_{0-10}$ alkyl,
$C_{3-8}$ cycloalkyl(oxy)$_{0-1}C_{0-10}$ alkyl,
$C_{3-8}$ heterocyclyl(oxy)$_{0-1}C_{0-10}$ alkyl,
$C_{3-8}$ heterocycloalkyl (oxy)$_{0-1}C_{0-10}$ alkyl,
$C_{1-10}$ alkoxyl,
aryl$C_{1-10}$ alkoxyl, and
hydroxy$C_{0-10}$alkyl;

wherein $R^1$, $R^2$, $R^3$, $R^4$, $R^6$, $R^7$, and D are optionally substituted with 1, 2, or 3 substituent $R^5$ chosen from:
halogen,
(carbonyl)$_{0-1}C_{1-10}$ alkyl,
(carbonyl)$_{0-1}C_{2-10}$ alkenyl,
(carbonyl)$_{0-1}C_{2-10}$ alkynyl,
$C_{1-10}$ alkylcarbonyl,
$C_{2-10}$ alkenylcarbonyl,
$C_{2-10}$ alkynylcarbonyl,
aryl $C_{0-10}$ alkyl,
$(C_{3-8})$heterocyclyl $C_{0-10}$ alkyl,
$C_{3-8}$ cycloalkyl $C_{0-10}$ alkyl,
$(C_{3-8})$heterocycloalkyl $C_{0-10}$ alkyl,
$C_{1-4}$acylamino $C_{0-10}$ alkyl,
$C_{0-10}$ alkylamino $C_{0-10}$ alkyl,
aryl$C_{0-10}$ alkylamino $C_{0-10}$ alkyl,
$C_{3-8}$ cycloalkyl $C_{0-10}$ alkylamino $C_{0-10}$ alkyl,
$C_{3-8}$ heterocyclyl $C_{0-10}$ alkylamino $C_{0-10}$ alkyl,
$C_{3-8}$ heterocycloalkyl $C_{0-10}$ alkylamino $C_{0-10}$ alkyl,
$C_{1-10}$alkyloxy $C_{0-10}$alkyl,
$(C_{1-10}$ alkyl)$_2$aminocarbonyloxy,
hydroxy $C_{0-10}$alkyl,
$C_{1-10}$ alkylsulfonyl,
$C_{1-10}$ alkylsulfonylamino,
aryl $C_{1-10}$ alkylsulfonylamino,
$C_{3-8}$ heterocyclyl $C_{1-10}$ alkylsulfonylamino,
$C_{3-8}$ heterocycloalkyl $C_{1-10}$ alkylsulfonylamino,
$C_{3-8}$ cycloalkyl $C_{1-10}$ alkylsulfonylamino,
cyano,
nitro,
perfluoro$C_{1-6}$alkyl, and
perfluoro$C_{1-6}$alkoxy;

wherein $R^5$ is optionally substituted with 1, 2, or 3 substituents chosen from hydrogen, hydroxy, $(C_{1-6})$alkoxyl, halogen, CO$_2$H, CN, O(C=O)C$_1$-C$_6$ alkyl, NO$_2$, trifluoromethoxy, trifluoroethoxy, —O$_{(0-1)}(C_{1-10})$perfluoroalkyl, and NH$_2$; and provided that when X is —COOR then L is isoxazoldiyl and D is phenyl.

2. A compound according to claim 1, wherein:
X is selected from —$(C_{0-3}$alkyl)PO(R')OR, —$(C_{0-3}$alkyl)PO(OR)$_2$, —$(C_{0-3}$alkyl)PO(NRR)$_2$, —SO$_3$R, —$(C_{0-3}$alkyl)PO$(C_{1-10}$alkyl)OR, —$(C_{0-3}$alkyl)PO$(C_{3-10}$cycloalkyl)OR, —$(C_{0-3}$alkyl)PO(H)OR, and —$(C_{0-3}$alkyl)PO(NHCR'R"COOR)$_2$; and $R^2$ and $R^3$ are each independently chosen from hydrogen, hydroxy, and $C_{1-6}$alkyl.

3. A compound according to claim 2, wherein L is —CONR$^4$—, or —NR$^4$CO—.

4. A compound according to claim 2, wherein L is a bond, aryl, or heteroaryl.

5. A compound according to claim 4, wherein L is heteroaryl.

6. A compound according to claim 5, wherein L is chosen from isoxazoldiyl, oxazoldiyl, pyrazoldiyl, imidazoldiyl, thazoldiyl, pyridindiyl, pyradizindiyl, and pyrimidindiyl.

7. A compound according to claim 6, wherein L is isoxazoldiyl.

8. A compound according to claim 2, wherein $R^1$ is selected from isoxazolyl, imidazolyl, oxazolyl, pyridinyl, pyradizinyl, and pyrimidinyl, optionally substituted with 1, 2, or 3 $R^5$ substituents.

9. A compound according to claim 8, wherein $R^1$ is selected from pyridindiyl, pyradizindiyl, and pyrimidindiyl, optionally substituted with 1, 2, or 3 $R^5$ substituents.

10. A compound according to claim 2, wherein $R^2$ is hydroxy.

11. A compound according to claim 6, wherein $R^3$ is hydrogen.

12. A compound according to claim 1, wherein $R^4$, $R^6$, and $R^7$ are each independently selected from hydrogen, aryl $C_{0-10}$ alkyl, $(C_{3-8})$heterocyclyl$C_{0-10}$ alkyl, $C_{3-8}$ cycloalkyl$C_{0-10}$ alkyl, $(C_{3-8})$heterocycloalkyl$C_{0-10}$ alkyl, $C_{1-10}$ alkyl, hydroxy$C_{0-10}$alkyl, and aryl$C_{1-10}$ alkoxyl.

13. A compound according to claim 12, wherein $R^4$, $R^6$, and $R^7$ are each independently selected from napthalenyl, phenylmethoxy, phenyl, methyl, ethyl, propyl, cyclohexyl, and hydrogen.

14. A compound selected from:
diethyl 4-((4-hydroxy-2-(pyridin-2-yl)pyrimidine-5-carboxamido)(4-methoxyphenyl)methyl)phenylphosphonate;
4-((4-hydroxy-2-(pyridin-2-yl)pyrimidine-5-carboxamido)(4-methoxyphenyl)methyl)phenylphosphonic acid;
(2S,2'S)-diethyl 2,2'-((4-((4-hydroxy-2-(pyridin-2-yl)pyrimidine-5-carboxamido)(4-methoxyphenyl)methyl)phenyl)phosphoryl)bis(azanediyl)dipropanoate;
diethyl 2,2'-((4-((4-hydroxy-2-(pyridin-2-yl)pyrimidine-5-carboxamido)(4-methoxyphenyl)methyl)phenyl)phosphoryl)bis(azanediyl)bis(2-methylpropanoate);
diethyl 2,2'-((4-((4-hydroxy-2-(pyridin-2-yl)pyrimidine-5-carboxamido)(4-methoxyphenyl)methyl)phenyl)phosphoryl)bis(azanediyl)diacetate;
4-((4-hydroxy-2-(pyridin-2-yl)pyrimidine-5-carboxamido)(4-methoxyphenyl)methyl)phenylphosphinic acid;
Diethyl 4-((4-hydroxy-2-(pyridin-2-yl)pyrimidine-5-carboxamido)(phenyl)methyl)phenyl phosphonate;
4-((4-hydroxy-2-(pyridin-2-yl)pyrimidine-5-carboxamido)(phenyl)methyl)phenyl phosphonic acid;
Ethyl 4-((4-hydroxy-2-(pyridin-2-yl)pyrimidine-5-carboxamido)(phenyl)methyl)phenylphosphonate;
ethyl 4-((4-hydroxy-2-(pyridin-2-yl)pyrimidine-5-carboxamido)(phenyl)methyl)phenyl(methyl)phosphinate;
4-((4-hydroxy-2-(pyridin-2-yl)pyrimidine-5-carboxamido)(phenyl)methyl)phenyl(methyl)phosphinic acid;
diethyl 4-(1-(4-hydroxy-2-(pyridin-2-yl)pyrimidine-5-carboxamido)ethyl)phenyl phosphonate;
4-(1-(4-hydroxy-2-(pyridin-2-yl)pyrimidine-5-carboxamido)ethyl)phenylphosphonic acid;
ethyl hydrogen 4-(1-(4-hydroxy-2-(pyridin-2-yl)pyrimidine-5-carboxamido)ethyl)phenylphosphonate;
diethyl (R)-4-(1-(4-hydroxy-2-(pyridin-2-yl)pyrimidine-5-carboxamido)ethyl)phenyl phosphonate;
(R)-4-(1-(4-hydroxy-2-(pyridin-2-yl)pyrimidine-5-carboxamido)ethyl)phenylphosphonic acid;
diethyl (S)-4-(1-(4-hydroxy-2-(pyridin-2-yl)pyrimidine-5-carboxamido)ethyl)phenyl phosphonate;
(S)-4-(1-(4-hydroxy-2-(pyridin-2-yl)pyrimidine-5-carboxamido)ethyl)phenylphosphonic acid;
(S)-4-(1-(4-hydroxy-2-(pyridazin-3-yl)pyrimidine-5-carboxamido)ethyl)phenylphosphonic acid;
diethyl 5-((4-hydroxy-2-(pyridin-2-yl)pyrimidine-5-carboxamido)(phenyl)methyl)pyridin-2-ylphosphonate;
ethyl hydrogen 5-((4-hydroxy-2-(pyridin-2-yl)pyrimidine-5-carboxamido)(phenyl)methyl)pyridin-2-ylphosphonate;
3-((4-hydroxy-2-(pyridin-2-yl)pyrimidine-5-carboxamido)(4-methoxyphenyl)methyl)phenylphosphonic acid;
diisopropyl (4-hydroxy-2-(pyridin-2-yl)pyrimidine-5-carboxamido)(phenyl)methyl phosphonate;
isopropyl Hydrogen (4-hydroxy-2-(pyridin-2-yl)pyrimidine-5-carboxamido)(phenyl)methylphosphonate;
isopropyl Hydrogen (4-hydroxy-2-(pyridin-2-yl)pyrimidine-5-carboxamido)(phenyl)methylphosphonate;
diethyl 4-(1-(4-hydroxy-2-(pyridin-2-yl)pyrimidin-5-ylamino)-1-oxopropan-2-yl)phenyl phosphonate;
ethyl 4-(1-(4-hydroxy-2-(pyridin-2-yl)pyrimidin-5-ylamino)-1-oxopropan-2-yl)phenylphosphonate;
diethyl 4-((4-hydroxy-2-(1H-pyrazol-1-yl)pyrimidine-5-carboxamido)(phenyl)methyl)phenylphosphonate;
ethyl hydrogen 4-((4-hydroxy-2-(1H-pyrazol-1-yl)pyrimidine-5-carboxamido)(phenyl)methyl)phenylphosphonate;
ethyl 4-((4-hydroxy-2-(1H-pyrazol-1-yl)pyrimidine-5-carboxamido)(phenyl)methyl)phenyl(methyl)phosphinate;
4-((4-Hydroxy-2-(1H-pyrazol-1-yl)pyrimidine-5-carboxamido)(phenyl)methyl)phenyl(methyl)phosphinic acid;
diethyl 4-((4-hydroxy-2-(pyridazin-3-yl)pyrimidine-5-carboxamido)(phenyl)methyl)phenylphosphonate;
4-((4-Hydroxy-2-(1H-pyrazol-1-yl)pyrimidine-5-carboxamido)(4-methoxyphenyl)methyl)phenylphosphinic acid;
4-((4-hydroxy-2-(pyridazin-3-yl)pyrimidine-5-carboxamido)(4-methoxyphenyl)methyl)phenylphosphinic acid;
diethyl (4-hydroxy-2-(1H-pyrazol-1-yl)pyrimidine-5-carboxamido)(4-methoxyphenyl)methylphosphonate;
diethyl 4-(1-(4-hydroxy-2-(1H-pyrazol-1-yl)pyrimidin-5-ylamino)-1-oxopropan-2-yl)phenylphosphonate;
diethyl 4-(1-(4-hydroxy-2-(1H-pyrazol-1-yl)pyrimidin-5-ylamino)-2-methyl-1-oxopropan-2-yl)phenylphosphonate;
diethyl 4-(1-(4-hydroxy-2-(1H-pyrazol-1-yl)pyrimidin-5-ylamino)-3-methyl-1-oxobutan-2-yl)phenylphosphonate;
diethyl 4-(2-(4-hydroxy-2-(1H-pyrazol-1-yl)pyrimidin-5-ylamino)-2-oxo-1-phenylethyl)phenylphosphonate;
diethyl 4-(2-(4-hydroxy-2-(pyridazin-3-yl)pyrimidin-5-ylamino)-2-oxo-1-phenylethyl)phenylphosphonate;
4-(1-(4-hydroxy-2-(1H-pyrazol-1-yl)pyrimidine-5-carboxamido)ethyl)phenylphosphonic acid;
(R)-4-(1-(4-hydroxy-2-(1H-pyrazol-1-yl)pyrimidine-5-carboxamido)ethyl)phenyl phosphonic acid;
(S)-4-(1-(4-hydroxy-2-(1H-pyrazol-1-yl)pyrimidine-5-carboxamido)ethyl)phenylphosphonic acid;
4-((4-hydroxy-2-(1H-pyrazol-1-yl)pyrimidine-5-carboxamido)(phenyl)methyl)phenyl(propyl)phosphinic acid;
4-((4-fluorophenyl)(4-hydroxy-2-(1H-pyrazol-1-yl)pyrimidine-5-carboxamido)methyl)phenyl(methyl)phosphinic acid;
4-((R)-(4-fluorophenyl)(4-hydroxy-2-(1H-pyrazol-1-yl)pyrimidine-5-carboxamido)methyl)phenyl(methyl)phosphinic acid;
4-((S)-(4-fluorophenyl)(4-hydroxy-2-(1H-pyrazol-1-yl)pyrimidine-5-carboxamido)methyl)phenyl(methyl)phosphinic acid;
4-((R)-(2,4-difluorophenyl)(4-hydroxy-2-(1H-pyrazol-1-yl)pyrimidine-5-carboxamido)methyl)phenyl(methyl)phosphinic acid;
4-((S)-(2,4-difluorophenyl)(4-hydroxy-2-(1H-pyrazol-1-yl)pyrimidine-5-carboxamido)methyl)phenyl(methyl)phosphinic acid;
4-((S)-(4-hydroxy-2-(1H-pyrazol-1-yl)pyrimidine-5-carboxamido)(phenyl)methyl)phenyl(methyl)phosphinic acid;
4-((R)-(4-hydroxy-2-(1H-pyrazol-1-yl)pyrimidine-5-carboxamido)(phenyl)methyl)phenyl(methyl)phosphinic acid;
3-((R)-(4-hydroxy-2-(1H-pyrazol-1-yl)pyrimidine-5-carboxamido)(phenyl)methyl)phenyl(methyl)phosphinic acid;
3-((S)-(4-hydroxy-2-(1H-pyrazol-1-yl)pyrimidine-5-carboxamido)(phenyl)methyl)phenyl(methyl)phosphinic acid;

4-((R)-cyclohexyl(4-hydroxy-2-(1H-pyrazol-1-yl)pyrimidine-5-carboxamido)methyl)phenyl(methyl)phosphinic acid;
4-((S)-cyclohexyl(4-hydroxy-2-(1H-pyrazol-1-yl)pyrimidine-5-carboxamido)methyl)phenyl(methyl)phosphinic acid;
4-((S)-(2-(4-fluoro-1H-pyrazol-1-yl)-4-hydroxypyrimidine-5-carboxamido)(4-fluorophenyl)methyl)phenyl(methyl)phosphinic acid;
4-((R)-(2-(4-fluoro-1H-pyrazol-1-yl)-4-hydroxypyrimidine-5-carboxamido)(4-fluorophenyl)methyl)phenyl(methyl)phosphinic acid;
(4-hydroxy-2-(pyridazin-3-yl)pyrimidine-5-carboxamido)(phenyl)methylphosphonic acid;
(4-Hydroxy-2-(pyridazin-3-yl)pyrimidine-5-carboxamido)(4-methoxyphenyl)methyl phosphonic acid;
(4-Hydroxy-2-(pyridazin-3-yl)pyrimidine-5-carboxamido)(naphthalen-2-yl)methyl phosphonic acid;
diethyl 2,2'-((4-((4-hydroxy-2-(pyridazin-3-yl)pyrimidine-5-carboxamido)(4-methoxyphenyl)methyl)phenyl)phosphoryl)bis(azanediyl)diacetate;
(2S,2'S)-Diethyl 2,2'-((4-((4-hydroxy-2-(pyridazin-3-yl)pyrimidine-5-carboxamido)(4-methoxyphenyl)methyl)phenyl)phosphoryl)bis(azanediyl)dipropanoate;
4-((4-hydroxy-2-(pyridazin-3-yl)pyrimidine-5-carboxamido)(4-methoxyphenyl)methyl)benzylphosphonic acid;
4-(5-(2-(4-hydroxy-2-(pyridazin-3-yl)pyrimidine-5-carboxamido)propan-2-yl)pyridine-2-yl)phenylphosphonic acid;
3-((4-hydroxy-2-(pyridazin-3-yl)pyrimidine-5-carboxamido)(4-methoxyphenyl)methyl)phenylphosphonic acid;
3-(2-(4-hydroxy-2-(pyridazin-3-yl)pyrimidin-5-ylamino)-2-oxoethyl)phenyl phosphonic acid;
(4-Hydroxy-2-(pyridazin-3-yl)pyrimidine-5-carboxamido)(4-methoxyphenyl)methyl phosphonic acid;
4-(5-(4-Hydroxy-2-(pyridin-2-yl)pyrimidin-5-yl)isoxazol-3-yl)benzoic acid; and
4-(5-(4-hydroxy-2-(pyridin-2-yl)pyrimidin-5-yl)isoxazol-3-yl)phenyl(methyl)phosphinic acid; or pharmaceutically acceptable salts, thereof.

15. A pharmaceutical composition comprising a compound of claim 1 and pharmaceutically acceptable carrier.

16. A method for the treatment of anemia in a mammal which comprises administering to the mammal an effective amount of a compound of claim 1, or a pharmaceutically acceptable salt thereof.

* * * * *